(12) United States Patent  
Castro Pineiro et al.

(10) Patent No.: US 7,105,507 B2  
(45) Date of Patent: Sep. 12, 2006

(54) CYCLOHEXANE DERIVATIVES AND THEIR USE AS THERAPEUTIC AGENTS

(75) Inventors: Jose Luis Castro Pineiro, Bishops Stortford (GB); Kevin Dinnell, Much Hadham (GB); Jason Matthew Elliott, Felsted (GB); Gregory John Hollingworth, Brentwood (GB); Duncan Edward Shaw, Bishops Stortford (GB); Christopher John Swain, Duxford (GB)

(73) Assignee: Merck Sharp & Dohme Limited, Hoddesdon (GB)

( * ) Notice: Subject to any disclaimer, the term of this patent is extended or adjusted under 35 U.S.C. 154(b) by 572 days.

(21) Appl. No.: 10/276,127

(22) PCT Filed: May 16, 2001

(86) PCT No.: PCT/GB01/02145

§ 371 (c)(1),  
(2), (4) Date: Nov. 13, 2002

(87) PCT Pub. No.: WO01/87838

PCT Pub. Date: Nov. 22, 2001

(65) Prior Publication Data

US 2003/0236250 A1 Dec. 25, 2003

(30) Foreign Application Priority Data

May 19, 2000 (GB) ................... 0012240.8

(51) Int. Cl.
| | |
|---|---|
| A61K 31/55 | (2006.01) |
| A61K 31/495 | (2006.01) |
| A61K 31/496 | (2006.01) |
| C07D 403/04 | (2006.01) |
| C07D 491/107 | (2006.01) |

(52) U.S. Cl. .............. 514/212.01; 514/227.5; 514/239.5; 514/252.14; 514/253.01; 514/254.1; 514/255.02; 514/255.03; 514/278; 514/307; 514/316; 514/327; 514/331; 514/249; 514/413; 514/429; 514/616; 540/610; 544/59; 544/166; 544/295; 544/350; 544/360; 544/366; 544/369; 544/374; 544/384; 544/400; 546/16; 546/19; 546/146; 546/190; 546/221; 546/234; 548/453; 548/578; 564/155

(58) Field of Classification Search ............... 546/16, 546/19, 190, 221, 234; 544/384, 400, 59, 544/166, 295, 360, 366, 369, 374; 514/255.03, 514/255.02, 278, 316, 331, 212.01, 252.14, 514/253.01, 254.1, 227.5, 239.5, 327, 429; 540/610; 548/578

See application file for complete search history.

(56) References Cited

U.S. PATENT DOCUMENTS 4,065,573 A * 12/1977 Lednicer ............... 514/462  
5,248,686 A * 9/1993 Kamenka et al. ......... 514/324  
5,849,795 A 12/1998 Arcamone et al.

OTHER PUBLICATIONS

Ohnmacht et al. Annual Reports in Medicinal Chemistry, vol.33, p. 71-80 (1998).*  
Chemical Abstracts, vol. 123, No. 15, Oct. 9, 1995 Columbus, Ohio, US; abstract No. 198390, Abdel-Kreem, M.F.M. et al: & Database Chemabs X)002172915 & Bull. Pharm. Sci., Asiut Univ. (1994). vol. date 1994, 17(2), 105-12.  
Ghazal, Abdel Rahim et al.:*Alexandria J. Pharm. Sci.* (1992), 6(1), 75-8.  
Shafik, Ragab M. et al: *Farmaco* (1995), 50(4), 273-9.

* cited by examiner

*Primary Examiner*—Emily Bernhardt  
(74) *Attorney, Agent, or Firm*—Curtis C. Panzer; David L. Rose

(57) ABSTRACT

The present invention relates compounds of formula (I), wherein ring A is a phenyl or pyridyl ring; X represents a linker selected from the group consisting of formulae: (a), (b), (c), (d), and (e); and $R^1$, $R^2$, $R^3$, $R^4$, $R^5$, $R^6$, $R^7$, $R^{13}$, $R^{14}$, $R^{15}$, $R^{16}$, $R^{17}$, $R^{21a}$ and $R^{21b}$ are as defined herein. The compounds are of particular use in the treatment or prevention of depression, anxiety, pain, inflammation, migraine, emesis or postherpetic neuralgia.

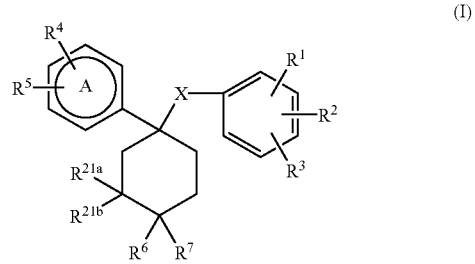

(I)

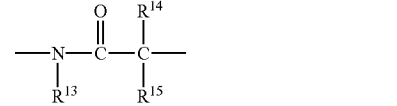

(a)

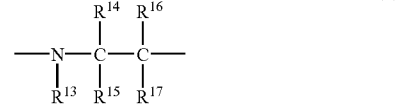

(b)

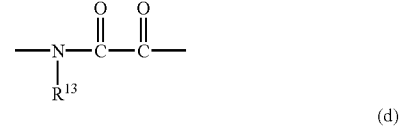

(c)

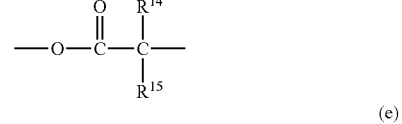

(d)

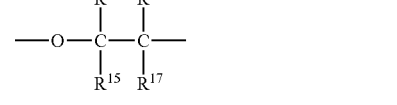

(e)

19 Claims, No Drawings

CYCLOHEXANE DERIVATIVES AND THEIR USE AS THERAPEUTIC AGENTS

CROSS REFERENCE TO RELATED APPLICATIONS

This application is a U.S. National Phase application under 35 U.S.C. §371 of PCT Application No. PCT/GB01/102,145, filed May 16, 2001, which claims priority under 35 U.S.C. §119 from GB Application No. 0012240.8, filed May 19, 2000.

This invention relates to a class of gem-disubstituted cyclohexane derivatives which are useful as tachykinin antagonists. More particularly, the compounds of the invention are useful as neurokinin 1 (NK-1) receptor antagonists.

The present invention provides compounds of the formula (I):

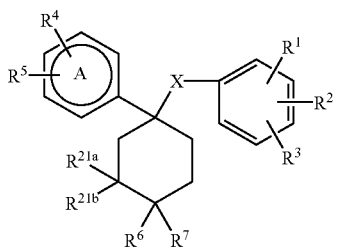

(I)

wherein
ring A is a phenyl or pyridyl ring;
X represents a linker selected from the group consisting of:

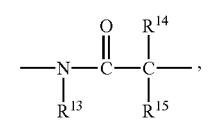

(a)

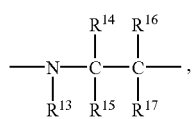

(b)

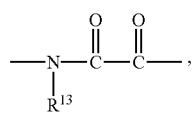

(c)

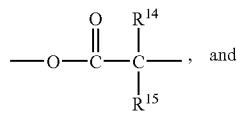

(d)

, and

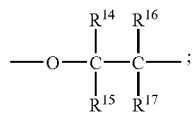

(e)

;

$R^1$ represents hydroxy, $C_{1-6}$alkyl, fluoro$C_{1-6}$alkyl, $C_{2-6}$alkenyl, $C_{3-7}$cycloalkyl, $C_{3-7}$cycloalkyl$C_{1-4}$alkyl, $C_{1-6}$alkoxy, fluoro$C_{1-6}$alkoxy, $C_{1-6}$alkoxy$C_{1-4}$alkyl, $C_{1-6}$alkoxy$C_{1-4}$alkoxy, fluoro$C_{1-6}$alkoxy$C_{1-4}$alkyl, $C_{2-6}$alkenyloxy, $C_{3-7}$cycloalkoxy, $C_{3-7}$cycloalkyl$C_{1-4}$alkoxy, phenoxy, cyano, halogen, $NR^aR^b$, $SR^a$, $SOR^a$, $SO_2R^a$, $OSO_2R^a$, $NR^aCOR^c$, $COR^a$, $CO_2R^a$ or $CONR^aR^b$ where $R^a$ and $R^b$ each independently represent hydrogen, $C_{1-4}$alkyl, $C_{3-5}$cycloalkyl, fluoro$C_{1-4}$alkyl or $CH_2CO_2C_{1-4}$alkyl, and $R^c$ represents $C_{1-6}$alkyl, $C_{1-6}$alkoxy, fluoro$C_{1-6}$alkyl or phenyl;

$R^2$ represents hydrogen, halogen, $C_{1-6}$alkyl or $C_{1-6}$alkoxy;

or when $R^2$ is adjacent to $R^1$, they may be joined together such that there is formed a 5- or 6-membered saturated or unsaturated ring containing one or two atoms selected from nitrogen, oxygen and sulphur, which ring is optionally substituted by a group selected from $C_{1-4}$alkyl, $CF_3$, =O or =S;

$R^3$ represents hydrogen, halogen, $C_{1-6}$alkyl, fluoro$C_{1-6}$alkyl, $C_{1-6}$alkoxy, fluoro$C_{1-6}$alkoxy, $C_{3-7}$cycloalkyl, $C_{3-7}$cycloalkyl$C_{1-4}$alkyl, cyano, $SR^a$, $SOR^a$, $SO_2R^a$, $NR^aR^b$, $NR^a$-$COR^{14}$, $COR^a$, $CO_2R^a$, $CONR^aR^b$ or $C_{1-4}$alkyl substituted by cyano, $CO_2R^a$ or $CONR^aR^b$ where $R^a$ and $R^b$ are as previously defined;

or $R^3$ represents a 5- or 6-membered aromatic heterocyclic group containing 1, 2, 3 or 4 heteroatoms, selected from nitrogen, oxygen and sulphur, which group is optionally substituted by one or two groups selected from $C_{1-6}$alkyl, $C_{1-6}$alkoxy, $C_{3-7}$cycloalkyl, $C_{3-7}$cycloalkyl$C_{1-4}$alkyl, trifluoromethyl, $OCF_3$, $NO_2$, $CN$, $SR^a$, $SOR^a$, $SO_2R^a$, $COR^a$, $CO_2R^a$, phenyl, —$(CH_2)_rNR^aR^b$, —$(CH_2)_rNR^aCOR^b$, —$(CH_2)_rCONR^aR^b$, or $CH_2C(O)R^a$, where $R^a$ and $R^b$ are as previously defined and r is zero, 1 or 2;

$R^4$ is hydrogen, halogen, $C_{1-6}$alkyl, $C_{1-6}$alkoxy, fluoro$C_{1-6}$alkyl, fluoro$C_{1-6}$alkoxy, hydroxy, $NO_2$, $CN$, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;

$R^5$ is hydrogen, halogen, $C_{1-6}$alkyl, fluoro$C_{1-6}$alkyl or $C_{1-6}$alkoxy substituted by $C_{1-4}$alkoxy;

$R^6$ represents hydrogen, hydroxy or a $C_{1-4}$alkyl group optionally substituted by a hydroxy group;

$R^7$ represents hydrogen, hydroxy, —$(CH_2)_nNR^8R^9$, —$(CH_2)_nCO_2R^a$, carbocyclyl, C-linked heterocyclyl or heteroaryl;

or $R^6$ and $R^7$ together represent =O, =CHCO$_2$R$^a$ or —O(CH$_2$)$_m$O—;

$R^8$ and $R^9$ each independently represent hydrogen, $C_{1-6}$alkyl, $C_{2-6}$alkenyl, hydroxy$C_{1-6}$alkyl, $(CH_2)_qC_{3-7}$cycloalkyl, $(CH_2)_q$aryl, $(CH_2)_q$heterocyclyl, $CHO$, $C(O)C_{1-6}$alkyl, $C(O)(CH_2)_qC_{3-7}$cycloalkyl, $C(O)(CH_2)_q$aryl, $C(O)(CH_2)_q$heterocyclyl, $C(O)(CH_2)_pNR^aR^b$, $(CH_2)_qCO_2C_{1-6}$alkyl, $CO_2(CH_2)_qC_{3-7}$cycloalkyl, $CO_2(CH_2)_q$aryl, $CO_2(CH_2)_q$heterocyclyl, $CO_2(CH_2)_pNR^aR^b$, $(CH_2)_pNR^aCOR^b$, $(CH_2)_pNR^aCO_2R^b$, $(CH_2)_qCONR^a$aryl or $(CH_2)_q$CONR$^a$heterocyclyl where $R^a$ and $R^b$ are as previously defined;

or $R^8$ and $R^9$, together with the nitrogen atom to which they are attached, represent a heteroaliphatic ring selected from the group consisting of:

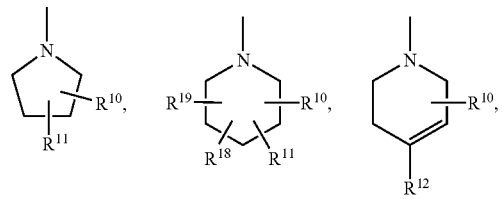

-continued

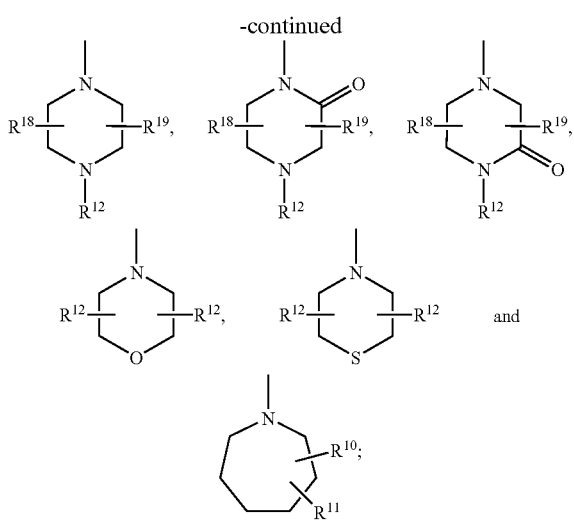

$R^{10}$ and $R^{11}$ each independently represent hydrogen, halogen, hydroxy, $C_{1-6}$alkyl, $C_{2-6}$alkenyl, $C_{2-6}$alkynyl, hydroxy$C_{1-6}$alkyl, fluoro$C_{1-6}$alkyl, $C_{1-6}$alkoxy, $(CH_2)_qC_{3-7}$cycloalkyl, $(CH_2)_q$aryl, $(C_{2-6}$alkenyl)aryl, $(C_{2-6}$alkynyl)aryl, $(CH_2)_q$heterocyclyl, $(CH_2)_qNR^aR^b$, $O(CH_2)_qC_{3-7}$cycloalkyl, $O(CH_2)_q$aryl, $O(CH_2)_q$heterocyclyl, $O(CH_2)_pNR^aR^b$, $OC(O)C_{1-6}$alkyl, $C(O)C_{1-6}$alkyl, $C(O)(CH_2)_q$aryl, $C(O)(CH_2)_q$heterocyclyl, $C(O)(CH_2)_qNR^aR^b$, $CO_2H$, $CO_2C_{1-6}$alkyl, $CO_2(CH_2)_qC_{3-7}$cycloalkyl, $CO_2(CH_2)_q$aryl, $CO_2(CH_2)_q$heterocyclyl or $CO_2(CH_2)_pNR^aR^b$, where $R^a$ and $R^b$ are as previously defined;

or, when they are attached to the same carbon atom, $R^{10}$ and $R^{11}$ may together represent =O, =CHCO$_2$R$^a$, —O(CH$_2$)$_m$O—, —CH$_2$O(CH$_2$)$_s$—, —CH$_2$OCH$_2$C(O)—, —CH$_2$OCH$_2$CH(OH)—, —CH$_2$OCH$_2$C(CH$_3$)$_2$—, —CH$_2$OC(CH$_3$)$_2$CH$_2$—, —C(CH$_3$)$_2$OCH$_2$CH$_2$—, —CH$_2$C(O)OCH$_2$—, —OC(O)CH$_2$CH$_2$—, —C(O)OCH$_2$CH$_2$—, —C(O)OC(CH$_3$)$_2$CH$_2$—, —C(O)OCH$_2$C(CH$_3$)$_2$—, —OCH$_2$(CH$_2$)$_s$—, —OC(CH$_3$)$_2$CH$_2$CH$_2$—, —OCH$_2$C(CH$_3$)$_2$CH$_2$—, —OCH$_2$CH$_2$C(CH$_3$)$_2$—, —OCH$_2$CH=CHCH$_2$—, —OCH$_2$CH(OH)CH$_2$CH$_2$—, —OCH$_2$CH$_2$CH(OH)CH$_2$—, —OCH$_2$C(O)CH$_2$CH$_2$—, —OCH$_2$CH$_2$C(O)CH$_2$—, or a group of the formula

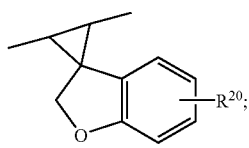

or, where they are attached to adjacent carbon atoms, $R^{10}$ and $R^{11}$ may together represent —OCH$_2$CH$_2$— or —OCH$_2$CH(OH)—, or $R^{10}$ and $R^{11}$ may together form a fused benzene ring;

or, $R^{10}$ and $R^{11}$ together form a $C_{1-2}$alkylene bridge across the pyrrolidine, piperidine or hexamethyleneimine ring to which they are attached;

$R^{12}$ represents hydrogen, $C_{1-6}$alkyl, $(CH_2)_qC_{3-7}$cycloalkyl, $(CH_2)_q$aryl, $(CH_2)_q$heterocyclyl, CHO, $C(O)C_{1-6}$alkyl, $C(O)(CH_2)_qC_{3-7}$cycloalkyl, $C(O)(CH_2)_q$aryl, $C(O)(CH_2)_q$heterocyclyl, $CO_2C_{1-6}$alkyl, $CO_2(CH_2)_qC_{3-7}$cycloalkyl, $CO_2(CH_2)_q$aryl, $CO_2(CH_2)_q$heterocyclyl or $CO_2(CH_2)_pNR^aR^b$, where $R^a$ and $R^b$ are as previously defined;

or, where they are attached to adjacent carbon atoms, $R^{12}$ and $R^{18}$ may together form a fused imidazolyl or triazolyl ring;

$R^{13}$ represents hydrogen, $C_{1-6}$alkyl or $C(O)C_{1-6}$alkyl;

$R^{14}$, $R^{15}$, $R^{16}$ and $R^{17}$ each independently represent hydrogen, hydroxy, $C_{1-6}$alkyl, $C_{1-6}$alkenyl, hydroxy$C_{1-6}$alkyl, $C_{1-4}$alkoxy$C_{1-4}$alkyl, $(CH_2)_pNR^aR^b$, CHO, $C(O)C_{1-6}$alkyl or $CO_2C_{1-6}$alkyl;

or, $R^{14}$ and $R^{15}$ together represent —CH$_2$CH$_2$—;

or, $R^{16}$ and $R^{17}$ together represent —CH$_2$CH$_2$—;

$R^{18}$ and $R^{19}$ each independently represent hydrogen, halogen, hydroxy, $C_{1-6}$alkyl or oxo (=O);

$R^{20}$ represents hydrogen, halogen, hydroxy, $C_{1-4}$alkyl, hydroxy$C_{1-4}$alkyl or fluoro$C_{1-4}$alkyl;

$R^{21a}$ represents hydrogen, halogen or hydroxy and $R^{21b}$ represents hydrogen;

or $R^{21a}$ and $R^{21b}$ both represent fluorine or together represent oxo (=O);

n is zero, 1 or 2;

m is 1 or 2;

p is 1, 2, 3 or 4;

q is zero, 1, 2, 3 or 4; and s is 1, 2 or 3;

and pharmaceutically acceptable salts and N-oxides thereof.

According to an alternative embodiment, the present invention also provides compounds of the formula (I'):

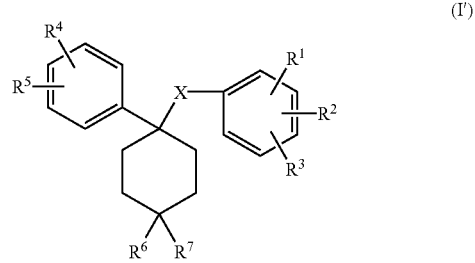

wherein

X represents a linker selected from the group consisting of:

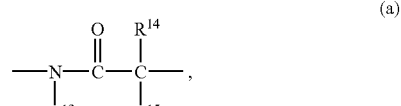

(a)

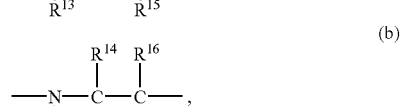

(b)

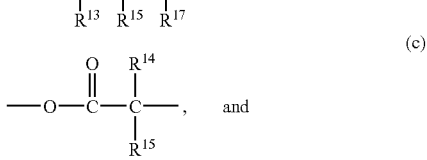

(c)

and

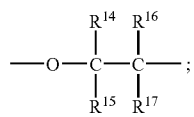

$R^6$ represents hydrogen or a $C_{1-4}$alkyl group optionally substituted by a hydroxy group;

$R^7$ represents hydrogen, hydroxy, —$(CH_2)_nNR^8R^9$, —$(CH_2)_nCO_2R^a$, carbocyclyl or heteroaryl;

or $R^6$ and $R^7$ together represent =O, =CHCO$_2R^a$ or —O(CH$_2)_m$O—;

$R^8$ and $R^9$ each independently represent hydrogen, $C_{1-6}$alkyl, $C_{2-6}$alkenyl, $(CH_2)_qC_{3-7}$cycloalkyl, $(CH_2)_q$aryl, $(CH_2)_q$heterocyclyl, CHO, C(O)C$_{1-6}$alkyl, C(O)(CH$_2)_qC_{3-7}$cycloalkyl, C(O)(CH$_2)_q$aryl, C(O)(CH$_2)_q$heterocyclyl, C(O)(CH$_2)_p$NR$^aR^b$, $(CH_2)_qCO_2C_{1-6}$alkyl, CO$_2$(CH$_2)_qC_{3-7}$cycloalkyl, CO$_2$(CH$_2)_q$aryl, CO$_2$(CH$_2)_q$heterocyclyl, CO$_2$(CH$_2)_p$NR$^aR^b$, $(CH_2)_p$NR$^a$COR$^b$ or $(CH_2)_p$NR$^a$CO$_2R^b$, where $R^a$ and $R^b$ are as previously defined;

or $R^8$ and $R^9$, together with the nitrogen atom to which they are attached, represent a heteroaliphatic ring selected from the group consisting of:

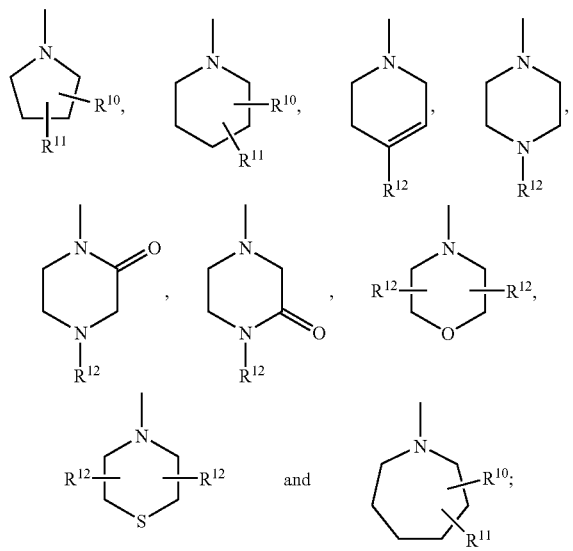

$R^{10}$ and $R^{11}$ each independently represent hydrogen, halogen, hydroxy, $C_{1-6}$alkyl, $C_{2-6}$alkenyl, $C_{2-6}$alkynyl, hydroxyC$_{1-6}$alkyl, $C_{1-6}$alkoxy, $(CH_2)_qC_{3-7}$cycloalkyl, $(CH_2)_q$ aryl, $(C_{2-6}$alkenyl)aryl, $(C_{2-6}$alkynyl)aryl, $(CH_2)_q$ heterocyclyl, $(CH_2)_q$NR$^aR^b$, O(CH$_2)_qC_{3-7}$cycloalkyl, O(CH$_2)_q$aryl, O(CH$_2)_q$heterocyclyl, O(CH$_2)_p$NR$^aR^b$, OC(O)C$_{1-6}$alkyl, C(O)C$_{1-6}$alkyl, C(O)(CH$_2)_q$aryl, C(O)(CH$_2)_q$heterocyclyl, C(O)(CH$_2)_q$NR$^aR^b$, CO$_2$H, CO$_2$C$_{1-6}$alkyl, CO$_2$(CH$_2)_qC_{3-7}$ cycloalkyl, CO$_2$(CH$_2)_q$aryl, CO$_2$(CH$_2)_q$heterocyclyl or CO$_2$(CH$_2)_p$NR$^aR^b$, where $R^a$ and $R^b$ are as previously defined;

or, when they are attached to the same carbon atom, $R^{10}$ and $R^{11}$ together represent =O, =CHCO$_2R^a$, O(CH$_2)_m$O—, —OCH$_2$CH$_2$CH$_2$—, —CH$_2$OCH$_2$CH$_2$— or —CH$_2$OCH$_2$C(O)—;

or, where they are attached to adjacent carbon atoms, $R^{10}$ and $R^{11}$ together form a fused benzene ring;

or, $R^{10}$ and $R^{11}$ together form a $C_{1-2}$alkylene bridge across the pyrrolidine, piperidine or hexamethyleneimine ring to which they are attached;

$R^{12}$ represents hydrogen, $C_{1-6}$alkyl, $(CH_2)_qC_{3-7}$cycloalkyl, $(CH_2)_q$aryl, $(CH_2)_q$heterocyclyl, CHO, C(O)C$_{1-6}$alkyl, C(O)(CH$_2)_qC_{3-7}$cycloalkyl, C(O)(CH$_2)_q$aryl, C(O)(CH$_2)_q$heterocyclyl, CO$_2$C$_{1-6}$alkyl, CO$_2$(CH$_2)_qC_{3-7}$cycloalkyl, CO$_2$(CH$_2)_q$aryl, CO$_2$(CH$_2)_q$heterocyclyl or CO$_2$(CH$_2)_p$NR$^aR^b$, where $R^a$ and $R^b$ are as previously defined;

$R^{14}$, $R^{15}$, $R^{16}$ and $R^{17}$ each independently represent hydrogen, hydroxy, $C_{1-6}$alkyl, $C_{1-6}$alkenyl, hydroxyC$_{1-6}$alkyl, $(CH_2)_p$NR$^aR^b$, CHO, C(O)C$_{1-6}$alkyl or CO$_2$C$_{1-6}$alkyl;

and $R^1$, $R^2$, $R^3$, $R^4$, $R^5$, $R^{13}$, n, m, p and q are as defined in relation to formula (I);

and pharmaceutically acceptable salts thereof.

A preferred class of compound of formula (I) is that wherein $R^1$ is hydroxy, $C_{1-6}$alkyl, fluoroC$_{1-6}$alkyl, $C_{2-6}$alkenyl, $C_{1-6}$alkoxy, fluoroC$_{1-6}$alkoxy, $C_{2-6}$alkenyloxy, $C_{3-7}$cycloalkoxy, $C_{3-7}$cycloalkylC$_{1-4}$alkoxy, cyano, NR$^aR^b$, SR$^a$, OSO$_2R^a$, or $R^1$ together with the group $R^2$ form a 5-membered saturated ring containing one oxygen atom.

A particularly preferred class of compound of formula (I) is that wherein $R^1$ is $C_{1-6}$alkyl, fluoroC$_{1-6}$alkyl, $C_{1-6}$alkoxy, fluoroC$_{1-6}$alkoxy, $C_{3-7}$cycloalkoxy or $C_{3-7}$cycloalkoxyC$_{1-4}$alkyl, especially methyl, trifluoromethyl, methoxy, trifluoromethoxy, 2,2,2-trifluoroethoxy, difluoromethoxy, cyclopropoxy or cyclopropylmethoxy.

Another preferred class of compound of formula (I) is that wherein $R^2$ is a hydrogen, fluorine or chlorine atom, especially a hydrogen atom.

A further preferred class of compound of formula (I) is that wherein $R^3$ is hydrogen, halogen, fluoroC$_{1-6}$alkyl, fluoroC$_{1-6}$alkoxy, cyano, NR$^aR^b$, NR$^a$COR$^d$ (where $R^d$ is methyl, methoxy, trifluoromethyl or phenyl), or a 5-membered aromatic heterocyclic group as previously defined.

Also preferred is the class of compound of formula (I) in which $R^3$ is $C_{1-6}$alkyl, fluoroC$_{1-6}$alkyl, fluoroC$_{1-6}$alkoxy or a 5-membered aromatic heterocyclic group as previously defined, especially methyl, trifluoromethyl, trifluoromethoxy or 5-trifluoromethyl-1,2,3,4-tetrazol-1-yl.

Certain particularly apt compounds of the present invention include those wherein $R^3$ is a group selected from pyrrole, furan, thiene, pyridine, pyrazole, imidazole, oxazole, isoxazole, thiazole, isothiazole, pyrazine, pyrimidine, pyridazine, triazole, oxadiazole, thiadiazole, triazine, and tetrazole, each heteroaryl group being optionally substituted as previously defined.

Preferred compounds of the present invention are those wherein $R^3$ is a group selected from furan, pyridine, pyrazole, imidazole, oxazole, isoxazole, pyrazine, pyrimidine, thiazole, 1,2,3-triazole, 1,2,4-triazole, 1,2,4-oxadiazole, 1,3,4-oxadiazole and tetrazole, each hetero group being optionally substituted as previously defined.

Particularly preferred compounds of the present invention are those wherein $R^3$ is a group selected from furan, pyridine, pyrimidine, 1,2,3-triazole, 1,2,4-triazole and tetrazole, each heteroaryl group being optionally substituted as previously defined.

An especially preferred class of compound of formula (I) is that wherein $R^3$ is the group

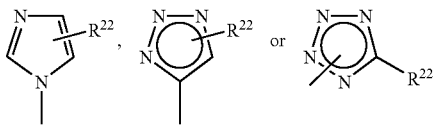

where R₂₂ is hydrogen, halogen, $C_{1-6}$alkyl, $C_{1-6}$alkoxy, $CF_3$, $OCF_3$, $NO_2$, CN, $SR^a$, $SOR^a$, $SO_2R^a$, $COR^a$, $CO_2R^a$, $(CH_2)_rCONR^aR^b$, $(CH_2)_rNR^aR^b$ or $(CH_2)_rNR^aCOR^b$, where $R^a$, $R^b$ and r are as previously defined.

$R^{22}$ is preferably hydrogen, $C_{1-4}$alkyl, especially methyl, $CF_3$, $(CH_2)_rCONR^aR^b$, $SOR^a$ or $SO_2R^a$ where $R^a$ and $R^b$ are preferably hydrogen, $C_{1-4}$alkyl or fluoro$C_{1-4}$alkyl and r is as previously defined. Most especially, $R^{22}$ is $CF_3$.

Preferably $R^1$ and $R^3$ are in the 3 and 5 positions of the phenyl ring.

More preferably $R^1$ is 3-fluoro or 3-$CF_3$.

More preferably $R^3$ is 5-fluoro or 5-$CF_3$.

More preferably $R^2$ is hydrogen.

Most preferably $R^1$ is 3-$CF_3$, $R^2$ is hydrogen and $R^3$ is 5-$CF_3$.

Another preferred class of compounds of formula (I) is that wherein $R^1$ and $R^3$ are in the 2- and 5-positions of the phenyl ring.

In this sub-class of compounds of formula (I), $R^1$ is preferably $C_{1-6}$alkoxy or $C_{3-7}$cycloalkoxy, especially methoxy or cyclopropoxy.

Also in this sub-class of compounds of formula (I), $R^2$ is preferably hydrogen.

Also, in this sub-class of compounds of formula (I) $R^3$ is preferably hydrogen, $C_{1-6}$alkoxy, fluoro$C_{1-6}$alkoxy or a 5-membered aromatic heterocyclic group as previously defined. Most especially, $R^3$ is hydrogen, methoxy or trifluoromethoxy.

A further preferred class of compound of formula (I) is that wherein $R^4$ is hydrogen.

Another preferred class of compounds of formula (I) is that wherein $R^5$ is hydrogen, fluorine, chlorine or $CF_3$, especially hydrogen or fluorine.

Preferably $R^4$ is hydrogen and $R^5$ is hydrogen or 4-fluoro.

Another further preferred class of compounds of formula (I) is that wherein $R^6$ is hydrogen.

A further preferred class of compounds of formula (I) is that wherein $R^7$ is hydroxy, —$(CH_2)_nNR^8R^9$, a C-linked heterocyclyl group or $R^6$ and $R^7$ together represent =O, —$O(CH_2)_mO$— or —$CH_2OCH_2C(O)$—.

Another preferred class of compounds of formula (I) is that wherein $R^7$ is hydroxy or —$(CH_2)_nNR^8R^9$, or $R^6$ and $R^7$ together represent =O, —$O(CH_2)_mO$— or —$CH_2OCH_2C(O)$—.

A further preferred class of compounds of formula (I) is that wherein $R^8$ represents hydrogen, $C_{1-6}$alkyl, $C_{2-6}$alkenyl, hydroxy$C_{1-6}$alkyl, $(CH_2)_qC_{3-7}$cycloalkyl, $(CH_2)_q$aryl, $(CH_2)_q$heterocyclyl, $C(O)C_{1-6}$alkyl, $C(O)(CH_2)_q$aryl, $C(O)(CH_2)_q$heterocyclyl, $C(O)(CH_2)_pNR^aR^b$, $(CH_2)_qCO_2C_{1-6}$alkyl, $(CH_2)_pNR^aCO_2R^b$ or $(CH_2)_qCONR^a$aryl;

and $R^9$ represents hydrogen, $C_{1-6}$alkyl, $(CH_2)_qC_{3-7}$cycloalkyl or $CO_2C_{1-6}$alkyl;

or $R^8$ and $R^9$ together with the nitrogen atom to which they are attached represent a heteroaliphatic ring selected from the group consisting of

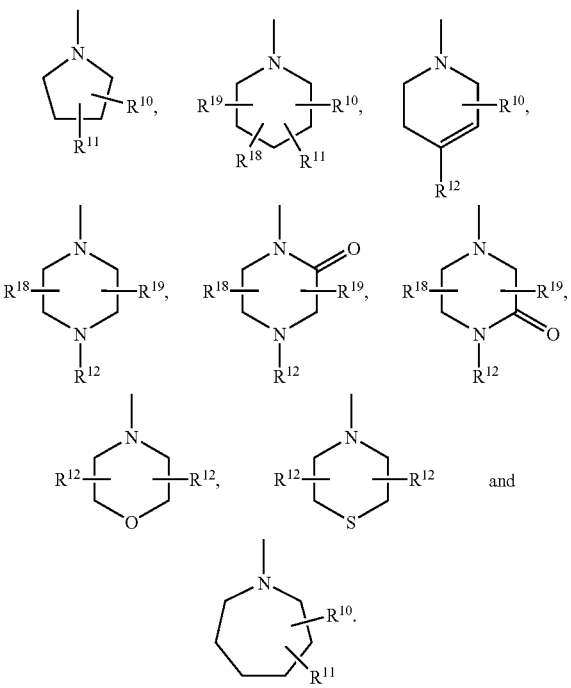

A yet further preferred class of compounds of formula (I) is that wherein $R^8$ represents hydrogen, $C_{1-6}$alkyl, $C_{2-6}$alkenyl, $(CH_2)_qC_{3-7}$cycloalkyl, $(CH_2)_q$aryl, $(CH_2)_q$heterocyclyl, $C(O)C_{1-6}$alkyl, $C(O)(CH_2)_q$aryl, $C(O)(CH_2)_q$heterocyclyl, $C(O)(CH_2)_pNR^aR^b$, $(CH_2)_qCO_2C_{1-6}$alkyl or $(CH_2)_pNR^aCO_2R^b$;

and $R^9$ represents hydrogen, $C_{1-6}$alkyl, $(CH_2)_qC_{3-7}$cycloalkyl or $CO_2C_{1-6}$alkyl;

or $R^8$ and $R^9$ together with the nitrogen atom to which they are attached represent a heteroaliphatic ring selected from the group consisting of

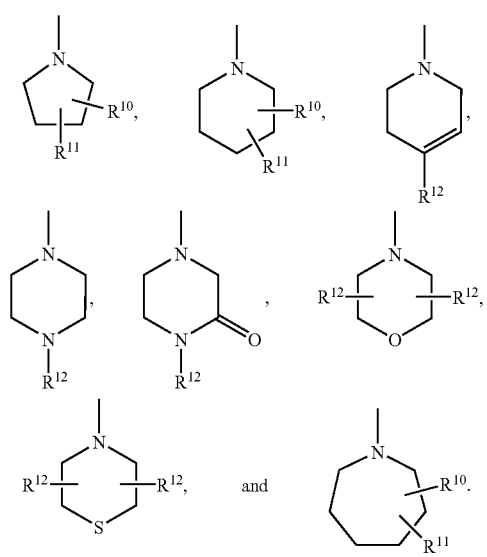

A further preferred class of compounds of formula (I) is that wherein $R^{10}$ represents hydrogen, hydroxy, $C_{1-6}$alkyl, $C_{2-6}$alkenyl, $C_{2-6}$alkynyl, hydroxy$C_{1-6}$alkyl, fluoroC$_{1-6}$alkyl, (C$_{2-6}$alkynyl)aryl, (CH$_2$)$_q$aryl, (CH$_2$)$_q$heterocyclyl, (CH$_2$)$_q$NR$^a$R$^b$, OC(O)C$_{1-6}$alkyl, C(O)(CH$_2$)$_q$NR$^a$R$^b$, CO$_2$H or —CO$_2$C$_{1-6}$alkyl;

and R$^{11}$ represents hydrogen, halogen, hydroxy, C$_{1-6}$alkyl or (CH$_2$)$_q$NR$^a$R$^b$;

or when they are attached to the same carbon atom, R$^{10}$ and R$^{11}$ may together represent =O, —O(CH$_2$)$_m$O—, —CH$_2$O(CH$_2$)$_s$—, —CH$_2$OCH$_2$C(O)—, —CH$_2$OCH$_2$CH(OH)—, —CH$_2$OCH$_2$C(CH$_3$)$_2$—, —CH$_2$OC(CH$_3$)$_2$CH$_2$—, —C(CH$_3$)$_2$OCH$_2$CH$_2$—, —CH$_2$C(O)OCH$_2$—, —OC(O)CH$_2$CH$_2$—, —C(O)OCH$_2$CH$_2$—, —C(O)OC(CH$_3$)$_2$CH$_2$—, —C(O)OCH$_2$C(CH$_3$)$_2$—, —OCH$_2$(CH$_2$)$_s$—, —OC(CH$_3$)$_2$CH$_2$CH$_2$—, —OCH$_2$CH=CHCH$_2$—, —OCH$_2$CH(OH)CH$_2$CH$_2$—, —OCH$_2$CH$_2$CH(OH)CH$_2$—, —OCH$_2$C(O)CH$_2$CH$_2$—, or a group of the formula

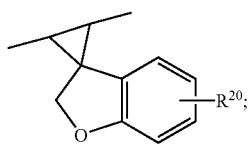

or, when they are attached to adjacent carbon atoms, R$^{10}$ and R$^{11}$ may together represent —OCH$_2$CH$_2$— or —OCH$_2$CH(OH)—, or R$^{10}$ and R$^{11}$ may together form a fused benzene ring;

or R$^{10}$ and R$^{11}$ together form a C$_{1-2}$alkylene bridge across the pyrrolidine or piperidine ring to which they are attached.

Another preferred class of compounds of formula (I) is that wherein R$^{10}$ represents hydrogen, hydroxy, C$_{1-6}$alkyl, C$_{2-6}$alkenyl, C$_{2-6}$alkynyl, hydroxyC$_{1-6}$alkyl, (C$_{2-6}$alkynyl)aryl, (CH$_2$)$_q$aryl, (CH$_2$)$_q$heterocyclyl, (CH$_2$)$_q$NR$^a$R$^b$, OC(O)C$_{1-6}$alkyl, C(O)(CH$_2$)$_q$NR$^a$R$^b$, CO$_2$H or CO$_2$C$_{1-6}$alkyl;

and R$^{11}$ represents hydrogen, halogen, hydroxy, C$_{1-6}$alkyl or (CH$_2$)$_q$NR$^a$R$^b$;

or when they are attached to the same carbon atom, R$^{10}$ and R$^{11}$ together represent =O or —O(CH$_2$)$_m$O—;

or, when they are attached to adjacent carbon atoms, R$^{10}$ and R$^{11}$ together form a fused benzene ring;

or R$^{10}$ and R$^{11}$ together form a C$_{1-2}$alkylene bridge across the pyrrolidine or piperidine ring to which they are attached.

A further preferred class of compounds of formula (I) is that wherein R$^{12}$ represents hydrogen, C$_{1-6}$alkyl, (CH$_2$)$_q$C$_{3-7}$cycloalkyl, (CH$_2$)$_q$aryl, (CH$_2$)$_q$heterocyclyl, CHO, C(O)C$_{1-6}$alkyl, C(O)C$_{3-7}$cycloalkyl, C(O)(CH$_2$)$_q$aryl or CO$_2$C$_{1-6}$alkyl.

A yet further preferred class of compounds of formula (I) is that wherein R$^9$ represents hydrogen, C$_{1-6}$alkyl, (CH$_2$)$_q$C$_{3-7}$cycloalkyl or CO$_2$C$_{1-6}$alkyl.

A particularly preferred class of compounds of formula (I) is that wherein R$^8$ represents hydrogen, C$_{1-6}$alkyl, C$_{2-4}$alkenyl, C$_{3-7}$cycloalkyl, CH$_2$C$_{3-7}$cycloalkyl, (CH$_2$)$_q$phenyl, (CH$_2$)$_q$furyl, (CH$_2$)$_q$pyridyl, (CH$_2$)$_q$triazolinone, C(O)C$_{1-4}$alkyl, C(O)(CH$_2$)$_q$phenyl, C(O)(CH$_2$)$_q$imidazolyl, C(O)(CH$_2$)$_q$tetrazolyl, C(O)(CH$_2$)pyrrolidinyl, C(O)(CH$_2$)$_p$NR$^a$R$^b$, CH$_2$C(O)C$_{1-4}$alkyl or (CH$_2$)$_p$NR$^a$CO$_2$C$_{1-4}$alkyl;

and R$^9$ represents hydrogen, C$_{1-6}$alkyl, CH$_2$C$_{3-5}$cycloalkyl or CO$_2$C$_{1-4}$alkyl;

or R$^8$ and R$^9$ together with the nitrogen atom to which they are attached represent a heteroaliphatic ring selected from the group consisting of:

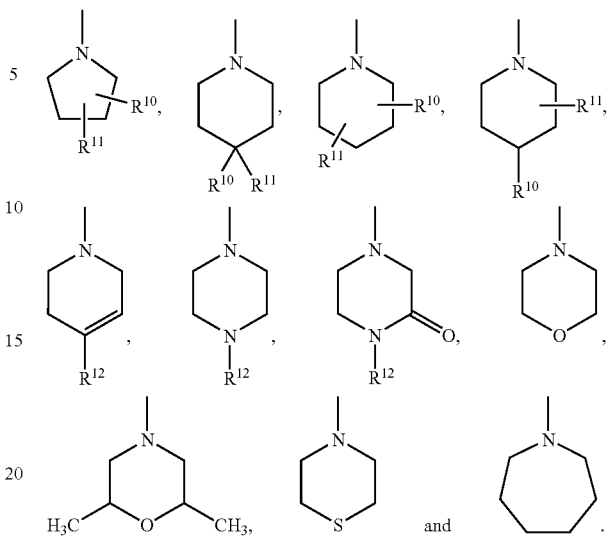

A further particularly preferred class of compounds of formula (I) is that wherein:

R$^{10}$ represents hydrogen, hydroxy, methyl, allyl, acetylene, hydroxyC$_{1-4}$alkyl, —C≡C(phenyl), phenyl, 4-fluorophenyl, CH$_2$phenyl, CH$_2$CH$_2$phenyl, heterocyclyl (wherein said heterocyclyl is selected from the group consisting of pyrrolidinyl, piperidinyl, piperazinyl, morpholinyl, thiomorpholinyl, and hexamethyleneimine, wherein each ring is optionally substituted by one or two groups selected from methyl, hydroxymethyl, cyclohexyl, dimethylamino and benzisothiazole or there is optionally a benzene ring fused to the ring, or there is optionally present a —CH$_2$CH$_2$— bridge across the ring), NR$^a$R$^b$, OC(O)CH$_3$, C(O)NR$^a$R$^b$, CO$_2$H or CO$_2$C$_{1-4}$alkyl; and R$^{11}$ represents hydrogen, fluorine, hydroxy, methyl or dimethylamino;

or, when they are attached to the same carbon atom, R$^{10}$ and R$^{11}$ together represent =O or —OCH$_2$CH$_2$O—;

or, when they are attached to adjacent carbon atoms, R$^{10}$ and R$^{11}$ together form a fused benzene ring;

or, R$^{10}$ and R$^{11}$ together form a —CH$_2$CH$_2$— bridge across the pyrrolidine or piperidine ring to which they are attached.

A yet further particularly preferred class of compounds of formula (I) is that wherein R$^{12}$ represents hydrogen, C$_{1-6}$alkyl, C$_{3-6}$cycloalkyl, CH$_2$C$_{3-6}$cycloalkyl (especially CH$_2$cyclopropyl or CH$_2$cyclohexyl), phenyl, CH$_2$phenyl, CH$_2$CH$_2$phenyl (wherein each of said phenyl groups are optionally substituted by one or two substituents selected from fluorine, CF$_3$ or methoxy), CH$_2$heterocyclyl (wherein said heterocyclyl is selected from the group consisting of 2-, 3- or 4-pyridine, 2- or 3-thiophene, 2- or 3-furan, thiazole, and benzisothiazole), CHO, C(O)C$_{1-4}$alkyl, C(O)C$_{3-6}$cycloalkyl (especially C(O)cyclopropyl or C(O)cyclohexyl), C(O)CH$_2$cycloalkyl (especially C(O)CH$_2$cyclopropyl or C(O)CH$_2$cyclohexyl), C(O)CH$_2$CH$_2$C$_{3-6}$cycloalkyl (especially C(O)CH$_2$CH$_2$cyclohexyl), C(O)phenyl or CO$_2$C$_{1-4}$alkyl.

Yet another particularly preferred class of compounds of formula (I) is that wherein R$^9$ represents hydrogen, C$_{1-6}$alkyl, CH$_2$C$_{3-5}$cycloalkyl or CO$_2$C$_{1-4}$alkyl.

Another preferred class of compound of formula (I) is that wherein the ring A is a phenyl ring.

Particularly preferred compounds of formula (I) are those wherein $R^7$ represents a group selected from:

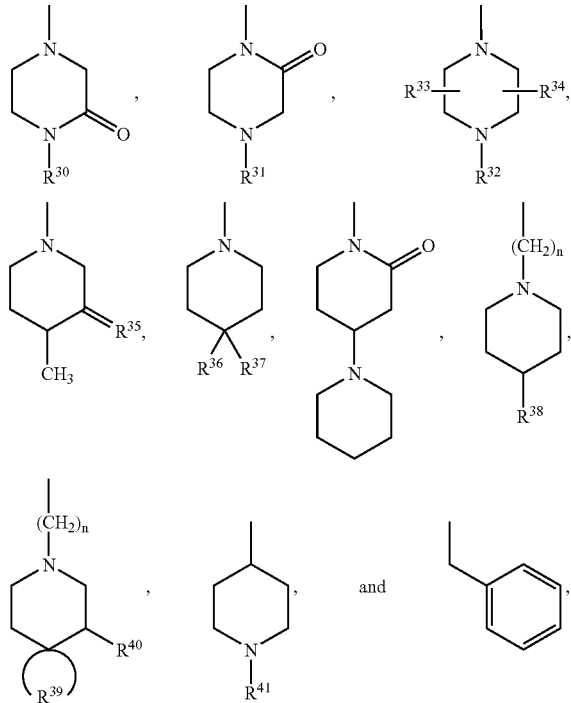

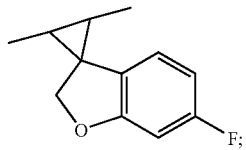

$R^{40}$ is hydrogen or hydroxy, especially hydrogen;
$R^{41}$ is $C_{1-3}$alkyl, especially isopropyl; and
n is zero, 1 or 2, especially zero.

Further preferred compounds of formula (I) are those wherein $R^7$ represents a group selected from:

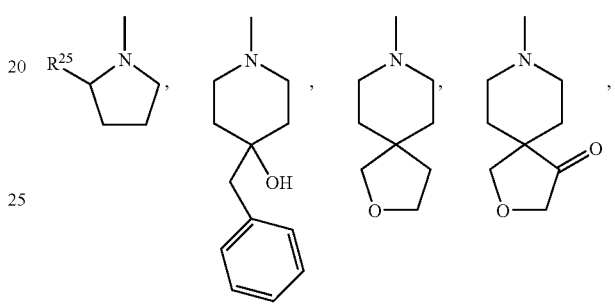

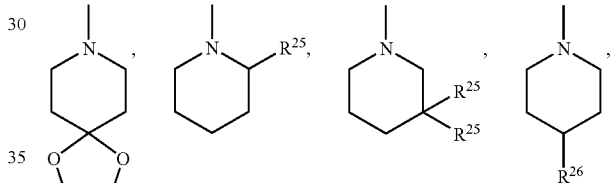

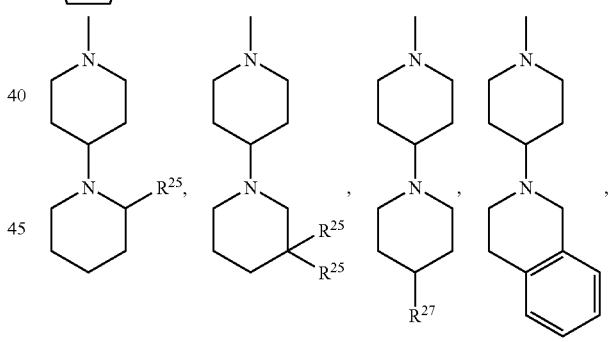

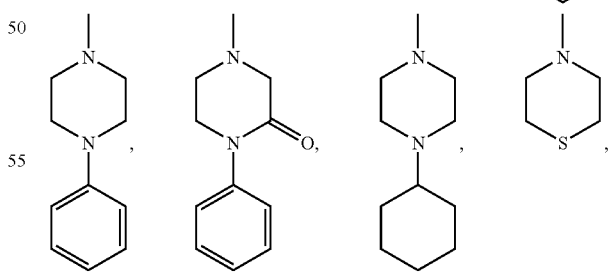

wherein $R^{30}$ represents 4-pyridyl, phenyl, phenyl mono-substituted by fluorine, chlorine, methyl, methoxy or $CO_2$methoxy, or phenyl disubstituted by methyl;

$R^{31}$ represents $C_{2-4}$alkyl or $(CH_2)_qC_{3-7}$cycloalkyl, especially tert-butyl, cyclopropylmethyl or cyclohexyl;

$R^{32}$ represents $C_{1-6}$alkyl, tetrahydropyranyl or benzyl;

$R^{33}$ and $R^{34}$, which may be attached to the same or different carbon atoms, each independently represent hydrogen or methyl;

$R^{35}$ represents hydroxy or methoxy;

$R^{36}$ represents hydroxy$C_{1-4}$alkyl (especially hydroxymethyl), $C_{1-4}$alkoxy (especially methoxy) or hydroxy;

$R^{37}$ represents methoxy $C_{2-4}$alkyl (especially methoxymethyl) or $C_{2-4}$alkyl;

$R^{38}$ represents hydrogen, oxo (=O), hydroxy, trifluoromethyl, $C_{1-3}$alkyl (especially isopropyl) or hydroxy$C_{1-3}$alkyl (especially hydroxymethyl or hydroxyethyl);

$R^{39}$ represents a ring-forming moiety selected from —OCH$_2$CH$_2$O—, —CH$_2$OCH$_2$CH$_2$—, —CH$_2$OCH$_2$CH$_2$CH$_2$—, —CH$_2$OCH$_2$C(O)—, —CH$_2$OCH$_2$CH(OH)—, —CH$_2$OC(CH$_3$)$_2$CH$_2$—, —C(CH$_3$)$_2$OCH$_2$CH$_2$—, —CH$_2$C(O)OCH$_2$, —C(O)OCH$_2$CH$_2$—, —C(O)OC(CH$_3$)$_2$CH$_2$—, —OCH$_2$CH$_2$CH$_2$—, —OCH$_2$CH$_2$CH$_2$CH$_2$—, —OC(CH$_3$)$_2$CH$_2$CH$_2$, —OCH$_2$CH=CHCH$_2$—, —OCH$_2$CH(OH)CH$_2$CH$_2$—, —OCH$_2$CH$_2$CH(OH)CH$_2$—, —OCH$_2$C(O)CH$_2$CH$_2$— and a group of the formula wherein R$^{25}$ represents hydrogen, methyl or hydroxymethyl;

R$^{26}$ represents hydrogen, methyl, hydroxy, methylamino, dimethylamino, cyclopropylamino, phenyl, or phenyl substituted by fluorine; and R$^{27}$ represents hydrogen, methyl, hydroxy, methylamino, dimethylamino or cyclopropylamino.

Another preferred class of compounds of formula (I) is that wherein X is the linker:

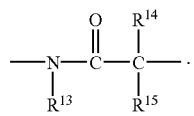

Another preferred class of compounds of formula (I) is that wherein R$^{13}$ represents hydrogen, methyl or acetyl. In particular, R$^{13}$ represents hydrogen.

A further preferred class of compounds of formula (I) is that wherein one of the groups R$^{14}$, R$^{15}$, R$^{16}$ and R$^{17}$ represents hydrogen, hydroxy, C$_{1-6}$alkyl, hydroxyC$_{1-6}$alkyl, (CH$_2$)$_p$NR$^a$R$^b$, CHO, C(O)C$_{1-6}$alkyl or CO$_2$C$_{1-6}$alkyl, and the other(s) of the groups R$^{14}$, R$^{15}$, R$^{16}$ and R$^{17}$ each represent hydrogen.

A particularly preferred class of compounds of formula (I) is that wherein one of the groups R$^{14}$, R$^{15}$, R$^{16}$ and R$^{17}$ represents methyl or hydroxymethyl, and the other(s) of groups R$^{14}$, R$^{15}$, R$^{16}$ and R$^{17}$ each represent hydrogen.

Another preferred class of compounds of formula (I) is that wherein R$^{21a}$ represents hydrogen, fluorine or hydroxy and R$^{21b}$ is hydrogen, or R$^{21a}$ and R$^{21b}$ both represent fluorine or together represent oxo (=O). In particular, R$^{21a}$ is preferably hydrogen, fluorine or hydroxy and R$^{21b}$ is hydrogen. Most especially, R$^{21a}$ and R$^{21b}$ are preferably both hydrogen.

Most especially, a preferred class of compounds of formula (I) is that wherein X is the linker:

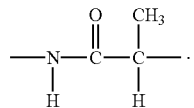

Another preferred class of compounds of formula (I) is that wherein n is zero.

A further preferred class of compounds of formula (I) is that wherein m is 2.

Another preferred class of compounds of formula (I) is that wherein p is 1, 2 or 3, particularly 1 or 2, and especially 1.

A further preferred class of compounds of formula (I) is that wherein q is zero, 1 or 2, particularly zero or 1.

One favoured group of compounds of the present invention are of the formula (Ia) and pharmaceutically acceptable salts thereof:

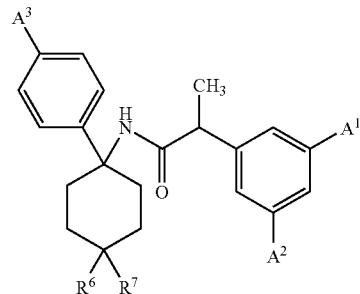

wherein

A$^1$ is fluorine or CF$_3$;

A$^2$ is fluorine or CF$_3$;

A$^3$ is fluorine or hydrogen; and

R$^6$ and R$^7$ are as defined in relation to formula (I).

When any variable occurs more than one time in formula (I) or formula (Ia) or in any substituent, its definition on each occurrence is independent of its definition at every other occurrence.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the term "hydroxyC$_{1-6}$alkyl" means a C$_{1-6}$alkyl group in which one or more (in particular 1 to 3, and especially 1) hydrogen atoms have been replaced by hydroxy groups. Particularly preferred are hydroxyC$_{1-3}$alkyl groups, for example, CH$_2$OH, CH$_2$CH$_2$OH, CH(CH$_3$)OH or C(CH$_3$)$_2$H, and most especially CH$_2$OH.

As used herein, the terms "fluoroC$_{1-6}$alkyl" and fluoroC$_{1-6}$alkoxy means a C$_{1-6}$alkyl or C$_{1-6}$alkoxy group in which one or more (in particular, 1 to 3) hydrogen atoms have been replaced by fluorine atoms. Particularly preferred are fluoroC$_{1-3}$alkyl and fluoroC$_{1-6}$alkoxy groups, for example, CF$_3$, CH$_2$CH$_2$F, CH$_2$CHF$_2$, CH$_2$CF$_3$, OCF$_3$, OCH$_2$CH$_2$F, OCH$_2$CHF$_2$ or OCH$_2$CF$_3$, and most especially CF$_3$, OCF$_3$ and OCH$_2$CF$_3$.

The cycloalkyl groups referred to herein may represent, for example, cyclopropyl, cyclobutyl, cyclopentyl or cyclohexyl. A suitable (CH$_2$)$_q$C$_{3-7}$cycloalkyl group where q is 1 may be, for example, cyclopropylmethyl or cyclohexylmethyl.

Similarly cycloalkoxy groups referred to herein may represent, for example, cyclopropoxy or cyclobutoxy.

As used herein, the terms "alkenyl" and "alkynyl" as a group or part of a group means that the group is straight or branched. Examples of suitable alkenyl groups include vinyl and allyl. A suitable alkynyl group is acetylene or propargyl.

When used herein the term "halogen" means fluorine, chlorine, bromine and iodine. The most apt halogens are fluorine and chlorine of which fluorine is preferred, unless otherwise stated.

As used herein, the term "aryl" as a group or part of a group means an aromatic radical such as phenyl, biphenyl or naphthyl, wherein said phenyl, biphenyl or naphthyl group may be optionally substituted by one, two or three groups independently selected from halogen, C$_{1-6}$alkyl, C$_{1-6}$alkoxy, fluoroC$_{1-6}$alkyl, fluoroC$_{1-6}$alkoxy, NO$_2$, cyano, SR$^a$, SOR$^a$, SO$_2$R$^a$, COR$^a$, CO$_2$R$^a$, CONR$^a$R$^b$, C$_{2-6}$alkenyl, C$_{2-6}$alkynyl, C$_{1-4}$alkoxyC$_{1-4}$alkyl or —O(CH$_2$)$_m$O—. Preferably said phenyl, biphenyl or naphthyl group is optionally substituted by one or two substituents, especially none or one. Particularly preferred substituents include fluorine, chlorine, bromine, C$_{1-4}$alkyl (especially methyl), C$_{1-4}$alkoxy (especially methoxy), trifluoromethyl, trifluoromethoxy or vinyl.

As used herein, the term "heterocyclyl" as a group or part of a group means a saturated, partially saturated or unsaturated heteroatom-containing ring-shaped radical, where the heteroatoms may be selected from nitrogen, oxygen and sulfur. Examples of saturated heterocyclyl radicals include N-linked saturated 3 to 6-membered heteromonocyclic groups containing 1 to 3 nitrogen atoms and optionally 1 oxygen or sulfur atom (for example, azetidinyl, pyrrolidinyl, piperidinyl, morpholinyl, thiomorpholinyl, piperazinyl or piperazinyl substituted on the nitrogen atom by a C$_{1-4}$alkyl group or a C$_{2-4}$alkyl group substituted by hydroxy or C$_{1-2}$alkoxy). Examples of saturated heterocyclyl radicals also include C-linked saturated 3 to 6-membered heteromonocyclic groups containing, for example, one oxygen atom (for instance, tetrahydrofuranyl or tetrahydropyranyl). Examples of partially saturated heterocyclyl radicals include N-linked partially saturated 3 to 6-membered heteromonocyclic groups containing 1 to 3 nitrogen atoms (for example, 3-pyrroline). Examples of unsaturated heterocyclyl radicals include heteroaromatic rings selected from pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indolyl, benzofuranyl, benzthiophenyl, benzimidazolyl, benzisoxazolyl, benzoxazolyl, benzthiazolyl or benzisothiazolyl.

Said saturated and partially saturated heterocyclyl radicals may be optionally substituted by one, two or three groups independently selected from halogen, C$_{1-6}$alkyl, C$_{1-6}$alkoxy, fluoroC$_{1-6}$alkyl, fluoroC$_{1-6}$alkoxy, NO$_2$, cyano, oxo (=O), NR$^a$R$^b$, SR$^a$, SOR$^a$, SO$_2$R$^a$, COR$^a$, CO$_2$R$^a$, CONR$^a$R$^b$, C$_{2-6}$alkenyl, C$_{2-6}$alkynyl, C$_{1-4}$alkoxyC$_{1-4}$alkyl, —O(CH$_2$)$_m$O—, —OCH$_2$CH$_2$CH$_2$—, —CH$_2$OCH$_2$CH$_2$— or —CH$_2$OCH$_2$C(O)—. Preferably said saturated or partially saturated heterocyclyl radical is optionally substituted by one or two substituents, especially none or one. Particularly preferred substituents include fluorine, chlorine, bromine, C$_{1-4}$alkyl (especially methyl), C$_{1-4}$alkoxy (especially methoxy), trifluoromethyl, trifluoromethoxy, oxo, vinyl, C$_{1-4}$alkylamino (especially methylamino) or di(C$_{1-4}$alkyl)amino (especially dimethylamino).

Said unsaturated heterocyclyl radicals may be optionally substituted by one, two or three groups independently selected from halogen, C$_{1-6}$alkyl, C$_{1-6}$alkoxy, fluoroC$_{1-6}$alkyl, fluoroC$_{1-6}$alkoxy, NO$_2$, cyano, NR$^a$R$^b$, SR$^a$, SOR$^a$, SO$_2$R$^a$, COR$^a$, CO$_2$R$^a$, CONR$^a$R$^b$, C$_{2-6}$alkenyl, C$_{2-6}$alkynyl, C$_{1-4}$alkoxyC$_{1-4}$alkyl or —O(CH$_2$)$_m$O—. Preferably said unsaturated heterocyclyl is optionally substituted by one or two substituents, especially none or one. Particularly preferred substituents include fluorine, chlorine, bromine, C$_{1-4}$alkyl (especially methyl), C$_{1-4}$alkoxy (especially methoxy), trifluoromethyl, trifluoromethoxy or vinyl.

As used herein, the term "carbocyclyl" as a group or part of a group means a 3 to 7-membered cycloalkyl radical such as cyclopropyl, cyclobutyl, cyclopentyl or cyclohexyl, wherein said cycloalkyl radical may be optionally substituted by one, two or three groups independently selected from halogen, C$_{1-6}$alkyl, C$_{1-6}$alkoxy, hydroxyC$_{1-6}$alkyl, fluoroC$_{1-6}$alkyl, fluoroC$_{1-6}$alkoxy, NO$_2$, cyano, SR$^a$, SOR$^a$, SO$_2$R$^a$, COR$^a$, CO$_2$R$^a$, CONR$^a$R$^b$, C$_{2-6}$alkenyl, C$_{2-6}$alkynyl, C$_{1-4}$alkoxyC$_{1-4}$alkyl or —O(CH$_2$)$_m$O—. Preferably said cycloalkyl radical is substituted by one or two substituents, especially one. Particularly preferred substituents include fluorine, chlorine, bromine, C$_{1-4}$alkyl (especially methyl), methoxy, hydroxyC$_{1-4}$alkyl (especially C(CH$_3$)$_2$OH), trifluoromethyl, trifluoromethoxy or vinyl.

Specific compounds within the scope of this invention include:

cis-(RS)-α-methyl-N-{4-[4-phenylmethyl-4-(dimethylamino)piperidin-1-yl]-1-phenylcyclohexyl}-3,5-bis(trifluoromethyl)benzeneacetamide;

trans-(RS)-α-methyl-N-{4-[4-phenylmethyl-4-(dimethylamino)piperidin-1-yl]-1-phenylcyclohexyl}-3,5-bis(trifluoromethyl)benzeneacetamide;

cis-(RS)-α-methyl-N-{4-[4-(phenylmethyl)-4-hydroxypiperidin-1-yl]-1-phenylcyclohexyl}-3,5-bis(trifluoromethyl)benzeneacetamide;

trans-(RS)-α-methyl-N-{4-[4-(phenylmethyl)-4-hydroxypiperidin-1-yl]-1-phenylcyclohexyl}-3,5-bis(trifluoromethylbenzeneacetamide;

cis-N-{4-[4-(4-fluorophenyl)piperidin-1-yl]-1-phenylcyclohexyl}-3,5-bis(trifluoromethyl)benzeneacetamide;

trans-N-{4-[4-(4-fluorophenyl)piperidin-1-yl]-1-phenylcyclohexyl}-3,5-bis(trifluoromethyl)benzeneacetamide;

trans-(RS)-α-methyl-N-{4-[(2-{[(1,1-dimethylethoxy)carbonyl]amino}ethyl)amino]-1-phenylcyclohexyl}-3,5-bis(trifluoromethyl)benzeneacetamide;

trans-(RS)-N-{4-[4-(4-fluorophenyl)piperidin-1-yl]-1-phenylcyclohexyl}-α-methyl-3,5-bis(trifluoromethyl)benzeneacetamide;

trans-(RS)-N-{4-[4-(4-fluorophenyl)piperidin-1-yl]-1-phenylcyclohexyl}-N,α-dimethyl-3,5-bis(trifluoromethyl)benzeneacetamide;

trans-(RS)-N-{4-[4-(4-fluorophenyl)piperidin-1-yl]-1-phenylcyclohexyl}-α,α-dimethyl-3,5-bis(trifluoromethyl)benzeneacetamide;

trans-(RS)-N-{4-[4-(4-fluorophenyl)piperidin-1-yl]-1-phenylcyclohexyl}-α-hydroxymethyl-3,5-bis(trifluoromethyl)benzeneacetamide;

trans-(RS)-α-methyl-N-[4-(4-oxopiperidin-1-yl)-1-phenylcyclohexyl]-3,5-bis(trifluoromethyl)benzeneacetamide;

trans-(RS)-α-methyl-N-{1-phenyl-4-[(phenylmethyl)amino]cyclohexyl}-3,5-bis(trifluoromethyl)benzeneacetamide;

trans-(RS)-α-methyl-N-{4-[N-methyl(phenylmethyl)amino]-1-phenylcyclohexyl}-3,5-bis(trifluoromethyl)benzeneacetamide;

trans-(RS)-α-methyl-N-(4-methylamino-1-phenylcyclohexyl)-3,5-bis(trifluoromethyl)benzeneacetamide;

trans-(RS)-N-[4-({1-oxo-2-[3,5-bis(trifluoromethyl)phenyl]propyl}amino)-4-phenylcyclohexyl]-N-(phenylmethyl)glycine methyl ester;

trans-(RS)-N-methyl-N-[4-({1-oxo-2-[3,5-bis(trifluoromethyl)phenyl]propyl}amino)-4-phenylcyclohexyl]glycine methyl ester;

trans-(RS)-α-methyl-N-{4-[2-(dimethylamino)acetylamino]-1-phenylcyclohexyl}-3,5-bis(trifluoromethyl)benzeneacetamide;

trans-(RS)-N-(4-aminomethyl-1-phenylcyclohexyl)-α-methyl-3,5-bis(trifluoromethyl)benzeneacetamide, trans-(RS)-α-methyl-N-(4-dimethylaminomethyl-1-phenylcyclohexyl)-3,5-bis(trifluoromethyl)benzeneacetamide;

trans-(RS)-α-methyl-N-[4-(piperidin-1-yl)methyl-1-phenylcyclohexyl]-3,5-bis(trifluoromethyl)benzeneacetamide;

trans-(RS)-4-[4-(4-fluorophenyl)piperidin-1-yl]-1-phenyl-N-{2-[3,5-bis(trifluoromethyl)phenyl]propyl}cyclohexylamine;

and pharmaceutically acceptable salts thereof.

Further particularly preferred compounds of the present invention include:

cis-(RS)- and trans-(RS)-α-methyl-N-{4-[4-hydroxymethyl-4-(methoxymethyl)piperidin-1-yl]-1-phenylcyclohexyl}-3,5-bis(trifluoromethylbenzeneacetamide;
trans-(RS)-α-methyl-N-[4-(1,4-oxa-8-azaspiro[4.5]decan-8-yl)-1-phenylcyclohexyl]-3,5-bis(trifluoromethyl)benzeneacetamide;
trans-(RS)-α-methyl-N-[4-(2-oxa-4-oxo-8-azaspiro[4.5]decan-8-yl)-1-phenylcyclohexyl]-3,5-bis(trifluoromethyl)benzeneacetamide;
trans-(RS)-α-methyl-N-[4-(1-oxa-9-azaspiro[5.5]undecan-9-yl)-1-phenylcyclohexyl]-3,5-bis(trifluoromethyl)benzeneacetamide;
trans-(2R*,3'R*)- and trans-(2R*,3'S*)-α-methyl-N-[4-(3-hydroxy-1-oxa-9-azaspiro[5.5]undecan-9-yl)-1-phenylcyclohexyl]-3,5-bis(trifluoromethyl)benzeneacetamide;
trans-(2R*,4'R*) and trans-(2R*,4'S*)-α-methyl-N-[4-(4-hydroxy-1-oxa-9-azaspiro[5.5]undecan-9-yl)-1-phenylcyclohexyl]-3,5-bis(trifluoromethyl)benzeneacetamide;
trans-(R,S)-α-methyl-N-[4-(1-oxa-3-oxa-9-azaspiro[5.5]undecan-9-yl)-1-phenylcyclohexyl]-3,5-bis(trifluoromethyl)benzeneacetamide;
trans-(RS)-α-methyl-N-{4-[4-(phenylmethyl)piperazin-1-yl]-1-phenylcyclohexyl}-3,5-bis(trifluoromethyl)benzeneacetamide;
trans-(RS)-α-methyl-N-[4-(4-methylpiperazin-1-yl)-1-phenylcyclohexyl]-3,5-bis(trifluoromethyl)benzeneacetamide;
trans-(RS)-α-methyl-N-{4-[4-(1-methylethyl)piperazin-1-yl]-1-phenylcyclohexyl}-3,5-bis(trifluoromethyl)benzeneacetamide;
trans-(RS)-α-methyl-N-{4-[4-(1-methylethyl)-2-oxo-1-piperazinyl]-1-phenylcyclohexyl}-3,5-bis(trifluoromethyl)benzeneacetamide;
trans-(RS)-α-methyl-N-[4-(2,2-dimethyl-4-phenylmethyl-1-piperazinyl)-1-phenylcyclohexyl]-3,5-bis(trifluoromethyl)benzeneacetamide;
trans-(RS)-α-methyl-N-{4-[4-(1,1-dimethylethyl)-2-oxo-1-piperazinyl]-1-phenylcyclohexyl}-3,5-bis(trifluoromethyl)benzeneacetamide;
trans-(RS)-α-methyl-N-{4-[4-(4-fluorophenyl)-3-oxo-1-piperazinyl]-1-phenylcyclohexyl}-3,5-bis(trifluoromethyl)benzeneacetamide;
trans-(S)-α-methyl-N-{4-[4-(4-fluorophenyl)-3-oxo-1-piperazinyl]-1-phenylcyclohexyl}-3,5-bis(trifluoromethyl)benzeneacetamide;
trans-(RS)-α-methyl-N-{4-[2-oxo-4-(piperidin-1-yl)piperidin-1-yl]-1-phenylcyclohexyl}-3,5-bis(trifluoromethyl)benzeneacetamide;
trans-(RS)-α-methyl-N-[4-(4-oxopiperidin-1-yl)methyl-1-phenylcyclohexyl]-3,5-bis(trifluoromethylbenzeneacetamide;
trans-(RS)-α-methyl-N-[4-(4-hydroxypiperidin-1-yl)methyl-1-phenylcyclohexyl]-3,5-bis(trifluoromethylbenzeneacetamide;
cis-(RS)-α-methyl-N-[4-hydroxy-4-(1-oxa-8-azaspiro[4.5]decan-8-yl)methyl-1-phenylcyclohexyl]-3,5-bis(trifluoromethyl)benzeneacetamide;
trans-(RS)-α-methyl-N-[1-phenyl-4-{1-(1-methylethyl)piperidin-4-yl]cyclohexyl}-3,5-bis(trifluoromethyl)benzeneacetamide;
(1R*,3S*,4R*)- and (1R*,3R*,4R)-α,α-dimethyl-N-[3-hydroxy-4-(1-oxa-8-azaspiro[4.5]decan-8-yl)-1-phenylcyclohexyl]-3,5-bis(trifluoromethyl)benzeneacetamide;
(1R*,3S*,4R*)-α,α-dimethyl-N-[3-fluoro-4-(2-oxa-8-azaspiro[4.5]decan-8-yl)-1-phenylcyclohexyl]-3,5-bis(trifluoromethyl)benzeneacetamide;

and pharmaceutically acceptable salts thereof.

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention have one or more asymmetric centres, and may accordingly exist both as enantiomers and as diastereoisomers. It is to be understood that all such isomers and mixtures thereof are encompassed within the scope of the present invention.

The preferred compounds of the formula (I) and (Ia) will have the stereochemistry of the 1- and 4-positions as shown in formula (Ib)

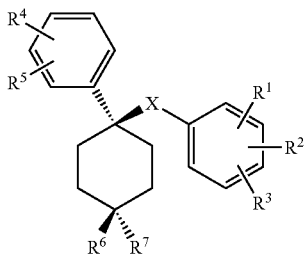

(Ib)

It will be appreciated that the preferred definitions of the various substituents recited herein may be taken alone or in combination and, unless otherwise stated, apply to the generic formula for compounds of the present invention as well as to the preferred classes of compound represented by formula (Ia) and formula (Ib).

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation. Oral compositions such as tablets, pills, capsules or wafers are particularly preferred.

A more detailed description of pharmaceutical compositions that are suitable for the formulation of compounds of the present invention is disclosed in U.S. Pat. No. 6,071,927, the content of which is incorporated herein by reference (see in particular, column 8, line 50 to column 10, line 4).

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. A comprehensive listing of clinical conditions, uses and methods of treatment for which the compounds of the present invention will be useful is disclosed in U.S. Pat. No. 6,071,927, the content of which is incorporated herein by reference (see, in particular, column 10, line 14 to column 22, line 18).

In particular, the compounds of the present invention are useful in the treatment of a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; and anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders.

The compounds of the present invention are also particularly useful in the treatment of nociception and pain. Diseases and conditions in which pain predominates, include soft tissue and peripheral damage, such as acute trauma, osteoarthritis, rheumatoid arthritis, musculo-skeletal pain, particularly after trauma, spinal pain, myofascial pain syndromes, headache, migraine, episiotomy pain, and burns.

The compounds of the present invention are also particularly useful in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; in the treatment of inflammatory diseases such as inflammatory bowel disease, psoriasis, fibrositis, osteoarthritis, rheumatoid arthritis, pruritis and sunburn; and in the treatment of allergic disorders such as eczema and rhinitis.

The compounds of the present invention are also particularly useful in the treatment of gastrointestinal (GI) disorders, including inflammatory disorders and diseases of the GI tract such as ulcerative colitis, Crohn's disease and irritable bowel syndrome.

The compounds of the present invention are also particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents, including those routinely used in cancer chemotherapy; by radiation including radiation therapy such as in the treatment of cancer; and in the treatment of post-operative nausea and vomiting.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

In the treatment of psychiatric disorders, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to a general process (A), compounds of formula (I), in which X is —N(R$^{13}$)C(O)CR$^{14}$R$^{15}$—, may be prepared by reaction of a compound of formula (II) with a compound of formula (III) or an activated derivative thereof

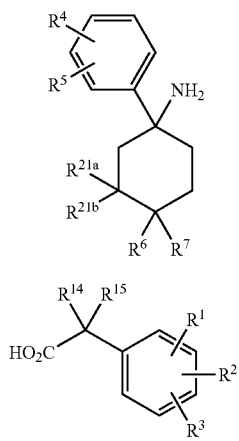

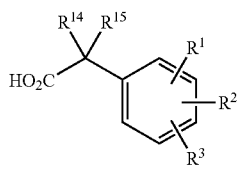

in the presence of a base and a coupling reagent.

Suitable bases of use in the reaction include tertiary amines, for example, triethylamine.

Suitable coupling reagents include any of the coupling reagents commonly used in peptide synthesis. A preferred coupling reagent is 1-(3-dimethylaminopropyl)-3-ethylcarbodiimide hydrochloride (EDC). Preferably the coupling reaction is effected in the presence of 1-hydroxybenzotrazole hydrate (HOBT).

The reaction is conveniently effected in a suitable organic solvent such as, for example, dimethylformamide.

According to an alternative general process (B), compounds of formula (I), in which X is —N(R$^{13}$)C(O)CR$^{14}$R$^{15}$—, may be prepared by the reaction of an amine of formula (II) with an activated carboxylic acid derivative of formula (IV)

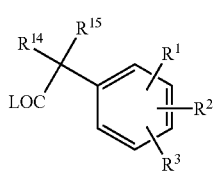

where L is a leaving group.

Suitable activated carboxylic acid derivatives represented in formula (IV) include acyl halides (e.g. acid chlorides) and acid anhydrides including mixed anhydrides (e.g. acid formic anhydride). These activated derivatives may be formed from the corresponding acid of formula (III) by well known procedures. For example, acid chlorides may be prepared by reaction with phosphorus pentachloride, thionyl chloride or oxalyl chloride and acid anhydrides may be prepared by reaction with an appropriate acid anhydride (e.g. trifluoroacetic anhydride), an acid chloride (e.g. acetyl chloride), an alkyl or aralkyl haloformate (e.g. ethyl or benzyl chloroformate) or methanesulphonyl chloride.

A particularly preferred reagent for activating the carboxylic acid group is bis(2-oxo-3-oxazolidinyl)phosphinic chloride (BOP-Cl).

Activated carboxylic acid derivatives of formula (IV) may also be prepared in situ by reaction of the corresponding acids of formula (III), with a coupling reagent such as carbonyldiimidazole, dicyclohexylcarbodiimide or diphenylphosphorylazide.

The conditions under which the activated carboxylic acid derivatives of formula (IV) are formed and subsequently reacted with the amines of formula (II) will depend upon the nature of the activated derivative. However, in general the reaction between the compounds (II) and (IV) may be carried out in a non-aqueous medium such as, for example, dimethylformamide, tetrahydrofuran, acetonitrile or a halogenated hydrocarbon such as dichloromethane at a temperature within the range −25° C. to +150° C. The reaction may optionally be carried out in the presence of a base such as triethylamine or pyridine and the base may also be used as the solvent for reaction.

Where acid chlorides are used, the reaction may be carried out using the Schotten-Baumann technique in the presence of a suitable base, for example, aqueous sodium hydroxide, conveniently at a temperature between 0° C. and 100° C., for example, room temperature.

According to another general process (C), compounds of formula (I), in which X is —N(R$^{13}$)CR$^{14}$R$^{15}$CR$^{16}$R$^{17}$—, may be prepared by the reaction of a compound of formula (II) with a compound of formula (V)

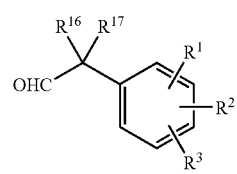

in the presence of a reducing agent.

Suitable reducing agents for use in this reaction include, for example, sodium cyanoborohydride or sodium triacetoxyborohydride.

The reaction is conveniently effected in a suitable solvent such as a halogenated hydrocarbon, for example, 1,2-dichloroethane, an alcohol, for example, methanol, acetic acid or a mixture thereof.

According to another general process (D), compounds of formula (I), in which X is —OC(O)CR$^{14}$R$^{15}$—, may be prepared by the reaction of a compound of formula (VI) with a compound of formula (VII)

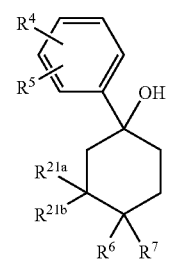

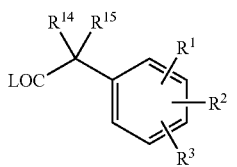

in the presence of a base (provided that R$^{21a}$ is not hydroxy).

Suitable bases of use in the reaction include aromatic amines such as pyridine or 4-(dimethylamino)pyridine (DMAP).

The reaction is conveniently effected in a suitable aprotic solvent such as, for example, dimethylformamide, or a halogenated hydrocarbon, for example, dichloromethane, or a mixture thereof.

According to another general process (E), compounds of formula (I), in which X is —OCR$^{14}$R$^{15}$CR$^{16}$R$^{17}$—, may be prepared by the reaction of a compound of formula (VI) with a compound of formula (VIII)

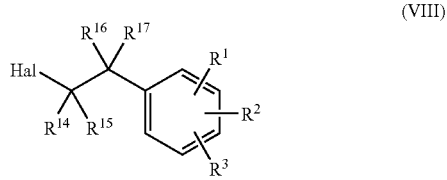

(VIII)

(wherein Hal is a halogen atom such as chlorine, iodine or, preferably, bromine), in the presence of a base such as sodium hydride.

The reaction is conveniently effected in a suitable aprotic solvent such as, for example, dimethylformamide.

It will be appreciated that compounds of formula (I) may also be prepared from other compounds of formula (I) by a variety of interconversion processes.

Thus, according to general process (F.1), compounds of formula (I) in which X is —N(R$^{13}$)CR$^{14}$R$^{15}$CR$^{16}$R$^{17}$—, may be prepared by the interconversion of a compound of formula (I) in which X is —N(R$^{13}$)C(O)CR$^{14}$R$^{15}$—, by reaction with a reducing agent.

Suitable reducing agents for use in this reaction include sodium borohydride or borane.tetrahydrofuran complex.

The reaction is conveniently effected in a solvent such as an ether, for example, tetrahydrofuran.

According to another general process (F.2), compounds of formula (I) in which R$^7$ is —(CH$_2$)$_n$NR$^8$R$^9$ (where n is zero) may be prepared by interconversion of a compound of formula (I) in which R$^6$ and R$^7$ together represent =O, by reaction with an appropriate amine, R$^8$R$^9$NH, in the presence of sodium cyanoborohydride and a Lewis acid, for example, zinc chloride, in a solvent such as an alcohol, for example, methanol, or in the presence of sodium triacetoxyborohydride in a solvent such as a halogenated hydrocarbon, for example, 1,2-dichloroethane.

Yet further interconversion reactions that may be effected using conventional procedures are shown in the following Scheme 1. The methods depicted in Scheme 1 are not exhaustive and illustrate just some of the possible routes to further compounds of formula (I).

Scheme 1

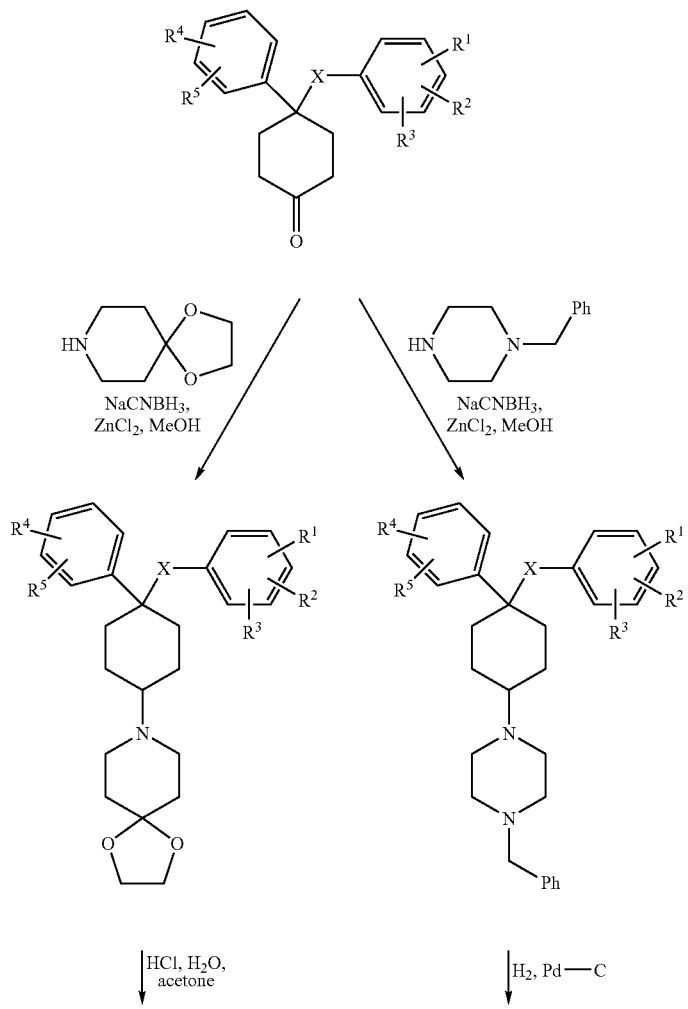

-continued
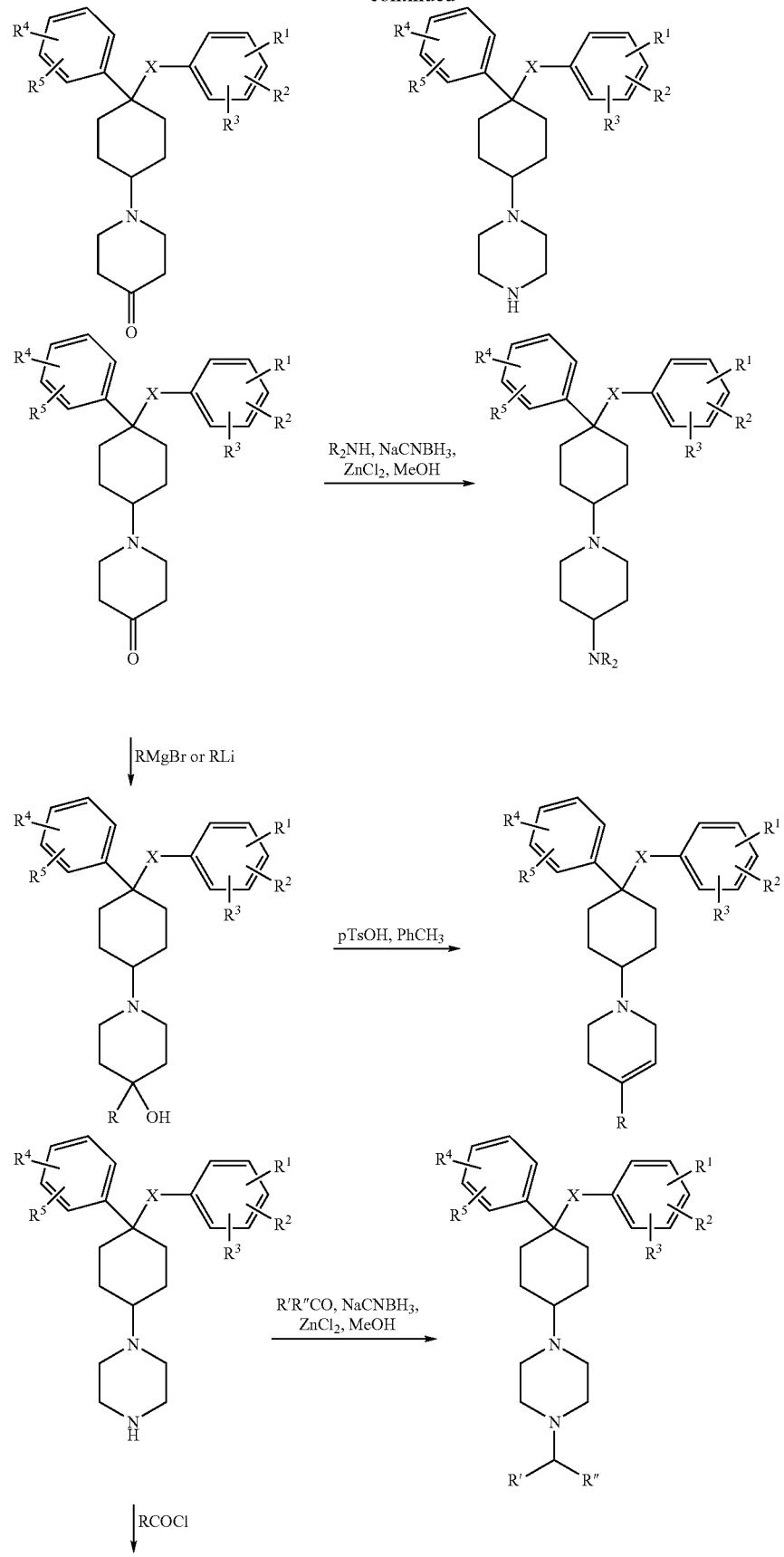

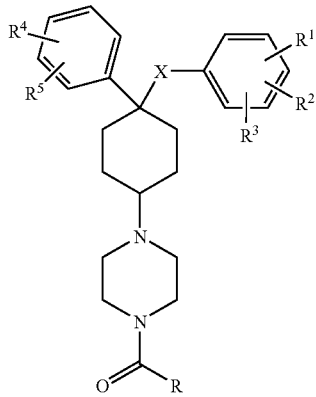

It will be appreciated that reference to R, R' and R" in Scheme 1 refers to suitable substituents within the scope of the definitions of formula (I), insofar as said substituents are compatible with the reaction conditions described in Scheme 1.

Preferably, where $R^{21a}$ is halogen or hydroxy, or $R^{21a}$ and $R^{21b}$ both represent fluorine or together represent oxo (=O), such substituents are introduced at a late stage by conventional methodology. It will be appreciated, however, that where such substituents are compatible with the reactions described above, then such groups may be present, even if not depicted in the above formulae.

Further details of suitable procedures for the preparation of compounds of formula (I) will be found in the accompanying Examples.

Compounds of formula (II) may be prepared by a variety of methods well known to those skilled in the art. Examples of suitable methods include, but are not limited to, the methods shown in Scheme 2.

Scheme 2

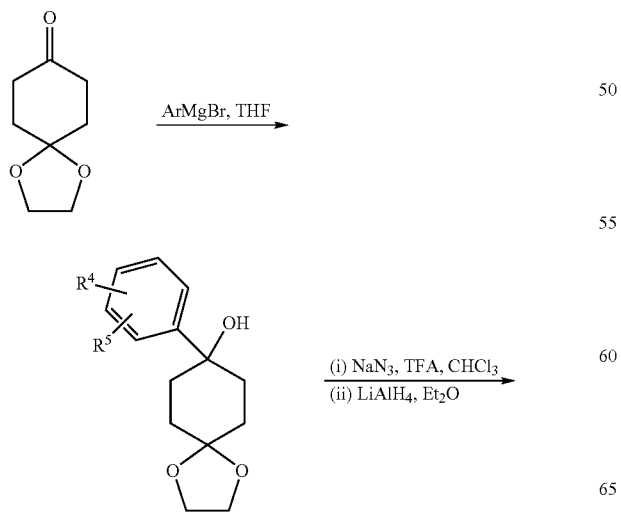

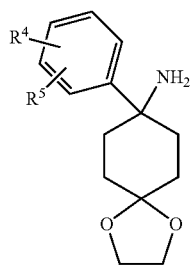

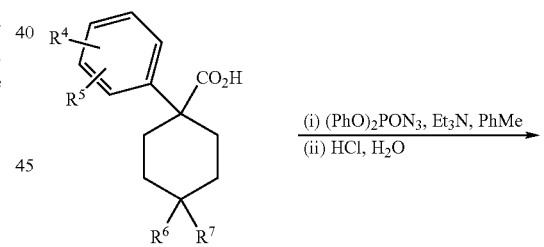

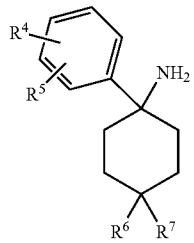

Compounds of formula (III) are either known compounds or may be prepared by a variety of methods well known to those skilled in the art. Examples of suitable methods for introducing the substituents $R^{14}$ and $R^{15}$ include, but are not limited to, the methods shown in Scheme 3.

Scheme 3

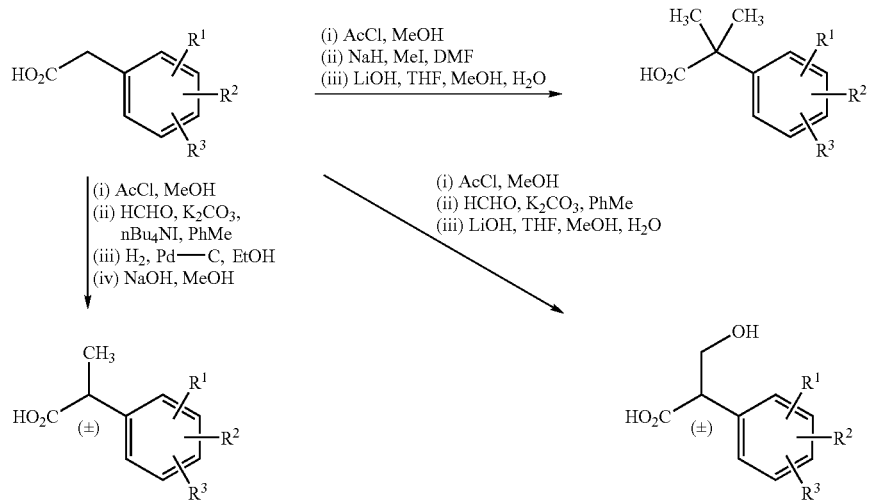

Compounds of formula (V) may be prepared by conventional methods such as partial reduction of a corresponding carboxylic acid of formula (III).

Compounds of formula (VI) may be prepared as shown, for instance, in the first step of Scheme 2, above.

Compounds of formula (VII) may be prepared from the corresponding carboxylic acids of formula (III) using methods analogous to those described herein for the synthesis of compounds of formula (IV).

Compounds of formula (VIII) are either known compounds or may be prepared by conventional methods, for instance, by methods analogous to those described herein.

Compounds of formula (I) in which the ring A is a pyridyl ring may be prepared in an analogous manner to the methods described above, replacing the phenyl ring depicted in the above formulae as appropriate.

It will be appreciated that the general methodology described above may be adapted, using methods that are readily apparent to one of ordinary skill in the art, in order to prepare further compounds of the present invention.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene and P. G. M. Wuts, Protective Groups in Organic Synthesis, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the $NK_1$ receptor of less than 100 nM on said test method.

The following non-limiting Examples serve to illustrate the preparation of compounds of the present invention:

DESCRIPTION 1

Methyl 3,5-Bis(trifluoromethyl)benzeneacetate

Sulfuric acid (conc., 1 mL) was added to a solution of 3,5-bis(trifluoromethyl)benzeneacetic acid (50.0 g, 0.18 mol) in methanol (400 mL) and the mixture was stirred at room temperature for 1 week. The solvent was evaporated and ethyl acetate (100 mL) and aqueous sodium hydrogen carbonate (saturated, 600 mL) were added. The layers were separated and the aqueous layer was extracted with ethyl acetate (2×300 mL). The combined organic fractions were washed with brine, dried ($MgSO_4$) and the solvent was evaporated under reduced pressure to give the title compound (49.0 g, 93%). $^1H$ NMR (400 MHz, $CDCl_3$) δ 7.80 (1H, s), 7.75 (2H, s), 3.77 (2H, s), and 3.75 (3H, s).

DESCRIPTION 2

Methyl 2-[3,5-Bis(trifluoromethyl)phenyl]-2-propenoate

A mixture of methyl 3,5-bis(trifluoromethyl)benzeneacetate (Description 1, 10.0 g, 35 mmol), paraformaldehyde (5.2 g, 175 mmol), potassium carbonate (14.5 g, 105 mmol) and tetra-n-butyl ammonium iodide (650 mg, 1.75 mmol) in toluene (200 mL) was heated at 80° C. for 4 hours, cooled and stirred at room temperature for 16 hours. The mixture was filtered through a bed of Celite™, washing with ethyl acetate (2×100 mL). The combined filtrates were washed with water (100 mL) and brine (100 mL), dried ($MgSO_4$) and the solvent was evaporated under reduced pressure. The residue was purified by flash column chromatography on silica gel, eluting with isohexane/EtOAc (100:0 increasing to 90:10) to give the title compound as a clear oil (6.2 g, 60%). $^1H$ NMR (400 MHz, $CDCl_3$) δ 3.86 (3H, s), 6.05 (1H, s), 6.59 (1H, s), 7.86 (1H, s) and 7.88 (2H, s).

DESCRIPTION 3

(RS)-Methyl α-Methyl-3,5-bis(trifluoromethyl)benzeneacetate

An aqueous slurry of palladium on carbon (50 mg) was added to a solution of methyl 2-[3,5-bis(trifluoromethyl) phenyl]-2-propenoate (Description 2, 1.0 g, 3.4 mmol) in ethanol (40 mL) and the mixture was shaken under an atmosphere of hydrogen (50 psi) for 1 hour. The mixture was filtered and the solvent was evaporated under reduced pressure to give the title compound as a colorless oil (0.97 g, 95%). $^1$H NMR (360 MHz, CDCl$_3$) δ 1.57 (3H, d, J 7.2 Hz), 3.71 (3H, s), 3.86 (1H, q, J 7.2 Hz), 7.76 (2H, s) and 7.79 (1H, s).

DESCRIPTION 4

(RS)-α-Methyl-3,5-bis(trifluoromethyl)benzeneacetic Acid

Aqueous sodium hydroxide (4M, 3 mL, 12 mmol) was added to a solution of (RS)-methyl α-methyl-3,5-bis(trifluoromethyl)benzeneacetate (Description 3, 0.96 g, 3.2 mmol) in methanol (5 mL) and the mixture was heated under reflux for 1 hour. The mixture was cooled and the solvent was evaporated under reduced pressure. The residue was diluted with water, acidified with hydrochloric acid (2M) and extracted with ethyl acetate (2×25 mL). The combined organic fractions were washed with brine, dried (MgSO$_4$) and the solvent was evaporated under reduced pressure to give the title compound as a colorless solid (0.92 g, 99%). $^1$H NMR (360 MHz, CDCl$_3$) δ 1.60 (3H, d, J 7.2 Hz), 3.90 (1H, q, J 7.2 Hz), 7.78 (2H, s) and 7.81 (1H, s).

DESCRIPTION 5

Methyl α,α-Dimethyl-3,5-bis(trifluoromethyl)benzeneacetate

Sodium hydride (60% in mineral oil, 2.1 g, 52.5 mmol) was added in portions to a solution of methyl 3,5-bis(trifluoromethyl)benzeneacetate (Description 1, 5 g, 17.5 mmol) in dimethylformamide (100 mL) and the mixture was stirred at room temperature for 10 minutes. Iodomethane (5.45 mL, 87.5 mmol) was added and the mixture was stirred at room temperature overnight. Aqueous ammonium chloride (saturated) was added and the mixture was extracted with ethyl acetate. The combined organic fractions were washed with water, dried (MgSO$_4$), and the solvent was evaporated under reduced pressure. The residue was purified by flash column chromatography on silica gel, eluting with isohexane/EtOAc (100:0 increasing to 90:10) to give the title compound as a colorless oil (5.34 g, 97%). $^1$H NMR (400 MHz, CDCl$_3$) δ 7.78 (3H, s), 3.69 (3H, s), and 1.65 (6H, s).

DESCRIPTION 6

α,α-Dimethyl-3,5-bis(trifluoromethyl)benzeneacetic Acid

Lithium hydroxide monohydrate (2.13 g, 50.6 mmol) was added to a suspension of methyl α,α-dimethyl-3,5-bis(trifluoromethyl)benzeneacetate (Description 5, 5.3 g, 16.88 mmol) in methanol (60 mL), water (20 mL) and tetrahydrofuran (20 mL) and the mixture was degassed and stirred at room temperature for 3 days. The solvent was evaporated under reduced pressure and the residue was suspended in hydrochloric acid (1M). The mixture was extracted with ethyl acetate and the combined organic fractions were dried (MgSO$_4$) and the solvent was evaporated under reduced pressure to give the title compound as a colorless solid (5.05 g, 100%). $^1$H NMR (400 MHz, CDCl$_3$) δ 7.84 (2H, s), 7.80 (1H, s), and 1.68 (6H, s).

DESCRIPTION 7

(RS)-Methyl α-(Hydroxymethyl)-3,5-bis(trifluoromethyl)benzeneacetate

A mixture of methyl 3,5-bis(trifluoromethyl)benzeneacetate (Description 1, 10.0 g, 35 mmol), paraformaldehyde (1.15 g, 38.5 mmol) and sodium hydrogen carbonate (84 mg, 1 mmol) in dimethylsulfoxide (10 mL) was heated at 45° C. for 1 hour, cooled and water (200 mL) was added. The mixture was extracted with ether (2×200 mL) and the combined organic fractions were washed with water (4×100 mL) and brine (100 mL), dried (MgSO$_4$) and the solvent was evaporated under reduced pressure. The residue was purified by flash column chromatography on silica gel, eluting with isohexane/EtOAc (75:25) to give the title compound as a colorless oil (2.0 g, 10%). $^1$H NMR (400 MHz, CDCl$_3$) δ 2.27 (1H, t, J 7.0 Hz), 3.76 (3H, s), 3.94–3.99 (2H, m), 4.01–4.15 (1H, m), 7.77 (2H, s) and 7.83 (1H, s).

DESCRIPTION 8

Lithium (RS)-α-(Hydroxymethyl)-3,5-bis(trifluoromethyl)benzeneacetate

Lithium hydroxide (168 mg, 4 mmol) in water (2 mL) was added to a solution of (RS)-methyl α-(hydroxymethyl)-3,5-bis(trifluoromethyl)benzeneacetate (Description 7, 500 mg, 1.6 mmol) in methanol (4 mL). Methanol (2 mL) and tetrahydrofuran (2 mL) were added and the mixture was stirred at room temperature for 2 hours. The solvent was evaporated under reduced pressure and the residue was dried azeotropically by evaporating toluene (×2) to to give the crude title compound as a colorless gum (870 mg), which was used without further purification. $^1$H NMR (400 MHz, CD$_3$OD) δ 3.73–3.79 (1H, m), 3.85–3.92 (1H, m), 4.02–4.06 (1H, m), 7.80 (1H, s) and 7.98 (2H, s).

DESCRIPTION 9

4-(4-Fluorophenyl)pyridine

A mixture of 4-fluorobenzeneboronic acid (38.7 g, 276 mmol), 4-bromopyridine hydrochloride (48.9 g, 250 mmol), [1,4-butanediylbis(diphenylphosphine-κP)] dichloropalladium (*Organometallics* 1998, 17, 661; 1.52 g, 2.5 mmol), 1,2-dimethoxyethane (500 mL) and sodium carbonate solution (2M, 440 mL) was degassed with bubbling nitrogen and stirred at 80° C. for 24 hours. The mixture was cooled and extracted with ethyl acetate. The combined organic fractions were dried (MgSO$_4$) and the solvent was evaporated under reduced pressure to give crude title compound as a brown solid (50.87 g) which was used without further purification. $^1$H NMR (360 MHz, CDCl$_3$) δ 8.65 (2H, m), 7.61 (2H, m), 7.49 (2H, dd, J 1.6, 4.6 Hz), and 7.09 (2H, m).

DESCRIPTION 10

4-(4-Fluorophenyl)-1,2,3,6-tetrahydro-1-(phenylmethyl)pyridine

Benzyl bromide (52.4 mL, 441 mmol) was added to a solution of 4-(4-fluorophenyl)pyridine (Description 9, 50.87 g, 294 mmol) in acetone (500 mL) and mixture was heated under reflux for 3 days. The mixture was cooled to room temperature and the solid was collected, washed with acetone and diethyl ether and dried in vacuo. The solid was dissolved in methanol (400 mL) and water (100 mL), cooled to 0° C. and sodium borohydride (20.6 g, 542 mmol) was added in portions. The mixture was stirred at room temperature for 1 hour, then heated under reflux for 18 hours. The mixture was cooled and the solvent was evaporated under reduced pressure. Dichloromethane (300 mL) and water (200 mL) were added and the layers were separated. The organic layer was dried (MgSO$_4$) and the solvent was evaporated under reduced pressure to give the title compound as a light brown oil (61.5 g, 78%). m/z (ES$^+$) 268 (M+1).

DESCRIPTION 11

4-(4-Fluorophenyl)piperidine

Palladium hydroxide on carbon(20%, 5 g) was added to a solution of 4-(4-fluorophenyl)-1,2,3,6-tetrahydro-1-(phenylmethyl)pyridine (Description 10, 60 g, 225 mmol) in methanol (500 mL) and the mixture was shaken under an atmosphere of hydrogen (50 psi) for 48 hours. The mixture was filtered through a glass fibre pad, washing with methanol, and the solvent was evaporated under reduced pressure. The residue was dissolved in ethyl acetate and ethereal hydrogen chloride (1M, 300 mL) was added. The solid was collected and recrystallised from 2-propanol to give 4-(4-fluorophenyl)piperidine hydrochloride as a colorless solid (30.5 g, 63%). m/z (ES$^+$) 180 (M+1).

A sample (1 g, 4.64 mmol) was suspended in ethyl acetate and washed with saturated aqueous sodium carbonate. The organic layer was dried (MgSO$_4$) and the solvent was evaporated under reduced pressure to give the title compound as a colorless oil (825 mg, 99%). m/z (ES$^+$) 180 (M+1).

DESCRIPTION 12

4-(Dimethylamino)-1-(phenylmethyl)-4-piperidinecarbonitrile

A solution of 1-(phenylmethyl)-4-piperidone (9.46 g, 50 mmol) in ethanol (20 mL) was added slowly to a stirred solution of potassium cyanide (3.58 g, 55 mmol) and dimethylamine hydrochloride (4.89 g, 60 mmol) in water (60 mL). The mixture was stirred at room temperature for 68 hours, then water (100 mL) was added. The solid was collected, suspended in aqueous sodium hydrogen carbonate (saturated, 100 mL) and water (50 mL) and extracted with dichloromethane (3×100 mL). The combined organic fractions were dried (MgSO$_4$) and the solvent was evaporated under reduced pressure to give the the title compound as a cream solid (11.69 g, 96%). m/z (ES$^+$) 244 (M+1).

DESCRIPTION 13

4-(Dimethylamino-1,4-bis(phenylmethyl)piperidine

A solution of 4-(dimethylamino)-1-(phenylmethyl)-4-piperidinecarbonitrile (Description 12, 4.86 g, 20 mmol) in ether (75 mL) was added to benzylmagnesium chloride (1.0M in ether, 100 mL, 100 mmol) and the mixture was heated under reflux for 6 hours. The mixture was cooled in ice and hydrochloric acid (1M, 100 mL) was added slowly. The layers were separated and the aqueous layer was extracted with hydrochloric acid (1M, 2×100 mL). The combined aqueous layers were washed with ether (100 mL) then adjusted to pH 10.0 with aqueous sodium hydroxide (4M). The mixture was extracted with ether (3×200 mL) and the combined organic fractions were evaporated under reduced pressure. Saturated aqueous sodium hydrogen carbonate (100 mL) and water (20 mL) were added and the mixture was extracted with dichloromethane (3×100 mL). The combined organic fractions were dried (MgSO$_4$) and the solvent was evaporated under reduced pressure. The residue was recrystallized from ethanol-water (2:1, 75 mL) to give the title compound as a colorless solid (5.15 g, 84%). m/z (ES$^+$) 309 (M+1).

DESCRIPTION 14

4-(Dimethylamino)-4-(phenylmethyl)piperidine

A suspension of palladium on carbon (10%, 2 g) was added to a solution of 4-(dimethylamino)-1,4-bis(phenylmethyl)piperidine (Description 13, 4.62 g, 15 mmol) and formic acid (90%, 1.4 mL) in methanol (100 mL). Ammonium formate (4.73 g, 75 mmol) was added and the mixture was stirred at room temperature for 20 hours. The mixture was filtered, washing with methanol, and the solvent was evaporated under reduced pressure. Ether (40 mL) was added and the mixture was extracted with hydrochloric acid (1M, 3×40 mL). The combined aqueous layers were washed with ether (40 mL), adjusted to pH 12.0 with aqueous sodium hydroxide (4M) and extracted with dichloromethane (3×40 mL). The combined organic fractions were dried (MgSO$_4$) and the solvent was evaporated under reduced pressure. The residue was triturated with hexane (20 mL) and the solid was collected and dried in vacuo to give the the title compound as a colorless solid (2.20 g, 67%). m/z (ES$^+$) 219 (M+1).

DESCRIPTION 15

1,4-Dioxa-8-phenylspiro[4.5]decan-8-amine

Sodium azide (1.67 g, 25.6 mmol) was added to a stirred, cooled (−5° C.) solution of 8-phenyl-1,4-dioxaspiro[4.5]decan-8-ol (*Synth. Commun.* (1994), 24(6), 799–807, 2.0 g, 8.5 mmol) in chloroform (20 mL) and the mixture was stirred at 5° C. for 10 minutes. Trifluoroacetic acid (3.3 mL, 42.5 mmol) was added dropwise over 5 minutes and the mixture was allowed to warm to room temperature and stirred overnight. The mixture was diluted with water (50 mL) and extracted with ether (2×50 mL). The combined organic fractions were washed with water (50 mL), aqueous ammonia (1N, 2×50 mL) and brine, dried (MgSO$_4$) and the solvent was evaporated under reduced pressure. The residue was dissolved in ether (20 mL) and added dropwise to lithium aluminum hydride (1M in ether, 25 mL, 25 mmol). The mixture was stirred at room temperature for 3 hours, then aqueous sodium hydroxide (1M, 3 mL) and water (3 mL) were added carefully. The ether was evaporated under reduced pressure, saturated aqueous sodium hydrogen carbonate was added and the mixture was extracted with dichloromethane (3×20 mL). The combined organic fractions were washed with brine, dried (MgSO$_4$) and the solvent was evaporated under reduced pressure. The residue was purified by flash column chromatography on silica gel, eluting with EtOAc to give the title compound as a brown gum (80 mg, 4%). m/z (ES$^+$) 234 (M+1) and 217 (M+1-NH$_3$).

DESCRIPTION 16

Dimethyl 4-Oxo-1-phenyl-1,3-cyclohexanedicarboxylate

Sodium hydride (60% in mineral oil, 35.8 g, 1.49 mol) was washed with hexane to remove the mineral oil, suspended in dimethylformamide (400 mL) and cooled to 0° C. Methyl phenyl acetate (42 mL, 0.3 mol) was added slowly with stirring. Methyl acrylate (59 mL, 0.65 mol) was added dropwise over 2 hours at 0° C. and the mixture was stirred at room temperature overnight. Aqueous ammonium chloride (saturated) was added and the mixture was extracted with dichloromethane (2×700 mL). The combined organic fractions were washed with water (5×500 mL), dried (MgSO$_4$) and the solvent was evaporated under reduced pressure. The residue purified by flash column chromatography on silica gel, eluting with isohexane/Et$_2$O (80:20) and the residue was triturated with isohexane-Et$_2$O (50:50). The solid was collected and dried iii vacuo to give the title compound as colorless crystals (30 g, 35%). $^1$H NMR (400 MHz, CDCl$_3$) δ 12.11 (1H, s), 7.36–7.25 (5H, m), 3.81 (3H, s), 3.64 (3H, s), 3.08 (1H, d, J 16.1 Hz), 2.73 (1H, d, J 16.1 Hz), 2.26–2.37 (2H, m), and 2.22–2.17 (2H, m).

DESCRIPTION 17

4-Oxo-1-phenylcyclohexanecarboxylic Acid

Lithium hydroxide monohydrate (11.08 g, 264 mmol) was added to a suspension of dimethyl 4-oxo-1-phenyl-1,3-cyclohexanedicarboxylate (Description 16, 25.5 g, 87.9 mmol) in methanol (250 mL), water (83 mL) and tetrahydrofuran (83 mL) and the mixture was heated under reflux for 3 days. The mixture was cooled and the tetrahydrofuran and methanol were evaporated under reduced pressure. The pH was adjusted to 1 with hydrochloric acid (5M) and the mixture was extracted with dichloromethane. The combined organic fractions were dried (MgSO$_4$) and the solvent was evaporated under reduced pressure to give the title compound as a light yellow solid (19 g, 99%). $^1$H NMR (400 MHz, CDCl$_3$) δ 7.50–7.29 (5H, m), 2.29–2.73 (2H, m), 2.62–2.55 (2H, m), 2.47–2.41 (2H, m), and 2.35–2.27 (2H, m).

DESCRIPTION 18

4-Oxo-1-phenylcyclohexylamine Hydrochloride

Diphenylphosphoryl azide (18.8 mL, 23.9 g, 87 mmol) was added to a solution of 4-oxo-1-phenylcyclohexanecarboxylic acid (Description 17, 17.1 g, 78 mmol) and triethylamine (24.4 mL, 17.7 g, 175 mmol) in toluene (260 mL) and the mixture was stirred at 90° C. for 90 minutes. The mixture was cooled, diluted with ethyl acetate (300 mL) and washed with sodium carbonate (2×250 mL). The combined aqueous fractions were extracted with ethyl acetate (300 mL) and the combined organic fractions were washed with brine (250 mL), dried (MgSO$_4$) and the solvent was evaporated under reduced pressure. The residue was suspended in hydrochloric acid (5M, 500 mL) and the mixture was heated under reflux for 2 hours. The mixture was cooled, the solvent was evaporated under reduced pressure and the residue was dried azeotropically by evaporating toluene under reduced pressure (4×) to give crude title compound which was used without further purification. m/z (ES$^+$) 190 (M+1)

DESCRIPTION 19

Methyl 4-Oxo-1-phenylcyclohexanecarboxylate

Acetyl chloride (0.46 mL, 0.50 g, 6.4 mmol) was added to a solution of 4-oxo-1-phenylcyclohexanecarboxylic acid (Description 17, 0.94 g, 4.3 mmol) in methanol (5 mL) and the mixture was heated under reflux for 20 hours. The mixture was cooled, poured into aqueous sodium hydrogen carbonate (saturated, 100 mL) and extracted with ethyl acetate (2×50 mL). The combined organic fractions were dried (Na$_2$SO$_4$) and the solvent was evaporated under reduced pressure. The residue was dissolved in tetrahydrofuran (2 mL), acetic acid (6 mL) and water (2 mL) were added and the mixture was stirred at 45° C. for 2 hours. The mixture was cooled, the solvent was evaporated under reduced pressure and aqueous sodium hydrogen carbonate (saturated, 100 mL) was added. The mixture was extracted with ethyl acetate (2×50 mL), the combined organic fractions were dried (Na$_2$SO$_4$) and the solvent was evaporated under reduced pressure to give the title compound (0.98 g, 98%). $^1$H NMR (250 MHz, CDCl$_3$) δ 7.45–7.26 (5H, m), 3.72 (3H, s), 2.77 (2H, m), 2.61–2.38 (4H, m), and 2.25 (2H, m).

DESCRIPTION 20

Cis-Methyl 4-[4-(4-Fluorophenyl)piperidin-1-yl]-1-phenylcyclohexanecarboxylate, Cis-4-[4-(4-Fluorophenyl)piperidin-1-yl]-1-phenylcyclohexanecarboxylic Acid, and Trans-Methyl 4-[4-(4-Fluorophenyl)piperidin-1-yl]-1-phenylcyclohexanecarboxylate A solution of sodium cyanoborohydride (0.93 g, 14.9 mmol) and zinc chloride (1.01 g, 7.45 mmol) in methanol (30 mL) was added to a solution of methyl 4-oxo-1-phenylcyclohexanecarboxylate (Description 19, 3.45 g, 14.9 mmol) and 4-(4-fluorophenyl)piperidine (Description 11, 3.2 g, 17.9 mmol) in methanol (50 mL) and the mixture was stirred at room temperature for 24 hours. The mixture was poured into water and extracted with ethyl acetate. The combined organic fractions were dried (MgSO$_4$), and the solvent was evaporated under reduced pressure. The residue was recrystallized from ethanol to give cis-methyl 4-[4-(4-fluorophenyl)piperidin-1-yl]-phenylcylohexanecarboxylate (0.9 g, 15%) as a colorless solid. m/z (ES$^+$) 396 (M+1).

The mother liquors from the recrystallisation were collected and the solvent was evaporated under reduced pressure. Methanol (20 mL) and hydrochloric acid (6M, 200 mL) were added and the mixture was heated under reflux for 3 days. The mixture was cooled and the solvent was evaporated under reduced pressure. The residue was dissolved in methanol (100 mL) and acetyl chloride (0.77 mL, 10.8 mmol) was added slowly. The mixture was heated under reflux for 6 hours cooled and the solvent was evaporated under reduced pressure. Ethyl acetate and aqueous sodium carbonate (saturated) were added and the layers were separated. The solid which formed in the organic layer was collected and dried in vacuo to give cis-4-[4-(4-fluorophenyl)piperidin-1-yl]-1-phenylcyclohexanecarboxylic acid as a colorless solid (1.2 g, 21%). m/z (ES$^+$) 382 (M+1).

The mother liquors from the recrystallisation were dried (MgSO$_4$) and the solvent was evaporated under reduced pressure to give trans-methyl 4-[4-(4-fluorophenyl)piperidin-1-yl]-1-phenylcyclohexanecarboxylate as a colorless solid, (1.6 g, 27%) m/z (ES$^+$) 396 (M+1).

DESCRIPTION 21

Trans-4-[4-(4-Fluorophenyl)piperidin-1-yl]-1-phenylcyclohexanecarboxylic Acid Hydrochloride Hydrochloric acid (6M, 100 mL) was added to a suspension of tran-smethyl 4-[4-(4-fluorophenyl)piperidin-1-yl]-1-phenylcyclohexanecarboxylate (Description 20, 1.6 g, 4.05 mmol) in methanol (10 mL) and the mixture was heated under reflux for 48 hours. The mixture was cooled and the solvent was evaporated under reduced pressure to give the title compound as a colorless solid (1.5 g, 89%). m/z (ES$^+$) 382 (M+1).

DESCRIPTION 22

Trans-4-[4-(4-Fluorophenyl)piperidin-1-yl]-1-phenylcyclohexylamine

Diphenylphosphoryl azide (114 µl, 0.53 mmol) and triethylamine (150 µl, 1.06 mmol) were added to a solution of trans-4-[4-(4-fluorophenyl)piperidin-1-yl]-1-phenylcyclohexanecarboxylic acid hydrochloride (Description 21, 200 mg, 0.48 mmol) in toluene (5 mL) and the mixture was heated at 90° C. for 2 hours. The mixture was cooled to room temperature, diluted with aqueous sodium carbonate (saturated, 40 mL) and extracted with ethyl acetate (2×25 mL). The combined organic fractions were washed with brine, dried (MgSO$_4$) and the solvent was evaporated under reduced pressure. Hydrochloric acid (5M, 10 mL) was added and the mixture was heated under reflux for 4 hours. The mixture was cooled and stirred at room temperature overnight. The mixture was diluted with water (10 mL) and washed with ethyl acetate (2×20 mL). The aqueous fraction was carefully basified with aqueous sodium hydroxide (4M) and extracted with ethyl acetate (2×20 mL). The combined organic fractions were washed with brine, dried (MgSO$_4$) and the solvent was evaporated under reduced pressure to give the title compound as a clear gum (121 mg, 72%). m/z (ES$^+$) 353 (M+1).

DESCRIPTION 23

Trans-1,1-Dimethylethyl 4-[4-(4-Fluorophenyl)piperidin-1-yl]-1-phenylcyclohexylcarbamate Di-tert-butyl dicarbonate (244 mg, 1.1 mmol) was added to a solution of trans-4-[4-(4-fluorophenyl)piperidin-1-yl]-1-phenylcyclohexylamine (Description 22, 200 mg, 0.56 mmol) and triethylamine (83 µl, 0.6 mmol) in dichloromethane (3 mL) and the mixture was stirred at room temperature for 20 hours. N,N-Dimethylethylenediamine (90 µl, 0.8 mmol) was added and the mixture was stirred for 1 hour. Dichloromethane (10 mL) was added and the mixture was washed with aqueous citric acid (10%, 2×20 mL) and brine, dried (MgSO$_4$) and the solvent was evaporated under reduced pressure to give the title compound as a colorless foam (263 mg, 100%). $^1$H NMR (400 MHz, CDCl$_3$) δ 1.32 (9H, s), 1.45–160 (4H, m), 1.88–1.91 (2H, m), 2.31–2.34 (3H, m), 2.60–2.62 (1H, m), 2.67–2.85 (6H, m), 3.29–3.37 (3×, m), 4.71 (1 h, s), 6.97 (2H, t, J 8.6 Hz), 7.20–7.24 (2H, m), 7.28 (1H, t, J 7.2 Hz), 7.38–7.41 (2H, m), 7.49 (2H, d, J 7.8 Hz), and 12.31 (1H, s).

DESCRIPTION 24

Trans-4-[4-(4-Fluorophenyl)piperidin-1-yl]-N-methyl-1-phenylcyclohexylamine

Lithium aluminum hydride (1M in tetrahydrofuran, 1.2 mL, 1.2 mmol) was added to a solution of trans-1,1-dimethylethyl 4-[4-(4-fluorophenyl)piperidin-1-yl]-1-phenylcyclohexylcarbamate (Description 23, 260 mg, 0.56 mmol) in tetrahydrofuran (10 mL) and the mixture was heated under reflux for 4 hours. The mixture was cooled in ice and water (50 µl), aqueous sodium hydroxide (4M, 150 µl) and water (150 µl) were added. The mixture was filtered through Celite™ and the solvent was evaporated under reduced pressure. The residue was purified by flash column chromatography on silica gel, eluting with CH$_2$Cl$_2$/MeOH/NH$_3$ (Aq.) (60:8:1), to give the title compound as a colorless oil (150 mg, 71%). m/z (ES$^+$) 367 (M+1).

DESCRIPTION 25

Trans-4-(4-Oxopiperidin-1-yl)-1-phenylcyclohexanecarboxylic Acid Hydrochloride

Sodium acetoxyborohydride (7.0 g, 32.9 mmol) was added to a degassed solution of 4-oxo-1-phenylcyclohexanecarboxylic acid (Description 17, 5.98 g, 27.4 mmol) and 1,4-dioxa-8-azaspiro[4.5]decane (4.32 g, 30.2 mmol) in dichloroethane (125 mL) and the mixture was stirred at room temperature for 20 hours. The solvent was evaporated under reduced pressure, methanol (120 mL) was added and the mixture was stirred at room temperature for 1 hour. The mixture was filtered and cooled to 0° C. Acetyl chloride (10 mL) was added slowly and the mixture was heated under reflux for 20 hours. The mixture was cooled, filtered and the solvent was evaporated under reduced pressure. Aqueous sodium carbonate (saturated, 200 mL) was added and the mixture was extracted with ethyl acetate (2×200 mL). The combined organic fractions were dried (Na$_2$SO$_4$) and the solvent was evaporated under reduced pressure. Hydrochloric acid (5M, 300 mL) was added and the mixture was heated under reflux for 20 hours. The mixture was cooled and the solvent was evaporated under reduced pressure to give the title compound (3.36 g, 36%). m/z (ES$^+$) 302 (M+1).

DESCRIPTION 26

Trans-1-(4-Isocyanato-4-phenylcyclohex-1-yl)piperidin-4-one

Diphenylphosphoryl azide (71 µl, 0.33 mmol) was added to a mixture of trans-4-(4-oxopiperidin-1-yl)-1-phenylcyclohexanecarboxylic acid hydrochloride (Description 25, 100 mg, 0.3 mmol) and triethylamine (92 µl, 0.66 mmol) in toluene (5 mL) and the mixture was stirred at room temperature for 1 hour, then at 90° C. for 1.5 hours. The mixture was cooled and ethyl acetate (25 mL) and aqueous sodium carbonate (10%, 20 mL) were added. The organic layer was washed with aqueous sodium carbonate (10%, 20 mL) and the combined aqueous fractions were extracted with ethyl acetate (25 mL). The combined organic fractions were washed with brine (25 mL), dried (MgSO$_4$) and the solvent was evaporated under reduced pressure. The residue was purified by flash column chromatography on silica gel, eluting with EtOAc, to give the title compound (30 mg, 34%). $^1$H NMR (400 MHz, CDCl$_3$) δ 7.51–7.49 (2H, m), 7.42–7.35 (2H, m), 7.31–7.27 (1H, m), 2.84–2.81 (4H, m), 2.59–2.57 (1H, m), 2.48–2.42 (6H, m), and 1.93–1.81 (6H, m).

DESCRIPTION 27

Trans-1-(4-Amino-4-phenylcyclohex-1-yl)piperidin-4-one Dihydrochloride

Trans-1-(4-Isocyanato-4-phenylcyclohex-1-yl)piperidin-4-one (Description 26, 30 mg, 0.1 mmol) in hydrochloric acid (5M, 6 mL) was heated under reflux overnight. The solvent was evaporated under reduced pressure to give the title compound (32 mg, 100%). $^1$H NMR (400 MHz, CD$_3$OD) δ 7.72–7.70 (2H, m), 7.58–7.54 (2H, m), 7.50–7.46 (1H, m), 3.49–3.36 (3H, m), 3.12–2.95 (4H, m), 2.30 (2H, br d, J 11.4 Hz), 2.12–2.03 (4H, m), 1.91–1.95 (2H, m), and 1.56–1.47 (2H, m).

DESCRIPTION 28

Cis-(RS)-N-(4-Hydroxy-1-phenylcyclohexyl)-α-methyl-3,5-bis(trifluoromethyl) benzeneacetamide Sodium borohydride (0.24 g, 6.3 mmol) in ethanol (10 mL) was added slowly to a stirred, cooled (−78° C.) solution of (RS)-α-methyl-N-[4-oxo-1-phenylcyclohexyl]-3,5-bis(trifluoromethyl)benzeneacetamide (Example 3, 1.9 g, 4.2 mmol) in ethanol (40 mL) and the mixture was stirred at −78° C. for 3.5 hours. Hydrochloric acid (1M, 10 mL) was added slowly and the mixture was warmed to room temperature. Aqueous sodium hydrogen carbonate (saturated) was added and the ethanol was evaporated under reduced pressure. Water (20 mL) was added and the mixture was extracted with ethyl acetate (2×50 mL). The combined organic fractions were washed with brine (20 mL), dried (MgSO$_4$) and the solvent was evaporated under reduced pressure to give the title compound as a colorless solid (1.6 g, 86%). $^1$H NMR (400 MHz, CD$_3$OD) δ 1.42–1.60 (5H, m), 1.79–1.88 (4H, m), 2.30–2.34 (1H, m), 2.56–2.61 (1H, m), 3.59–3.66 (1H, m), 4.03 (1H, q, J 7.0 Hz), 7.09–7.28 (5H, m), 7.85 (1H, s), 7.92 (2H, s) and 8.20 (1H, s).

DESCRIPTION 29

Cis-(RS)-N-(4-Methanesulfonyloxy-1-phenylcyclohexyl)-α-methyl-3,5-bis(trifluoromethyl) benzeneacetamide Methanesulfonyl chloride (0.91 mL, 1.35 g, 11.8 mmol) was added to a stirred, cooled (0° C.) solution of Cis-(RS)-N-(4-hydroxy-1-phenylcyclohexyl)α-methyl-3,5-bis(trifluoromethyl) benzeneacetamide (Description 28, 1.8 g, 3.9 mmol) and pyridine (1.6 mL, 1.55 g, 19.6 mmol) in dichloromethane (40 mL) and the mixture was stirred at room temperature for 18 hours. Dichloromethane (50 mL) was added and the mixture was washed with aqueous citric acid (10%, 2×50 mL) and aqueous sodium hydroxide (1M, 2×50 mL). The mixture was dried (MgSO$_4$) and the solvent was evaporated under reduced pressure to give the title compound as a colorless solid (1.97 g, 94%). $^1$H NMR (400 MHz, CD$_3$OD) δ 1.46 (3H, d, J 7.0 Hz), 1.53–1.65 (1H, m), 1.77–2.00 (4H, m), 2.02–2.58 (1H, m), 2.41–245 (1H, m), 2.55–2.58 (1H, m), 4.03 (1H, q, J 7.0 Hz), 4.66–4.70 (1H, m), 7.13–7.26 (5H, m), 7.87 (1H, s), 7.92 (2H, s) and 8.25 (1H, s).

DESCRIPTION 30

Trans-(RS)-N-(4-Azido-1-phenylcyclohexyl)-α-methyl-3,5-bis(trifluoromethyl) benzeneacetamide Sodium azide (0.91 g, 14 mmol) was added to a solution of cis-(RS)-N-(4-methanesulfonyloxy-1-phenylcyclohexyl)-α-methyl-3,5-bis(trifluoromethyl)benzeneacetamide (Description 29, 1.5 g, 2.8 mmol) in dimethylformamide and the mixture was stirred at 90° C. for 19 hours. The mixture was cooled, poured into aqueous ammonium chloride (saturated, 50 mL) and water (50 mL) and extracted with ethyl acetate (2×50 mL). The combined organic fractions were washed with water (3×50 mL) and brine (50 mL), dried (MgSO$_4$) and the solvent was evaporated under reduced pressure to give the crude title compound (1.9 g) which was used without further purification. m/z (ES$^+$) 484 (M+1).

DESCRIPTION 31

Trans-(RS)-N-(4-Cyano-1-phenylcyclohexyl)-α-methyl-3,5-bis(trifluoromethyl) benzeneacetamide Tetrabutylammonium cyanide (750 mg, 2.8 mmol) was dried azeotropically by evaporating toluene under reduced pressure, then a solution of Cis (RS)-N-(4-methanesulfonyloxy-1-phenylcyclohexyl)-α-methyl-3,5-bis(trifluoromethyl)benzeneacetamide (Description 29, 250 mg, 0.46 mmol) in toluene (25 mL) was added and the mixture was stirred at 70° C. for 24 hours. The mixture was cooled, poured into water (75 mL) and extracted with ethyl acetate (75 mL). The layers were separated and the organic layer was washed with brine (50 mL), dried (MgSO$_4$) and the solvent was evaporated under reduced pressure. The residue was purified by flash column chromatography on silica gel, eluting with isohexane/EtOAc (80:20), to give the title compound (146 mg, 70%). $^1$H NMR (400 MHz, CD$_3$OD) δ 1.46 (3H, d, J 7.2 Hz), 1.67–1.83 (4H, m), 2.16–2.20 (2H, m), 2.37–2.49 (2H, m), 2.80–2.84 (1H, m), 3.61–3.65 (1H, m), 5.56 (1H, br s), 7.23–7.30 (5H, m), 7.71 (2H, s), and 7.79 (1H, s).

DESCRIPTION 32

Dicyclohexylammonium (RS)-α-Methyl-3,5-bis(trifluoromethyl)benzeneacetate n-Butyllithium (2.5M solution in hexanes, 67.6 mL, 169 mmol) was added slowly to a stirred, cooled (−78° C.) solution of 3,5-bis(trifluoromethyl)benzeneacetic acid (20.0 g, 73.5 mmol) in tetrahydrofuran (400 mL) and the mixture was stirred at −78° C. for 1 hour. Iodomethane (6.87 mL, 110 mmol) was added slowly and the mixture was allowed to warm to room temperature and stirred overnight. Aqueous sodium bisulfite (20%) was added until the mixture was acidic. The mixture was extracted with ethyl acetate, the combined organic fractions were dried (MgSO$_4$) and the solvent was evaporated under reduced pressure. The residue was dissolved in ethyl acetate (400 mL), dicyclohexylamine (10 mL, 80.85 mmol) was added and the mixture was heated under reflux for 1 hour. The mixture was cooled and the solid was collected and dried in vacuo to give the title compound as a colorless solid (31.13 g, 91%). $^1$H NMR (400 MHz, CDCl$_3$) δ 7.83 (2H, s), 7.68 (1H, s), 3.66 (1H, q, J 7.1 Hz), 2.83–2.75 (2H, m), 1.87–1.84 (4H, m), 1.71–1.68 (4H, m), 1.60–1.57 (2H, m), 1.48 (3H, d, J 7.1 Hz), 1.28–1.08 (8H, m), and 1.03–0.92 (2H, m).

DESCRIPTION 33

(RS)-α-Methyl-3,5-bis(trifluoromethyl)benzeneacetic Acid

Dicyclohexylammonium (RS)-α-methyl-3,5-bis(trifluoromethyl)benzeneacetate (Description 32, 31.13 g, 67 mmol) was suspended in ethyl acetate, washed with aqueous citric acid (25%) and water, dried (MgSO$_4$) and the solvent was evaporated under reduced pressure to give the title compound as a colorless solid (19.0 g, 100%). $^1$H NMR (400 MHz, CDCl$_3$) δ 7.81 (1H, s), 7.78 (2H, s), 3.90 (1H, q, J 7.2 Hz), and 1.60 (3H, d, J 7.2 Hz).

DESCRIPTION 34

Dicyclohexylammonium (RS)-α-(2-Propenyl)-3,5-bis(trifluoromethyl)benzeneacetate Prepared from 3,5-bis(trifluoromethyl)benzeneacetic acid and 3-bromo-1-propene according to the method of Description 32. $^1$H NMR (400 MHz, CD$_3$OD) δ 7.95 (2H, s), 7.75 (1H, s), 5.82–5.70 (1H, m), 5.01 (1H, br d, J 17 Hz), 4.93 (1H, br d, J 10 Hz), 3.65 (1H, t, J 7 Hz), 3.20–3.10 (2H, m), 2.87–2.77 (1H, m), 2.53–2.43 (1H, m), 2.10–2.00 (4H, m), 1.90–1.80 (4H, m), 1.75–1.65 (2H, m), and 1.45–1.12 (10H, m).

DESCRIPTION 35

(RS)-α-(2-Propenyl)-3,5-bis(trifluoromethyl)benzeneacetic Acid

Prepared from dicyclohexylammonium (RS)-α-(2-propenyl)-3,5-bis(trifluoromethyl)benzeneacetate (Description 34) according to the method of Description 33. $^1$H NMR (400 MHz, CDCl$_3$) δ 7.81 (1H, s), 7.78 (2H, s), 5.68 (1H, m), 5.15–5.05 (2H, m), 3.82 (1H, t, J 7.6 Hz), 2.90 (1H, ddd, J 14, 7, 7 Hz), and 2.58 (1H, ddd, J 14, 7, 7 Hz).

DESCRIPTION 36

(4S)3-[3,5-Bis(trifluoromethyl)benzeneacetyl]-4-(phenylmethyl)-2-oxazolidinone Sodium bis(trimethylsilyl)amide (1M in tetrahydrofuran, 52.4 mL) was added dropwise to a stirred, cooled (−30° C.) solution of (S)-4-(phenylmethyl)-2-oxazolidinone (9.27 g, 52.4 mmol) in tetrahydrofuran (150 mL) and the mixture was allowed to warm to 0° C. and stirred for 1 hour. The mixture was added via cannula to a stirred, cooled (−30° C.) solution of freshly prepared 3,5-bis(trifluoromethyl)benzeneacetyl chloride (prepared from [3,5-bis(trifluoromethyl)phenyl]acetic acid (15 g, 55.1 mmol), oxalyl chloride (9.63 mL, 110.3 mmol) and dimethylformamide (2 drops) in dichloromethane (150 mL), followed by evaporation of solvent under reduced pressure) in tetrahydrofuran (100 mL). The mixture was stirred at −30° C. for 1 hour, then allowed to warm slowly to room temperature and stirred overnight. Hydrochloric acid (1M) was added and the mixture was extracted with ethyl acetate. The combined organic fractions were dried (MgSO$_4$) and the solvent was evaporated under reduced pressure. The residue was purified by flash column chromatography on silica gel, eluting with isohexane:EtOAc (80:20), to give the title compound as a colorless oil, (9.0 g, 40%). $^1$H NMR (360 MHz, CDCl$_3$) δ 7.83 (1H, s), 7.79 (2H, s), 7.34–7.23 (3H, m), 7.18–7.14 (2H, m), 4.74–4.68 (1H, m), 4.49–4.37 (2H, m), 4.29–4.21 (2H, m), 3.29 (1H, dd, J 34, 13.4 Hz), and 2.80 (1H, dd, J 9.5, 13.4 Hz).

DESCRIPTION 37

(4R)-3-[3,5-Bis(trifluoromethyl)benzeneacetyl]-4-phenylmethyl)-2-oxazolidinone Prepared from (R)-4-(phenylmethyl)-2-oxazolidinone and 3,5-bis(trifluoromethyl)benzeneacetyl chloride according to the method of Description 36. $^1$H NMR (400 MHz, CDCl$_3$) δ 7.83 (1H s), 7.79 (2H, s), 7.33–7.26 (3H, m), 7.17–7.15 (2H, m), 4.73–4.69 (1H, m), 4.48–4.37 (2H, m), 4.29–4.22 (2H, m), 3.29 (1H, dd, J 3.4, 13.4 Hz), and 2.80 (1H, dd, J 9.5, 13.4 Hz).

DESCRIPTION 38

(4S)-3-{(2S)-1-Oxo-2-[3,5-bis(trifluoromethyl)phenyl]propyl}-4-(phenylmethyl)-2-oxazolidinone Sodium bis(trimethylsilyl)amide (1M in tetrahydrofuran, 19.3 mL) was added slowly to a stirred, cooled (−78° C.) solution of (4S)-3-[3,5-bis(trifluoromethyl)benzeneacetyl]-4-(phenylmethyl)-2-oxazolidinone (Description 36, 7.25 g, 16.8 mmol) in tetrahydrofuran (60 mL) and the mixture was stirred at −78° C. for 1 hour. Iodomethane (21 mL, 33.6 mmol) was added and the mixture was stirred at −78° C. for 30 minutes, at 0° C. for 1 hour, then at room temperature overnight. Saturated aqueous ammonium chloride was added and the mixture was extracted with ethyl acetate. The combined organic fractions were dried (MgSO$_4$) and the solvent was evaporated under reduced pressure. The residue was purified by flash column chromatography on silica gel, eluting with isohexane:EtOAc (90:10 increasing to 85:15), to give the title compound as a colorless oil (5.14 g, 69%). $^1$H NMR (360 MHz, CDCl$_3$) δ 7.84 (2H, s), 7.78 (1H, s), 7.38–7.27 (3H, m), 7.23–7.21 (2H, m), 5.26 (1H, q, J 7.0 Hz), 4.68–4.64 (1H, m), 4.19–4.15 (2H, m), 3.34 (1H, dd, J 3.3, 13.3 Hz), 2.83 (1H, dd, J 9.5, 13.3 Hz), and 1.60 (3H, d, J 7.0 Hz).

DESCRIPTION 39

(4R)-3-{(2R)-1-Oxo-2-[3,5-bis(trifluoromethyl)phenyl]propyl}-4-(phenylmethyl)-2-oxazolidinone Prepared from (4R)-3-[3,5-bis(trifluoromethyl)benzeneacetyl]-4-phenylmethyl)-2-oxazolidinone (Description 37) according to the method of Description 38. $^1$H NMR (400 MHz, CDCl$_3$) δ 7.84 (2H, s), 7.78 (1H, s), 7.37–7.28 (3H, m), 7.23–7.21 (2H, m), 5.26 (1H, q, J 7.0 Hz), 4.68–4.64 (1H, m), 4.19–4.16 (2H, m), 3.34 (1H, dd, J 3.3, 13.3 Hz), 2.83 (1H, dd, J 9.5, 13.3 Hz), and 1.60 (3H, d, J 7.0 Hz).

DESCRIPTION 40

(S)-α-Methyl-3,5-bis(trifluoromethyl)benzeneacetic Acid

Aqueous hydrogen peroxide (30%, 14 mL) then lithium hydroxide monohydrate (944 mg, 22.4 mmol) were added to a stirred, degassed, cooled (0° C.) solution of (4S)-3-{(2S)-1-oxo-2-[3,5-bis(trifluoromethyl)phenyl]propyl}-4-(phenylmethyl)-2-oxazolidinone (Description 38, 5.0 g, 11.2 mmol) in tetrahydrofuran/water (4:1, 50 mL) and the mixture was stirred at 0° C. for 2.5 hours. Aqueous sodium bisulfite (10%) was added slowly, maintaining the internal temperature below 5° C., until the mixture was acidic. The mixture was extracted with ethyl acetate, the combined organic fractions were dried ($MgSO_4$) and the solvent was evaporated under reduced pressure. The residue was triturated with isohexane and filtered, washing with isohexane. The solvent was evaporated under reduced pressure and the residue was dissolved in ethyl acetate (10 mL/g) and heated to reflux. Dicyclohexylamine (2.45 mL, 12.3 mmol) was added and the mixture was cooled. The solid was collected, suspended in ethyl acetate and washed with aqueous citric acid (10%). The organic layer was washed with water, dried ($MgSO_4$) and the solvent was evaporated under reduced pressure to give the title compound as a colorless solid (1.7 g, 53%). $^1$H NMR (400 MHz, $CDCl_3$) δ 7.81 (1H, s), 7.78 (2H, s), 3.90 (1H, q, J 7.2 Hz), and 1.60 (3H, d, J 7.2 Hz). e.e. (determined by 500 MHz, $^1$H NMR of a mixture of 140 mmol of acid and 70 mmol of (1R,2R)-1,2-diphenyl-1,2-ethanediamine, at 284K in $CDCl_3$)>99%.

DESCRIPTION 41

(R)-α-Methyl-3,5-bis(trifluoromethyl)benzeneacetic Acid

Prepared from (4R)-3-{(2R)-1-oxo-2-[3,5-bis(trifluoromethyl)phenyl]propyl}-4-(phenylmethyl)-2-oxazolidinone (Description 39) according to the method of Description 38. $^1$H NMR (400 MHz, $CDCl_3$) δ 7.81 (1H, s), 7.78 (2H, s), 3.90 (1H, q, J 7.2 Hz), and 1.60 (3H, d, J 7.2 Hz). e.e (determined by 500 MHz $^1$H NMR of a mixture of 140 mmol of acid and 70 mmol of (1R,2R)-1,2-diphenyl-1,2-ethanediamine, at 284K in $CDCl_3$) 98.6%.

DESCRIPTION 42

Methyl α,α-Diethyl-3,5-bis(trifluoromethyl)benzeneacetate

Prepared from methyl 3,5-bis(trifluoromethyl)benzeneacetate (Description 1) and iodoethane according to the method of Description 5. $^1$H NMR (400 MHz, $CDCl_3$) δ 0.76 (6H, t, J 7.4 Hz), 2.08–2.16 (4H, m), 3.69 (3H, s), 770 (2H, s), and 777 (1H, s).

DESCRIPTION 43

Methyl 1-[3,5-Bis(trifluoromethyl)phenyl]cyclopropanecarboxylate

Prepared from methyl 3,5-bis(trifluoromethyl)benzeneacetate (Description 1) and 1,2-dibromoethane according to the method of Description 5. $^1$H NMR (400 MHz, $CDCl_3$) δ 1.25 (2H, m), 1.73 (2H, m), 3.65 (3H, s), and 7.79 (3H, s).

DESCRIPTION 44

α,α-Diethyl-3,5-bis(trifluoromethyl)benzeneacetic Acid

Prepared from methyl α,α-diethyl-3,5-bis(trifluoromethyl)benzeneacetate (Description 42) according to the method of Description 6. $^1$H NMR (400 MHz, $CDCl_3$) δ 0.80 (6H, t, J 7.4 Hz), 2.03–2.19 (4H, m), 7.77 (2H, s), and 7.79 (1H, s).

DESCRIPTION 45

1-[3,5-Bis(trifluoromethyl)phenyl]cyclopropanecarboxylic Acid

Prepared from methyl α,α-diethyl-3,5-bis(trifluoromethyl)benzeneacetate (Description 43) according to the method of Description 6. $^1$H NMR (400, $CDCl_3$) δ 1.32–1.35 (2H, m), 1.78–1.81 (2H, m), and 7.79 (3H, s).

DESCRIPTION 46

(RS)-Methyl α-(Methoxymethyl)-3,5-bis(trifluoromethyl)benzeneacetate (Diazomethyl)trimethylsilane (1.6 mL, 3.2 mmol) was added dropwise to a stirred, cooled (0° C.) mixture of (RS)-methyl α-(hydroxymethyl)-3,5-bis(trifluoromethyl)benzeneacetate (Description 7, 1.0 g, 3.2 mmol) and aqueous fluoroboric acid (48%, 585 mg, 3.2 mmol) in dichloromethane (10 mL) and the mixture was stirred at room temperature for 20 minutes. Further (diazomethyl)trimethylsilane (0.8 mL, 1.6 mmol) was added and the mixture was stirred at room temperature for 20 minutes. Further (diazomethyl)trimethylsilane (0.4 mL, 0.8 mmol)) was added and the mixture was stirred at room temperature for 20 minutes. Further (diazomethyl)trimethylsilane (0.4 mL, 0.8 mmol)) was added and the mixture was stirred at room temperature for 30 minutes, poured into water (40 mL) and extracted with dichloromethane (2×40 mL). The combined organic fractions were dried ($MgSO_4$), the solvent was evaporated under reduced pressure and the residue was purified by flash column chromatography on silica gel, eluting with isohexane/EtOAc (90:10), to give the title compound as a colorless oil (834 mg, 80%). $^1$H NMR (400 MHz, $CDCl_3$) δ 3.36 (3H, s), 3.69–3.73 (1H, m), 3.74 (3H, s), 3.92–3.96 (1H, m), 3.99–4.03 (1H, m), and 7.80–7.81 (3H, m).

DESCRIPTION 47

(RS)-α-(Methoxymethyl)-3,5-bis(trifluoroethyl)benzeneacetic Acid

Aqueous sodium hydroxide (4 MHz, 1 mL, 4 mmol) was added to a solution of (RS)-methyl α-(methoxymethyl)-3,5-bis(trifluoromethyl)benzeneacetate (Description 46, 834 mg, 2.5 mmol) in methanol (4 mL) and the mixture was stirred at room temperature for 20 hours. The solvent was evaporated under reduced pressure and the mixture was acidified with hydrochloric acid (1M). The mixture was extracted with dichloromethane (2×20 mL), the combined organic fractions were dried ($MgSO_4$) and the solvent was evaporated under reduced pressure. The residue was purified by flash column chromatography on silica gel, eluting with $CH_2Cl_2$/MeOH (95:5), to give the title compound as a colorless oil (126 mg 16%) $^1$H NMR (400 MHz, CDCl$_3$) δ 3.39 (3H, s), 3.71–3.77 (1H, m), 3.92–3.96 (1H, m), 4.02–4.05 (1H, m), and 7.78–7.83 (3H, m).

DESCRIPTION 48

3,5-Bis(trifluoromethyl)-α-oxobenzeneacetic Acid

A mixture of 1-[3,5-bis(trifluoromethyl)phenyl]ethanone (3.84 g, 15 mmol) and selenium (IV) oxide (2.50 g, 22.5 mmol) in pyridine (25 mL) was stirred at 100° C. for 2 hours, filtered, cooled and the solvent was evaporated under reduced pressure. Hydrochloric acid (2M, 50 mL) was added and the mixture was extracted with ethyl acetate (3×50 mL). The combined organic fractions were washed with hydrochloric acid (2M, 50 mL) and brine (50 mL), dried (MgSO$_4$) and the solvent was evaporated under reduced pressure to give an orange solid (4.19 g). The residue was dissolved in propan-2-ol (50 mL) and dicyclohexylamine (2.92 mL, 2.66 g, 14.6 mmol) was added. The solvent was evaporated under reduced pressure and the residue was recrystallised from ethanol-water (1:1, 60 mL). The solid was collected, suspended in ether (50 mL) and the mixture was extracted with aqueous sodium hydroxide (1M, 3×25 mL). The combined aqueous fractions were washed with ether (2×25 mL) and hydrochloric acid (5M, 25 mL) was added. The mixture was extracted with dichloromethane (3×50 mL) and the combined organic fractions were dried (MgSO$_4$) and the solvent was evaporated under reduced pressure. The residue was triturated with isohexane (40 mL) and the solid was collected and dried in vacuo to give the title compound as a tan solid (1.32 g, 31%). m/z (ES$^-$) 285 (M−1).

DESCRIPTION 49

1,1-Dimethylethyl 4-Methoxy-1-piperidinecarboxylate

Sodium hydride (60% dispersion in mineral oil, 2.98 g, 74.5 mmol) was added to a solution of 1,1-dimethylethyl 4-hydroxy-1-piperidinecarboxylate (5.0 g, 24.8 mmol) in dimethylformamide (30 mL) and the mixture was stirred for 5 minutes. Methyl iodide (4.64 mL, 74.5 mmol) was added and the mixture was stirred for 30 minutes. Water (50 mL) was added and the mixture was extracted with diethyl ether (2×50 mL). The combined organic fractions were washed with water (4×50 mL) and brine, dried (MgSO$_4$) and the solvent was evaporated under reduced pressure to give the title compound (5.3 g, 99%). m/z (ES$^+$) 216 (M+1).

DESCRIPTION 50

4-Methoxypiperidine

Prepared from 1,1-dimethylethyl 4-methoxy-1-piperidinecarboxylate (Description 49) according to the method of Description 75. $^1$H NMR (360 MHz, CDCl$_3$) δ 3.35 (3H, s), 3.29–3.23 (1H, m), 3.11–3.05 (2H, m), 2.64–2.57 (2H, m), 1.96–1.90 (2H, m), and 1.46–1.36 (2H, m).

DESCRIPTION 51

1,1-Dimethylethyl 4-Ethyl-4-hydroxy-1-piperidinecarboxylate 1,1-Dimethylethyl 4-oxo-1-piperidinecarboxylate (10.1 g, 50.7 mmol) in tetrahydrofuran (40 mL) was added dropwise over 30 minutes to a stirred, cooled (0° C.) solution of ethyl magnesium bromide (1.0M in tetrahydrofuran, 50.7 mL, 50.7 mmol) in tetrahydrofuran (30 mL). The mixture was allowed to warm to room temperature and stirred for 4 hours. The mixture was poured into saturated aqueous ammonium chloride (150 mL) and extracted with ethyl acetate (2×150 mL). The combined organic fractions were washed with brine, dried (MgSO$_4$) and the solvent was evaporated under reduced pressure. The residue was purified by flash column chromatography on silica gel, eluting with 3:1 isohexane:ethyl acetate, to give the title compound (8.5 g, 73%). m/z (ES$^+$) 230 (M+1).

DESCRIPTION 52

1,1-Dimethylethyl 4-Ethyl-4-methoxy-1-piperidinecarboxylate

Prepared from 1,1-dimethylethyl 4-ethyl-4-hydroxy-1-piperidinecarboxylate (Description 51) according to the method of Description 54. m/z (ES$^+$) 244 (M+1).

DESCRIPTION 53

4-Ethyl-4-methoxypiperidine

Prepared from 1,1-dimethylethyl 4-ethyl-4-methoxy-1-piperidinecarboxylate (Description 52) according to the method of Description 75. m/z (ES$^+$) 144 (M+1).

DESCRIPTION 54

Trans-(RS)-3-Methoxy-4-methyl-1-(phenylmethyl) piperidine Hydrochloride

Sodium hydride (60% dispersion in mineral oil, 374 mg, 9.75 mmol) was added in portions to a solution of trans-(RS)-4-methyl-1-phenylmethyl)-3-piperidinol (*Tetrahedron* 1970, 26, 5519–5527, 1 g, 4.88 mmol) in dimethylformamide (30 mL) and the mixture was stirred at room temperature for 1 hour. Iodomethane (304 μL, 4.88 mmol) was added and the mixture was stirred at room temperature for 30 minutes. The mixture was poured into water (300 mL) and extracted with diethyl ether (2×200 mL). The combined organic fractions were dried (MgSO$_4$) and the solvent was evaporated under reduced pressure. The residue was suspended in diethyl ether (50 mL) and ethereal hydrogen chloride (1M, 5 mL) was added. The solid was collected and dried in vacuo to give the title compound (720 mg, 60%). m/z (ES$^+$) 220 (M+1).

DESCRIPTION 55

Trans-(RS)-3-Methoxy-4-methylpiperidine Hydrochloride

A slurry of palladium on carbon (10%, 100 mg) in ethanol (10 mL) was added to a solution of trans-(RS)-3-methoxy-4-methyl-1-(phenylmethyl)piperidine hydrochloride (Description 54, 720 mg, 2.82 mmol) in ethanol (20 mL) and hydrochloric acid (2M, 10 mL) and the mixture was shaken under hydrogen (50 psi) for 24 hours. The mixture was filtered through Celite™ and the solvent was evaporated under reduced pressure to give the title compound as a colorless solid (488 mg, 99%). m/z (ES$^+$) 130 (M+1).

DESCRIPTION 56

Trans-(RS)-4-Methyl-3-piperidinol Hydrochloride

A slurry of palladium on carbon (10%, 600 mg) in ethanol (10 mL) was added to a solution of trans-(RS)-4-methyl-1-(phenylmethyl)-3-piperidinol (*Tetrahedron* 1970, 26, 5519–5527, 6 g, 29.2 mmol) and hydrochloric acid (2M, 10 mL) in ethanol (100 mL) and the mixture was shaken under hydrogen (50 psi) for 42 hours. The mixture was filtered through Celite™ and the solvent was evaporated under reduced pressure. Toluene (50 mL) was added and evaporated under reduced pressure to give the title compound as a colorless solid (4.4 g, 99%). m/z (ES$^+$) 115 (M+1).

DESCRIPTION 57

Trans-(RS)-1,1-Dimethylethyl 3-Hydroxy-4-methylpiperidinecarboxylate

Di-tert-butyl dicarbonate (4.32 g, 20 mmol) was added to a solution of trans-(RS)-4-methyl-3-piperidinol hydrochloride (Description 56, 2.93 g, 19.4 mmol) and triethylamine (4.1 mL, 29 mmol) in dichloromethane (150 mL) and the mixture was stirred at room temperature for 16 hours. N,N-Dimethylethylenediamine (506 μL) was added and the mixture was stirred at room temperature for 16 hours. The mixture was washed with aqueous citric acid (10%, 100 mL), dried (MgSO$_4$), and the solvent was evaporated under reduced pressure to give the title compound as a colorless oil (4.0 g, 96%). m/z (ES$^+$) 159 (M+1).

DESCRIPTION 58

Trans-(RS)-3-Fluoro-4-methylpiperidine Hydrochloride

Diethylaminosulphur trifluoride (880 μL, 6.66 mmol) was added to a stirred, cooled (−40° C.) solution of trans-(RS)-1,1-dimethylethyl 3-hydroxy-4-methylpiperidinecarboxylate (Description 57, 500 mg, 2.22 mmol) in dichloromethane (50 mL). The mixture was allowed to warm to room temperature and stirred for 16 hours. Ice (5 g) and water (5 mL) were added and the mixture was stirred for 20 minutes. The layers were separated and the aqueous layer was extracted with dichloromethane (2×50 mL). The combined organic fractions were washed with brine (50 mL), dried (MgSO$_4$) and the solvent was evaporated under reduced pressure. The residue was suspended in diethyl ether (50 mL) and treated with methanolic hydrogen chloride (1M, 3 mL). The mixture was stirred at room temperature for 30 minutes, then the solvent was evaporated under reduced pressure to give the title compound as a solid (303 mg, 78%). m/z (ES$^+$) 118 (M+1).

DESCRIPTION 59

(RS)-1,1-Dimethylethyl 4-Methyl-3-oxopiperidinecarboxylate 1,1,1-Tris(acetyloxy)-1,1-dihydro-1,2-benziodoxol-3(1H)-one (4.17 g, 0.13 mmol) was added to a solution of trans-(RS)-1,1-dimethylethyl 3-hydroxy-4-methylpiperidinecarboxylate (Description 57, 2 g, 9.3 mmol) in dichloromethane (60 mL) and the mixture was stirred at room temperature for 60 minutes. Aqueous sodium bisulfite (10%, 50 mL) was added and the mixture was stirred at room temperature for 5 minutes. Saturated aqueous sodium hydrogen carbonate (50 mL) was added and the layers were separated. The organic fraction was dried (MgSO$_4$) and the solvent was evaporated under reduced pressure to give the title compound (1.96 g, 99%). m/z (ES$^+$) 157 (M+1).

DESCRIPTION 60

(RS)-3,3-Difluoro-4-methylpiperidine Hydrochloride

Diethylaminosulphur trifluoride (1.18 mL, 8.97 mmol) was added to a stirred, cooled (0° C.) solution of (RS)-1,1-dimethylethyl 4-methyl-3-oxopiperidinecarboxylate (Description 59, 500 mg, 2.24 mmol) in dichloromethane and the mixture was stirred at room temperature for 16 hours. Ice (5 g) and water (5 mL) were added and the mixture was stirred at room temperature for 20 minutes. The layers were separated and the aqueous layer was extracted with dichloromethane (2×50 mL). The combined organic fractions were washed with brine (50 mL), dried (MgSO$_4$) and the solvent was evaporated under reduced pressure. The residue was suspended in diethyl ether (50 mL) and treated with methanolic hydrogen chloride (1M, 3 mL). The mixture was stirred at room temperature for 30 minutes then the solvent was evaporated under reduced pressure to give the title compound as a solid (303 mg, 78%). m/z (ES$^+$) 136 (M+1).

DESCRIPTION 61

(RS)-10-Methyl-7-(phenylmethyl)-1,4-dioxa-7-azaspiro[4.5]decane Hydrochloride p-Toluenesulfonic acid (31 mg) was added to a solution of (RS)-4-methyl-1-phenylmethyl)-3-piperidinone (*Tetrahedron* 1970, 26, 5519–5527, 1.55 g, 7.6 mmol) and ethylene glycol (20 mL, 0.35 mol) in toluene (76 mL) and the mixture was heated under reflux with azeotropic removal of water overnight. The mixture was cooled, poured into saturated aqueous potassium carbonate (150 mL) and extracted with dichloromethane (3×100 mL). The combined organic fractions were washed with water, dried (MgSO$_4$) and the solvent was evaporated under reduced pressure. The residue was purified by flash column chromatography on silica gel, eluting with CH$_2$Cl$_2$/MeOH/NH$_3$(Aq.) (96.5:3.5:1). The residue was suspended in diethyl ether (50 mL) and ethereal hydrogen chloride (1M, 3 mL) was added. The solid was collected and dried in vacuo to give the title compound (750 mg, 35%). m/z (ES$^+$) 248 (M+1).

DESCRIPTION 62

(RS)-10-Methyl-1,4-dioxa-7-azaspiro[4.5]decane Hydrochloride

A slurry of palladium on carbon (10%, 90 mg) in ethanol (10 mL) was added to a solution of (RS)-10-methyl-7-phenylmethyl)-1,4-dioxa-7-azaspiro[4.5]decane hydrochloride (Description 61, 750 mg, 2.65 mmol) in ethanol (30 mL) and the mixture was shaken under hydrogen (50 psi) for 24 hours. The mixture was filtered through Celite™ and the

DESCRIPTION 63

1,2,3,6-Tetrahydro-1-(phenylmethyl)-4-pyridineethanol

Benzyl bromide (4.4 mL, 41 mmol) was added to a solution of 4-pyridineethanol (5 g, 41 mmol) in acetone (100 mL) and the mixture was heated under reflux for 16 hours. The mixture was cooled and the solid was collected, washed with acetone (50 mL) and diethyl ether (2×50 mL) then dissolved in methanol (100 mL) and treated with sodium borohydride (6.2 g 164 mmol). The mixture was heated under reflux for 16 hours, cooled, and the solvent was evaporated under reduced pressure. Ethyl acetate (200 mL) and aqueous sodium hydrogen carbonate (10%, 150 mL) were added and the layers were separated. The aqueous layer was extracted with ethyl acetate (2×100 mL), the combined organic fractions were dried (MgSO$_4$) and the solvent was evaporated under reduced pressure. The residue was purified by flash column chromatography on silica gel, eluting with CH$_2$Cl$_2$/MeOH/NH$_3$(Aq.) (92:8:1), to give the title compound as a colorless oil (1.65 g, 18%). m/z (ES$^+$) 218 (M+1).

DESCRIPTION 64

Trans-(RS)-3-Hydroxy-1-(phenylmethyl)-4-piperidineethanol

Borane-tetrahydrofuran complex (1M in tetrahydrofuran, 16 mL) was added to a solution of 1,2,3,6-tetrahydro-1-(phenylmethyl)-4-pyridineethanol (Description 63, 1 g, 4.6 mmol) in tetrahydrofuran (30 mL) and the mixture was stirred at room temperature for 16 hours. Further borane-tetrahydrofuran complex (1M in tetrahydrofuran, 70 mL) was added and the solution was heated under reflux for 72 hours. The mixture was cooled, a mixture of aqueous sodium hydroxide (4M, 200 mL) and aqueous hydrogen peroxide (37%, 200 mL) was added and the mixture was stirred at room temperature for 2 hours. The mixture was extracted with ethyl acetate (2×25 mL), the combined organic fractions were washed with brine (100 mL), dried (MgSO$_4$) and the solvent was evaporated under reduced pressure. The residue was purified by flash column chromatography on silica gel, eluting with CH$_2$Cl$_2$/MeOH/Et$_3$N (95:5:1 increasing to 90:10:1), to give the title compound (260 mg, 24%). m/z (ES$^+$) 236 (M+1).

DESCRIPTION 65

Trans-(RS)-Octahydro-6-(phenylmethyl)furo[2,3-c]pyridine

Diethyl diazenedicarboxylate (191 µL, 1.2 mmol) was added to a solution of trans-(RS)-3-hydroxy-1-phenylmethyl)-4-piperidineethanol (Description 64, 260 mg, 1.1 mmol) and triphenylphosphine (328 mg, 1.2 mmol) in tetrahydrofuran (60 mL) and the mixture was stirred at room temperature for 36 hours. The solvent was evaporated under reduced pressure, dichloromethane and water were added and the layers were separated. The organic layer was dried (MgSO$_4$) and the solvent was evaporated under reduced pressure. The residue was dissolved in methanol (1.5 mL) and poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure and the residue was purified by preparative thin layer chromatography on silica gel, eluting with CH$_2$Cl$_2$/MeOH/NH$_3$(Aq.) (96:4:1), to give the title compound (78 mg, 32%). m/z (ES$^+$) 218 (M+1).

DESCRIPTION 66

Trans-(RS)-Octahydrofuro[2,3-c]pyridine Hydrochloride

A slurry of palladium on carbon (10%, 3 mg) in ethanol (10 mL) and concentrated hydrochloric acid (1 mL) was added to a solution of trans-(RS)-octahydro-6-(phenylmethyl)furo[2,3-c]pyridine (Description 65, 78 mg) in ethanol (10 mL) and the mixture was shaken under hydrogen (50 psi) for 16 hours. The mixture was filtered through Celite™ and the solvent was evaporated under reduced pressure. Toluene (2×5 mL) was added and evaporated under reduced pressure and the residue was dried in vacuo to give the title compound (58 mg, 99%). m/z (ES$^+$) 128 (M+1).

DESCRIPTION 67

1,1-Dimethylethyl 4,4-Bis(hydroxymethyl)-1-piperidinecarboxylate

A solution of 1-(1,1-dimethylethyl) 4-ethyl 1,4-piperidinedicarboxylate (10 g, 39 mmol) in tetrahydrofuran (100 mL) was added to a stirred, cooled (−78° C.) solution of lithium diisopropylamide in tetrahydrofuran (0.82M, 140 mL) and the mixture was stirred at −78° C. for 2 h, then at −40° C. for 3 hours. The mixture was cooled to −78° C., ethyl chloroformate (13 mL, 136 mmol) in tetrahydrofuran (80 mL) was added and the mixture was allowed to warm to room temperature over 16 hours. Saturated aqueous ammonium chloride (50 mL), hydrochloric acid (1M, 2000 mL) and ethyl acetate (3000 mL) were added and the layers were separated. The aqueous layer was extracted with ethyl acetate (3×150 mL), the combined organic fractions were dried (MgSO$_4$) and the solvent was evaporated under reduced pressure. The residue was dissolved in toluene/tetrahydrofuran (1:1, 400 mL) and lithium borohydride (4.5 g, 207 mmol) was added. The mixture was heated at 60° C. for 16 hours, cooled and saturated aqueous ammonium chloride was added slowly until the organic layer was a clear solution. The mixture was adjusted to pH 12 with saturated aqueous sodium carbonate and the layers were separated. The aqueous layer was extracted with ethyl acetate (2×150 mL), the combined organic fractions were dried (MgSO$_4$) and the solvent was evaporated under reduced pressure. The residue was purified by flash column chromatography on silica gel, eluting with isohexane/EtOAc (50:50 increasing to 0:100), to give the title compound (6.1 g, 63%). m/z (ES$^+$) 190 (M+1-C$_4$H$_8$).

DESCRIPTION 68

1,1-Dimethylethyl 4-Hydroxymethyl-4-methanesulfonyloxymethyl-1-piperidinecarboxylate Methanesulfonyl chloride (44 µL, 0.56 mmol) in dichloromethane (10 mL) was added slowly to a stirred, cooled (0° C.) solution of 1,1-dimethylethyl 4,4-bis(hydroxymethyl)-1-piperidinecarboxylate (Description 67, 140 mg, 0.56 mmol) and triethylamine (95 µL, 0.68 mmol) in dichloromethane (50 mL). The mixture was allowed to warm to room temperature and stirred for 16 hours. Water (10 mL) was added and the layers were separated. The aqueous layer was extracted with dichloromethane (2×40 mL), the combined organic fractions were dried (MgSO$_4$) and the solvent was evaporated under reduced pressure. The residue was purified by flash column chromatography on silica gel, eluting with isohexane/EtOAc (80:20 increasing to 0:100), to give the title compound (98 mg, 54%). m/z (ES$^+$) 324 (M+1).

DESCRIPTION 69

1,1-Dimethylethyl 2-Oxa-7-azaspiro[3.5]nonane-7-carboxylate

A solution of 1,1-dimethylethyl 4-hydroxymethyl-4-methanesulfonyloxymethyl-1-piperidinecarboxylate (Description 68, 3 g, 9.3 mmol) in tetrahydrofuran (200 mL) was added dropwise to a stirred suspension of sodium hydride (60% dispersion in mineral oil, 2.2 g, 55.8 mmol) in tetrahydrofuran (50 mL) and the mixture was stirred at room temperature for 72 hours. Water (5 mL) was added and the mixture was extracted with ethyl acetate (3×400 mL). The combined organic fractions were dried (MgSO$_4$) and the solvent was evaporated under reduced pressure. The residue was purified by flash column chromatography on silica gel, eluting with isohexane/EtOAc (80:20 increasing to 50:50), to give the title compound (1.5 g, 71%). m/z (ES$^+$) 228 (M+1).

DESCRIPTION 70

2-Oxa-7-azaspiro[3.5]nonane

Trifluoroacetic acid (5 mL) was added to a solution of 1,1-dimethylethyl 2-oxa-7-azaspiro[3.5]nonane-7-carboxylate (Description 69, 80 mg, 0.625 mmol) in dichloromethane (15 mL) and the mixture was stirred at room temperature for 3 hours. Saturated aqueous sodium hydrogen carbonate (3 mL) and dichloromethane (5 mL) were added and the layers were separated. The aqueous layer was extracted with dichloromethane (3×3 mL) and the combined organic fractions were poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure to give the title compound as a colorless solid (8 mg, 17%). m/z (ES$^+$) 128 (M+1).

DESCRIPTION 71

1,1-Dimethylethyl 4-Hydroxy-4-(3-trimethylsilyloxypropynyl)-1-piperidinecarboxylate Trimethyl(2-propynyloxy)silane (11.54 mL, 9.62 g, 75 mmol) was added dropwise to a stirred, cooled (−5° C.) solution of ethyl magnesium bromide (1M in tetrahydrofuran, 75 mL, 75 mmol) in tetrahydrofuran (150 mL), maintaining the internal temperature below 0° C. The mixture was stirred at 0° C. for 30 minutes, then at room temperature for 90 minutes. The mixture was cooled to −5° C. and 1,1-methylethyl 4-oxo-1-piperidinecarboxylate (15.0 g, 75 mmol) was added slowly, maintaining the internal temperature below 0° C. The mixture was stirred at 0° C. for 3 h then at room temperature for 96 hours. Saturated aqueous ammonium chloride (300 mL), water (100 mL) and ethyl acetate (300 mL) were added and the layers were separated. The aqueous layer was extracted with ethyl acetate (200 mL) and the combined organic fractions were dried (MgSO$_4$) and the solvent was evaporated under reduced pressure to give the title compound (24.4 g, 100%). $^1$H NMR (400 MHz, CDCl$_3$) δ 4.36 (2H, s), 3.80–3.70 (2H, m), 3.35–3.25 (2H, m), 1.95–1.85 (2H, m), 1.78–1.60 (3H, m), 1.48 (9H, s), and 0.2 (9H, s).

DESCRIPTION 72

1,1-Dimethylethyl 4-Hydroxy-4-(3-hydroxypropynyl)-1-piperidinecarboxylate

Tetrabutylammonium fluoride (1M in tetrahydrofuran, 80 mL, 80 mmol) was added to a solution of 1,1-dimethylethyl 4-hydroxy-4-(3-trimethylsilyloxypropynyl)-1-piperidinecarboxylate (Description 71, 24.4 g, 75 mmol) in tetrahydrofuran (300 mL) and the mixture was stirred at room temperature for 18 hours. The solvent was evaporated under reduced pressure and water (200 mL) was added, The mixture was extracted with ethyl acetate (2×200 mL) and the combined organic fractions were washed with water (2×200 mL) and brine (200 mL), dried (MgSO$_4$) and the solvent was evaporated under reduced pressure to give the title compound as an orange oil (16.8 g, 88%). $^1$H NMR (400 MHz, CDCl$_3$) δ 4.32 (2H, s), 3.80–3.68 (2H, m), 3.32–3.22 (2H, m), 1.93–1.83 (2H, m), 1.75–1.65 (2H, m), 1.62 (1H, br s), and 1.46 (9H, s).

DESCRIPTION 73

1,1-Dimethylethyl 4-Hydroxy-4-(3-proxypropyl)-1-piperidinecarboxylate

Palladium on carbon (5%, 800 mg) was added to a solution of 1,1-dimethylethyl 4-hydroxy-4-(3-hydroxypropynyl)-1-piperidinecarboxylate (Description 72, 8.37 g, 32.8 mmol) in ethanol (400 mL), acetic acid (40 mL) and water (5 mL) and the mixture was shaken under an atmosphere of hydrogen (40 psi) for 20 hours. The mixture was filtered through Hyflo™ and the solvent was evaporated under reduced pressure. The residue was purified by flash column chromatography on silica gel, eluting with isohexane/EtOAc (50:50 increasing to 0:100), to give the title compound (4.84 g, 57%). $^1$H NMR (400 MHz, CDCl$_3$) δ 3.85–3.75 (2H, m), 3.70 (2H, t, J 6 Hz), 3.18 (2H, br t, J 14 Hz), 2.00 (2H, br s), 1.73–1.65 (2H, m), 1.63–1.48 (6H, m), and 1.46 (9H, s).

DESCRIPTION 74

1,1-Dimethylethyl 1-Oxa-8-azaspiro[4.5]decane-8-carboxylate

A solution of diethyl diazenedicarboxylate (3.35 mL, 21.3 mmol) in tetrahydrofuran (50 mL) was added over 15 minutes to a stirred, cooled (0° C.) solution of 1,1-dimethylethyl 4-hydroxy-4-(3-hydroxypropyl)-1-piperidinecarboxylate (Description 73, 4.6 g, 17.8 mmol) and triphenylphosphine (5.58 g, 21.3 mmol) in tetrahydrofuran (150 mL) and the mixture was stirred at 0° C. for 1 hour, then at room temperature for 24 hours. The solvent was evaporated under reduced pressure and the residue was purified by flash column chromatography on silica gel, eluting with isohexane/EtOAc (75:25 increasing to 50:50), to give the title compound (3.18 g, 70%). m/z (ES$^+$) 242 (M+1).

DESCRIPTION 75

1-Oxa-8-azaspiro[4.5]decane Hydrochloride

Methanolic hydrogen chloride (3M, 20 mL) was added over 10 minutes to a stirred, cooled (0° C.) solution of 1,1-dimethylethyl 1-oxa-8-azaspiro[4.5]decane-8-carboxylate (Description 74, 3.18 g, 13.2 mmol) in methanol (10 mL) and the mixture was stirred at room temperature for 3 hours. The solvent was evaporated under reduced pressure to give the title compound (2.29 g, 98%). m/z (ES$^+$) 142 (M+1).

DESCRIPTION 76

1,1-Dimethylethyl 4-(3-Ethoxy-3-oxo-1-propynyl)-4-hydroxy-1-piperidinecarboxylate n-Butyllithium (175 mL, 0.28 mol) was added dropwise over 45 minutes to a stirred, cooled (−70° C.) solution of ethyl propiolate (32 mL, 0.32 mol) in tetrahydrofuran (250 mL). The mixture was stirred at −70° C. for 10 minutes, then a solution of 1,1-dimethylethyl 4-oxo-1-piperidinecarboxylate (18.6 g, 0.093 mol) in tetrahydrofuran (250 mL) was added dropwise over 1 hour maintaining the internal temperature below −70° C. The mixture was stirred at −70° C. for 1 hour, acetic acid (21 mL) in tetrahydrofuran (50 mL) was added. The mixture was warmed to room temperature and the solvent was evaporated under reduced pressure. Saturated aqueous sodium hydrogen carbonate (300 mL) and ethyl acetate (650 mL) were added and the layers were separated. The aqueous fraction was extracted with ethyl acetate (2×650 mL) and the combined organic fractions were washed with brine, dried (Na$_2$SO$_4$) and the solvent was evaporated under reduced pressure. The residue was purified by chromatography on a short silica gel column, eluting with 1:1 isohexane:ethyl acetate, to give the title compound (29.2 g, contains trace impurity). m/z (ES$^+$) 298 (M+1).

DESCRIPTION 77

1,1-Dimethylethyl 4-(3-Ethoxy-3-oxoprop-1-yl)-4-hydroxy-1-piperidinecarboxylate

Palladium on carbon (5%, 1 g) in water (10 mL) was added to a solution of 1,1-dimethylethyl 4-(3-ethoxy-3-oxo-1-propynyl)-4-hydroxy-1-piperidinecarboxylate (Description 76, 14.6 g, 0.046 mol) in ethanol (200 mL) and the mixture was shaken under hydrogen (45 psi) for 90 minutes. The mixture was filtered through a glass fibre pad and the solvent was evaporated under reduced pressure to give the title compound. m/z (ES$^+$) 302 (M+1).

DESCRIPTION 78

1,1-Dimethylethyl 1-Oxa-2-oxo-8-azaspiro[4.5]decane-8-carboxylate p-Toluenesulphonic acid (1.75 g, 9.2 mmol) was added to a solution of 1,1-dimethylethyl 4-(3-ethoxy-3-oxoprop-1-yl)-4-hydroxy-1-piperidinecarboxylate (Description 77, 27.63 g, 0.092 mol) in toluene (250 mL) and the mixture was heated under reflux for 3 hours. The mixture was cooled and the solvent was evaporated under reduced pressure. Water (400 mL) and ethyl acetate (400 mL) were added and the layers were separated. The aqueous fraction was extracted with ethyl acetate (200 mL). The combined organic fractions were washed with brine, dried (MgSO$_4$) and the solvent was evaporated under reduced pressure to give the title compound (20.86 g, 88%). m/z (ES$^+$) 256 (M+1).

DESCRIPTION 79

1-Oxa-8-azaspiro[4.5]decan-2-one Hydrochloride

Prepared from 1,1-dimethylethyl 1-oxa-2-oxo-8-azaspiro[4.5]decane-8-carboxylate (Description 78) according to the method of Description 75. m/z (ES$^+$) 156 (M+1).

DESCRIPTION 80

1,1-Dimethylethyl 4-Hydroxy-4-(3-hydroxy-3-methylbut-1-yl)-1-piperidinecarboxylate 1,1-Dimethylethyl 1-oxa-2-oxo-8-azaspiro[4.5]decane-8-carboxylate (Description 78, 5.0 g, 19.58 mmol) in tetrahydrofuran (150 mL) was added dropwise over 45 minutes to a stirred, cooled (0° C.) solution of methyl magnesium chloride (3M in tetrahydrofuran, 19.58 mL, 58.75 mmol) in tetrahydrofuran (150 mL). The mixture was allowed to warm to room temperature and stirred overnight. The mixture was poured into saturated aqueous ammonium chloride (200 mL) and extracted with ethyl acetate (200 mL). The organic fraction was washed with brine, dried (Na$_2$SO$_4$) and the solvent was evaporated under reduced pressure. The residue was purified by flash column chromatography on silica gel, eluting with ethyl acetate, to give the title compound (3.9 g, 69%). m/z (ES$^+$) 214 (M+1-C$_4$H$_8$—H$_2$O).

DESCRIPTION 81

2,2-Dimethyl-1-oxa-8-azaspiro[4.5]decane

Trifluoroacetic acid (10 mL) was added to a solution of 1,1-dimethylethyl 4-hydroxy-4-(3-hydroxy-3-methylbut-1-yl)-1-piperidinecarboxylate (Description 80, 3.9 g, 13.57 mmol) in dichloromethane (10 mL) and the mixture was stirred at room temperature overnight. The solvent was evaporated under reduced pressure and the residue was purified by flash column chromatography on silica gel, eluting with CH$_2$Cl$_2$/MeOH/NH$_3$(Aq.) (90:10:1) to give the title compound (2.04 g, 89%). m/z (ES$^+$) 170 (M+1).

DESCRIPTION 82

1-(1,1-Dimethylethyl) 4-Ethyl 4-(2-Propenyl)-1,4-piperidinedicarboxylate

A solution of 1-(1,1-Dimethylethyl) 4-ethyl 1,4-piperidinedicarboxylate (25.0 g, 97 mmol) in tetrahydrofuran (100 mL) was added slowly to a stirred, cooled (−78° C.) solution of potassium hexamethyldisilazide (29.0 g, 145 mmol) in tetrahydrofuran (150 mL), maintaining the internal temperature below −65° C. The mixture was stirred at −78° C. for 30 minutes, then 3-bromopropene (12.6 mL, 145 mmol) was added dropwise over 10 minutes. The mixture was stirred at −78° C. for 1 hour, then saturated aqueous ammonium chloride (400 mL) and water (100 mL) were added and the mixture was warmed to room temperature. The mixture was extracted with ethyl acetate (3×400 mL) and the combined organic fractions were washed with aqueous citric acid (10%, 2×250 mL), saturated aqueous sodium hydrogen carbonate (400 mL) and brine (200 mL), dried (MgSO$_4$) and the solvent was evaporated under reduced pressure to give the title compound (29.3 g, 100%). $^1$H NMR (400 MHz, CDCl$_3$) δ 5.75–5.60 (1H, m), 5.10–5.00 (2H, m), 4.16 (2H, q, J 7 Hz), 3.92–3.78 (2H, m), 2.90 (2H, br t, J 14 Hz), 2.26 (2H, d, J 7 Hz), 2.08 (2H, br d, J 14 Hz), 1.45 (9H, s), 1.45–1.30 (2H, m), and 1.26 (3H, t, J 7 Hz).

DESCRIPTION 83

1,1-Dimethylethyl 1-Oxo-2-oxa-8-azaspiro[4.5]decane-8-carboxylate 1-(1,1-Dimethylethyl) 4-ethyl 4-(2-propenyl)-1,4-piperidinedicarboxylate (Description 82, 20.0 g, 67.2 mmol) was dissolved in methanol (300 mL) and dichloromethane (300 mL) and cooled to −78° C. Oxygen was bubbled through the solution for 10 minutes, then ozone for 75 minutes, to give a persistant blue coloration. Oxygen was bubbled through the solution for 10 minutes, then nitrogen for 10 minutes. Sodium borohydride (5.1 g, 135 mmol) was added and the mixture was stirred at −78° C. for 1 hour. Further sodium borohydride (5.1 g, 135 mmol) was added and the mixture was stirred at room temperature for 16 hours. Acetone (75 mL) was added and the mixture was stirred at room temperature for 10 minutes. Water (50 mL) was added and the organic solvent was evaporated under reduced pressure. Saturated aqueous ammonium chloride (500 mL) was added and the mixture was extracted with ethyl acetate (2×500 mL). The combined organic fractions were washed with aqueous citric acid (10%, 500 mL), saturated aqueous sodium hydrogen carbonate (500 mL) and brine (200 mL), dried (Na$_2$SO$_4$) and the solvent was evaporated under reduced pressure to give the title compound (15.0 g, 88%). $^1$H NMR (400 MHz, CDCl$_3$) δ 4.31 (2H, t, J 7 Hz), 3.97–3.87 (2H, m), 3.17–3.07 (2H, m), 2.20 (2H, t, J 7 Hz), 1.92–1.82 (2H, m), 1.60–1.45 (2H, m), and 1.45 (9H, s).

DESCRIPTION 84

1,1-Dimethylethyl 4-(2-hydroxyethyl)-4-(hydroxymethyl)-1-piperidinecarboxylate

Diisobutylaluminium hydride (1.0M in dichloromethane, 3.60 mL, 3.60 mmol) was added over 10 minutes to a stirred, cooled (−78° C.) solution of 1,1-methylethyl 1-oxo-2-oxa-8-azaspiro[4.5]decane-8-carboxylate (Description 83, 400 mg, 1.57 mmol) in dichloromethane (4 mL) and the mixture stirred at −78° C. for 3 hours, then at 0° C. for 2 hours. Water (1.6 mL) was added very slowly at 0° C. and the mixture was warmed to room temperature and stirred overnight. The mixture was filtered through Hyflo™, washing with dichloromethane, and the solvent was evaporated under reduced pressure. The residue was purified by flash column chromatography on silica gel, eluting with ethyl acetate, to give the title compound (255 mg, 63%). m/z (ES$^+$) 260 (M+1).

DESCRIPTION 85

1,1-Dimethylethyl 2-Oxa-8-azaspiro[4.5]decane-8-carboxylate

Diethyl azodicarboxylate (183 μl, 1.16 mmol) in tetrahydrofuran (0.5 mL) was added dropwise to a stirred, cooled (0° C.) solution of 1,1-demethylethyl 4-(2-hydroxyethyl)-4-(hydroxymethyl)-1-piperidinecarboxylate (Description 84, 250 mg, 0.96 mmol) and triphenylphosphine (303 mg, 1.16 mmol) in tetrahydrofuran (10 mL) and the mixture was stirred at 0° C. for 90 minutes then at room temperature overnight. The mixture was cooled to 0° C. and further triphenylphosphine (126 mg, 0.48 mmol) and diethyl azodicarboxylate (76 μl, 0.48 mmol) were added. The mixture was stirred at room temperature for 2.5 hours, then the solvent was evaporated under reduced pressure and the residue was purified by flash column chromatography on silica gel, eluting with 4:1 isohexane:ethyl acetate, to give the title compound as a colorless oil (150 mg, 65%). m/z (ES$^+$) 186 (M+1-C$_4$H$_8$).

DESCRIPTION 86

2-Oxa-8-azaspiro[4.5]decane

Methanolic hydrogen chloride (3M, 3 mL) was added to a stirred, cooled (0° C.) solution of 1,1-dimethylethyl 2-oxa-8-azaspiro[4.5]decane-8-carboxylate (Description 85, 150 mg, 0.62 mmol) in methanol and the mixture was stirred at room temperature for 24 hours. The solvent was evaporated under reduced pressure and the residue was dissolved in methanol and passed through Amberlyst 26 ion exchange resin, eluting with methanol. The solvent was evaporated under reduced pressure and the residue was dissolved in dichloromethane, dried (Na$_2$SO$_4$) and the solvent was evaporated under reduced pressure to give the title compound (77 mg, 88%). m/z (ES$^+$) 142 (M+1).

DESCRIPTION 87

1,1-Dimethylethyl 4-(2-Hydroxyethyl)-4-(2-hydroxy-2-methylprop-1-yl)-1-piperidinecarboxylate Prepared from 1,1-dimethylethyl 1-oxo-2-oxa-8-azaspiro[4.5]decane-8-carboxylate (Description 83) according to the method of Description 80. m/z (ES$^+$) 288 (M+1).

DESCRIPTION 88

1,1-Dimethyl-2-oxa-8-azaspiro]4,5-decane

Prepared from 1,1-dimethylethyl 4-(2-hydroxyethyl)-4-(2-hydroxy-2-methylprop-1-yl)-1-piperidinecarboxylate (Description 87) according to the method of Description 81. m/z (ES$^+$) 170 (M+1).

DESCRIPTION 89

1-(1,1-Dimethylethyl) 4-Ethyl 4-(2-Methyl-2-propenyl)-1,4-piperidinedicarboxylate A solution of 1-(1,1-dimethylethyl) 4-ethyl 1,4-piperidinedicarboxylate (12.85 g, 50 mmol) in tetrahydrofuran (50 mL) was added slowly to a stirred, cooled (−78° C.) solution of potassium hexamethyldisilazide (14.96 g, 75 mmol) in tetrahydrofuran (75 mL), maintaining the internal temperature below −65° C. The mixture was stirred at −78° C. for 30 minutes, then 3-bromo-2-methylpropene (7.56 mL, 10.12 g, 75 mmol) was added dropwise over 5 minutes. The mixture was stirred at −78° C. for 1 hour, then saturated aqueous ammonium chloride (200 mL) was added and the mixture was warmed to room temperature. Water (100 mL) was added and the mixture was extracted with ethyl acetate (3×200 mL). The combined organic fractions were washed with aqueous citric acid (10%, 3×200 mL), saturated aqueous sodium hydrogen carbonate (200 mL) and brine (200 mL), dried (MgSO$_4$) and the solvent was evaporated under reduced pressure to give the title compound as a pale yellow oil (15.48 g, 99%). m/z (ES$^+$) 256 (M+1-C$_4$H$_8$).

DESCRIPTION 90

1-(1,1-Dimethylethyl) 4-(Hydroxymethyl)-4-(2-methyl-2-propenyl)-1-piperidinecarboxylate Lithium borohydride (0.44 g, 20 mmol) was added to a solution of 1-(1,1-dimethylethyl) 4-ethyl 4-(2-methyl-2-propenyl)-1,4-piperidinedicarboxylate (Description 89, 3.11 g, 10 mmol) in tetrahydrofuran and the mixture was stirred under reflux for 18 hours. The mixture was cooled, toluene (20 mL) and lithium borohydride (0.44 g, 20 mmol) were added and the mixture was stirred under reflux for 6 hours. The mixture was cooled and saturated aqueous ammonium chloride (20 mL) and water (50 mL) were added. The mixture was extracted with ethyl acetate (3×500 mL) and the combined organic fractions were washed with aqueous citric acid (10%, 50 mL), saturated aqueous sodium hydrogen carbonate (50 mL) and brine (50 mL), dried (MgSO$_4$) and the solvent was evaporated under reduced pressure. The residue was purified by flash column chromatography on silica gel, eluting with isohexane/EtOAc (70:30) to give the title compound as a colorless foam (1.81 g, 67%). $^1$H NMR (400 MHz, CDCl$_3$) shows two slowly equilibrating tautomers; major; δ 4.92 (1H, s), 4.77 (1H, s), 3.86–3.20 (10H, m), 2.14 (2H, s), 1.82 (3H, s), and 1.46 (9H, s); minor; δ 4.87 (1H, s), 4.66 (1H, s), 3.86–3.20 (10H, m), 2.11 (2H, s), 1.76 (3H, s), and 1.46 (9H, s). m/z (ES$^+$) 270 (M+1).

DESCRIPTION 91

3,3-Dimethyl-2-oxa-8-azaspiro[4.5]decane

Trifluoroacetic acid (20 mL) was added to a solution of 1-(1,1-dimethylethyl) 4-(hydroxymethyl)-4-(2-methyl-2-propenyl)-1-piperidinecarboxylate (Description 90, 1.14 g, 4.2 mmol) in dichloromethane (4 mL) and the mixture was stirred at room temperature for 2 hours. The solvent was evaporated under reduced pressure and water (40 mL) was added. The pH was adjusted to 12 with aqueous sodium hydroxide (4M) and the mixture was extracted with ethyl acetate (4×40 mL). The combined organic fractions were dried (MgSO$_4$) and the solvent was evaporated under reduced pressure. The residue was dissolved in ethanol (10 mL) and ethereal hydrogen chloride (1M, 10 mL) was added. The solvent was evaporated under reduced pressure and the residue was triturated with ethyl acetate (15 mL). The solid was collected and dried in vacuo to give the title compound as a colorless solid (483 mg, 56%). m/z (ES$^+$) 170 (M+1).

DESCRIPTION 92

3,3-Dimethyl-2-oxa-8-azaspiro[4.5]decan-1-one

Trifluoroacetic acid (50 mL) was added to a solution of 1-(1,1-dimethylethyl) 4-ethyl 4-(2-methyl-2-propenyl)-1,4-piperidinedicarboxylate (Description 89, 10.86 g, 35 mmol) in dichloromethane (10 mL) and the mixture was stirred at 50 C for 8 hours. The mixture was cooled and the solvent was evaporated under reduced pressure. Ether (50 mL) was added and the mixture was extracted with hydrochloric acid (1M, 3×50 mL). The combined aqueous fractions were washed with ether (2×50 mL), adjusted to pH 12 with aqueous sodium hydroxide (4M) and the mixture was extracted with ethyl acetate (6×50 mL). The combined organic fractions were dried (MgSO$_4$) and the solvent was evaporated under reduced pressure. The residue was dissolved in ethanol (50 mL), cooled in ice and and ethereal hydrogen chloride (1M, 35 mL) was added slowly. The solvent was evaporated under reduced pressure, ethanol (75 mL) was added and the mixture was heated under reflux for 15 minutes. The mixture was cooled and the solid was collected and dried in vacuo to give the title compound as a colorless solid (5.59 g, 73%), m.p.>280° C. m/z (ES$^+$) 184 (M+1).

DESCRIPTION 93

8-(Phenylmethyl)-2-oxa-8-azaspiro[4.5]decan-3-one

Borane-tetrahydrofuran complex (1.0M in tetrahydrofuran, 60 mL, 60 mmol) was added to a suspension of α-ethyl 4-carboxy-1-(phenylmethyl)-4-piperidineacetate hydrochloride (*Helv. Chim. Acta* 1972, 55, 2432–2438, 10.24 g, 30 mmol) in tetrahydrofuran (150 mL) and the mixture was stirred at room temperature for 3 days. Further borane-tetrahydrofuran complex (1.0M in tetrahydrofuran, 60 mL, 60 mmol) was added and the mixture was stirred at room temperature for 1 day. Methanol (20 mL) was added and the solvent was evaporated under reduced pressure. Methanol (200 mL) was added and the solvent was evaporated under reduced pressure. Methanol (200 mL) was added and the solvent was evaporated under reduced pressure. Hydrochloric acid (2M, 200 mL) was added and the mixture was heated under reflux for 4 hours. The mixture was cooled. Ether (200 mL) was added and the layers were separated. The organic layer was extracted with hydrochloric acid (2M, 2×100 mL) and the combined aqueous fractions were washed with ether (2×100 mL), adjusted to pH 10 with saturated aqueous potassium carbonate and extracted with dichloromethane (3×100 mL). The combined organic fractions were dried (MgSO$_4$) and the solvent was evaporated under reduced pressure. The residue was purified by flash column chromatography on silica gel, eluting with CH$_2$Cl$_2$/MeOH/NH$_3$ (aq.) (96:4:0.4), to give the title compound (3.4 g, 46%). m/z (ES$^+$) 246 (M+1).

DESCRIPTION 94

2-Oxa-8-azaspiro[4.5]decan-3-one Hydrochloride

Palladium on carbon (5%, 300 mg) was added to a solution of 8-(phenylmethyl)-2-oxa-8-azaspiro[4.5]decan-3-one (Description 93, 2.80 g, 11.4 mmol) in methanol/formic acid(10:1, 50 mL) and the mixture was stirred at room temperature for 20 hours. Further palladium on carbon (5%, 300 mg) and formic acid (5 mL) were added and the mixture was stirred at room temperature for 6 hours. Further palladium on carbon (5%, 300 mg) and formic acid (5 mL) were added and the mixture was stirred at room temperature for 66 hours. The mixture was filtered and the solvent was evaporated under reduced pressure. Portions of hydrochloric acid (1M, 2×200 mL) then ethanol (3×100 mL) were added and evaporated under reduced pressure. The residue was triturated with ethanol (50 mL) and refrigerated. The solid was collected and dried in vacuo to give to give the title compound as a colorless solid (2.09 g, 95%), m.p. 225–228° C. m/z (ES$^+$) 156 (M+1).

DESCRIPTION 95

1,1-Dimethylethyl 4-(Hydroxymethyl)-4-(phenyl-methoxymethyl)-1-piperidinecarboxylate Finely ground potassium hydroxide (248 mg, 44 mmol) was added to a stirred, cooled (10° C.) solution of 1,1-dimethylethyl 4,4-bis(hydroxymethyl)-1-piperidinecarboxylate (Description 67, 1.83 g, 7.4 mmol), 18-crown-6 (196 mg, 0.74 mmol) and benzyl bromide (884 µL, 7.4 mmol) in tetrahydrofuran (80 mL) and the mixture was stirred at room temperature for 16 hours. Brine (40 mL) was added and the layers were separated. The organic layer was dried (MgSO$_4$) and the solvent was evaporated under reduced pressure. The residue was purified by flash column chromatography on silica gel, eluting with isohexane/EtOAc (80:20 increasing to 50:50) to give the title compound (1.0 g, 40%). m/z (ES$^+$) 336 (M+1).

DESCRIPTION 96

1,1-Dimethylethyl 4-Ethenyl-4-(phenylmethoxymethyl)-1-piperidinecarboxylate 1,1,1-Tris(acetyloxy)-1,1-dihydro-1,2-benziodoxol-3(1H)-one (1.38 g, 3.3 mmol) was added to a solution of 1,1-dimethylethyl 4-(hydroxymethyl)-4-(phenylmethoxymethyl)-1-piperidinecarboxylate (Description 95, 1.06 g, 3 mmol) in dichloromethane (40 mL) and the mixture was stirred at room temperature for 4 hours. Aqueous sodium bisulfite (10%, 10 mL) was added and the mixture was stirred at room temperature for 5 minutes. Saturated aqueous sodium hydrogen carbonate (20 mL) was added and the layers were separated. The organic layer was dried (MgSO$_4$) and the solvent was evaporated under reduced pressure. The residue was dissolved in tetrahydrofuran (20 mL), and added to a stirred, cooled (0° C.) solution of triphenylphosphoranylidine (0.1M, 50 mL). The mixture was stirred at room temperature for 16 hours, then the solvent was evaporated under reduced pressure. Ethyl acetate (40 mL) and aqueous sodium hydrogen carbonate (10%, 40 mL) were added and the layers were separated. The organic layer was dried (MgSO$_4$) and the solvent was evaporated under reduced pressure. The residue was purified by flash column chromatography on silica gel, eluting with isohexane/EtOAc (75:25) give the title compound (1.01 g, 99%). m/z (ES$^+$) 332 (M+1).

DESCRIPTION 97

(RS)-1,1-Dimethylethyl 4-(1,2-Dihydroxyethyl)-4-(phenylmethoxymethyl)-1-piperidinecarboxylate Osmium tetroxide (2.5 wt % solution in tert-butanol, 240 mL) was added to a mixture of 1,1-dimethylethyl 4-ethenyl-4-(phenylmethoxymethyl)-1-piperidinecarboxylate (Description 96, 1.01 g, 3 mmol) and N-methylmorpholine-N-oxide (460 mg, 4 mmol) in water (4 mL) and tetrahydrofuran (12 mL). The mixture was stirred at room temperature for 24 hours then saturated aqueous sodium hydrogen sulphate (5 mL) was added. The mixture was extracted with ethyl acetate (2×15 mL), the combined organic fractions were dried (MgSO$_4$) and the solvent was evaporated under reduced pressure to give the title compound (1.05 g, 96%). m/z (ES$^+$) 366 (M+1).

DESCRIPTION 98

(RS)-1,1-Dimethylethyl 4-Hydroxymethyl-4-(1,2-dihydroxyethyl)-1-piperidinecarboxylate A slurry of palladium on carbon (10%, 100 mg) in ethanol (10 mL) was added to a solution of (RS)-1,1-dimethylethyl 4-(1,2-dihydroxyethyl)-4-(phenylmethoxymethyl)-1-piperidinecarboxylate (Description 97, 1.05 g, 2.9 mmol) in ethanol (30 mL) and the mixture was shaken under hydrogen (50 psi) for 72 hours. The mixture was filtered through Celite™ and the solvent was evaporated under reduced pressure to give the title compound as a pale oil (615 mg, 77%). m/z (ES$^+$) 276 (M+1).

DESCRIPTION 99

(RS)-4-Hydroxy-2-oxa-8-azaspiro[4.5]decane Hydrochloride

Methanesulfonyl chloride (173 µL, 2.2 mmol) in dichloromethane (100 mL) was added dropwise to a solution of (RS)-1,1-dimethylethyl 4-hydroxymethyl-4-(1,2-dihydroxyethyl)-1-piperidinecarboxylate (Description 98, 615 mg, 2.2 mmol) and triethylamine (933 µL, 6.6 mmol) in dichloromethane (150 mL) and the mixture was stirred at room temperature for 16 hours. Water (100 mL) was added and the layers were separated. The aqueous fraction was extracted with dichloromethane (2×100 mL), the combined organic fractions were dried (MgSO$_4$) and the solvent was evaporated under reduced pressure. The residue was purified by flash column chromatography on silica gel, eluting with isohexane/EtOAc (50:50) and the residue was suspended in diethyl ether (50 mL) and treated with methanolic hydrogen chloride (0.25M, 3 mL). The mixture was stirred at room temperature for 30 minutes, then the solvent was evaporated under reduced pressure to give the title compound as a solid (150 mg, 35%). m/z (ES$^+$) 158 (M+1).

DESCRIPTION 100

(RS)-1-(1,1-Dimethylethyl) 4-Ethyl 3-Oxo-1,4-piperidinedicarboxylate

Palladium hydroxide on carbon (20%, 2.9 g) and hydrochloric acid (2M, 50 mL) were added to a solution of (RS)-ethyl 3-oxo-1-(phenylmethyl)piperidinecarboxylate hydrochloride (25 g, 83.95 mmol) in ethanol (320 mL) and the mixture was shaken under hydrogen (50 psi) overnight. The mixture was filtered through a glass fibre pad and the solvent was evaporated under reduced pressure. Dichloromethane (200 mL), aqueous potassium carbonate (20%, 200 mL) and di-tert-butyl dicarbonate (25.65 g, 117.53 mmol) were added and the mixture was stirred at room temperature overnight. The layers were separated and N,N-dimethylethylenediamine (4.4 mL, 40 mmol) was added to the organic fraction. The mixture was stirred for at room temperature for 1 h, washed with aqueous citric acid (10%, 3×200 mL), water (2×200 mL) and brine, dried (MgSO$_4$) and the solvent was evaporated under reduced pressure to give the title compound (21.8 g, 93%). m/z (ES$^+$) 216 (M+1-C$_4$H$_8$).

DESCRIPTION 101

(RS)-1-1,1-Dimethylethyl) 4-Ethyl 3-Oxo-4-(2-propenyl)-1,4-piperidinedicarboxylate Sodium hydride (60% dispersion in mineral oil, 1.47 g, 36.9 mmol) was added to a stirred, cooled (0° C.) solution of (RS)-1-(1,1-dimethylethyl) 4-ethyl 3-oxo-1,4-piperidinedicarboxylate (Description 100, 29 g, 107 mmol) in dimethylformamide (100 mL) and the mixture was stirred at room temperature for 10 minutes. The mixture was cooled to (0° C.) and allyl bromide (4.68 mL, 55.3 mmol) was added slowly. The mixture was warmed to room temperature and stirred overnight. Water (100 mL) was added and the mixture was extracted with ethyl acetate (2×100 mL). The combined organic fractions were washed with water (4×100 mL) and brine, dried (Na$_2$SO$_4$) and the solvent was evaporated under reduced pressure to give the title compound (32.8 g, 98%). m/z ES$^+$ 256 (M+1-C$_4$H$_8$).

DESCRIPTION 102

Cis-(RS)- and Trans-(RS)-1-(1,1-Dimethylethyl) 4-Ethyl 3-Hydroxy-4-(2-propenyl)-1,4-piperidinedicarboxylate Sodium borohydride (4.05 g, 107 mmol) was added to a solution of (RS)-1-(1,1-dimethylethyl) 4-ethyl 3-oxo-4-(2-propenyl)-1,4-piperidinedicarboxylate (Description 101, 32.8 g, 105 mmol) in ethanol (300 mL) and the mixture was stirred at room temperature for 2 hours. Additional sodium borohydride (2 g, 53 mmol) was added and the mixture was stirred at room temperature overnight. Saturated aqueous ammonium chloride (100 mL) was added and the mixture was basified with aqueous sodium carbonate (10%). The mixture was extracted with ethyl acetate (2×350 mL) and the combined organic fractions were washed with brine, dried (Na$_2$SO$_4$) and the solvent was evaporated under reduced pressure. The residue was purified by flash column chromatography on silica gel, eluting with isohexane:EtOAc (80:20), to give the title compound as a mixture of cis- and trans-isomers (6.1 g, 18%). m/z ES$^+$ 258 (M+1-C$_4$H$_8$).

DESCRIPTION 103

Cis-(RS)-1-(1,1-Dimethylethyl) 4-Ethyl 3-(Phenylmethoxy)-4-(2-propenyl)-1,4-piperidinedicarboxylate and Trans-(RS)-1-(1,1-Dimethylethyl) 4-Ethyl 3-(Phenylmethoxy)-4-(2-propenyl)-1,4-piperidinedicarboxylate Sodium hydride (919 mg, 23 mmol) was added to a solution of cis-(RS)- and trans-(RS)-1-(1,1-dimethylethyl) 4-ethyl 3-hydroxy-4-(2-propenyl)-1,4-piperidinedicarboxylate (Description 102, 6.0 g, 19.1 mmol) in dimethylformamide (50 mL) and the mixture was stirred at room temperature for 5 minutes. Benzyl bromide (2.73 mL, 23 mmol) was added and the mixture was stirred at room temperature overnight. Water (50 mL) was added and the mixture was extracted with ethyl acetate (2×50 mL). The combined organic fractions were washed with water (3×50 mL) and brine, dried (MgSO$_4$) and the solvent was evaporated under reduced pressure. The residue was purified by flash column chromatography on silica gel, eluting with 9:1 isohexane:ethyl acetate. The residue was purified by MPLC on silica gel, eluting with isohexane/ethyl acetate (90:10), to give trans-(RS)-1-(1,1-dimethylethyl) 4-ethyl 3-(phenylmethoxy)-4-(2-propenyl)-1,4-piperidinedicarboxylate; $^1$H NMR (400 MHz, DMSO-d$_6$) δ 7.38–7.24 (5H, m), 5.67–5.56 (1H, m), 5.00 (1H, d, J 1.8, Hz), 4.97 (1H, d, J 8.8 Hz), 4.72–4.68 (1H, m), 4.40 (1H, d, J 11.4 Hz), 4.23 (1H, d, J 14.0 Hz), 4.12 (2H, q, J 7 Hz), 3.84 (1H, d, J 13.1 Hz), 3.75 (1H, d, J 2.5 Hz), 2.86 (1, d, J 14.4 Hz), 2.74 (1H, m), 2.46–2.41 (1H, m), 2.26–2.21 (1H, m), 1.80 (1H, d, J 13.4 Hz), 1.59 (1H, dt, J 4.5, 12.8 Hz), 1.35 (9H, s), and 1.19 (3H, t, J 7 Hz); m/z (ES$^+$) 404 (M+1); and cis-(RS)-1-(1,1-dimethylethyl) 4-ethyl 3-(phenylmethoxy)-4-(2-propenyl)-1,4-piperidinedicarboxylate; $^1$H NMR (400 MHz, DMSO-d$_6$) δ 7.33–7.21 (5H, m), 5.64–5.53 (1H, m), 5.11–4.98 (2H, m), 4.63–4.58 (1H, m), 4.32 (1H, d, J 11.3 Hz), 4.18 (1H, d, J 14.0 Hz), 4.09–395 (2H, m), 3.84 (1H, d, J 13.4 Hz), 3.58 (1H, s), 3.05 (1H, d, J 14.5 Hz), 2.91 (1H, m), 2.56–2.49 (1H, m), 2.35–2.29 (1H, m), 1.93 (1H, dt, J 4.8, 13.5 Hz), 1.47 (1H, d, J 14.1 Hz), 1.34 (9H, s), and 1.12 (3H, t, J 7 Hz); m/z (ES$^+$) 348 (M+1-C$_4$H$_8$).

DESCRIPTION 104

Trans-(RS)-1,1-Dimethylethyl 6-(Phenylmethoxy)-1-oxo-2-oxa-8-azaspiro[4.5]decane-8-carboxylate Prepared from trans-(RS)-1-(1,1-dimethylethyl) 4-ethyl 3-phenylmethoxy)-4-(2-propenyl)-1,4-piperidinedicarboxylate (Description 103) according to the method of Description 124. m/z (ES$^+$) 362 (M+1).

DESCRIPTION 105

Trans-(RS)-1,1-Dimethylethyl 6-Hydroxy-1-oxo-2-oxa-8-azaspiro[4,5]-decane-8-carboxylate Prepared from trans-(RS)-1,1-dimethylethyl 6-(phenylmethoxy)-1-oxo-2-oxa-8-azaspiro[4.5]decane-8-carboxylate (Description 104) according to the method of Description 98. m/z (ES$^+$) 272 (M+1)

DESCRIPTION 106

Trans-(RS)-6-Hydroxy-2-oxa-8-azaspiro[4.5]decan-1-one Hydrochloride

Prepared from trans-(RS)-1,1-dimethylethyl 6-hydroxy-1-oxo-2-oxa-8-azaspiro[4.5]decane-8-carboxylate (Description 105) according to the method of Description 75. m/z (ES$^+$) 172 (M+1).

DESCRIPTION 107

Cis-(RS)-1,1-Dimethylethyl 6-(Phenylmethoxy)-1-oxo-2-oxa-8-azaspiro[4.5]decane-8-carboxylate Prepared from cis-(RS)-1-(1,1-dimethylethyl) 4-ethyl 3-(phenylmethoxy)-4-(2-propenyl)-1,4-piperidinedicarboxylate (Description 103) according to the method of Description 124. m/z (ES$^+$) 328 (M+1-C$_4$H$_8$).

DESCRIPTION 108

Cis-(RS)-1,1-Dimethylethyl 6-Hydroxy-1-oxo-2-oxa-8-azaspiro[4.5]decane-8-carboxylate Prepared from cis-(RS)-1,1-dimethylethyl 6-(phenylmethoxy)-1-oxo-2-oxa-8-azaspiro[4.5]decane-8-carboxylate (Description 107) according to the method of Description 98. $^1$H NMR (400 MHz, DMSO-$d_6$) δ 5.41 (1H, d, J 4.5 Hz), 4.25–4.15 (2H, m), 3.78 (1H, dd, J 12, 5 Hz), 3.65 (1H, br d, J 13 Hz), 3.50–3.42 (1H, m), 3.28–3.05 (2H, m), 2.45–2.35 (1H, m), 2.00 (1H, dt, J 13, 8 Hz), 1.85 (1H, dt, J 14, 3 Hz), 1.50 (1H, dt, J 14, 5 Hz), and 1.40 (9H, s).

DESCRIPTION 109

Cis-(RS)-6-Hydroxy-2-oxa-8-azaspiro[4.5]decan-1-one Hydrochloride

Prepared from cis-(RS)-1,1-dimethylethyl 6-hydroxy-1-oxo-2-oxa-8-azaspiro[4.5]decane-8-carboxylate (Description 108) according to the method of Description 75. m/z (ES$^+$) 172 (M+1).

DESCRIPTION 110

Trans-(RS)-1,1-Dimethylethyl 4-(2-Hydroxyethyl)-4-(hydroxymethyl)-3-(phenylmethoxy)-1-piperidinecarboxylate Prepared from trans-(RS)-1,1-dimethylethyl 6-(phenylmethoxy)-1-oxo-2-oxa-8-azaspiro[4.5]decane-8-carboxylate (Description 104) according to the method of Description 114. m/z (ES$^+$) 366 (M+1).

DESCRIPTION 111

Trans-(RS)-1,1-Dimethylethyl 6-(Phenylmethoxy)-2-oxa-8-azaspiro[4.5]decane-8-carboxylate Prepared from trans-(RS)-1,1-dimethylethyl 4-(2-hydroxyethyl)-4-(hydroxymethyl)-3-(phenylmethoxy)-1-piperidinecarboxylate (Description 110) according to the method of Description 115. m/z (ES$^+$) 292 (M+1-$C_4H_8$).

DESCRIPTION 112

Trans-(RS)-1,1-Dimethylethyl 6-Hydroxy-2-oxa-8-azaspiro[4.5]decane-8-carboxylate Prepared from trans-(RS)-1,1-dimethylethyl 6-(phenylmethoxy)-2-oxa-8-azaspiro[4.5]decane-8-carboxylate (Description 111) according to the method of Description 116. m/z (ES$^+$) 202 (M+1-$C_4H_8$).

DESCRIPTION 113

Trans-(RS)-2-Oxa-8-azaspiro[4.5]decan-6-ol Hydrochloride

Prepared from trans-(RS)-1,1-dimethylethyl 6-hydroxy-2-oxa-8-azaspiro[4.5]decane-8-carboxylate (Description 112) according to the method of Description 75. m/z (ES$^+$) 158 (M+1).

DESCRIPTION 114

Cis-(RS)-1,1-Dimethylethyl 4-(2-Hydroxyethyl)-4-(hydroxymethyl)-3-(phenylmethoxy)-1-piperidinecarboxylate Lithium borohydride (523 mg, 24.0 mmol) was added to a solution of cis-(RS)-1,1-dimethylethyl 6-(phenylmethoxy)-1-oxo-2-oxa-8-azaspiro[4.5]decane-8-carboxylate (Description 107, 2.9 g, 8.0 mmol) in tetrahydrofuran/toluene (3:1, 40 mL) and the mixture was stirred at 50° C. overnight. Further lithium borohydride (261 mg, 12 mmol) was added and the mixture was stirred at 50° C. for 5 hours. The mixture was cooled, acidified with hydrochloric acid (1M) and extracted with ethyl acetate (2×100 mL). The combined organic fractions were washed with brine, dried ($Na_2SO_4$) and the solvent was evaporated under reduced pressure. The residue was purified by flash column chromatography on silica gel, eluting with 1:3 isohexane:ethyl acetate, to give the title compound (2.5 g, 85%). m/z (ES$^+$) 310 (M+1-$C_4H_8$).

DESCRIPTION 115

Cis-(RS)-1,1-Dimethylethyl 6-(Phenylmethoxy)-2-oxa-8-azaspiro[4.5]decane-8-carboxylate A solution of methanesulphonyl chloride (514 μl, 6.62 mmol) in dichloromethane (150 mL) was added over 30 minutes to a solution of cis-(RS)-1,1-dimethylethyl 4-(2-hydroxyethyl)-4-(hydroxymethyl)-3-(phenylmethoxy)-1-piperidinecarboxylate (Description 114, 2.42 g, 6.62 mmol) and pyridine (1.61 mL, 19.86 mmol) in dichloromethane (150 mL) and the mixture was stirred at room temperature overnight. Further batches of of methanesulphonyl chloride (514 μl, 6.62 mmol) and pyridine (1.61 mL, 19.86 mmol) were added at two-hourly intervals until all the starting material was consumed by TLC. The mixture was washed with aqueous citric acid (10%, 300 mL), aqueous sodium hydroxide (1M, 300 mL) and brine, dried ($Na_2SO_4$) and the solvent was evaporated under reduced pressure. The residue was purified by flash column chromatography on silica gel, eluting with 4:1 isohexane:ethyl acetate, to give the title compound (1.47 g, 64%). m/z (ES$^+$) 191 (M+1-$C_4H_8$).

DESCRIPTION 11

Cis-(RS)-1,1-Dimethylethyl 6-Hydroxy-2-oxa-8-azaspiro[4.5]decane-8-carboxylate

Palladium on carbon (5%, 500 mg) was added to a solution of cis-(RS)-1,1-dimethylethyl 6-(phenylmethoxy)-2-oxa-8-azaspiro[4.5]decane-8-carboxylate (Description 115, 1.47 g, 4.23 mmol) and acetic acid (2.5 mL) in methanol (50 mL) and the mixture was shaken under hydrogen (50 psi) overnight. The mixture was filtered through a glass fibre pad and the solvent was evaporated under reduced pressure to give the title compound (1.03 g, 95%). m/z (ES$^+$) 202 (M+1-$C_4H_8$).

DESCRIPTION 117

Cis-(RS)-2-Oxa-8-azaspiro[4.5]decan-6-ol Hydrochloride

Prepared from cis-(RS)-1,1-dimethylethyl 6-hydroxy-2-oxa-8-azaspiro[4.5]decane-8-carboxylate (Description 116) according to the method of Description 75. m/z (ES$^+$) 158 (M+1).

DESCRIPTION 118

Trans-(RS)-1,1-Dimethylethyl 6-Fluoro-1-oxo-2-oxa-8-azaspiro[4.5]decane-8-carboxylate (Diethylamino)sulphur trifluoride (772 μl, 5.9 mmol) was added slowly to a stirred, cooled (−40° C.) solution of cis-(RS)-1,1-dimethylethyl 6-hydroxy-1-oxo-2-oxa-8-azaspiro[4,5]decane-8-carboxylate (Description 108, 200 mg, 0.74 mmol) in dichloromethane (20 mL) and the mixture was stirred at −40° C. for 3 h and at room temperature overnight. Water (50 mL) and dichloromethane (30 mL) were added and the layers were separated. The organic fraction was washed with brine, dried (Na$_2$SO$_4$) and the solvent was evaporated under reduced pressure to give crude title compound (225 mg,). m/z (ES$^+$) 218 (M+1-C$_4$H$_8$).

DESCRIPTION 119

Trans-(RS)-6-Fluoro-2-oxa-8-azaspiro[4.5]decan-1-one Hydrochloride

Prepared from trans-(RS)-1,1-dimethylethyl 6-fluoro-1-oxo-2-oxa-8-azaspiro[4.5]decane-8-carboxylate (Description 118) according to the method of Description 75. m/z (ESP) 174 (M+1).

DESCRIPTION 120

Trans-(RS)-1,1-Dimethylethyl 2-Oxa-6-oxo-8-azaspiro[4.5]decane-8-carboxylate 1,1,1-Tris(acetyloxy)-1,1-dihydro-1,2-benziodoxol-3(1H)-one (758 mg, 1.79 mmol) was added to a solution of trans-(RS)-1,1-dimethylethyl 6-hydroxy-2-oxa-8-azaspiro[4.5]decane-8-carboxylate (Description 112, 230 mg, 0.89 mmol) in dichloromethane (10 mL) and the mixture was stirred at room temperature for 1 hour. Aqueous sodium bisufite (10%, 15 mL) and saturated aqueous sodium hydrogen carbonate (15 mL) were added and the mixture was stirred at room temperature for 20 minutes. The mixture was extracted with dichloromethane (2×15 mL) and the combined organic fractions were washed with brine, dried (Na$_2$SO$_4$) and the solvent was evaporated under reduced pressure to give the title compound (230 mg, 100%). m/z (ES$^+$) 200 (M+1-C$_4$H$_8$).

DESCRIPTION 121

Trans-(RS)-1,1-Dimethylethyl 6,6-Difluoro-2-oxa-8-azaspiro[4.5]decane-8-carboxylate (Diethylamino)sulphur trifluoride (436 μl, 3.56 mmol) was added to a stirred, cooled (−40° C.) solution of trans-(RS)-1,1-dimethylethyl 2-oxa-4-oxa-8-azaspiro[4.5]decane-8-carboxylate (Description 120, 230 mg, 0.89 mol) in dichloromethane (10 mL) and the mixture was stirred at −40° C. for 2 h then at room temperature for 2 hours. Water (20 mL) was added carefully and the mixture was extracted with dichloromethane (2×20 mL). The combined organic fractions were washed with brine, dried (Na$_2$SO$_4$) and the solvent was evaporated under reduced pressure. The residue was purified by flash column chromatography on silica gel, eluting with 4:1 isohexane:ethyl acetate, to give the title compound (46 mg, 19%). $^1$H NMR (400 MHz, CDCl$_3$) δ 3.99 (1H, d, J 10 Hz), 3.93–3.83 (2H, m), 3.75–3.64 (1H, m), 3.59 (1H, d, J 10 Hz), 3.58–3.50 (2H, m), 3.4–3.3 (1H, m), 2.23–2.15 (1H, m), 1.8–1.65 (2H, m), and 1.47 (10H, s).

DESCRIPTION 122

(RS)-6,6-Difluoro-2-oxa-8-azaspiro[4.5]decane

Prepared from trans-(RS)-1,1-dimethylethyl 6,6-difluoro-2-oxa-8-azaspiro[4.5]decane-8-carboxylate (Description 121) according to the method of Description 193. m/z (ES$^+$) 178 (M+1).

DESCRIPTION 123

(RS)-1-(1,1-Dimethylethyl) 3-Ethyl 3-(2-Propenyl)-1,3-piperidinedicarboxylate 1-(1,1-Dimethylethyl) 3-ethyl 1,3-piperidinedicarboxylate (12.85 g, 50 mmol) in tetrahydrofuran (50 mL) was added slowly to a stirred, cooled (−78° C.) solution of potassium hexamethyldisilazide (14.96 g, 75 mmol) in tetrahydrofuran (75 mL). The mixture was stirred at −78° C. for 30 minutes, then 3-bromo-1-propene (6.49 mL, 9.07 g, 75 mmol) was added dropwise over 5 minutes. The mixture was stirred at −78° C. for 1 hour, then saturated aqueous ammonium chloride (200 mL) and water (100 mL) were added. The mixture was allowed to warm to room temperature and extracted with ethyl acetate (3×200 mL). The combined organic fractions were washed with aqueous citric acid (10%, 3×200 mL), saturated aqueous sodium hydrogen carbonate (200 mL) and brine (200 mL), dried (MgSO$_4$) and the solvent was evaporated under reduced pressure to give to give the title compound as a pale yellow oil (13.46 g, 91%). m/z (ES$^+$) 298 (M+1).

DESCRIPTION 124

(RS)-1,1-Dimethylethyl 2-Oxa-1-oxo-7-azaspiro[4.5]decan-7-carboxylate (RS)-1-(1,1-Dimethylethyl) 3-ethyl 3-(2-propenyl)-1,3-piperidinedicarboxylate (Description 123, 13.46 g, 45 mmol) was dissolved in methanol (200 mL) and dichloromethane (320 mL) and cooled to −78° C. Oxygen was bubbled through the solution for 10 minutes, then ozone for 75 minutes, to give a persistan blue coloration. Oxygen was bubbled through the solution for 10 minutes, then nitrogen for 10 minutes. Sodium borohydride (3.43 g, 90 mmol) was added and the mixture was stirred at −78° C. for 1 hour. Further sodium borohydride (3.43 g, 90 mmol) was added and the mixture was stirred at 0–5° C. for 1 hour. Acetone (50 mL) was added and the mixture was stirred at room temperature for 1 hour. Saturated aqueous ammonium chloride (200 mL) was added and the organic solvent was evaporated under reduced pressure. Water (100 mL) was added and the mixture was extracted with ethyl acetate (3×200 mL). The combined organic fractions were washed with aqueous citric acid (10%, 200 mL), saturated aqueous sodium hydrogen carbonate (200 mL) and brine (200 mL), dried (MgSO$_4$) and the solvent was evaporated under reduced pressure. The residue was recrystallised from hexane/EtOAc (96:4, 50 mL) and the solid was collected and dried in vacuo to give the title compound as a colorless solid (9.20 g, 80%). m/z (ES$^+$) 199 (M+1-C$_4$H$_8$).

DESCRIPTION 125

(RS)-2-Oxa-7-azaspiro[4.5]decan-1-one Hydrochloride

Trifluoroacetic acid (50 mL) was added to a solution of (RS)-1,1-dimethylethyl 2-oxa-1-oxo-7-azaspiro[4.5]decan-7-carboxylate (Description 124, 7.67 g, 30 mmol) in dichloromethane (10 mL) and the mixture was stirred at room temperature for 4 hours. The solvent was evaporated under reduced pressure, ether (40 mL) was added and the mixture was extracted with hydrochloric acid (1M, 3×40 mL). The combined aqueous fractions were washed with ether (2×40 mL), adjusted to pH 12.0 with saturated aqueous potassium carbonate and extracted with dichloromethane (10×50 mL). The combined organic fractions were dried (MgSO$_4$) and the solvent was evaporated under reduced pressure. The residue was dissolved in ethanol (30 mL) and ethereal hydrogen chloride (1M, 30 mL) was added. The mixture was refrigerated and the solid was collected and dried in vacuo. The residue was suspended in propan-2-ol (50 mL) and the mixture was heated under reflux for 15 minutes. The mixture was cooled and the solid was collected and dried in vacuo at 40° C. to give the title compound as a cream solid (3.09 g, 54%), m.p. 197–200° C. m/z (ES$^+$) 156 (M+1).

DESCRIPTION 126

(RS)-1,1-Dimethylethyl 3-(2-Hydroxyethyl)-3-(hydroxymethyl)-1-piperidinecarboxylate Prepared from (RS)-1,1-dimethylethyl 2-oxa-1-oxo-7-azaspiro[4.5]decane-7-carboxylate (Description 124) according to the method of Description 84. m/z (ES$^+$) 160 (M+1).

DESCRIPTION 127

(RS)-1,1-Dimethylethyl 2-Oxa-7-azaspiro[4.5]decane-7-carboxylate

Methanesulfonyl chloride (0.295 mL, 382 mmol) was added to a stirred, cooled (0° C.) solution of (RS)-1,1-dimethylethyl 3-(2-hydroxyethyl)-3-hydroxymethyl)-1-piperidinecarboxylate (Description 126, 989 mg, 3.82 mmol) and pyridine (0.925 mL, 11.4 mmol) in dichloromethane (10 mL) and the mixture was stirred at room temperature for 2 hours. Aqueous citric acid (10%, 50 mL) was added and the mixture was extracted with dichloromethane (3×30 mL). The combined organic fractions were dried (Na$_2$SO$_4$), the solvent was evaporated under reduced pressure and the residue was purified by flash column chromatography on silica gel, eluting with isohexane/EtOAc (90:10), to give the title compound (315 mg, 34%). $^1$H NMR (360 MHz, CDCl$_3$) δ 3.85–3.70 (2H, m), 3.60 (1H, d, J 10 Hz), 3.55–3.35 (3H, m), 3.31–3.23 (1H, m), 3.18 (1H, d, J 14 Hz), 1.85–1.75 (1H, m), 1.65–1.50 (5H, m), and 1.45 (9H, s).

DESCRIPTION 128

(RS)-2-Oxa-7-azaspiro[4.5]decane Hydrochloride

Prepared from (RS)-1,1-dimethylethyl 2-oxa-7-azaspiro[4.5]decane-7-carboxylate (Description 127) according to the method of Description 75. m/z (ES$^+$) 142 (M+1).

DESCRIPTION 129

1,1-Dimethylethyl 4-Hydroxy-4-(2-propenyl)-1-piperidinecarboxylate

Prepared from 1,1-dimethylethyl 4-oxo-1-piperidinecarboxylate according to the method of Description 51, substituting allyl magnesium chloride for ethyl magnesium bromide. m/z (ES$^+$) 186 (M+1-C$_4$H$_8$).

DESCRIPTION 130

1,1-Dimethylethyl 4-(2-Propenyl)-4-(2-propenyloxy)-1-piperidinecarboxylate

Sodium hydride (60% dispersion in mineral oil, 12 g, 0.3 mol) was added slowly to a stirred, cooled (0° C.) solution of 1,1-dimethylethyl 4-hydroxy-4-(2-propenyl)-1-piperidinecarboxylate (Description 129, 23.1 g, 0.096 mol) in dimethylformamide (200 mL) and the mixture was stirred at 0° C. for 10 minutes. Allyl bromide (25.4 ml, 0.3 mol) was added and the mixture was stirred at 0° C. for 5 minutes, then at room temperature for 45 minutes. The mixture was cooled to 0° C. and water (200 mL) was added. The mixture was extracted with diethyl ether (2×200 mL) and the combined organic fractions were washed with water (4×200 mL) and brine (150 mL), dried (MgSO$_4$) and the solvent was evaporated under reduced pressure. The residue was purified by flash column chromatography on silica gel, eluting with isohexane/EtOAc (9:1), to give the title compound (5.5 g, 20%). m/z (E) 226 (M+1-C$_4$H$_8$).

DESCRIPTION 131

1,1-Dimethylethyl 1-Oxa-9-azaspiro[5.5]undec-3-en-9-carboxylate

Solutions of 1,1-dimethylethyl 4-(2-propenyl)-4-(2-propenyloxy)-1-piperidinecarboxylate (Description 130, 4.9 g, 17.4 mmol) in dichloromethane (1.2 L) and bis(tricyclohexylphosphine)benzylidine ruthenium (IV) dichloride (717 mg, 0.87 mmol) in dichloromethane (1.2 L) were added dropwise simultaneously to dichloromethane (600 mL) over a period of 8 hours, and the mixture was stirred at room temperature overnight. The solvent was evaporated under reduced pressure and the residue was purified by flash column chromatography on silica gel, eluting with 9:1 isohexane:ethyl acetate, to give the title compound (3.3 g, 75%). m/z (ES$^+$) 254 (M+1).

DESCRIPTION 132

1-Oxa-9-azaspiro[5.5]undec-3-ene

Prepared from 1,1-dimethylethyl 1-oxa-9-azaspiro[5.5]undec-3-en-9-carboxylate (Description 131) according to the method of Description 193. m/z (ES$^+$) 154 (M+1).

DESCRIPTION 133

(RS)-1,1-Dimethylethyl 3-Hydroxy-1-oxa-9-azaspiro[5.5]undecane-9-carboxylate and (RS)-1,1-Dimethylethyl 4-Hydroxy-1-oxa-9-azaspiro[5.5]undecane-9-carboxylate Borane tetrahydrofuran complex (1M in tetrahydrofuran, 23.68 mL, 23.68 mmol) was added dropwise to a solution of 1,1-dimethylethyl 1-oxa-9-azaspiro[5.5]undec-3-en-9-carboxylate (Description 131, 2.0 g, 7.89 mmol) in tetrahydrofuran (30 mL) and the mixture was stirred at room temperature for 6.5 hours. Water (25 mL), aqueous sodium hydroxide (4M, 25 mL) and hydrogen peroxide (37%, 25 mL) were added and the mixture was stirred at room temperature for 20 minutes. Water (100 mL) and diethyl ether (100 mL) were added and the layers were separated. The aqueous fraction was extracted with diethyl ether (100 mL) and the combined organic fractions were washed with brine, dried (MgSO$_4$) and the solvent was evaporated under reduced pressure. The residue was purified by flash column chromatography on silica gel, eluting with ethyl acetate. The residue was purified by MPLC on silica gel, eluting with ethyl acetate, to give 1,1-dimethylethyl 3-hydroxy-1-oxa-9-azaspiro[5.5]undecane-9-carboxylate (520 mg, 24%); $^1$H NMR (360 MHz, CDCl$_3$) δ 3.76–3.71 (4H, m), 3.50–3.45 (1H, m), 3.16–3.07 (2H, m), 1.92–1.85 (3H, m), 1.75–1.63 (2H, m), 1.46 (9H, s), and 1.45–1.35 (3H, m); and 1,1-dimethylethyl 4-hydroxy-1-oxa-9-azaspiro[5.5]undecane-9-carboxylate (200 mg, 9%);. $^1$H NMR (400 MHz, CDCl$_3$) δ 4.02–3.93 (1H, m), 3.87–3.83 (1H, m), 3.75–3.71 (2H, m), 3.57 (1H, dt, J 2.3, 11.7 Hz), 3.19 (1H, t, J 11.3 Hz), 3.03 (1H, t, J 11.7 Hz), 1.95–1.87 (2H, m), 1.86–1.81 (1H, m), 1.68–1.65 (1H, m), 1.57–1.47 (2H, m), 1.45 (9H, s), and 1.41–1.28 (2H, m).

DESCRIPTION 134

(RS)-1-Oxa-9-azaspiro[5.5]undecan-3-ol

Prepared from of 1,1-dimethylethyl 3-hydroxy-1-oxa-9-azaspiro[5.5]undecane-9-carboxylate (Description 133) according to the method of Description 193. m/z (ES$^+$) 172 (M+1).

DESCRIPTION 135

1-(1,1-Dimethylethyl) 4-Phenylmethyl 4-(3-Butenyl)-1,4-piperidinedicarboxylate Lithium hexamethyldisilazide (1M in tetrahydrofuran, 15.7 mL, 15.7 mmol) was added dropwise to a stirred, cooled (−78° C.) solution of 1-(1,1-dimethylethyl) 4-phenylmethyl 1,4-piperidinedicarboxylate (2.50 g, 7.83 mmol) in tetrahydrofuran (50 mL) and the mixture was stirred at −78° C. for 2 hours. 4-Bromo-1-butene (1.99 mL, 19.6 mmol) was added dropwise and the mixture was stirred at −78° C. for 1 hour, then at room temperature for 2 hours. Water (100 mL) was added and the mixture was extracted with ethyl acetate (2×100 mL). The combined organic fractions were dried (MgSO$_4$) and the solvent was evaporated under reduced pressure. The residue was purified by flash column chromatography on silica gel, eluting with isohexane/EtOAc (90:10) to give the title compound (1.07 g, 37%). $^1$H NMR (400 MHz CDCl$_3$) δ 7.4–7.3 (5H, m), 5.75–5.6 (1H, m), 5.15 (2H, s), 4.93 (1H, br d, J 7 Hz), 4.90 (1H, br s), 3.95–3.75 (2H, m), 2.93–2.78 (2H, m), 2.13 (2H, br d, J 10 Hz), 1.95–1.85 (2H, m), 1.65–1.55 (2H, m), 1.44 (9H, s), and 1.43–1.30 (2H, m).

DESCRIPTION 136

1-(1,1-Dimethylethyl) 4-Phenylmethyl 4-(3-Hydroxypropyl)-1,4-piperidinedicarboxylate A solution of 1-(1,1-dimethylethyl) 4-phenylmethyl 4-(3-butenyl)-1,4-piperidinedicarboxylate (Description 135, 1.06 g, 2.84 mmol) in dichloromethane/methanol (50:50, 20 mL) was cooled to −78° C. and oxygen was bubbled through the mixture for 10 minutes. Ozone was bubbled through the mixture until a blue coloration persisted. Oxygen was bubbled through the mixture for 10 minutes, then nitrogen for 10 minutes. Sodium borohydride (1.1 g, 28.9 mmol) was added over 5 minutes and the mixture was allowed to warm to room temperature. The solvent was evaporated under reduced pressure and water (40 mL) was added. The mixture was extracted with ethyl acetate (3×40 mL), the combined organic fractions were dried (Na$_2$SO$_4$) and the solvent was evaporated under reduced pressure to give the title compound (1.06 g, 99%). $^1$H NMR (400 MHz, CDCl$_3$) δ 7.4–7.3 (5H, m), 5.15 (2H, s), 3.95–3.75 (2H, m), 3.52 (2H, t, J 7 Hz), 2.95–2.80 (2H, m), 2.12 (2H, br d, J 10 Hz), 1.65–1.30 (7H, m), and 1.44 (9H, s).

DESCRIPTION 137

1,1-Dimethylethyl 4-(Hydroxymethyl)-4-(3-hydroxypropyl)-1-piperidinecarboxylate Lithium borohydride (500 mg, 22.7 mmol) was added to a solution of 1-(1,1-dimethylethyl) 4-phenylmethyl 4-(3-hydroxypropyl)-1,4-piperidinedicarboxylate (Description 136, 1.05 g, 2.79 mmol) in tetrahydrofuran/toluene (50:50, 20 mL). and the mixture was stirred at 60° C. for 4 hours. The mixture was cooled and hydrochloric acid (2M, 10 mL) was added. The mixture was poured into aqueous sodium carbonate (10%, 100 mL) and extracted with ethyl acetate (3×50 mL). The combined organic fractions were dried (Na$_2$SO$_4$) and the solvent was evaporated under reduced pressure. The residue was purified by flash column chromatography on silica gel, eluting with EtOAc/MeOH (100:0 increasing to 95:5) to give the title compound (563 mg, 74%). $^1$H NMR (400 MHz, CDCl$_3$) δ 3.67 (2H, t, J 7 Hz), 3.48 (2H, s), 3.47–3.40 (2H, m), 3.35–3.25 (2H, m), 1.7 (2H, br s), 1.6–1.3 (8H, m), and 1.44 (9H, s).

DESCRIPTION 138

1,1-Dimethylethyl 2-Oxa-9-azaspiro[5.5]undecane-9-carboxylate

Diethyl diazenedicarboxylate (390 μL, 2.46 mmol) was added to a solution of 1,1-dimethylethyl 4-(hydroxymethyl)-

4-(3-hydroxypropyl)-1-piperidinecarboxylate (Description 137, 560 mg, 2.05 mmol) and triphenylphosphine (646 mg, 2.46 mmol) in tetrahydrofuran (10 mL) and the mixture was stirred at room temperature for 24 hours. Further triphenylphosphine (646 mg, 2.46 mmol) and diethyl diazenedicarboxylate (390 µL, 2.46 mmol) were added and the mixture was stirred at room temperature for 24 hours. Methanol (5 mL) was added and the solvent was evaporated under reduced pressure. The residue was purified by flash column chromatography on silica gel, eluting with isohexane/EtOAc (75:25), to give the title compound (78 mg, 15%). m/z (ES$^+$) 256 (M+1).

DESCRIPTION 139

2-Oxa-9-azaspiro[5.5]undecane

Acetyl chloride (1 mL) was added to stirred, cooled (0° C.) methanol (10 mL) and the mixture was stirred at 0° C. for 5 minutes. 1,1-Dimethylethyl 2-oxa-9-azaspiro[5.5]undecane-9-carboxylate (Description 138, 78 mg, 0.27 mmol) was added and the mixture was stirred at room temperature for 3 hours. The solvent was evaporated under reduced pressure, aqueous sodium carbonate (10%, 10 mL) was added and the mixture was extracted with dichloromethane (3×10 mL). The combined organic fractions were dried (Na$_2$SO$_4$) and the solvent was evaporated under reduced pressure to give the title compound (50 mg, 100%). m/z (ES$^+$) 156 (M+1).

DESCRIPTION 140

Phenylmethyl 4-[(1-Methyl-1H-1,2,4-triazol-5-yl)methyl]-3-oxo-1-piperazinecarboxylate Sodium hydride (60% dispersion in mineral oil, 281 mg, 7.0 mmol) was added to a solution of phenylmethyl 3-oxo-1-piperazinecarboxylate (1.5 g, 6.4 mmol) in dry dimethyl formamide (5 mL) and the mixture was stirred at room temperature for 30 minutes. 5-(Chloromethyl)-1-methyl-1H-1,2,4-triazole (WO0023449, 920 mg, 7.0 mmol) was added and the mixture was stirred at room temperature for 16 hours. The mixture was poured into water (150 mL) and extracted with diethyl ether (2×100 mL). The combined organic fractions were dried (MgSO$_4$) and the solvent was evaporated under reduced pressure to give the title compound as a pale oil (2 g, 94%). m/z (ES$^+$) 330 (M+1).

DESCRIPTION 141

1-[(1-Methyl-1H-1,2,4-triazol-5-yl)methyl]-2-oxopiperazine

A slurry of palladium on carbon (10%, 1.7 g) and 1,4-cyclohexadiene (4.1 g, 51 mmol) in ethanol (10 mL) was added to a solution of phenylmethyl 4-[(1-methyl-1H-1,2,4-triazol-5-yl)methyl]-3-oxo-1-piperazinecarboxylate (Description 140, 1.7 g, 5.2 mmol) in ethanol (40 mL) and the mixture was stirred at room temperature for 2 hours. The mixture was filtered through Celite™ and the solvent was evaporated under reduced pressure. The residue was recrystallized from propan-2-ol to give the title compound (500 mg, 49%). m/z (ES$^+$) 196 (M+1).

DESCRIPTION 142

2-[(2-Hydroxyethyl)amino]-N-(3-pyridinyl)acetamide

Chloroacetyl chloride (2.2 mL, 27.6 mmol) was added dropwise over 10 minutes to a stirred, cooled (0° C.) solution of 3-pyridinamine (2 g, 21 mmol) and triethylamine (4 mL, 28 mmol) in tetrahydrofuran (30 mL). The mixture was allowed to warm to room temperature, then 2-aminoethanol (5 mL, 120 mmol) in methanol (5 mL) was added. The mixture was stirred at 60° C. for 4 hours, cooled and the solvent was evaporated under reduced pressure. The residue was purified by flash column chromatography on silica gel, eluting with CH$_2$Cl$_2$/MeOH/NH$_3$(Aq.) (90:10:1), to give the title compound (2.53 g, 62%). m/z (ES$^+$) 196 (M+1).

DESCRIPTION 143

1-(3-Pyridinyl)piperazin-2-one

Bis(1,1-dimethylethyl)diazenedicarboxylate (4.1 g, 18 mmol) in tetrahydrofuran (100 mL) was added dropwise to a stirred, cooled (0° C.) solution of 2-[(2-hydroxyethyl)amino]-N-(3-pyridinyl)acetamide (Description 142, 2.5 g, 13 mmol) and tributylphosphine (4.2 mL, 16.9 mmol) in tetrahydrofuran (300 mL) and the mixture was stirred at room temperature for 16 hours. Ethereal hydrogen chloride (1M, 10 mL) was added and the mixture was stirred at room temperature for 1 hour. Triethylamine (6 mL, 42 mmol) was added the solvent was evaporated under reduced pressure and the residue was purified by flash column chromatography on silica gel, eluting with CH$_2$Cl$_2$/MeOH/NH$_3$(Aq.) (90:10:1), to give the title compound (800 mg, 35%). m/z (ES$^+$) 178 (M+1).

DESCRIPTION 144

2-[(2-Hydroxyethyl)amino]-N-(2-thiazolyl)acetamide

Prepared from 2-thiazolamine according to the method of Description 142. m/z (ES$^+$) 202 (M+1).

DESCRIPTION 145

1-(2-Thiazolyl)piperazin-2-one

Prepared from 2-[(2-hydroxyethyl)amino]-N-(2-thiazolyl)acetamide (Description 144) according to the method of Description 143. m/z (ES$^+$) 184 (M+1).

DESCRIPTION 146

N-Phenylmethyl-N'-(2-pyridinyl)-1,2-ethanediamine

2-Bromopyridine (6.1 mL, 64 mmol) was added to N-(phenylmethyl)-1,2-ethanediamine (50 ml, 322 mmol) and the mixture was heated at 130–140° C. for 2 hours. The mixture was cooled, diluted with ethyl acetate (500 mL), washed with water (3×150 mL), dried (MgSO$_4$) and the solvent was evaporated under reduced pressure. The residue was purified by flash column chromatography on silica gel, eluting with CH$_2$Cl$_2$/MeOH/NH$_3$(Aq.) (90:8:1), to give the title compound as a yellow oil (5.7 g, 40%). m/z (ES$^+$) 228 (M+1).

DESCRIPTION 147

N-Phenylmethyl-N'-(4-pyridinyl)-1,2-ethanediamine

Prepared from 4-bromopyridine according to the method of Description 146. m/z (ES$^+$) 228 (M+1).

DESCRIPTION 148

N-Phenylmethyl-N'-(6-chloro-2-pyridinyl)-1,2-ethanediamine

Prepared from 2,6-dichloropyridine according to the method of Description 146. m/z (ES$^+$) 262, 264 (M+1).

DESCRIPTION 149

N-(Phenylmethylaminoethyl)-2-pyrazinamine

Prepared from 2-bromopyrazine according to the method of Description 146. m/z (ES$^+$) 229 (M+1).

DESCRIPTION 150

4-Phenylmethyl-1-(2-pyridinyl)piperazin-2-one

Glyoxal trimeric dihydrate (15.8 g, 75 mmol) was added to a mixture of N-phenylmethyl-N'-(2-pyridinyl)-1,2-ethanediamine (Description 146, 5.7 g, 25 mmol) and hydrochloric acid (2N, 100 mL) and the mixture was stirred at room temperature for 24 hours. Further glyoxal trimeric dihydrate (5.3 g, 25 mmol) was added and the mixture was stirred at room temperature for 20 hours. The mixture was basified with aqueous sodium hydroxide (4M) and extracted with ethyl acetate (2×200 mL). The combined organic fractions were dried (MgSO$_4$) and the solvent was evaporated under reduced pressure. The residue was purified by flash column chromatography on silica gel eluting with isohexane/EtOAc (40:60 increasing to 30:70), to give the title compound as a light brown oil (3.6 g, 54%). m/z (ES$^+$) 268 (M+1).

DESCRIPTION 151

4-Phenylmethyl-1-(4-pyridinyl)piperazin-2-one

Prepared from N-phenylmethyl-N'-4-pyridinyl)-1,2-ethanediamine (Description 147) according to the method of Description 150. m/z (ES$^+$) 268 (M+1).

DESCRIPTION 152

4-Phenylmethyl-1-(6-chloro-2-pyridinyl)piperazin-2-one

Prepared from N-phenylmethyl-N'-(6-chloro-2-pyridinyl)-1,2-ethanediamine (Description 148) according to the method of Description 150. m/z (ES$^+$) 302, 304 (M+1).

DESCRIPTION 153

4-Phenylmethyl-1-pyrazinylpiperazinone

Prepared from N-(phenylmethylaminoethyl)-2-pyrazinamine (Description 149) according to the method of Description 150. $^1$H NMR (400 MHz, CDCl$_3$) δ 9.41 (1H, d, J 1.5 Hz), 8.36 (1H, dd, J 2.5, 1.5 Hz), 8.33 (1H, d, J 2.5 Hz), 7.40–7.25 (5H, m), 3.98 (2H, t, J 5.5 Hz), 3.65 (2H, s), 3.40 (2H, s), and 2.85 (2H, t, J 5.5 Hz).

DESCRIPTION 154

1-(2-Pyridyl)piperazin-2-one

A slurry of palladium on carbon (5%, 3.6 g) in water was added to a solution of 4-phenylmethyl-1-(2-pyridinyl)piperazin-2-one (Description 150, 3.6 g, 13.48 mmol) and ammonium formate (4.25 g, 67.5 mmol) in methanol (100 mL) and the mixture was heated under reflux for 4 hours, cooled and filtered through Hyflo™, washing with methanol. The solvent was evaporated under reduced pressure and the residue was purified by flash column chromatography on silica gel eluting with CH$_2$Cl$_2$/MeOH (90:10), to give the title compound as an orange oil (1.1 g, 46%). m/z (ES$^+$) 178 (M+1).

DESCRIPTION 155

1-(4-Pyridinyl)piperazin-2-one

Prepared from 4-phenylmethyl-1-(4-pyridinyl)piperazin-2-one (Description 151) according to the method of Description 154. m/z (ES$^+$) 178 (M+1).

DESCRIPTION 156

1-Pyrazinylpiperazin-2-one

Prepared from 4-phenylmethyl-1-pyrazinylpiperazinone (Description 153) according to the method of Description 154. m/z (ES$^+$) 179 (M+1).

DESCRIPTION 157

1-(6-chloro-2-pyridinyl)piperazin-2-one

1-Chloroethylchloroformate (143 μL, 1.33 mmol) was added slowly to a stirred, cooled (−18° C.) solution of 4-phenylmethyl-1-(6-chloro-2-pyridinyl)piperazin-2-one (Description 152, 400 mg, 1.33 mmol) in dichloromethane (10 mL) and the mixture was stirred at −14° C. for 3 hours. The solvent was evaporated under reduced pressure, methanol (10 mL) was added and the mixture was heated under reflux for 30 minutes. The mixture was cooled, the solvent was evaporated under reduced pressure and methanolic ammonia (2M, 10 mL) was added. The solvent was evaporated under reduced pressure and the residue was purified by flash column chromatography on silica gel, eluting with CH$_2$Cl$_2$/MeOH/NH$_3$(Aq.) (120:8:1), to give the title compound as a tan gum (118 mg, 42%). m/z (ES$^+$) 212, 214 (M+1)$^+$.

DESCRIPTION 158

N-[(1,1-Dimethylethoxy)carbonyl]-N-(1,1-dimethylethyl)glycine Methyl Ester

Di-tert-butyl dicarbonate (6.0 g, 28 mmol) was added to a solution of N-(1,1-dimethylethyl)glycine methyl ester (*J. Org. Chem* 1995, 60, 5814, 4.0 g, 28 mmol) in dichloromethane (20 mL) and the mixture was stirred at room temperature for 16 hours. Further di-tert-butyl dicarbonate (3.0 g, 14 mmol) was added and mixture was stirred at room temperature for 72 hours. N,N-dimethylethylenediamine (3.2 mL, 28 mmol) was added and the mixture was stirred at room temperature for 1 hour. The mixture was washed with aqueous citric acid (10%, 2×40 mL), saturated aqueous sodium hydrogen carbonate (30 mL) and brine (30 mL), dried (MgSO$_4$) and the solvent was evaporated under reduced pressure to give the title compound as a yellow oil (5.6 g, 82%). $^1$H NMR (400 MHz, CDCl$_3$) δ 1.40 (9H, s), 1.45 (9H, s), 3.72 (3H, s), and 4.05 (2H, s).

DESCRIPTION 159

N-[(1,1-Dimethylethoxy)carbonyl]-N-(1,1-dimethylethyl)glycine

Aqueous sodium hydroxide (4M, 5 mL) was added to a solution of N-[(1,1-dimethylethoxy)carbonyl]-N-(1,1-dimethylethyl)glycine methyl ester (Description 158, 2.0 g, 8.2 mmol) in methanol (10 mL) and the mixture was stirred at room temperature for 40 hours. The solvent was evaporated under reduced pressure, hydrochloric acid (2M, 20 mL) was added and the mixture was extracted with dichloromethane (3×40 mL). The combined organic fractions were washed with brine, dried (MgSO$_4$) and the solvent was evaporated under reduced pressure to give the title compound as a colorless oil (1.6 g, 88%). $^1$H NMR (400 MHz, CDCl$_3$) δ 1.41 (9H, s), 1.46 (9H, s), and 4.08 (2H, s).

DESCRIPTION 160

1,1-Dimethylethyl N-(1,1-Dimethylethyl)-N-(2-oxoethyl)carbamate

Diisobutylaluminium hydride (1M in toluene, 3.7 mL, 3.7 mmol) was added to a stirred, cooled (−78° C.) solution of N-[(1,1-dimethylethoxy)carbonyl]-N-(1,1-dimethylethyl) glycine methyl ester (Description 158, 900 mg, 3.7 mmol) in toluene (5 mL) and the mixture was stirred at −78° C. for 3 hours. Hydrochloric acid (1M, 5 mL) was added and the mixture was allowed to warm to room temperature. The mixture was extracted with ethyl acetate (2×40 mL) and the combined organic fractions were washed with brine, dried (MgSO$_4$) and the solvent was evaporated under reduced pressure to give the title compound as a colorless oil (688 mg, 86%). $^1$H NMR (400 MHz, CDCl$_3$) δ 1.39 (9H, s), 1.45 (9H, s), 4.01 (2H, s), and 9.54 (1H, s).

DESCRIPTION 161

N-(2-Chloroethyl)-1-[[2-(trimethylsilyl)ethoxy]methyl]-1H-Imidazole-2-methanamine A mixture of 2-chloroethylamine hydrochloride (8.23 g, 71 mmol), triethylamine (15.8 mL, 0.11 mol) and 1-(2-trimethylsilyl)ethoxymethyl-2-imidazolecarboxaldehyde (12.9 g, 57 mmol) in 1,2-dichloroethane (400 mL) was heated under reflux until all the solids dissolved. The mixture was cooled and sodium triacetoxyborohydride (15.0 g, 71 mmol) was then added in portions over 15 minutes. The mixture was stirred at room temperature for 3 h, then poured into aqueous sodium hydroxide (1M, 250 mL). The layers were separated and the aqueous layer was extracted with ethyl acetate (3×200 mL). The combined organic fractions were washed with brine (150 mL), dried (MgSO$_4$) and the solvent was evaporated under reduced pressure. The residue was purified by flash column chromatography on silica gel, eluting with CH$_2$Cl$_2$/MeOH (95:5), to give the title compound as a colorless oil (5.0 g, 30%). m/z (ES$^+$) 290 (M+1).

DESCRIPTION 162

1,1-Dimethylethyl N-(2-Chloroethyl)-N-(1-{[2-(trimethylsilyl)ethoxy]methyl}-1H-imidazole-2-ylmethyl)carbamate Di-tert-butyl dicarbonate (4.14 g, 19 mmol) was added in portions over 2 minutes to a stirred, cooled (0° C.) solution of N-(2-chloroethyl)-1-[[2-(trimethylsilyl)ethoxy]methyl]-1H-imidazole-2-methanamine (Description 161, 5.0 g, 17.3 mmol) in dichloromethane (200 mL) and the mixture was at 0° C. for 10 minutes, then at room temperature for 1 hour. The solvent was evaporated under reduced pressure and the residue was purified by flash column chromatography on silica gel, eluting with CH$_2$Cl$_2$/MeOH (98:2), to give the title compound (2.52 g, 34%). m/z (ES$^+$) 390 (M+1).

DESCRIPTION 163

1,1-Dimethylethyl 5,6,7,8-Tetrahydroimidazo[1,2-a]pyrazin-7-carboxylate

Tetrabutylammonium fluoride (1M in tetrahydrofuran, 7.1 mL, 7.1 mmol) was added to a solution of 1,1-dimethylethyl N-(2-chloroethyl)-N-(1-{[2-(trimethylsilyl)ethoxy]methyl}-1H-imidazole-2-ylmethyl)carbamate (Description 162, 2.52 g, 6.5 mmol) in tetrahydrofuran (50 mL) and the mixture was heated under reflux for 1.5 hours. Further tetrabutylammonium fluoride (1M in tetrahydrofuran, 7.1 mL, 7.1 mmol) was added and the mixture was heated under reflux for 20 hours. The mixture was cooled and the solvent was evaporated under reduced pressure. The residue was purified by flash column chromatography on silica gel, eluting with CH$_2$Cl$_2$/MeOH (97:3), to give the title compound (505 mg, 35%). m/z (ES$^+$) 224 (M+1).

DESCRIPTION 164

5,6,7,8-Tetrahydroimidazo[1,2-a]pyrazine Trifluoroacetate 1,1-Dimethylethyl 5,6,7,8-tetrahydroimidazo[1,2-a]pyrazin-7-carboxylate (Description 163, 505 mg, 2.26 mmol) in dichloromethane (2.5 mL) was added to stirred, cooled (0° C.) trifluoroacetic acid (5 mL) and the mixture was stirred at 0° C. for 15 minutes, then at room temperature for 45 minutes. The solvent was evaporated under reduced pressure to give the title compound. m/z (ES$^+$) 124 (M+1).

DESCRIPTION 165

1-{[(2-Trimethylsilyl)ethoxy]methyl}-1H-imidazole-4-methanol and 1-{[(2-Trimethylsilyl)ethoxy]methyl}-1H-imidazole-5-methanol 1H-Imidazole-4-methanol hydrochloride (5.0 g, 37.2 mmol) in dimethylformamide (100 mL) was added dropwise over 30 minutes to a suspension of sodium hydride (60% dispersion in mineral oil, 2.97 g, 74.3 mmol) in dimethylformamide (200 mL) and the mixture was stirred at room temperature for 2 hours. The mixture was cooled to 0° C. and a solution of [2-(chloromethoxy)ethyl]trimethysilane (6.59 mL, 37.2 mmol) in tetrahydrofuran (50 mL) was added dropwise over 15 minutes. The mixture was stirred at room temperature overnight, then water (100 mL) was added and the solvent was evaporated under reduced pressure. Toluene (200 mL) was added and evaporated under reduced pressure. Water (100 mL) was added and the mixture was extracted with ethyl acetate (3×150 mL). The combined organic fractions were washed with water (100 mL) and brine (150 mL), dried (MgSO$_4$) and the solvent was evaporated under reduced pressure. The residue was purified by flash column chromatography on silica gel, eluting with CH$_2$Cl$_2$/MeOH (95:5 increasing to 90:10), to give the title compound as a mixture of isomers (4.82 g, 57%). $^1$H NMR (400 MHz, CDCl$_3$) δ Major isomer, δ 0.00 (9H, s), 0.84–0.96 (2H, m), 3.43–3.56 (2H, m), 4.62 (2H, s), 5.24 (2H, s), 6.99 (1H, s), and 7.56 (1H, s); Minor isomer, δ 0.00 (9H, s), 0.84–0.96 (2H, m), 3.43–3.56 (2H, m), 4.67 (2H, s), 5.36 (2H, s), 7.05 (1H, s), and 7.56 (1H, s). m/z (ES$^+$) 229 (M+1).

DESCRIPTION 166

1-(2-Trimethylsilyl)ethoxymethyl-4-imidazolecarboxaldehyde and 1-(2-Trimethylsilyl)ethoxymethyl-5-imidazolecarboxaldehyde Manganese (IV) oxide (18.4 g, 0.21 mol) was added in portions over 5 minutes to a solution of 1-{[(2-trimethylsilyl)ethoxy]methyl}-1H-imidazole-4-methanol and 1-{[(2-trimethylsilyl)ethoxy]methyl}-1H-imidazole-5-methanol (Mixture of isomers, Description 165, 4.82 g, 21.1 mmol) in dichloromethane (500 mL) and the mixture was stirred at room temperature overnight. The mixture was filtered through Celite™, washing with dichloromethane (200 mL), and the solvent was evaporated under reduced pressure to give the title compound as a mixture of isomers (4.78 g, 99%). $^1$H NMR (400 MHz, CDCl$_3$) δ Major isomer, 0.00 (9H, s), 0.87–0.93 (2H, m), 3.56–3.65 (2H, m), 5.72 (2H, s), 7.84 (1H, s), 7.89 (1H, s), and 9.81 (1H, s); Minor isomer, 0.02 (9H, s), 0.87–0.97 (2H, m), 3.47–3.58 (4H, m), 5.35 (2H, s), 7.70 (1H, s), 7.75 (1H, s), and 9.93 (1H, s).

DESCRIPTION 167

N-(2-Chloroethyl)-1-[[2-(trimethylsilyl)ethoxy]methyl]-1H-imidazole-4-methanamine and N-(2-Chloroethyl)-1-[[2-(trimethylsilyl)ethoxy]methyl]-1H-imidazole-5-methanamine Prepared from 1-(2-trimethylsilyl)ethoxymethyl-4-imidazolecarboxaldehyde and 1-(2-trimethylsilyl)ethoxymethyl-5-imidazolecarboxaldehyde (Mixture of isomers, Description 166) according to the method of Description 161, followed by purification by flash column chromatography on silica gel, eluting with CH$_2$Cl$_2$/MeOH (95:5 increasing to 85:15), to give N-(2-chloroethyl)-1-[[2-(trimethylsilyl)ethoxy]methyl]-1H-imidazole-4-methanamine (1.97 g, 45%); $^1$H NMR (400 MHz, CDCl$_3$) δ 0.00 (9H, s), 0.92 (2H, t, J 8.3 Hz), 2.95 (2H, t, J 5.7 Hz), 3.44–3.53 (2H, m), 3.60–3.68 (2H, m), 3.88 (2H, s), 5.39 (2H, s), 6.99 (1H, s), and 7.61 (1H, s); m/z (ES$^+$) 290 (M+1); and N-(2-chloroethyl)-1-[[2-(trimethylsilyl)ethoxy]methyl]-1H-imidazole-5-methanamine (1.02 g, 23%); $^1$H NMR (400 MHz, CDCl$_3$) δ 0.00 (9H, s), 0.92 (2H, t, J 8.1 Hz), 3.08 (2H, t, J 6.0 Hz), 3.44–3.53 (2H, m), 3.73 (2H, t, J 6.0 Hz), 3.88 (2H, s), 5.24 (2H, s), 7.06 (1H, s), and 7.60 (1H, s); m/z (ES$^+$) 290 (M+1).

DESCRIPTION 168

1,1-Dimethylethyl N-(2-Chloroethyl)-N-(1-{[2-(trimethylsilyl)ethoxy]methyl}-1H-imidazole-4-ylmethyl)carbamate Prepared from N-(2-chloroethyl)-1-[[2-(trimethylsilyl)ethoxy]methyl]-1-imidazole-4-methanamine (Description 167) according to the method of Description 162. m/z (ES$^+$) 390 (M+1).

DESCRIPTION 169

1,1-Dimethylethyl 5,6,7,8-Tetrahydroimidazo[1,5-a]pyrazin-7-carboxylate

Prepared from 1,1-dimethylethyl N-(2-chloroethyl)-N 1-{[2-trimethylsilyl)ethoxy]methyl}-1H-imidazole-4-ylmethyl)carbamate (Description 168) according to the method of Description 163. $^1$H NMR (360 MHz, CDCl$_3$) δ 1.49 (9H, s), 3.80 (2H, t, J 5.5 Hz), 4.03 (2H, t, J 5.5 Hz), 4.65 (2H, s), 6.85 (1H, s), and 7.44 (1H, s).

DESCRIPTION 170

5,6,7,8-Tetrahydroimidazo[1,5-a]pyrazine Trifluoroacetate

Prepared from 1,1-dimethylethyl 5,6,7,8-tetrahydroimidazo[1,5-a]pyrazin-7-carboxylate (Description 169) according to the method of Description 164. m/z (ES$^+$) 124 (M+1).

DESCRIPTION 171

Methyl 2-Fluorobenzeneacetate

Prepared from 2-fluorobenzeneacetic acid according to the method of Description 1. $^1$H NMR (400 MHz, CDCl$_3$) δ 7.28–7.24 (2H, m), 7.13–7.04 (2H, m), 3.71 (3H, s), and 3.68 (2H, s).

DESCRIPTION 172

Methyl 3-Fluorobenzeneacetate

Prepared from 3-fluorobenzeneacetic acid according to the method of Description 1. $^1$H NMR (400 MHz, CDCl$_3$) δ 7.31–7.26 (1H, m), 7.06–6.95 (3H, m), 3.71 (3H, s), and 3.62 (2H, s).

DESCRIPTION 173

Methyl 4-Fluorobenzeneacetate

Prepared from 4-fluorobenzeneacetic acid according to the method of Description 1. $^1$H NMR (360 MHz, CDCl$_3$) δ 7.25–7.22 (2H, m), 7.03–6.99 (2H, m), 3.70 (3H, s), and 3.60 (2H, s).

DESCRIPTION 174

Dimethyl 1-(2-Fluorophenyl)-4-oxo-1,3-cyclohexanedicarboxylate

Prepared from methyl 2-fluorobenzeneacetate (Description 171) according to the method of Description 16. $^1$H NMR (400 MHz, CDCl$_3$) δ 12.12 (1H, s), 7.29–7.24 (1H, m), 7.22–7.17 (1H, m), 7.12–7.00 (2H, m), 3.83 (3H, s), 3.69 (3H, s), 2.37–2.32 (3H, m), 2.28–2.27 (1H, m), and 1.96–1.82 (2H, m).

DESCRIPTION 175

Dimethyl 1-(3-Fluorophenyl)-4-oxo-1,3-cyclohexanedicarboxylate

Prepared from methyl 3-fluorobenzeneacetate (Description 172) according to the method of Description 16. $^1$H NMR (360 MHz, CDCl$_3$) δ 12.11 (1H, s), 7.33–7.26 (1H, m), 7.13 (1H, m), 7.06 (1H, dt, J 2.2, 10.6 Hz), 6.99–6.95 (1H, m), 3.83 (3H, s), 3.65 (3H, s), 3.07 (1H, dd, J 1.4, 16.1 Hz), 2.71 (1H, d, J 16.1 Hz), 2.47–2.38 (2H, m), and 2.22–2.16 (2H, m).

DESCRIPTION 176

Dimethyl 1-(4-Fluorophenyl)-4-oxo-1,3-cyclohexanedicarboxylate

Prepared from methyl 4-fluorobenzeneacetate (Description 173) according to the method of Description 16. $^1$H NMR (400 MHz, CDCl$_3$) δ 12.10 (1H, s), 7.34–7.31 (2H, m), 7.04–7.00 (2H, m), 3.81 (3H, s), 3.64 (3H, s), 3.06 (1H, dd, J 1.2, 16.1 Hz), 2.71 (1H, d, J 16.1 Hz), 2.44–2.37 (2H, m), and 2.21–2.14 (2H, m).

DESCRIPTION 177

1-(2-Fluorophenyl)-4-oxocyclohexanecarboxylic Acid

Prepared from dimethyl 1-(2-fluorophenyl)-4-oxo-1,3-cyclohexanedicarboxylate (Description 174) according to the method of Description 17. $^1$H NMR (360 MHz, CDCl$_3$) δ 741–7.29 (2H, m), 7.2–16.97 (21 m), 2.78–2.65 (3H, m), and 2.46–2.21 (5H, m).

DESCRIPTION 178

1-(3-Fluorophenyl)-4-oxocyclohexanecarboxylic Acid

Prepared from dimethyl 1-(3-fluorophenyl)-4-oxo-1,3-cyclohexanedicarboxylate (Description 175) according to the method of Description 17. $^1$H NMR (360 MHz, CDCl$_3$) δ 7.39–7.35 (1H, m), 7.31–7.25 (1H, m), 7.21–7.18 (1H, m), 7.05–7.00 (1H, m), 2.78–2.73 (2H, m), 2.63–2.55 (2H, m), 2.47–2.41 (2H, m), and 2.30–2.23 (2H, m).

DESCRIPTION 179

1-(4-Fluorophenyl)-4-oxocyclohexanecarboxylic Acid

Prepared from dimethyl 1-(4-fluorophenyl)-4-oxo-1,3-cyclohexanedicarboxylate (Description 176) according to the method of Description 17. $^1$H NMR (360 MHz, CDCl$_3$) δ 7.48–7.46 (2H, m), 7.11–7.02 (2H, m), 2.79–2.73 (2H, m), 2.62–2.53 (2H, m), 2.46–2.34 (2H, m), and 2.30–2.22 (2H, m).

DESCRIPTION 180

1-(2-Fluorophenyl)-4-oxocyclohexylamine Hydrochloride

Prepared from 1-(2-fluorophenyl)-4-oxocyclohexanecarboxylic Acid (Description 177) according to the method of Description 18. $^1$H NMR (400 MHz, DMSO-d$_6$) δ 8.93 (3H, br s), 7.70–7.65 (1H, m), 7.55–7.51 (1H, m), 7.41–7.37 (2H, m), 2.75–2.61 (4H, m), 2.45–2.37 (2H, m), and 2.33–2.29 (2H, m).

DESCRIPTION 181

1-(3-Fluorophenyl)-4-oxocyclohexylamine Hydrochloride

Prepared from 1-(3-fluorophenyl)-4-oxocyclohexanecarboxylic Acid (Description 178) according to the method of Description 18. $^1$H NMR (400 MHz, DMSO-d$_6$) δ 8.94 (3H, br s), 7.62–7.54 (3H, m), 7.31–7.24 (1H, m), 2.69–2.59 (4H, m), 2.42–2.34 (2H, m), and 2.28–2.20 (2H, m).

DESCRIPTION 182

1-(4-Fluorophenyl)-4-oxocyclohexylamine Hydrochloride

Prepared from 1-(4-fluorophenyl)-4-oxocyclohexanecarboxylic Acid (Description 179) according to the method of Description 18. $^1$H NMR (400 MHz, DMSO-d$_6$) δ 8.88 (3H, br s), 7.81–7.76 (2H, m), 7.36–7.28 (2H, m), 2.70–2.55 (4H, m), 2.43–2.36 (2H, m), and 2.25–2.18 (2H, m).

DESCRIPTION 183

4-Oxo-1-(2-pyridyl)cyclohexanecarboxylic Acid Hydrochloride

Ethyl 2-pyridineacetate (30.0 g, 27.7 mL, 182 mmol) was added over 30 minutes to a stirred, cooled (0° C.) suspension of sodium hydride (60% dispersion in mineral oil, 23.2 g, 581 mmol) in dimethylformamide (400 mL) (internal temperature<2° C.) and the mixture was stirred at 0° C. for 30 minutes. Methyl 2-propenoate (37.6 mL, 418 mmol) was added dropwise over 2 hours (internal temperature<10° C.) and the mixture was stirred at room temperature for 24 hours. The mixture was cooled to 0° C. and the pH was adjusted to 3.0 with hydrochloric acid (2M, 300 mL). The mixture was extracted with ethyl acetate (2×400 mL) and the combined organic fractions were washed with brine (200 mL), dried (Na$_2$SO$_4$) and the solvent was evaporated under reduced pressure. The residue was purified by flash column chromatography on silica gel, eluting with isohexane/EtOAc (75:25), to give a solid (18.7 g). A portion (9.27 g) was suspended in hydrochloric acid (5M, 250 mL) and heated under reflux for 20 hours. The mixture was cooled, the solvent was evaporated under reduced pressure and the residue was dried in vacuo to give the title compound (7.62 g, 32%). $^1$H NMR (400 MHz, CD$_3$OD) δ 9.24 (1H, m), 8.57 (1H, t, J 7 Hz), 8.15 (1H, d, J 7 Hz), 8.10 (1H, t, J 7 Hz), 2.55–2.40 (4H, m), 2.25–2.10 (2H, m), and 1.95–1.80 (2H, m)

DESCRIPTION 184

4-Oxo-1-(2-pyridyl)cyclohexanecarboxyl Azide

Oxalyl chloride (3.41 mL, 39.7 mmol) was added to a mixture of 4-oxo-1-(2-pyridyl)cyclohexanecarboxylic acid hydrochloride (Description 183, 2.03 g, 7.94 mmol) and dimethylformamide (2 drops) in dichloromethane (20 mL). The mixture was heated under reflux for 2.5 hours, cooled and the solvent was evaporated under reduced pressure. Dichloromethane (2×10 mL) was added and evaporated under reduced pressure. The residue was suspended in dichloromethane (20 mL) and a solution of sodium azide (1.55 g, 23.8 mmol) and tetrabutylammonium bromide (250 mg, 0.77 mmol) in water (15 mL) was added. The mixture was stirred at room temperature for 18 hours, then aqueous potassium carbonate (10%, 100 mL) was added. The mixture was extracted with dichloromethane (2×50 mL), the combined organic fractions were washed with water (2×50 mL), dried (Na$_2$SO$_4$) and the solvent was evaporated under reduced pressure. The residue was purified by flash column chromatography on silica gel, eluting with isohexane/EtOAc (66:33 increasing to 50:50), to give the title compound as a colorless oil (0.57 g, 29%). $^1$H NMR (400 MHz, CDCl$_3$) δ 8.63 (1H, br d, J 4 Hz), 7.74 (1H, dt, J 8, 2 Hz), 7.39 (1H, br d, J 8 Hz), 7.26 (1H, m), and 2.75–2.35 (8H, m)

DESCRIPTION 185

4-Isocyanato-4-(2-pyridyl)cyclohexan-1-one

4-Oxo-1-(2-pyridyl)cyclohexanecarboxyl azide (Description 184, 377 mg, 1.54 mmol) in toluene (5 mL) was stirred at 90° C. for 1.25 hours, cooled and the solvent was evaporated under reduced pressure to to give the title compound (330 mg, 99%). m/z (ES$^+$) 217 (M+1).

DESCRIPTION 186

Trans-Methyl 4-[4-(Phenylmethyl)piperazin-1-yl]-1-phenylcyclohexanecarboxylate

Sodium triacetoxyborohydride (10 g, 46.79 mmol) was added to a solution of 4-oxo-1-phenylcyclohexanecarboxylic acid (Description 17, 8.5 g, 38.99 mmol) and 1-(phenylmethyl)piperazine (6.2 mL, 38.99 mmol) in dichloroethane (200 mL) and the mixture was stirred at room temperature for 18 hours. The solvent was evaporated under reduced pressure and the residue was triturated with methanol. The solid was collected, washed with methanol, suspended in methanol (200 mL) and acetyl chloride (4.2 mL, 58.5 mmol) was added dropwise. The mixture was heated under reflux for 2 days, cooled and basified with saturated aqueous sodium hydrogen carbonate. The methanol was evaporated under reduced pressure and the mixture was extracted with ethyl acetate. The combined organic fractions were dried (MgSO$_4$) and the solvent was evaporated under reduced pressure. The residue was crystallised from propan-2-ol (4 mL/g) to give the title compound as a colorless solid (5.65 g, 36%). m/z (ES$^+$) 393 (M+1).

DESCRIPTION 187

Trans-4-[4-(phenylmethyl)piperazin-1-yl]-1-phenylcyclohexanecarboxylic Acid Dihydrochloride Trans-Methyl 4-[4-(phenylmethyl)piperazin-1-yl]-1-phenylcyclohexanecarboxylate (Description 186, 5 g, 12.76 mmol) was dissolved in hydrochloric acid (5M, 150 mL) and heated under reflux for 3 days. The mixture was cooled, the solvent was evaporated under reduced pressure and the residue was dried in vacuo to give the title compound as a colorless solid, (5.37 g, 93%). m/z (ES$^+$) 379 (M+1).

DESCRIPTION 188

Trans-4-[4-(phenylmethyl)piperazin-1-yl]-1-phenylcyclohexylamine

Diphenylphosphoryl azide (5.1 mL, 23.75 mmol) was added to a suspension of trans-4-[4-(phenylmethyl)piperazin-1-yl]-1-phenylcyclohexanecarboxylic acid dihydrochloride (Description 187, 4.3 g, 9.5 mmol) and triethylamine (6.6 mL, 47.5 mmol) in toluene (150 mL) and the mixture was heated to 50° C. for 3 hours. The mixture was cooled, diluted with ethyl acetate, washed with a saturated solution of sodium carbonate, dried (MgSO$_4$) and the solvent was evaporated under reduced pressure. The residue was suspended in hydrochloric acid (5M, 100 mL) and the mixture was stirred at room temperature for 24 hours. The mixture was basified with aqueous sodium hydroxide (4M) and extracted with ethyl acetate. The combined organic fractions were dried (MgSO$_4$) and the solvent was evaporated under reduced pressure. The residue was dissolved in ethanol (100 mL), potassium hydroxide (10 g) was added and the mixture was heated under reflux for 4 days. The mixture was cooled, poured into water and extracted with ethyl acetate. The combined organic fractions were washed with water, dried (MgSO$_4$) and the solvent was evaporated under reduced pressure to give the title compound as a brown oil (3.07 g, 93%). m/z (ES$^+$) 350 (M+1).

DESCRIPTION 189

1,1-Dimethylethyl 4-Oxo-1-phenylcyclohexylcarbamate

Di-tert-butyl dicarbonate (13.55 g, 62.1 mmol) was added to a solution of 4-oxo-1-phenylcyclohexylamine (Description 18, 9.78 g, 51.7 mmol) in dichloromethane (150 mL) and the mixture was stirred at room temperature for 18 hours, then under reflux for 6 hours. Further di-tert-butyl dicarbonate (8.00 g, 36.7 mmol) was added and the mixture was stirred under reflux for 60 hours. The mixture was cooled and the solvent was evaporated under reduced pressure. The residue was purified by flash column chromatography on silica gel, eluting with isohexane/EtOAc (75:25 increasing to 67:33), to give the title compound as a colorless solid (8.35 g, 56%). $^1$H NMR (400 MHz, CDCl$_3$) δ 7.45–7.22 (5H, m), 5.02 (1H, br s), 2.75–2.50 (4H, m), 2.39 (2H, br d, J 12 Hz), 2.28 (2H, b. t, J 12 Hz), and 1.40 (9H, br s)

DESCRIPTION 190

Trans-1,1-Dimethylethyl 4-(3-Oxo-4-phenyl-1-piperazinyl)-1-phenylcyclohexylcarbamate Sodium triacetoxyborohydride (985 mg, 4.7 mmol) was added to a solution of 1,1-dimethylethyl 4-oxo-1-phenylcyclohexylcarbamate (Description 189, 3.2 g, 11 mmol) and 1-(phenyl)piperazinone (2.1 g, 12.1 mmol) in 1,2-dichloroethane (100 mL) and the mixture was stirred at room temperature for 19 hours. Saturated aqueous sodium hydrogen carbonate (100 mL) and water (50 mL) were added and the mixture was extracted with dichloromethane (3×50 mL). The combined organic fractions were dried (MgSO$_4$), the solvent was evaporated under reduced pressure and the residue was recrystallised twice from methanol. The residue was purified by flash column chromatography on silica gel, eluting with isohexane/EtOAc (20:80), to give the title compound as a colorless foam (1.1 g, 23%). m/z (ES$^+$) 450 (M+1).

DESCRIPTION 191

Trans-1,1-Dimethylethyl 4-[3-Oxo-4-(2-chlorophenyl)-1-piperazinyl]-1-phenylcyclohexylcarbamate Prepared from 1,1-dimethylethyl 4-oxo-1-phenylcyclohexylcarbamate (Description 189) and 1-(2-chlorophenyl)piperazinone (*Tetrahedron Lett.* 1998, 39, 7459–7462) according to the method of Description 190. m/z (ES$^+$) 484, 486 (M+1).

DESCRIPTION 192

Trans-1,1-Dimethylethyl 4-[3-Oxo-4-(2-methylphenyl)-1-piperazinyl]-1-phenylcyclohexylcarbamate Prepared from 1,1-dimethylethyl 4-oxo-1-phenylcyclohexylcarbamate (Description 189) and 1-(2-methylphenyl)piperazinone (*Tetrahedron Lett.* 1998, 39, 7459–7462) according to the method of Description 190. m/z (ES$^+$) 464 (M+1).

DESCRIPTION 193

Trans-4-(3-Oxo-4-phenyl-1-piperazinyl)-1-phenylcyclohexylamine

Trifluoroacetic acid (4 mL) was added to a stirred, cooled (0° C.) solution of trans-1,1-dimethylethyl 4-(3-oxo-4-phenyl-1-piperazinyl)-1-phenylcyclohexylcarbamate (Description 190, 1.0 g, 2.2 mmol) in dichloromethane (20 mL) and the mixture was stirred at 0° C. for 15 minutes, then at room temperature for 2 hours. The solvent was evaporated under reduced pressure, saturated aqueous sodium hydrogen carbonate (50 mL) was added and the mixture was extracted with dichloromethane (3×50 mL). The combined organic fractions were dried (MgSO$_4$) and the solvent was evaporated under reduced pressure to give the title compound as a colorless foam (780 mg, 100%). m/z (ES$^+$) 350 (M+1).

DESCRIPTION 194

Trans-4-[3-Oxo-4-(2-chlorophenyl)-1-piperazinyl]-1-phenylcyclohexylamine

Prepared from trans-1,1-dimethylethyl 4-[3-oxo-4-(2-chlorophenyl)-1-piperazinyl]-1-phenylcyclohexylcarbamate (Description 191) according to the method of Description 193. m/z (ES$^+$) 384,386 (M+1).

DESCRIPTION 195

Trans-4-[3-Oxo-4-(2-methylphenyl)-1-piperazinyl]-1-phenylcyclohexylamine

Prepared from trans-1,1-dimethylethyl 4-[3-oxo-4-(2-methylphenyl)-1-piperazinyl]-1-phenylcyclohexylcarbamate (Description 192) according to the method of Description 193. m/z (ES$^+$) 364 (M+1).

DESCRIPTION 196

Trans-N-Ethyl-4-(3-oxo-4-phenyl-1-piperazinyl)-1-phenylcyclohexylamine

Acetaldehyde (81 µL, 1.45 mmol) was added to a solution of trans-4-(3-oxo-4-phenyl-1-piperazinyl)-1-phenylcyclohexylamine (Description 193, 100 mg, 0.29 mmol) in methanol (2 mL) and the mixture was stirred at room temperature for 16 hours. Sodium borohydride (57 mg, 1.5 mmol) was added and the mixture was stirred at room temperature for 1 hour. The solvent was evaporated under reduced pressure and saturated aqueous sodium hydrogen carbonate (4 mL) was added. The mixture was extracted with dichloromethane (3×15 mL) and the combined organic fractions were poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure and the residue was purified by preparative thin layer chromatography on silica gel, eluting with CH$_2$Cl$_2$/MeOH/NH$_3$(Aq.) (90:8:1), to give the title compound as a colorless gum (28 mg, 26%). m/z (ES$^+$) 378 (M+1).

DESCRIPTION 197

Trans-N-Ethyl-4-[3-oxo-4-(2-chlorophenyl)-1-piperazinyl]-1-phenylcyclohexylamine Prepared from trans-4-[3-oxo-4-(2-chlorophenyl)-1-piperazinyl]-1-phenylcyclohexylamine (Description 194) according to the method of Description 196. m/z (ES$^+$) 412, 414 (M+1).

DESCRIPTION 198

Trans-N-Ethyl-4-[3-oxo-4-(2-methylphenyl)-1-piperazinyl]-1-phenylcyclohexylamine Prepared from trans-4-[3-oxo-4-(2-methylphenyl)-1-piperazinyl]-1-phenylcyclohexylamine (Description 195) according to the method of Description 196. m/z (ES$^+$) 392 (M+1).

DESCRIPTION 199

Cis- and trans-1,1-Dimethylethyl 4-(2-Hydroxyethylamino)-1-phenylcyclohexylcarbamate Sodium triacetoxyborohydride (1.4 g, 6.9 mmol) was added to a solution of 1,1-dimethylethyl 4-oxo-1-phenylcyclohexylcarbamate (Description 189, 1 g, 3.5 mmol) and ethanolamine (229 µL, 3.8 mmol) in 1,2-dichloroethane (10 mL) and the mixture was stirred at room temperature overnight. Saturated aqueous sodium hydrogen carbonate (3 mL) and dichloromethane (5 mL) were added and the layers were separated. The organic layer was dried (MgSO$_4$) and the solvent was evaporated under reduced pressure. The residue was purified by flash column chromatography on silica gel, eluting with CH$_2$Cl$_2$/MeOH/NH$_3$(Aq.) (92:8;1), to give the title compound as a 2:1 mixture of cis- and trans-isomers (920 mg, 79%). m/z (ES$^+$) 335 (M+1).

DESCRIPTION 200

Cis- and Trans-1,1-Dimethylethyl 4-{N-(2-hydroxyethyl)[(2-chlorophenyl)aminocarbonylmethyl]amino}-1-phenylcyclohexylcarbamate Cis- and trans-1,1-dimethylethyl 4-(2-hydroxyethylamino)-1-phenylcyclohexylcarbamate (mixture of diastereoisomers, Description 199. 920 mg. 2.75 mmol) in acetonitrile (75 mL) and 2-bromo-N-(2-chlorophenyl)acetamide (2 g, 8.25 mmol) were added simultaneously to a suspension of potassium carbonate (2 g, 13.8 mmol) in acetonitrile (50 mL) and the mixture was heated at 80° C. for 16 hours. The mixture was cooled and the solvent was evaporated under reduced pressure. Dichloromethane and water were added and the layers were separated. The organic layer was dried (MgSO$_4$) and the solvent was evaporated under reduced pressure. The residue was purified by flash column chromatography on silica gel, eluting with CH$_2$Cl$_2$/MeOH/NH$_3$(Aq.) (98:2:1) to give the title compound as a 2:1 mixture of cis- and trans-isomers (1.03 g, 73%). $^1$H NMR (400 MHz, CD$_3$OD) δ 1.09–1.44 (10H, m), 1.70–1.88 (5H, m), 2.37–2.68 (1H, m), 2.68–2.89 (4H, m), 3.16 and 3.42 (total 2H, each s), 3.59–3.71 (2H, m), 7.07–7.51 (8H, m), and 8.21–8.33 (1H, m). m/z (ES$^+$) 502, 504 (M+1).

DESCRIPTION 201

Cis- and Trans-1,1-Dimethylethyl 4-[4-(2-Chlorophenyl)-3-oxopiperazin-1-yl]-1-phenylcyclohexylcarbamate Prepared as a 2:1 mixture of cis- and trans-isomers from cis- and trans-1,1-dimethylethyl 4-{N-(2-hydroxyethyl)[(2-chlorophenyl)aminocarbonylmethyl]amino}-1-phenylcyclohexylcarbamate (Mixture of diastereoisomers, Description 200) according to the method of Example 230. m/z (ES$^+$) 484, 486 (M+1).

DESCRIPTION 202

Trans-4-[4-(2-Chlorophenyl)-3-oxopiperazin-1-yl]-1-phenylcyclohexylamine

Trifluoroacetic acid (1.5 mL) was added to a solution of cis- and trans-1,1-dimethylethyl 4-[4-(2-chlorophenyl)-3-oxopiperazin-1-yl]-1-phenylcyclohexylcarbamate (mixture of diastereoisomers, Description 201, 1.03 g, 2.05 mmol) in dichloromethane (10 mL) and the mixture was stirred at room temperature for 3 hours. Saturated aqueous sodium hydrogen carbonate (3 mL) and dichloromethane (5 mL) were added and the layers were separated. The aqueous layer was extracted with dichloromethane (3×3 mL) and the combined organic fractions were poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure and the residue was purified by preparative thin layer chromatography on silica gel, eluting with CH$_2$Cl$_2$/MeOH/NH$_3$(Aq.) (92:8:0.8), to give the title compound (140 mg, 14%). m/z (ES$^+$) 384, 386 (M+1).

DESCRIPTION 203

(2R*,1'R*)- and (2S*,1'R*)-α-Methyl-N-(1-phenyl-4-{[(trifluoromethyl)sulfonyl]oxy}cyclohex-3-enyl)-3,5-bis(trifluoromethyl)benzeneacetamide (RS)-α-Methyl-N-(4-oxo-1-phenylcyclohexyl)-3,5-bis(trifluoromethyl)benzeneacetamide (Example 3, 638 mg, 1.4 mmol) in tetrahydrofuran (10 mL) was added to a stirred, cooled (−78° C.) solution of lithium diisopropylamide in tetrahydrofuran (0.1M, 30 mL). The mixture was stirred at −78° C. for 3 hours, then allowed to warm to −10° C. over 30 minutes. The mixture was cooled to −78° C., then 1,1,1-trifluoro-N-phenyl-N-[(trifluoromethyl)sulfonyl]methanesulfonamide (499 mg, 1.4 mmol) in tetrahydrofuran (10 mL) was added. The mixture was allowed to warm to room temperature and stirred for 16 hours. Saturated aqueous ammonium chloride (10 mL), water (50 mL) and ethyl acetate (50 mL) were added and the layers were separated. The aqueous fraction was extracted with ethyl acetate (2×50 mL), the combined organic fractions were dried (MgSO$_4$) and the solvent was evaporated under reduced pressure. The residue was purified by flash column chromatography on silica gel, eluting with isohexane/EtOAc (100:0 increasing to 90:10) to give the title compound as a mixture of regioisomers (540 mg, 65%). m/z (ES$^+$) 590 (M+1).

DESCRIPTION 204

(RS)-α,α-Dimethyl-N-{1-phenyl-4-[(trimethylsilyl)oxy]cyclohex-3-enyl}-3,5-bis(trifluoromethyl)benzeneacetamide Lithium bis(trimethylsilyl)amide (1M in tetrahydrofuran, 0.47 mL) was added to a stirred, cooled (0° C.) solution of α,α-dimethyl-N-[4-oxo-1-phenylcyclohexyl]-3,5-bis(trifluoromethyl)benzeneacetamide (Example 57, 100 mg, 0.2 mmol) in tetrahydrofuran (5 mL) and the mixture was stirred at 0° C. for 30 minutes. Chlorotrimethylsilane (29 µL, 0.22 mmol) was added and the mixture was stirred at room temperature for 1 hour. Saturated aqueous sodium hydrogen carbonate was added and the mixture was extracted with ethyl acetate. The combined organic fractions were dried (MgSO$_4$), filtered through alumina and the solvent was evaporated under reduced pressure to give the title compound as a pale yellow oil (110 mg, 95%). $^1$H NMR (400 MHz, CDCl$_3$) δ 7.80 (1H, s), 7.77 (2H, s), 7.29–7.20 (5H, m), 5.53 (1H, s), 4.67–4.65 (1H, m), 2.80–2.74 (1H, m), 2.53–2.45 (1H, m), 2.23–2.14 (1H, m), 1.97–1.93 (1H, m), 1.55 (6H, s), 1.56–1.47 (1H, m), and 0.15 (9H, s).

EXAMPLE 1

N-(1,4-Dioxa-8-phenylspiro[4.5]decan-8-yl)-3,5-bis(trifluoromethyl)benzeneacetamide Oxalyl chloride (116 µl, 1.4 mmol) and dimethylformamide (1 drop) were added to a suspension of 3,5-bis(trifluoromethyl)benzeneacetic acid (0.38 g, 1.4 mmol) in dichloromethane (2 mL) and the mixture was stirred at room temperature for 1 hour. The solvent was evaporated under reduced pressure and toluene (10 mL) was added. The solvent was evaporated under reduced pressure and further toluene (10 mL) was added. The solvent was evaporated under reduced pressure and a solution of 1,4-dioxa-8-phenylspiro[4.5]decan-8-amine (Description 15, 80 mg, 0.34 mmol) in dichloroethane (3 mL) and triethylamine (0.2 mL, 1.4 mmol) were added. The mixture was stirred at room temperature overnight, diluted with saturated aqueous sodium hydrogen carbonate and extracted with dichloromethane (3×20 mL). The combined organic fractions were washed with brine, dried (MgSO$_4$) and the solvent was evaporated under reduced pressure to give the title compound as a brown gum (170 mg, 100%). m/z (ES$^+$) 488 (M+1).

EXAMPLE 2

N-(4-Oxo-1-phenylcyclohexyl)-3,5-bis(trifluoromethyl)benzeneacetamide

Hydrochloric acid (2M, 6 mL) was added to a solution of N-(1,4-dioxa-8-phenylspiro[4.5]decan-8-yl)-3,5-bis(trifluoromethyl)benzeneacetamide (example 1, 170 mg, 0.34 mmol) in acetone (7 mL) and the mixture was stirred at room temperature for 16 hours. The solvent was evaporated under reduced pressure, aqueous sodium hydroxide was added and the mixture was extracted with ethyl acetate (2×20 mL). The combined organic fractions were washed with brine, dried (MgSO$_4$) and the solvent was evaporated under reduced pressure to give the title compound as a colorless gum (76 mg, 49%). m/z (ES$^+$) 444 (M+1).

EXAMPLE 3

(RS)-α-Methyl-N-(4-oxo-1-phenylcyclohexyl)-3,5-bis(trifluoromethyl)benzeneacetamide Prepared from (RS)-α-methyl-3,5-bis(trifluoromethyl)benzeneacetic acid (Description 4) and 4-oxo-1-phenylcyclohexylamine hydrochloride (Description 18) according to the method of Example 1. $^1$H NMR (400 MHz, CDCl$_3$) δ 7.80 (1H, s), 7.72 (2H, s), 7.29 (5H, m), 5.71 (1H, s), 3.70 (1H, q, J 7.0 Hz), 2.81 (1H, m), 2.64 (1H, m), 2.47–2.04 (5H, m), 1.60 (1H, m), and 1.52 (3H, d, J 7.0 Hz).

EXAMPLE 4

Cis-(RS)-α-Methyl-N-{4-[4-Phenylmethyl-4-(dimethylamino)piperidin-1-yl]-1-phenylcyclohexyl}-3,5-bis(trifluoromethyl)benzeneacetamide and Trans-(RS)-α-Methyl-N-{4-[4-Phenylmethyl-4-(dimethylamino)piperidin-1-yl]-1-phenylcyclohexyl}-3,5-bis(trifluoromethyl)benzeneacetamide A solution of sodium cyanoborohydride (6.3 mg, 100 µmol) and zinc chloride (6.8 mg. 50 µmol) in methanol (1 mL) was added to a solution of (RS)-α-methyl-N-(4-oxo-1-phenylcyclohexyl)-3,5-bis(trifluoromethyl)benzeneacetamide (Example 3, 23 mg, 50 µmol) and 4-(dimethylamino)-4-(phenylmethyl)piperidine (Description 14, 22 mg, 100 µmol) in methanol (2 mL) and the mixture was stirred at room temperature for 2 hours. The solvent was evaporated in a stream of nitrogen, water (3 mL) and aqueous potassium carbonate (saturated, 1.5 mL) were added and the mixture was extracted with dichloromethane (3×1.5 mL). The combined organic fractions were poured onto an SCX cartridge (Varian Bond Eluta™; 10 mL/500 mg), and the cartridge was washed with methanol (4×1.5 mL) and eluted with methanolic ammonia (2M, 3×1.5 mL). The solvent was evaporated under reduced pressure and the residue was purified by preparative thin layer chromatography on silica gel, eluting with CH$_2$Cl$_2$/MeOH/NM(aq.) (90:10:1), to give:

cis-(RS)-N-{4-[4-phenylmethyl-4-(dimethylamino)piperidin-1-yl]-phenylcyclohexyl}-3,5-bis(trifluoromethyl)-α-methylbenzeneacetamide (12 mg, 35%), $^1$H NMR (400 MHz, CD$_3$OD) δ 7.93 (2H, s) 7.86 (1H, s), 7.27–7.13 (10H, m), 4.01 (1H, q, J 7.0 Hz), 2.68 (2H, s), 2.58–2.34 (7H, m), 2.30 (6H, s), 1.84–1.64 (6H, m), 1.46 (3H, m), 1.42 (3H, d, J 7.0 Hz), and 1.25 (1H, m); m/z (ES$^+$) 660 (M+1); and trans-(RS)-N-{4-[4-phenylmethyl-4-(dimethylamino)piperidin-1-yl]-1-phenylcyclohexyl}-3,5-bis(trifluoromethyl)-α-methylbenzeneacetamide, (6 mg, 19%), $^1$H NMR (400 MHz, CD$_3$OD) δ 7.82 (1H, s) 7.74 (2H, s), 7.37–7.10 (10H, m), 3.77 (1H, q, J 7.0 Hz), 2.86 (1H, m), 2.66 (2H, s), 2.68–2.29 (6H, m), 2.27 (6H, s), 1.86–1.25 (10H, m), and 1.32 (3H, d, J 7.0 Hz); m/z (ES$^+$) 660 (M+1).

EXAMPLE 5

Cis-(RS)-α-Methyl-N-{4-[4-(phenylmethyl)-4-hydroxypiperidin-1-yl]-1-phenylcyclohexyl}-3,5-bis(trifluoromethyl)benzeneacetamide and Trans-(RS)-α-Methyl-N-{4-[4-(Phenylmethyl)-4-hydroxypiperidin-1-yl]-1-phenylcyclohexyl}-3,5-bis(trifluoromethylbenzeneacetamide Prepared from (RS)-α-methyl-N-(4-oxo-1-phenylcyclohexyl)-3,5-bis(trifluoromethyl)benzeneacetamide (Example 3) and 4-(phenylmethyl)piperidin-4-ol according to the method of Example 4:

Cis-(RS)-N-{4-[4-(Phenylmethyl)-4-hydroxypiperidin-1-yl]-1-phenylcyclohexyl}-3,5-bis(trifluoromethyl)-α-methylbenzeneacetamide; $^1$H NMR (400 MHz, CD$_3$OD) δ 1.28–1.38 (1H, m), 1.44 (3H, d, J 7.0 Hz), 1.50–1.54 (3H, m), 1.62–1.78 (6H, m), 1.84–1.87 (2H, m), 2.43–2.63 (8H, m), 2.75 (2H, s), 4.02 (1H, q, J 7.0 Hz), 7.11–7.29 (10H, m), 7.86 (2H, s) and 7.93 (1H, s); m/z (ES$^+$) 633 (M+1);

Trans-(RS)-N-{4-[4-(Phenylmethyl)-4-hydropiperidin-1-yl]-1-phenylcyclohexyl}-3,5-bis(trifluoroethyl)-α-methyl-benzeneacetamide; $^1$H NMR (400 MHz, CD$_3$OD) δ 1.32 (3H, d, J 7.0 Hz), 1.41–1.49 (4H, m), 1.53–1.59 (2H, m), 1.62–1.7 (2H, m), 1.75–1.90 (4H, m), 2.42–2.55 (4H, m), 2.64–2.74 (6H, m), 2.89–2.92 (1, m), 3.78 (1H, q, J 7.0 Hz), 7.13–7.29 (8H, m), 7.38–7.41 (21 m), 7.75 (2H, s) and 7.79 (1H, s); m/z (ES$^+$) 633 (M+1).

EXAMPLE 6

Cis-N-{4-[4-(4-Fluorophenyl)piperidin-1-yl]-1-phenylcyclohexyl}-3,5-bis(trifluoromethyl)benzeneacetamide Hydrochloride; and Trans-N-{4-[4-(4-Fluorophenyl)piperidin-1-yl]-1-phenylcyclohexyl}-3,5-bis(trifluoromethyl)benzeneacetamide Prepared from N-(4-oxo-1-phenylcyclohexyl)-3,5-bis(trifluoromethyl)benzeneacetamide (Example 2) and 4-(4-fluorophenyl)piperidine (Description 11) according to the method of Example 4:

Cis-N-{4-[4-(4-Fluorophenyl)piperidin-1-yl]-1-phenylcyclohexyl}-3,5-bis(trifluoromethyl) benzeneacetamide; $^1$H NMR (400 MHz, CDCl$_3$) δ 1.37–1.49 (2H, m), 1.69–1.87 (6H, m), 1.92–1.95 (2H, m), 2.23 (2H, t, J 10.7 Hz), 2.34–2.39 (R$^1$, m), 2.43–2.54 (3H, m), 3.04 (2H, br d, J 9.9 Hz), 3.67 (2H, s), 5.67 (1H, s), 6.95–7.01 (2H, m), 7.16–7.26 (3H, m), 7.27–7.34 (4H, m), 7.75 (2H, s) and 7.79 (1H, s); m/z (ES$^+$) 607 (M+1);

Trans-N-{4-[4-(4-Fluorophenyl)piperidin-1-yl]-1-phenylcyclohexyl}-3,5-bis(trifluoromethyl) benzeneacetamide Hydrochloride; m.p. 247–250° C., $^1$H NMR (400 MHz, DMSO-d$_6$) δ 1.42–1.55 (2H, m), 1.93–2.06 (9H, m), 2.77–2.80 (3H, m), 2.90–3.02 (2H, m), 3.49 (2H, br d, J 11.5 Hz), 3.60 (2H, s), 7.14 (2H, t, J 8.8 Hz), 7.21–7.25 (3H, m), 7.31 (2H, t, J 7.5 Hz), 7.49 (2H, d, J 7.9 Hz), 7.83 (2H, s), 7.94 (1H, s), 8.42 (1H, s) and 9.40 (1H, s); m/z (ES$^+$) 607 (M+1).

The following compounds were prepared as mixtures of cis- and trans-isomers from (RS)-α-methyl-N-(4-oxo-1-phenylcyclohexyl)-3,5-bis(trifluoromethyl)benzeneacetamide (Example 3) according to the method of Example 4, substituting a suitable amine for 4-(dimethylamino)-4-(phenylmethyl)piperidine.

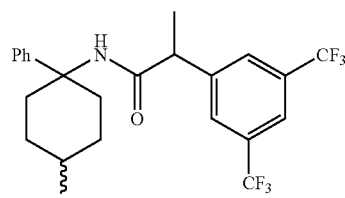

Cis-(RS) & Trans-(RS)

| Ex. | —NR$_2$ | Formula | M.W. | m/z (ES$^+$) (M + 1). |
|---|---|---|---|---|
| 7 | piperidine | C28H32F6N2O | 526 | 527 |
| 8 | NHMe | C24H26F6N2O | 472 | 473 |
| 9 | NMe2 | C25H28F6N2O | 486 | 487 |

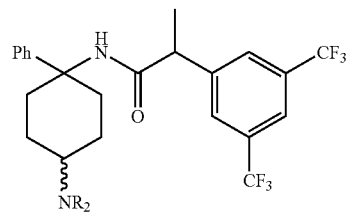

Cis-(RS) & Trans-(RS)

| Ex. | —NR$_2$ | Formula | M.W. | m/z (ES$^+$) (M + 1). |
|---|---|---|---|---|
| 10 | NHCH2Ph | C30H30F6N2O | 548 | 549 |
| 11 | morpholine | C27H30F6N2O2 | 528 | 529 |
| 12 | 4-hydroxypiperidine | C28H32F6N2O2 | 542 | 543 |
| 13 | 1,4-dioxa-8-azaspiro[4.5]decane | C30H34F6N2O3 | 584 | 585 |
| 14 | NHCH2-cyclopropyl | C27H30F6N2O | 512 | 513 |
| 15 | 4-(ethoxycarbonyl)piperidine | C31H36F6N2O3 | 598 | 599 |
| 16 | pyrrolidine | C27H30F6N2O | 512 | 513 |
| 17 | 4-(dimethylamino)piperidine | C30H37F6N3O | 569 | 570 |
| 18 | 4-methylpiperidine | C29H34F6N2O | 540 | 541 |
| 19 | 1,2,3,4-tetrahydroisoquinoline | C32H32F6N2O | 574 | 575 |
| 20 | 3-methylpiperidine | C29H34F6N2O | 540 | 541 |

-continued

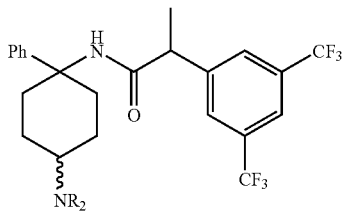

Cis-(RS) & Trans-(RS)

| Ex. | —NR₂ | Formula | M.W. | m/z (ES⁺) (M + 1). |
|---|---|---|---|---|
| 21 | N-methylpiperazinyl-benzisothiazole | C34H34F6N4OS | 660 | 661 |
| 22 | N-methylazepane | C29H34F6N2O | 540 | 541 |
| 23 | N-methyl-2-methylpyrrolidine | C28H32F6N2O | 526 | 527 |
| 24 | N-methylthiomorpholine | C27H30F6N2OS | 544 | 545 |
| 25 | N-methyl-azabicyclic | C29H32F6N2O | 538 | 539 |
| 26 | —NH—CH2CO2Me | C26H28F6N2O3 | 530 | 531 |
| 27 | N-methyl-4-cyclohexylpiperazine | C33H41F6N3O | 609 | 610 |
| 28 | N-methyl-3,3-dimethylpiperidine | C30H36F6N2O | 554 | 555 |

-continued

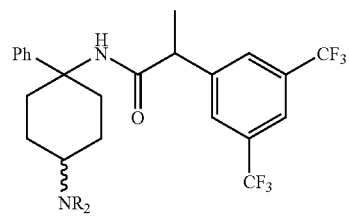

Cis-(RS) & Trans-(RS)

| Ex. | —NR₂ | Formula | M.W. | m/z (ES⁺) (M + 1). |
|---|---|---|---|---|
| 29 | N-methyl-3-(hydroxymethyl)piperidine | C29H34F6N2O2 | 556 | 557 |
| 30 | N-methyl-2,6-dimethylmorpholine | C29H34F6N2O2 | 556 | 557 |
| 31 | —NH-cyclopropyl | C26H28F6N2O | 498 | 499 |
| 32[1] | N-methyl-4-fluoro-4-benzylpiperidine | C35H37F7N2O | 634 | 635 |

[1] 4-Fluoro-A-(phenylmethyl)piperidine: WO 97/18202

EXAMPLE 33

Trans-(RS)-α-Methyl-N-{4-[(2-{[(1,1-dimethylethoxy)carbonyl]amino}ethyl)amino]-1-phenylcyclohexyl}-3,5-bis(trifluoromethyl)benzeneacetamide Sodium acetoxyborohydride (238 mg, 1.12 mmol) was added to a cooled (0° C.) solution of (RS)-α-methyl-N-(4-oxo-1-phenylcyclohexyl)-3,5-bis(trifluoromethyl)benzeneacetamide (Example 3, 394 mg, 0.86 mmol) and 1,1-dimethylethyl (2-aminoethyl)carbamate (166 mg, 1.03 mmol) in dichloroethane (15 mL) and the mixture was stirred at 0° C. for 1 hour, then at room temperature for 2 hours. Aqueous sodium hydroxide (1M, 30 mL) was added and the mixture was extracted with dichloromethane (3×30 mL). The combined organic fractions were dried (MgSO₄) and the solvent was evaporated under reduced pressure. The residue was recrystallised from isohexane/EtOAc (80:20, 10 mL). The solid was collected and recrystallised from isohexane/EtOAc (65:35, 12 mL). The solid was collected and dried in vacuo to give the title compound as a colorless solid (333 mg, 64%). m/z (ES⁺) 602 (M+1).

EXAMPLE 34

Trans-(RS)-N-{4-[4-(4-Fluorophenyl)piperidin-1-yl]-1-phenylcyclohexyl}-α-methyl-3,5-bis(trifluoromethyl)benzeneacetamide Hydrochloride Prepared from trans-4-[4-(4-fluorophenyl)piperidin-1-yl]-1-phenylcyclohexylamine (Description 22) and (RS)-α-methyl-3,5-bis(trifluoromethyl)benzeneacetic acid (Description 4) according to the method of Example 1. m/z (ES$^+$) 621 (M+1).

EXAMPLE 35

Trans-(RS)-N-{4-[4-(4-Fluorophenyl)piperidin-1-yl]-1-phenylcyclohexyl}-N,α-dimethyl-3,5-bis(trifluoromethyl)benzeneacetamide Hydrochloride Prepared from trans-4-[4-(4-fluorophenyl)piperidin-1-yl]-N-methyl-1-phenylcyclohexylamine (Description 24) and (RS)-α-methyl-3,5-bis(trifluoromethyl)benzeneacetic acid (Description 4) according to the method of Example 1. m/z (ES$^+$) 635 (M+1).

EXAMPLE 36

Trans-(RS)-N-{4-[4-(4-Fluorophenyl)piperidin-1-yl]-1-phenylcyclohexyl}-α,α-dimethyl-3,5-bis(trifluoromethyl)benzeneacetamide Hydrochloride Prepared from trans-4-[4-(4-fluorophenyl)piperidin-1-yl]-1-phenylcyclohexylamine (Description 22) and α,α-dimethyl-3,5-bis(trifluoromethyl)benzeneacetic acid, (Description 6) according to the method of Example 1. m/z (ES$^+$) 635 (M+1).

EXAMPLE 37

Trans-(RS)-N-{4-[4-(4-Fluorophenyl)piperidin-1-yl]-1-phenylcyclohexyl}-α-hydroxymethyl-3,5-bis(trifluoromethyl)benzeneacetamide Hydrochloride 1-(Dimethylaminopropyl)-3-ethylcarbodiimide hydrochloride (115 mg, 0.6 mmol) was added to a solution of trans-4-[4-(4-fluorophenyl)piperidin-1-yl]-1-phenylcyclohexylamine (Description 22, 50 mg, 0.14 mmol), lithium (RS)-α-(hydroxymethyl)-3,5-bis(trifluoromethyl)benzeneacetate (Description 8, 110 mg, 0.2 mmol), 1-hydroxybenzotriazole (81 mg, 0.6 mmol) and triethylamine (0.28 mL, 0.20 g, 2 mmol) in tetrahydrofuran (5 mL) and dimethylformamide (6 mL) and the mixture was stirred at room temperature for 48 hours. Aqueous sodium hydrogen carbonate (saturated, 30 mL) and water (30 mL) were added and the mixture was extracted with ethyl acetate (2×30 mL) The combined organic fractions were washed with water (3×20 mL) and brine (20 mL), dried (MgSO$_4$) and the solvent was evaporated under reduced pressure. The residue was purified by preparative thin layer chromatography on silica gel, eluting with CH$_2$Cl$_2$/MeOH/NH$_3$ (Aq.) (90:8:1), to give the title compound as a colorless solid (18 mg, 20%). m/z (ES$^+$) 637 (M+1).

EXAMPLE 38

Trans-(RS)-α-Methyl-N-[4-(4-oxopiperidin-1-yl)-1-phenylcyclohexyl]-3,5 bis(trifluoromethyl) benzeneacetamide Prepared from trans-1-(4-amino-4-phenylcyclohex-1-yl)piperidin-4-one dihydrochloride (Description 27) and (RS)-α-methyl-3,5-bis(trifluoromethyl)benzeneacetic acid (Description 4) according to the method of Example 1. $^1$H NMR (400 MHz, CDCl$_3$) δ 7.76 (1H, s), 7.65 (2H, s), 7.40–7.24 (5H, m), 5.49 (1H, s), 3.50 (1H, q, J 7.0 Hz), 2.75–2.72 (4H, m), 2.66–2.55 (3H, m), 2.39–2.36 (3H, m), 2.23–2.16 (2H, m), 1.75–1.69 (3H, m), 1.51–37 (2H, m), and 1.43 (3H, d, J 7.0 Hz).

EXAMPLE 39

Trans-(RS)-N-(4-Amino-1-phenylcyclohexyl)-α-methyl-3,5-bis(trifluoromethyl) benzeneacetamide Triphenylphosphine (1.5 g, 5.6 mmol) and water (2 mL) were added to a solution of crude trans-(RS)-N-(4-azido-1-phenylcyclohexyl)-α-methyl-3,5-bis(trifluoromethyl) benzeneacetamide [Description 30, from cis-(RS)-N-(4-methanesulfonyloxy-1-phenylcyclohexyl)-α-methyl-3,5-bis (trifluoromethyl)benzeneacetamide (Description 29, 1.5 g, 2.8 mmol)] in tetrahydrofuran (20 mL) and the mixture was heated under reflux for 22 hours. The mixture was cooled and the solvent was evaporated under reduced pressure. The residue was dissolved in ethyl acetate (100 mL) and washed with hydrochloric acid (1M, 100 mL) and brine (100 mL), dried (MgSO$_4$) and the solvent was evaporated under reduced pressure. The residue was purified by flash column chromatography on silica gel, eluting with CH$_2$Cl$_2$/MeOH/NH(Aq.), to give the title compound as a colorless solid (0.91 g, 71%). m/z (ES$^+$) 459 (M+1).

EXAMPLE 40

Trans-(RS)-α-Methyl-N-{1-phenyl-4-[(phenylmethyl)amino]cyclohexyl}-3,5-bis(trifluoromethyl) benzeneacetamide Sodium triacetoxyborohydride (0.72 g, 3.4 mmol) was added to a solution of trans-(RS)-N-(4-amino-1-phenylcyclohexyl)-α-methyl-3,5-bis(trifluoromethyl)benzeneacetamide (Example 39, 0.78 g, 1.7 mmol) and benzaldehyde (0.17 mL, 0.18 g, 1.7 mmol) in dichloroethane (25 mL) and the mixture was stirred at room temperature for 2 hours. The mixture was washed with aqueous sodium hydrogen carbonate (saturated) and water, dried (MgSO$_4$) and the solvent was evaporated under reduced pressure. The residue was purified by flash column chromatography on silica gel, eluting with EtOAc, to give the title compound (0.77 g, 83%). m/z (ES$^+$) 549 (M+1).

EXAMPLE 41

Trans-(RS)-α-Methyl-N-{4-[N-methyl(phenylmethyl)amino]-1-phenylcyclohexyl}-3,5-bis(trifluoromethyl)benzeneacetamide Sodium cyanoborohydride (148 mg, 2.4 mmol) was added to a solution of trans-(RS)-α-methyl-N-{1-phenyl-4-[(phenylmethyl)amino]cyclohexyl}-3,5-bis(trifluoromethyl) benzeneacetamide (Example 40, 650 mg, 1.2 mmol) and aqueous formaldehyde (37%, 0.44 mL, 6.0 mmol) in acetonitrile (20 mL) and the mixture was stirred at room temperature for 15 minutes. Acetic acid was added until the pH was neutral and the mixture was stirred at room temperature for 30 minutes, adding further acetic acid to maintain neutral pH. The solvent was evaporated under reduced pressure and aqueous sodium hydroxide (1M) and dichloromethane were added. The layers were separated and the aqueous layer was extracted dichloromethane (2×). The combined organic fractions were washed with water and brine, dried (MgSO$_4$) and the solvent was evaporated under reduced pressure to give the title compound (644 mg, 97%). m/z (ES$^+$) 563 (M+1).

EXAMPLE 42

Trans-(RS)-α-Methyl-N-(4-methylamino-1-phenylcyclohexyl)-3,5-bis(trifluoromethyl) benzeneacetamide Palladium hydroxide on carbon (20%, 10 mg) was added to a mixture of trans-(RS)-α-methyl-N-{(4-[N-methyl(phenylmethyl)amino]-1-phenylcyclohexyl}-3,5-bis(trifluoromethyl) benzeneacetamide (Example 41, 583 mg, 1.04 mmol), hydrochloric acid (1M, 2 mL) and acetic acid (2.5 mL) in ethyl acetate (25 mL) and the mixture was shaken under an atmosphere of hydrogen (40 psi) for 18 hours. The mixture was filtered through a glass fibre pad, washing with ethyl acetate, and the solvent was evaporated under reduced pressure. The residue was dissolved in ethyl acetate and aqueous sodium carbonate (10%) was added. The layers were separated and the aqueous layer was extracted with ethyl acetate (2×). The combined organic fractions were washed with brine, dried (MgSO$_4$) and the solvent was evaporated under reduced pressure. The residue was purified by flash column chromatography on silica gel, eluting with CH$_2$Cl$_2$/MeOH/NH$_3$ (Aq.) (95:5:0.5), to give the title compound (415 mg, 84%). m/z (ES$^+$) 473 (M+1).

EXAMPLE 43

Trans-(RS)-N-[4-({1-Oxo-2-[3,5-bis(trifluoromethyl)phenyl]propyl}amino)-4-phenylcyclohexyl]-N-(phenylmethyl)glycine Methyl Ester Methyl bromoacetate (28 μl, 0.31 mmol) was added to a mixture of trans-(RS)-α-methyl-N-{1-phenyl-4-[(phenylmethyl)amino]cyclohexyl}]-3,5-bis(trifluoromethyl)benzeneacetamide (Example 40, 84 mg, 0.15 mmol) and potassium carbonate (207 mg, 1.5 mmol) in dimethylformamide (2 mL) and the mixture was stirred at 100° C. overnight. The mixture was cooled, poured into ethyl acetate (25 mL) and washed with water (25 mL) and brine (25 mL), dried (MgSO$_4$) and the solvent was evaporated under reduced pressure. The residue was purified by flash column chromatography on silica gel, eluting with isohexane/EtOAc (80:20 increasing to 0:100) to give the title compound (19 mg, 20%). m/z (ES$^+$) 621 (M+1).

EXAMPLE 44

Trans-(RS)-N-Methyl-N-[4-({1-oxo-2-[3,5-bis(trifluoromethyl)phenyl]propyl}amino)-4-phenylcyclohexyl]glycine Methyl Ester Prepared from trans-(RS)-α-methyl-N-(4-methylamino-1-phenylcyclohexyl)-3,5-bis(trifluoromethyl)benzeneacetamide (Example 42) according to the method of Example 43. m/z (ES$^+$) 545 (M+1).

EXAMPLE 45

Trans-(RS)-α-Methyl-N-{4-[2-(dimethylamino)acetylamino]-1-phenylcyclohexyl}-3,5-bis(trifluoromethyl)benzeneacetamide Prepared from trans-(RS)-N-(4-amino-1-phenylcyclohexyl)-α-methyl-3,5-bis(trifluoromethyl)benzeneacetamide (Example 39) according to the method of Example 37. m/z (ES$^+$) 544 (M+1).

EXAMPLE 46

Trans-(RS)-N-(4-Aminomethyl-1-phenylcyclohexyl)-α-methyl-3,5-bis(trifluoromethyl) benzeneacetamide Hydrochloride Raney nickel (20 mg) was added to a solution of trans-(RS)-N-(4-cyano-1-phenylcyclohexyl)-α-methyl-3,5-bis(trifluoromethyl)benzeneacetamide (Description 31, 146 mg, 0.31 mmol) in methanolic ammonia (2M, 5 mL) and the mixture was shaken under an atmosphere of hydrogen (40 psi) for 2 hours. The mixture was filtered through Celite™, washing with ethanol, and the solvent was evaporated under reduced pressure. The residue was dissolved in methanol (1.5 mL) and poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure and the residue was dissolved in EtOAc/isohexane (3:1, 4 mL). Ethereal hydrogen chloride (1M, 0.5 mL) was added and the solid was collected and dried in vacuo to give the title compound as a colorless solid (101 mg, 69%); m/z (ES$^+$) 473 (M+1).

EXAMPLE 47

Trans-(RS)-α-Methyl-N-(4-dimethylaminomethyl-1-phenylcyclohexyl)-3,5-bis(trifluoromethyl)benzeneacetamide Hydrochloride Prepared from trans-(RS)-N-(4-aminomethyl-1-phenylcyclohexyl)-α-methyl-3,5-bis(trifluoromethyl)benzeneacetamide Example 46) according to the method of Example 41. m/z (ES$^+$) 501 (M+1).

EXAMPLE 48

Trans-(RS)-α-Methyl-N-[4-(piperidin-1-yl)methyl-1-phenylcyclohexyl]-3,5-bis(trifluoromethyl)benzeneacetamide 1,5-Dibromopentane (9 μl, 16 mg, 0.07 mmol) was added to a mixture of trans-(RS)-N-(4-aminomethyl-1-phenylcyclohexyl)-α-methyl-3,5-bis(trifluoromethyl)benzeneacetamide hydrochloride (Example 46, 35 mg, 0.07 mmol), potassium carbonate (36 mg, 0.26 mmol) and sodium iodide (5 mg, 0.03 mmol) in dimethylformamide (10 mL) and the mixture was stirred at 100° C. for 16 hours. Ethyl acetate and water were added and the layers were separated. The aqueous layer was extracted with ethyl acetate and the combined organic fractions were washed with water and brine, dried (MgSO$_4$) and the solvent was evaporated under reduced pressure. The residue was dissolved in methanol (2 mL) and poured onto an SCX cartridge (Varian Bond Elut™; 10 mL 500 mg). The cartridge was washed with methanol (4×2 mL), then eluted with methanolic ammonia (2M, 2×2 mL). The solvent was evaporated under reduced pressure and the residue was purified by preparative thin layer chromatography on silica gel, eluting with CH$_2$Cl$_2$/MeOH/Et$_3$N (95:5:1), to give the title compound as a colorless solid (10 mg, 28%). m/z (ES$^+$) 541 (M+1).

EXAMPLE 49

Trans-(RS)-4-[4-(4-fluorophenyl)piperidin-1-yl]-1-phenyl-N-{2-[3,5-bis(trifluoromethyl)phenyl]propyl}cyclohexylamine Dihydrochloride Borane tetrahydrofuran complex (1M in tetrahydrofuran, 1 mL, 1 mmol) was added to a solution of trans-(RS)-N-{4-[4-(4-fluorophenyl)piperidin-1-yl]-1-phenylcyclohexyl}-α-methyl-3,5-bis(trifluoromethyl)benzeneacetamide (Example 34, 100 mg, 0.16 mmol), in tetrahydrofuran (5 mL), and the mixture was stirred at room temperature for 2 hours, then under reflux for 16 hours. The mixture was cooled and methanol (5 mL) was added slowly. The mixture was heated under reflux for 10 minutes, cooled to room temperature and the solvent was evaporated under reduced pressure. Methanol (5 mL) was added and the solvent was evaporated under reduced pressure. Hydrochloric acid (1M) was added and the mixture was stirred at room temperature for 1 hour. The mixture was basified with aqueous sodium hydroxide (4M) and extracted with ethyl acetate (2×25 mL). The combined organic fractions were washed with brine, dried (MgSO$_4$) and the solvent was evaporated under reduced pressure. The residue was purified by flash column chromatography on silica gel, eluting with CH$_2$Cl$_2$/MeOH/NH$_3$ (Aq.) (120:8:1). The residue was dissolved in ethanol and ethereal hydrogen chloride (1M) was added. The solvent was evaporated under reduced pressure to give the title compound as a colorless solid (19.5 mg, 18%). m/z (ES$^+$) 607 (M+1).

EXAMPLE 50

(S)-α-Methyl-N-(4-oxo-1-phenylcyclohexyl)-3,5-bis(trifluoromethyl)benzeneacetamide Bis(2-oxo-3-oxazolidinyl)phosphinic chloride (672 mg, 2.64 mmol) was added to a solution of (S)-α-methyl-3,5-bis(trifluoromethyl)benzeneacetic acid (Description 40, 500 mg, 1.76 mmol) and pyridine (284 μL, 3.52 mmol) in dichloromethane (15 mL) and the mixture was stirred at room temperature for 5 minutes. 4-Oxo-1-phenylcyclohexylamine hydrochloride (Description 18, 500 mg, 2.64 mmol) was added and the mixture was stirred at room temperature for 48 hours. The mixture was diluted with dichloromethane and washed with saturated aqueous sodium carbonate. The organic layer was dried (MgSO$_4$) and the solvent was evaporated under reduced pressure. The residue was purified by flash column chromatography on silica gel, eluting with isohexane:EtOAc (65:35). The residue was crystallised twice from propan-2-ol/water (50:50, 20 mL) and the solid was collected and dried in vacuo to give the title compound as a colorless solid (200 mg, 37%). $^1$H NMR (400 MHz, CDCl$_3$) δ 7.80 (1H, s), 7.72 (2H, s), 7.29 (5H m), 5.71 (1H, s), 3.70 (1H, q, J 7.0 Hz), 2.81 (1H, m), 2.64 (1H, m), 2.47–2.04 (5H, m), 1.60 (1H, m), and 1.52 (3H, d, J 7.0 Hz). e.e. [Determined by chiral HPLC (Chiralcel OD-H 250×4.6 mm i.d.; isohexane/EtOH (96:4); 1 mL/min; 210 nm]>99%.

EXAMPLE 51

(R)-α-Methyl-N-(4-oxo-1-phenylcyclohexyl)-3,5-bis(trifluoromethyl)benzeneacetamide Prepared from (R)-α-methyl-3,5-bis(trifluoromethyl)benzeneacetic acid (Description 41) and 4-oxo-1-phenylcyclohexylamine hydrochloride (Description 18) according to the method of Example 50. $^1$H NMR (400 MHz, CDCl$_3$) δ 7.80 (1H, s), 7.72 (2H, s), 7.29 (5H, m), 5.71 (1H, s), 3.70 (1H, q, J 7.0 Hz), 2.81 (1H, m), 2.64 (1H, m), 2.47–2.04 (5H, m), 1.60 (1H, m), and 1.52 (3H, d, J 7.0 Hz). e.e. [Determined by chiral HPLC (Chiralcel OD-H 250×4.6 mm i.d.; isohexane/EtOH (96:4); 1 mL/min; 210 nm]>99%.

EXAMPLE 52

(RS)-N-(4-Oxo-1-phenylcyclohexyl)-α-(2-propenyl)-3,5-bis(trifluoromethyl)benzeneacetamide Prepared from (RS)-α-(2-propenyl)-3,5-bis(trifluoromethyl)benzeneacetic acid (Description 35) and 4-oxo-1-phenylcyclohexylamine hydrochloride (Description 18) according to the method of Example 1. $^1$H NMR (400 MHz, CDCl$_3$) δ 7.80 (1H, s), 7.73 (2H, s), 7.35–7.2 (5H, m), 5.80 (1H, br s), 5.75–5.63 (1H, m), 5.13–5.05 (2H, m), 3.56 (1H, dd, J 7, 6 Hz), 2.90–2.80 (2H, m), 2.65–2.55 (1H, m), and 2.52–2.30 (7H, m).

EXAMPLE 53

(RS)-α-Methyl-N-[1-(2-Fluorophenyl)-4-oxocyclohexyl]-3,5-bis(trifluoromethyl)benzeneacetamide Prepared from (RS)-α-methyl-3,5-bis(trifluoromethyl)benzeneacetic acid (Description 4) and 1-(2-fluorophenyl)-4-oxocyclohexylamine hydrochloride (Description 180) according to the method of Example 1. $^1$H NMR (360 MHz, CDCl$_3$) δ 7.79 (1H, s), 7.68 (2H, s), 7.40–7.35 (1H, m), 7.27–7.21 (1H, m), 7.14–7.10 (1H, m), 6.93–6.86 (1H, m), 5.95 (1H, s), 3.71 (1H, q J 7.0 Hz), 3.08–3.00 (1H, m), 2.86–2.78 (1H, m), 2.56–2.20 (6H, m), and 1.49 (3H, d, J 7.0 Hz).

EXAMPLE 54

(RS)-α-Methyl-N-[1-(3-Fluorophenyl)-4-oxocyclohexyl]-3,5-bis(trifluoromethyl)benzeneacetamide Prepared from (RS)-α-methyl-3,5-bis(trifluoromethyl)benzeneacetic acid (Description 4) and 1-(3-fluorophenyl)-4-oxocyclohexylamine hydrochloride (Description 181) according to the method of Example 1. $^1$H NMR (360 MHz, CDCl$_3$) δ 7.81 (1H, s), 7.73 (2H, s), 7.29–7.24 (1H, m), 7.06–7.03 (1H, m), 6.97–6.94 (2H, m), 5.78 (1H, s), 3.72 (1H, q, J 7.0 Hz), 2.81–2.75 (1H, m), 2.63–2.57 (1×, m), 2.44–2.24 (6H, m), and 1.53 (3H, d, J 7.0 Hz).

EXAMPLE 55

(RS)-α-Methyl-N-[1-(4-Fluorophenyl)-4-oxocyclohexyl]-3,5-bis(trifluoromethyl)benzeneacetamide Prepared from (RS)-α-methyl-3,5-bis(trifluoromethyl)benzeneacetic acid (Description 4) and 1-(4-fluorophenyl)-4-oxocyclohexylamine hydrochloride (Description 182) according to the method of Example 1. $^1$H NMR (400 MHz, CDCl$_3$) δ 7.81 (1H, s), 7.71 (2H, s), 7.29–7.25 (2H, m), 7.01–6.96 (2H, m), 5.73 (1H, s), 3.69 (1H, q, J 7.0 Hz), 2.80–2.77 (1H, m), 2.62–2.57 (1H, m), 2.44–2.28 (6H, m), and 1.51 (3H, d, J 7.0 Hz).

EXAMPLE 56

(RS)-α-Methyl-N-[4-oxo-1-(2-pyridyl)cyclohexyl]-3,5-bis(trifluoromethyl)benzeneacetamide 4-Isocyanato-4-(2-pyridyl)cyclohexan-1-one (Description 185, 327 mg, 1.51 mmol) was dissolved in hydrochloric acid (5M, 5 mL) and the mixture was heated under reflux for 24 hours. Further hydrochloric acid (5M, 2 mL) was added and the mixture was heated under reflux for 24 hours. The mixture was cooled and the solvent was evaporated under reduced pressure. Toluene (2×5 mL) was added and evaporated under reduced pressure and the residue was suspended in dichloromethane (10 mL). (RS)-α-Methyl-3,5-bis(trifluoromethyl)benzeneacetyl chloride [prepared from (RS)-methyl-3,5-bis(trifluoromethyl)benzeneacetic acid (Description 4, 430 mg, 1.5 mmol), oxalyl chloride (0.65 mL, 7.45 mmol) and dimethylformamide (2 drops) in dichloromethane (10 mL), followed by evaporation of solvent under reduced pressure] in dichloromethane (10 mL) then pyridine (1 mL) were added and the mixture was stirred at room temperature for 18 hours. Aqueous potassium carbonate (10%, 50 mL) was added and the mixture was extracted with dichloromethane (2×50 mL). The combined organic fractions were dried (Na$_2$SO$_4$) and the solvent was evaporated under reduced pressure. The residue was purified by flash column chromatography on silica gel, eluting with CH$_2$Cl$_2$/MeOH/NH$_3$(Aq.) (97.5:2.5:0.25), to give the title compound (140 mg, 20%). m/z (ES$^+$) 459 (M+1).

EXAMPLE 57

α,α-Dimethyl-N-[4-oxo-1-phenylcyclohexyl]-3,5-bis(trifluoromethyl)benzeneacetamide Oxalyl chloride (5.8 mL, 66.6 mmol) was added slowly to a solution of α,α-dimethyl-3,5-bis(trifluoromethyl)benzeneacetic acid (Description 6, 10 g, 33.3 mmol) and dimethylformamide (1 drop) in dichloromethane (100 mL) and. the mixture was stirred at room temperature for 24 hours. The solvent was evaporated under reduced pressure and the residue was dissolved in dichloromethane (20 mL) and added slowly to a solution of 4-oxo-1-phenylcyclohexylamine hydrochloride (Description 18, 8.2 g, 43.4 mmol) and pyridine (5.7 mL, 66.3 mmol) in dichloromethane (100 mL). The mixture was stirred at room temperature for 24 hours, then hydrochloric acid (2M, 100 mL) was added. The layers were separated and the aqueous layer was extracted with dichloromethane. The combined organic fractions were dried (MgSO$_4$) and the solvent was evaporated under reduced pressure. The residue was purified by flash column chromatograph on silica gel, eluting with isohexane:EtOAc (75:25), to give the title compound as a colorless solid (6.5 g, 41%). $^1$H NMR (400 MHz, CDCl$_3$) δ 7.83 (1H, s), 7.77 (2H, s), 7.35–7.26 (5H, m), 5.44 (1H, s), 2.70–2.66 (2H, m), 2.40–2.30 (6H, m), and 1.62 (6H, s).

EXAMPLE 58

(1R*,3S*)-α,α-Dimethyl-N-[3-fluoro-4-oxo-7-phenylcyclohexyl]-3,5-bis(trifluoromethyl)benzeneacetamide A solution of (RS)-α,α-dimethyl-N-{1-phenyl-4-[(trimethylsilyl)oxy]cyclohex-3-enyl}-3,5-bis(trifluoromethyl)benzeneacetamide (Description 204, 1.0 g, 1.78 mmol) in acetonitrile (10 mL) was added via a syringe pump over 1 hour to a solution of 1-chloromethyl-4-fluoro-1,4-diazoniabicyclo[2.2.2]octane bis(tetrafluoroborate) (1.83 g, 5.34 mmol) in acetonitrile (20 mL) and the mixture was stirred at room temperature for 30 minutes. The solvent was evaporated under reduced pressure and the residue was purified by flash column chromatography on silica gel, eluting with isohexane:EtOAc (75:25 increasing to 70:30), to give the title compound as a colorless foam (0.75 g, 83%). $^1$H NMR (400 MHz, CDCl$_3$) δ 7.85 (1H, s), 7.77 (2H, s), 7.34–7.26 (3H, m), 7.20–7.18 (2H, m), 5.53 (1H, s), 4.94 (1H, dq, J 47.7, 6.3 Hz), 3.46–3.40 (1H, m), 2.78–2.72 (1H, m), 2.54–2.49 (1H, m), 2.43–2.27 (2H, m), 2.17–2.09 (1H, m), and 1.66 (6H, d), J 11.0 Hz).

EXAMPLE 59

Cis-(RS)- and Trans-(RS)-α,α-Dimethyl-N-(3-hydroxy-4-oxo-1-phenylcyclohexyl)-3,5-bis(trifluoromethyl)benzeneacetamide Osmium tetroxide (2.5% in t-butanol, 0.25 mL) was added to a mixture of (RS)-α,α-dimethyl-N-{1-phenyl-4-[(trimethylsilyl)oxy]cyclohex-3-enyl}-3,5-bis(trifluoromethyl) benzeneacetamide (Description 204, 1.81 g, 3.33 mmol) and 4-methylmorpholine-N-oxide (487 mg, 4.16 mmol) in tetrahydrofuran (20 mL) and water (8 mL) and the mixture was stirred at room temperature for 24 hours. Further 4-methylmorpholine-N-oxide (100 mg) and tetrahydrofuran (8 mL) were added and the mixture was stirred at room temperature for 4 hours. Further osmium tetroxide (2.5% in t-butanol, 0.25 mL) was added and the mixture was stirred at room temperature for 2 hours. The solvent was evaporated under reduced pressure and toluene (2×30 mL) was added and evaporated under reduced pressure. The residue was purified by flash column chromatography on silica gel, eluting with isohexane/EtOAc (70:30 increasing to 50:50). The residue was further purified by flash column chromatography on silica gel, eluting with CH$_2$Cl$_2$/EtOAc (85:15), to give the title compound as a 4:1 mixture of diastereoisomers. $^1$H NMR (400 MHz, CDCl$_3$ major diastereoisomer) δ 7.85 (1H, s), 7.78 (2H, s), 7.35–7.15 (5H, m), 5.53 (1H, br s), 4.14 (1H, dd, J 12, 6.5 Hz), 3.48 (1H, br s), 3.15–3.05 (1H, m), 3.05–2.95 (1H, m), 2.58 (1H, br d, J 13 Hz), 2.45 (1H, dt, J 14, 5.5 Hz), 2.16 (1H, dt, J 14, 4.6 Hz), 1.95 (1H, dd, J 13.5, 12.5 Hz), 1.64 (3H, s), and 1.63 (3H, s).

The following compounds were prepared according to the method of Example 33, substituting a suitable ketone for (RS)-α-methyl-N-(4-oxo-1-phenylcyclohexyl)-3,5-bis(trifluoromethyl)benzeneacetamide and a suitable amine for 1,1-dimethylethyl (2-aminoethyl)carbamate, followed by separation of diastereoisomers by chromatography on silica gel.

| Ex. | X | A | B | —NR$_2$ | Stereochemistry | Formula | M.W. | m/z (ES$^+$) (M + 1) |
|---|---|---|---|---|---|---|---|---|
| 60 | H | Me | H | 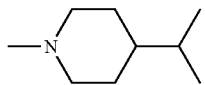 | Cis-(2R, 2'S)- Cis-(2S, 2'S)- Trans-(2R, 2'S)- Trans-(2S, 2'S)- | $C_{28}H_{32}F_6N_2O_2$ | 542 | 543 |
| 61[1] | H | Me | H | 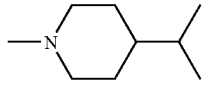 | Cis-(RS)- | $C_{31}H_{38}F_6N_2O$ | 568 | 569 |
| 62[1] | H | Me | H | 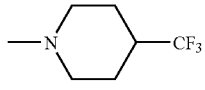 | Trans-(RS)- | $C_{31}H_{38}F_6N_2O$ | 568 | 569 |
| 63 | H | Me | H | 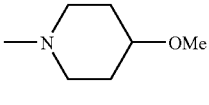 | Trans-(RS)- | $C_{29}H_{31}F_9N_2O$ | 594 | 595 |
| 64 | H | Me | H | 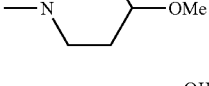 | Cis-(RS)- | $C_{29}H_{34}F_6N_2O_2$ | 556 | 557 |
| 65 | H | Me | H | 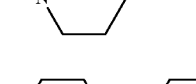 | Trans-(RS)- | $C_{29}H_{34}F_6N_2O_2$ | 556 | 557 |
| 66 | H | Me | H | 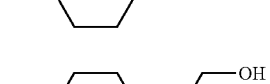 | Cis-(RS)- Trans-(RS)- | $C_{29}H_{34}F_6N_2O_2$ | 556 | 557 |
| 67 | H | Me | H | 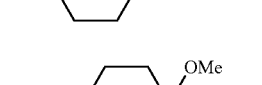 | Cis-(RS)- | $C_{30}H_{36}F_6N_2O_2$ | 570 | 571 |
| 68 | H | Me | H | 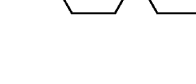 | Trans-(RS)- | $C_{30}H_{36}F_6N_2O_2$ | 570 | 571 |
| 69 | H | Me | H |  | Cis-RS)- Trans-(RS)- | $C_{31}H_{38}F_6N_2O_2$ | 584 | 585 |

-continued

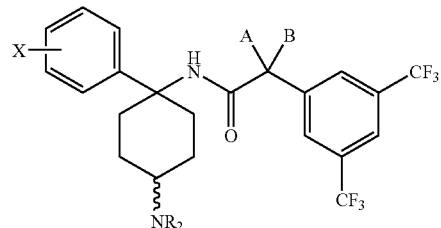

| Ex. | X | A | B | —NR₂ | Stereochemistry | Formula | M.W. | m/z (ES⁺) (M + 1) |
|---|---|---|---|---|---|---|---|---|
| 70 | H | Me | H | N-piperidine with OMe and Et at 4-position | Trans-(RS)- | $C_{31}H_{38}F_6N_2O_2$ | 584 | 585 |
| 71 | 3-F | Me | H | N-piperidine with CH₂Ph and OH at 4-position | Trans-(RS)- | $C_{35}H_{37}F_7N_2O_2$ | 650 | 651 |
| 72 | H | Me | H | N-piperidine with Me and CO₂CH₂Ph at 4-position | Trans-(RS)- | $C_{37}H_{40}F_6N_2O_3$ | 674 | 675 |
| 73 | H | Me | H | N-piperidine with Me and CO₂Et at 3-position (R)- | Trans-(RR) | $C_{32}H_{38}F_6N_2O_3$ | 612 | 613 |
| 74 | H | Me | H | N-piperidine with Me at 4 and OH at 3 | Cis-(2R*, 3'R*, 4'S*)- Cis-(2S*, 3'R*, 4'S*)- | $C_{29}H_{34}F_6N_2O_2$ | 556 | 557 |
| 75 | H | Me | H | N-piperidine with Me at 4 and OH at 3 | Trans-(2R* 4'S*)- Trans-(2S*, 3'R*, 4'S*)-, 3'R*, | $C_{29}H_{34}F_6N_2O_2$ | 556 | 557 |
| 76 | H | Me | H | N-piperidine with Me at 4 and OMe at 3 | Trans-(2R*, 3'R*, 4'S*)- Trans-(2S*, 3'R*, 4'S*)- | $C_{30}H_{36}F_6N_2O_2$ | 570 | 571 |
| 77 | H | Me | H | N-piperidine with Me at 4 and F at 3 | Trans-(2R*, 3'R*, 4'S*)- Trans-(2S*, 3'R*, 4'S*)- | $C_{29}H_{33}F_7N_2O$ | 558 | 559 |
| 78 | H | Me | H | N-piperidine with OH at 3 | Cis-(2R*, 3'R*)- Cis-(2S*, 3'R*)- Trans-(2R*, 3'R*)- Trans-(2S*, 3'R*)- | $C_{28}H_{32}F_6N_2O_2$ | 542 | 543 |
| 79 | H | Me | H | N-piperidine with CO₂Et at 3 | Cis-(2R, 3'R)- Cis-(2S, 3'R)- Trans-(2R, 3'R)- Trans-(2S, 3'R)- | $C_{32}H_{38}F_6N_2O_3$ | 612 | 613 |

-continued

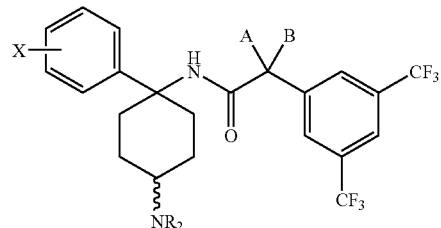

| Ex. | X | A | B | —NR₂ | Stereochemistry | Formula | M.W. | m/z (ES⁺) (M + 1). |
|---|---|---|---|---|---|---|---|---|
| 80 | H | Me | H | (octahydrofuro[3,2-c]pyridine, N-Me) | Trans-(2R*, 3aR*, 7aR*)- Trans-(2S*, 3aR*, 7aR*)- | $C_{30}H_{34}F_6N_2O_2$ | 568 | 569 |
| 81 | H | Me | H | (2-oxa-7-azaspiro[3.5]nonane, N-Me) | Trans-(RS) | $C_{30}H_{34}F_6N_2O_2$ | 568 | 569 |
| 82 | H | Me | H | (1-oxa-8-azaspiro[4.5]decane, N-Me) | Cis-(RS)- | $C_{31}H_{36}F_6N_2O_2$ | 582 | 583 |
| 83 | H | Me | H | (1-oxa-8-azaspiro[4.5]decane, N-Me) | Trans-(RS)- | $C_{31}H_{36}F_6N_2O_2$ | 582 | 583 |
| 84 | 2-F | Me | H | (1-oxa-8-azaspiro[4.5]decane, N-Me) | Trans-(RS)- | $C_{31}H_{35}F_7N_2O_2$ | 600 | 601 |
| 85 | 3-F | Me | H | (1-oxa-8-azaspiro[4.5]decane, N-Me) | Trans-(RS)- | $C_{31}H_{35}F_7N_2O_2$ | 600 | 601 |
| 86 | 4-F | Me | H | (1-oxa-8-azaspiro[4.5]decane, N-Me) | Cis-(RS)- | $C_{31}H_{35}F_7N_2O_2$ | 600 | 601 |
| 87 | 4-F | Me | H | (1-oxa-8-azaspiro[4.5]decane, N-Me) | Trans-(RS)- | $C_{31}H_{35}F_7N_2O_2$ | 600 | 601 |
| 88 | H | Me | H | (2,2-dimethyl-1-oxa-8-azaspiro[4.5]decane, N-Me) | Cis-(RS)- | $C_{33}H_{40}F_6N_2O_2$ | 610 | 611 |
| 89 | H | Me | H | (2,2-dimethyl-1-oxa-8-azaspiro[4.5]decane, N-Me) | Trans-(RS)- | $C_{33}H_{40}F_6N_2O_2$ | 610 | 611 |
| 90 | H | Me | H | (1-oxa-8-azaspiro[4.5]decan-2-one, N-Me) | Cis-(RS)- Trans-(RS)- | $C_{31}H_{34}F_6N_2O_3$ | 596 | 597 |
| 91 | H | Me | H | (2-oxa-8-azaspiro[4.5]decane, N-Me) | Cis-(RS)- | $C_{31}H_{36}F_6N_2O_2$ | 582 | 583 |

-continued
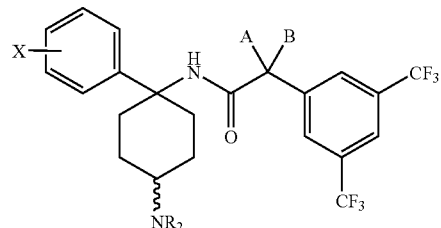
| Ex. | X | A | B | —NR₂ | Stereochemistry | Formula | M.W. | m/z (ES⁺) (M + 1). |
|---|---|---|---|---|---|---|---|---|
| 92 | H | Me | H | | Trans-(RS)- | $C_{31}H_{36}F_6N_2O_2$ | 582 | 583 |
| 93 | H | Allyl | H | | Cis-(RS)-<br>Trans-(RS)- | $C_{33}H_{38}F_6N_2O_2$ | 608 | 609 |
| 94 | H | Me | Me | | Trans- | $C_{32}H_{38}F_6N_2O_2$ | 596 | 597 |
| 95 | 2-F | Me | H | | Trans-(RS)- | $C_{31}H_{35}F_7N_2O_2$ | 600 | 601 |
| 96 | 3-F | Me | H | | Trans-(RS)- | $C_{31}H_{35}F_7N_2O_2$ | 600 | 601 |
| 97 | 4-F | Me | H | | Trans-(RS)- | $C_{31}H_{35}F_7N_2O_2$ | 600 | 601 |
| 98 | H | Me | H | | Cis-(RS)- | $C_{33}H_{40}F_6N_2O_2$ | 610 | 611 |
| 99 | H | Me | H | | Trans-(RS)- | $C_{33}H_{40}F_6N_2O_2$ | 610 | 611 |
| 100 | 3-F | Me | H | | Trans-(RS))- | $C_{33}H_{39}F_7N_2O_2$ | 628 | 629 |
| 101 | H | Me | Me | | Trans- | $C_{34}H_{42}F_6N_2O_2$ | 624 | 625 |
| 102 | H | Me | H | | Trans-(RS)- | $C_{33}H_{40}F_6N_2O_2$ | 610 | 611 |

-continued

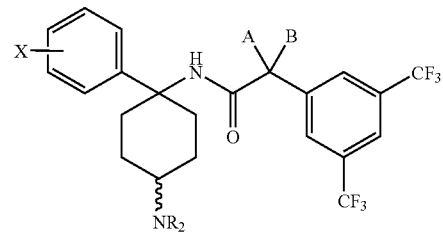

| Ex. | X | A | B | —NR₂ | Stereochemistry | Formula | M.W. | m/z (ES⁺) (M + 1). |
|---|---|---|---|---|---|---|---|---|
| 103 | H | Me | H | (N-piperidinyl spiro-tetrahydrofuran with HO) | Cis-(2R*, 4'S*)- Cis-(2S*, 4'S*)- | $C_{31}H_{36}F_6N_2O_3$ | 598 | 599 |
| 104 | H | Me | H | (N-piperidinyl spiro-tetrahydrofuran with HO) | Trans-(2R*, 4'S*)- Trans-(2S*, 4'S*)- | $C_{31}H_{36}F_6N_2O_3$ | 598 | 599 |
| 105 | H | Me | H | (N-piperidinyl spiro-tetrahydrofuran with OH) | Cis-(2R*, 5'R*, 6'R*)- Cis-(2S*, 5'R*, 6'R*)- | $C_{31}H_{36}F_6N_2O_3$ | 598 | 599 |
| 106 | H | Me | H | (N-piperidinyl spiro-tetrahydrofuran with OH) | Trans-(2R*, 5'R*, 6'R*)- Trans-(2S*, 5'R*, 6'R*)- | $C_{31}H_{36}F_6N_2O_3$ | 598 | 599 |
| 107 | H | Me | H | (N-piperidinyl spiro-tetrahydrofuran with OH) | Cis-(2R*, 5'R*, 6'S*)- Cis-(2S*, 5'R*, 6'S*)- | $C_{31}H_{36}F_6N_2O_3$ | 598 | 599 |
| 108 | H | Me | H | (N-piperidinyl spiro-tetrahydrofuran with OH) | Trans-(2R*, 5'R*, 6'S*)- Trans-(2S*, 5'R*, 6'S*)- | $C_{31}H_{36}F_6N_2O_3$ | 598 | 599 |
| 109 | H | Me | H | (N-piperidinyl spiro-tetrahydrofuran with F, F) | Trans-(2R*, 5'R*)- Trans-(2S*, 5'R*)- | $C_{31}H_{34}F_8N_2O_2$ | 618 | 619 |
| 110 | H | Me | H | (N-piperidinyl spiro-γ-butyrolactone) | Cis-(RS)- | $C_{31}H_{34}F_6N_2O_3$ | 596 | 597 |
| 111 | H | Me | H | (N-piperidinyl spiro-γ-butyrolactone) | Trans-(RS)- | $C_{31}H_{34}F_6N_2O_3$ | 596 | 597 |

-continued

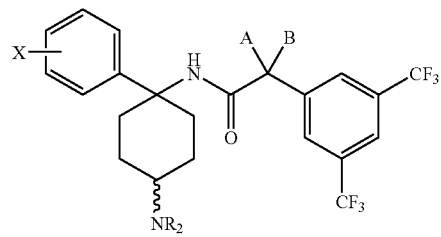

| Ex. | X | A | B | —NR₂ | Stereochemistry | Formula | M.W. | m/z (ES⁺) (M + 1). |
|---|---|---|---|---|---|---|---|---|
| 112 | H | Me | H | N-methyl-piperidine-spiro-γ-butyrolactone | Cis-(R)- | $C_{31}H_{34}F_6N_2O_3$ | 596 | 597 |
| 113 | H | Me | H | N-methyl-piperidine-spiro-γ-butyrolactone | Trans-(R)- | $C_{31}H_{34}F_6N_2O_3$ | 596 | 597 |
| 114 | H | Me | H | N-methyl-piperidine-spiro-dimethyl lactone | Cis-(RS)- | $C_{33}H_{38}F_6N_2O_3$ | 624 | 625 |
| 115 | H | Me | H | N-methyl-piperidine-spiro-dimethyl lactone | Trans-(RS)- | $C_{33}H_{38}F_6N_2O_3$ | 624 | 625 |
| 116 | H | Me | H | N-methyl-piperidine-spiro-hydroxy-lactone | Cis-(2R*, 5'R*, 6'R*)- Cis-(2S*, 5'R*, 6'R*)- | $C_{31}H_{34}F_6N_2O_4$ | 612 | 613 |
| 117 | H | Me | H | N-methyl-piperidine-spiro-hydroxy-lactone | Trans-(2R*, 5'R*, 6'R*)- Trans-(2S*, 5'R*, 6'R*)- | $C_{31}H_{34}F_6N_2O_4$ | 612 | 613 |
| 118 | H | Me | H | N-methyl-piperidine-spiro-hydroxy-lactone | Cis-(2R*, 5'R*, 6'S*)- Cis-(2S*, 5'R*, 6'S*)- | $C_{31}H_{34}F_6N_2O_4$ | 612 | 613 |
| 119 | H | Me | H | N-methyl-piperidine-spiro-hydroxy-lactone | Trans-(2R*, 5'R*, 6'S*)- Trans-(2S*, 5'R*, 6'S*)- | $C_{31}H_{34}F_6N_2O_4$ | 612 | 613 |

-continued
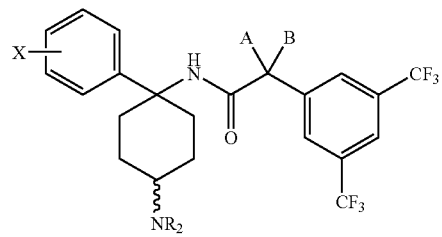
| Ex. | X | A | B | —NR₂ | Stereochemistry | Formula | M.W. | m/z (ES⁺) (M + 1). |
|---|---|---|---|---|---|---|---|---|
| 120 | H | Me | H | | Trans-(2R*, 5'R*, 6'R*)- Trans-(2S*, 5'R*, 6'R*)- | $C_{31}H_{33}F_7N_2O_3$ | 614 | 615 |
| 121 | H | Me | H | | Trans-(RS)- | $C_{35}H_{35}F_7N_2O_2$ | 648 | 649 |
| 122 | H | Me | H | | Cis-(RS)- | $C_{32}H_{36}F_6N_2O_2$ | 594 | 595 |
| 123 | H | Me | H | | Trans-(RS)- | $C_{32}H_{36}F_6N_2O_2$ | 594 | 595 |
| 124 | H | Me | H | | Cis-(2R*, 6'R*)- Cis-(2S*, 6'R*)- Trans-(2R*, 6'R*)- Trans-(2S*, 6'R*)- | $C_{32}H_{38}F_6N_2O_3$ | 612 | 613 |
| 125 | H | Me | H | | Trans-(RS)- | $C_{32}H_{38}F_6N_2O_2$ | 596 | 597 |
| 126 | H | Me | H | | Cis-(2R*, 5'R*)- Cis-(2S*, 5'R*)- Trans-(2R*, 5'R*)- Trans-(2S*, 5'R*)- | $C_{31}H_{36}F_6N_2O_2$ | 582 | 583 |
| 127 | H | Me | H | | Cis-(2R*, 5'R*)- Cis-(2S*, 5'R*)- Trans-(2R*, 5'R*)- Trans-(2S*, 5'R*)- | $C_{31}H_{34}F_6N_2O_3$ | 596 | 597 |
| 128 | H | Me | H | | Trans-(2R*, 10'S*)- Trans-(2S*, 10'S*)- | $C_{31}H_{36}F_6N_2O_3$ | 598 | 599 |

-continued

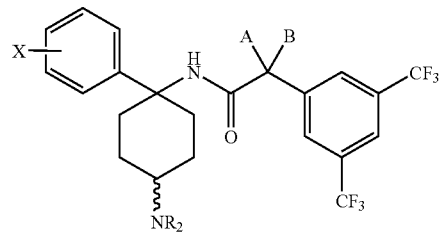

| Ex. | X | A | B | —NR₂ | Stereochemistry | Formula | M.W. | m/z (ES⁺) (M + 1). |
|---|---|---|---|---|---|---|---|---|
| 129[2] | H | Me | H | N-methyl, N'-isopropyl piperazinone | Trans-(RS)- | $C_{30}H_{35}F_6N_3O_2$ | 583 | 584 |
| 130 | H | Me | H | N-methyl, N'-phenyl piperazinone | Cis-(RS)- | $C_{33}H_{33}F_6N_3O_2$ | 617 | 618 |
| 131 | H | Me | H | N-methyl, N'-phenyl piperazinone | Trans-(RS)- | $C_{33}H_{33}F_6N_3O_2$ | 617 | 618 |
| 132 | H | Me | H | N-methyl, N'-phenyl piperazinone | Trans-(R)- | $C_{33}H_{33}F_6N_3O_2$ | 617 | 618 |
| 133 | H | Me | H | N-methyl, N'-phenyl piperazinone | Trans-(S)- | $C_{33}H_{33}F_6N_3O_2$ | 617 | 618 |
| 134 | 2-F | Me | H | N-methyl, N'-phenyl piperazinone | Cis-(RS)- | $C_{33}H_{32}F_7N_3O_2$ | 635 | 636 |
| 135 | 2-F | Me | H | N-methyl, N'-phenyl piperazinone | Trans-(RS)- | $C_{33}H_{32}F_7N_3O_2$ | 635 | 636 |
| 136 | 3-F | Me | H | N-methyl, N'-phenyl piperazinone | Cis-(RS)- | $C_{33}H_{32}F_7N_3O_2$ | 635 | 636 |
| 137 | 3-F | Me | H | N-methyl, N'-phenyl piperazinone | Trans-(RS)- | $C_{33}H_{32}F_7N_3O_2$ | 635 | 636 |

-continued

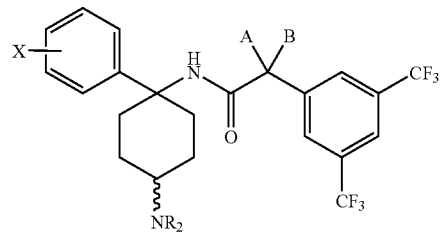

| Ex. | X | A | B | —NR₂ | Stereochemistry | Formula | M.W. | m/z (ES⁺) (M + 1). |
|---|---|---|---|---|---|---|---|---|
| 138 | 4-F | Me | H | (4-methyl-3-oxo-1-phenylpiperazinyl) | Cis-(RS)- | $C_{33}H_{32}F_7N_3O_2$ | 635 | 636 |
| 139 | 4-F | Me | H | (4-methyl-3-oxo-1-phenylpiperazinyl) | Trans-(RS)- | $C_{33}H_{32}F_7N_3O_2$ | 635 | 636 |
| 140 | H | Me | Me | (4-methyl-3-oxo-1-(2-methylphenyl)piperazinyl) | Trans- | $C_{35}H_{37}F_6N_3O_2$ | 645 | 646 |
| 141 | H | Me | H | (4-methyl-3-oxo-1-(2-pyridyl)piperazinyl) | Trans-(R)- | $C_{32}H_{32}F_6N_4O_2$ | 618 | 619 |
| 142 | H | Me | Me | (4-methyl-3-oxo-1-(2-pyridyl)piperazinyl) | Cis- | $C_{33}H_{34}F_6N_4O_2$ | 632 | 633 |
| 143 | H | Me | Me | (4-methyl-3-oxo-1-(2-pyridyl)piperazinyl) | Trans- | $C_{33}H_{34}F_6N_4O_2$ | 632 | 633 |
| 144 | H | Me | H | (4-methyl-3-oxo-1-(3-pyridyl)piperazinyl) | Trans-(RS)- | $C_{32}H_{32}F_6N_4O_2$ | 618 | 619 |
| 145 | H | Me | H | (4-methyl-3-oxo-1-(4-pyridyl)piperazinyl) | Trans-(R)- | $C_{32}H_{32}F_6N_4O_2$ | 618 | 619 |
| 146 | H | Me | Me | (4-methyl-3-oxo-1-(4-pyridyl)piperazinyl) | Cis- | $C_{33}H_{34}F_6N_4O_2$ | 632 | 633 |

-continued

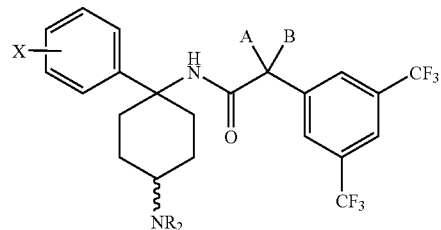

| Ex. | X | A | B | —NR₂ | Stereochemistry | Formula | M.W. | m/z (ES⁺) (M + 1). |
|---|---|---|---|---|---|---|---|---|
| 147 | H | Me | Me | (N-methylpiperazinone-N'-4-pyridyl) | Trans- | $C_{33}H_{34}F_6N_4O_2$ | 632 | 633 |
| 148 | H | Me | H | (N-methylpiperazinone-N'-(6-chloropyridin-2-yl)) | Trans-(R)- | $C_{32}H_{31}ClF_6N_4O_2$ | 652 / 654 | 653 / 655 |
| 149 | H | Me | Me | (N-methylpiperazinone-N'-(6-chloropyridin-2-yl)) | Trans- | $C_{33}H_{33}ClF_6N_4O_2$ | 666 / 668 | 667 / 669 |
| 150 | H | Me | H | (N-methylpiperazinone-N'-pyrazinyl) | Trans-(RS)- | $C_{31}H_{31}F_6N_5O_2$ | 619 | 620 |
| 151 | H | Me | Me | (N-methylpiperazinone-N'-pyrazinyl) | Trans- | $C_{32}H_{33}F_6N_5O_2$ | 633 | 634 |
| 152 | H | Me | H | (N-methylpiperazinone-N'-thiazol-2-yl) | Trans-(RS)- | $C_{30}H_{30}F_6N_4O_2S$ | 624 | 625 |
| 153 | H | Me | H | (N-methylpiperazinone-N'-((1-methyl-1,2,4-triazol-5-yl)methyl)) | Cis-(RS)- | $C_{31}H_{34}F_6N_6O_2$ | 636 | 637 |
| 154 | H | Me | H | (N-methylpiperazinone-N'-((1-methyl-1,2,4-triazol-5-yl)methyl)) | Trans-(RS)- | $C_{31}H_{34}F_6N_6O_2$ | 636 | 637 |

-continued

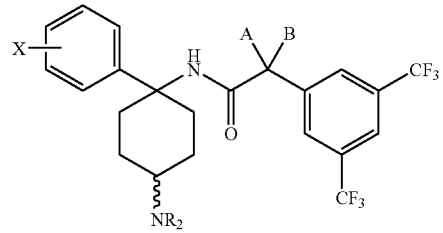

| Ex. | X | A | B | —NR₂ | Stereochemistry | Formula | M.W. | m/z (ES⁺) (M + 1) |
|-----|---|---|---|------|-----------------|---------|------|-------------------|
| 155[3] | H | Me | H | (5,6,7,8-tetrahydro[1,2,4]triazolo[1,5-a]pyrazinyl) | Cis-(RS)- Trans-(RS)- | $C_{28}H_{29}F_6N_5O$ | 565 | 566 |
| 156 | H | Me | H | (imidazo[1,2-a]pyrazinyl) | Cis-(RS)- Trans-(RS)- | $C_{29}H_{30}F_6N_4O$ | 564 | 565 |
| 157 | H | Me | H | (imidazo[1,5-a]pyrazinyl) | Cis-(RS)- | $C_{29}H_{30}F_6N_4O$ | 564 | 565 |
| 158 | H | Me | H | (imidazo[1,5-a]pyrazinyl) | Trans-(RS)- | $C_{29}H_{30}F_6N_4O$ | 564 | 565 |

[1] 4-(1-methylethyl)piperidine: WO9908699
[2] 1-(1-methylethyl)piperazinone: DE2519400
[3] 5,6,7,8-tetrahydro[1,2,4]Triazolo[1,5-a]pyrazine: WO9937645

The following compounds were prepared from (RS)-α-methyl-N-[4-oxo-1-(2-pyridyl)cyclohexyl]-3,5-bis(trifluoromethyl)benzeneacetamide (Example 56) and 2-oxa-8-azaspiro[4.5]decane (Description 86) according to the method of Example 33, followed by separation of diastereoisomers by preparative HPLC on silica gel.

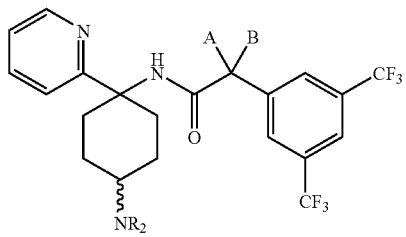

| Ex. | A | B | —NR₂ | Stereochemistry | Formula | M.W. | m/z (ES⁺) (M + 1) |
|-----|---|---|------|-----------------|---------|------|-------------------|
| 159 | Me | Me | (2-oxa-8-azaspiro[4.5]decyl) | Cis-(RS)- | $C_{30}H_{35}F_6N_3O_2$ | 583 | 584 |
| 160 | Me | Me | (2-oxa-8-azaspiro[4.5]decyl) | Trans-(RS)- | $C_{30}H_{35}F_6N_3O_2$ | 583 | 584 |

EXAMPLE 161

Trans-(RS)-α-Methyl-N-{4-[(2-hydroxyethyl)amino]-1-phenylcyclohexyl}-3,5-bis(trifluoromethyl)benzeneacetamide Ethanolamine (471 μL, 7.8 mmol) was added to a solution of (RS)-α-methyl-N-(4-oxo-1-phenylcyclohexyl)-3,5-bis(trifluoromethyl)benzeneacetamide (Example 3, 3.5 g, 7.6 mmol) in 1,2-dichloroethane (150 mL) and the mixture was stirred at room temperature for 15 minutes. The mixture was cooled to 0° C., sodium triacetoxyborohydride (3.3 g, 15.6 mmol) was added and the mixture was stirred at room temperature for 60 hours. Saturated aqueous sodium hydrogen carbonate (100 mL) and water (100 mL) were added and the mixture was extracted with dichloromethane (3×200 mL). The combined organic fractions were dried (MgSO$_4$) and the solvent was evaporated under reduced pressure. The residue was dissolved in ethanol (30 mL), ethereal hydrogen chloride (1M, 20 mL) was added and the mixture was stirred at room temperature for 10 minutes. The solvent was evaporated under reduced pressure and ethanol (20 mL) was added and evaporated under reduced pressure. Ethyl acetate (100 mL) was added and the mixture was heated under reflux for 1 hour. The mixture was cooled to 4° C. and aged for 16 hours. The solid was collected, washed with cold ethyl acetate and dried in vacuo at 80° C. for 2 hours to give the title compound as a colorless solid (1.6 g, 40%). m/z (ES$^+$) 503 (M+1).

EXAMPLE 162

Trans-(RS)-α-Methyl-N-[4-(3-fluoro-1,2,5,6-tetrahydro-4-methylpyrid-1-yl)-1-phenylcyclohexyl]-3,5-bis(trifluoromethylbenzeneacetamide, Cis-(RS)-α-Methyl-N-[4-(3-fluoro-1,2,5,6-tetrahydro-4-methylpyrid-1-yl)-1-phenylcyclohexyl]-3,5-bis(trifluoromethylbenzeneacetamide and (2R*,4'R*)-Trans-, (2S*,4'R*)-Trans-, (2R*,4'R*)-Cis-, and (2S*,4'R*)-Cis-α-Methyl-N-[4-(3,3-difluoro-4-methylpiperidin-1-yl)-1-phenylcyclohexyl]-3,5-bis(trifluoromethylbenzeneacetamide Sodium triacetoxyborohydride (140 mg, 0.66 mmol) was added to a solution of (RS)-3,3-difluoro-4-methylpiperidine hydrochloride (Description 60, 67 mg, 0.44 mmol), (RS)-α-methyl-N-(4-oxo-1-phenylcyclohexyl)-3,5-bis(trifluoromethyl)benzeneacetamide (Example 3, 150 mg, 0.33 mmol) and triethylamine (110 mL, 0.88 mmol) in dichloroethane (30 mL) and the mixture was stirred at room temperature for 72 hours. Saturated aqueous sodium hydrogen carbonate (3 mL) and dichloromethane (5 mL) were added and the layers were separated. The organic fraction was poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure and the residue was purified by flash column chromatography on silica gel, eluting with CH$_2$Cl$_2$/MeOH/NH$_3$(Aq.) (95:5:1), to give trans-(RS)-α-methyl-N-[4-(3-fluoro-1,2,5,6-tetrahydro-4-methylpyrid-1-yl)-1-phenylcyclohexyl]-3,5-bis(trifluoromethylbenzeneacetamide (16 mg, 7%); $^1$H NMR (360 MHz, CD$_3$OD) δ 1.33 (3H, d, J 6.5 Hz), 1.35–2.05 (9H, m), 1.63 (3H, s), 2.36–2.63 (4H, m), 2.74–2.78 (1H, m), 2.95–3.05 (1H, m), 3.83 (1H, q, J 7.2 Hz), 7.12–7.39 (5H, m), 7.79 (2H, s), and 7.81 (1H, s); m/z (ES$^+$) 557 (M+1); cis-(RS)-α-methyl-N-[4-(3-fluoro-1,2,5,6-tetrahydro-4-methylpyrid-1-yl)-1-phenylcyclohexyl]-3,5-bis(trifluoromethylbenzeneacetamide (12 mg, 5%); $^1$H NMR (400 MHz, CD$_3$OD) δ 1.22–1.28 (1H, m), 1.44 (3H, d, J 6.8 Hz), 1.43–1.54 (1H, m), 1.62 (3H, s), 1.72–1.85 (4H, m), 2.00–2.09 (2H, m), 2.42–2.61 (5H, m), 2.91–3.00 (2H, m), 4.02 (1H, q, J 6.8 Hz), 7.12–7.28 (5H, m), 7.94 (2H, s), and 8.14 (1H, s);. m/z (ES$^+$) 557 (M+1); (2R*,4'R*)-trans-, (2S*,4'R*)-trans-, (2R*,4'R*)-cis-, and (2S*,4'R*)-cis-α-methyl-N-[4-(3,3-difluoro-4-methylpiperidin-1-yl)-1-phenylcyclohexyl]-3,5-bis(trifluoromethylbenzeneacetamide as a mixture of diastereoisomers (13 mg, 5%); $^1$H NMR (360 MHz, CD$_3$OD) δ 1.36 (3H, d, J 7.2 Hz), 1.45 (3H, d, J 6.8 Hz), 1.53–1.83 (6H, m), 1.84–1.98 (2H, m), 2.09–2.25 (2H, m), 2.37–2.51 (2H, m), 2.58–2.92 (3H, m), 2.98–3.03 (1H, m), 3.89 and 4.09 (total 1H, each q, J 7.2 Hz)}, 7.13–736 (5H, m), and 7.80–8.18 (3H, m); m/z (ES$^+$) 577 (M+1).

EXAMPLE 163

Cis-(RS)- and Trans-(RS)-α-Methyl-N-{4-[4-hydroxymethyl-4-(methoxymethyl)piperidin-1-yl]-1-phenylcyclohexyl}-3,5-bis(trifluoromethylbenzeneacetamide 1,1-Dimethylethyl 2-oxa-7-azaspiro[3.5]nonane-7-carboxylate (Description 69, 1.5 g, 6.57 mmol) was dissolved in methanolic hydrogen chloride (1M, 400 mL), the mixture was stirred at room temperature for 4 hours, and the solvent was evaporated under reduced pressure. A portion of the residue (150 mg, 0.87 mmol) was dissolved in dry dichloroethane (30 mL) and (RS)-α-methyl-N-(4-oxo-1-phenylcyclohexyl)-3,5-bis(trifluoromethyl)benzeneacetamide (Example 3, 490 mg, 1.04 mmol) and sodium triacetoxyborohydride (379 mg, 1.74 mmol) were added. The mixture was stirred at room temperature overnight, then saturated aqueous sodium hydrogen carbonate (3 mL) and dichloromethane (5 mL) were added. The layers were separated and the organic fraction was poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure and the residue was purified by flash column chromatography on silica gel, eluting with CH$_2$Cl$_2$/MeOH/NH$_3$(Aq.) (95:5:1), to give the title compound (45 mg, 10%). $^1$H NMR (400 MHz, CD$_3$OD) δ 1.14 (3H, m), 1.37–1.46 (4H, m), 1.73–1.88 (4H, m), 1.92–2.08 (1H, m), 2.36–2.53 (4H, m), 2.62–2.65 (1H, m), 2.86–2.88 (1H, m), 3.25–3.28 (3H, s), 3.30–3.63 (6H, m) 3.74–4.01 (1H, m), 7.15–7.48 (5H, m), and 7.73–7.95 (3H, m). m/z (ES$^+$) 601 (M+1).

EXAMPLE 164

Trans-(RS)-α-Methyl-N-{4-({N-[(1,1-dimethylethoxy)carbonyl]-(1,1-dimethylethyl)amino}acetylamino)-1-phenylcyclohexyl}-3,5-bis(trifluoromethyl)benzeneacetamide 1-(Dimethylaminopropyl)-3-ethylcarbodiimide hydrochloride (110 mg, 0.57 mmol) was added to a mixture of N-[(1,1-dimethylethoxy)carbonyl]-N-(1,1-dimethylethyl) glycine (Description 159, 92 mg, 0.4 mmol), trans-(RS)-N-(4-amino-1-phenylcyclohexyl)-α-methyl-3,5-bis(trifluoromethyl)benzeneacetamide (Example 39, 150 mg, 0.33 mmol), 1-hydroxybenzotriazole (135 mg, 1 mmol) and triethylamine (230 μL, 1.65 mmol) in tetrahydrofuran (5 mL) and the mixture was stirred at room temperature for 16 hours. Saturated aqueous sodium hydrogen carbonate (15 mL) was added and the mixture was extracted with ethyl acetate (3×20 mL). The combined organic fractions were washed with brine, dried (MgSO$_4$) and the solvent was evaporated under reduced pressure. The residue was purified by preparative thin layer chromatography on silica gel, eluting with CH$_2$Cl$_2$/MeOH/NH$_3$(Aq.) (200:8:1), to give the title compound as a colorless foam (220 mg, 99%). m/z (ES$^+$) 672 (M+1).

EXAMPLE 165

Trans-4-(RS)-α-Methyl-N-{4-{[(1,1-dimethylethyl)amino]acetylamino}-1-phenylcyclohexyl}-3,5-bis(trifluoromethyl)benzeneacetamide Trifluoroacetic acid (1 mL) was added to a solution of trans-(RS)-α-methyl-N-{4-({N-[(1,1-dimethylethoxy)carbonyl]-(1,1-dimethylethyl)amino}acetylamino)-1-phenylcyclohexyl}-3,5-bis(trifluoromethyl)benzeneacetamide (Example 164) in dichloromethane (8 mL) and the mixture was stirred at room temperature for 2 hours. The solvent was evaporated under reduced pressure, the pH was adjusted to 12.0 with aqueous sodium hydroxide (1M) and the mixture was extracted with dichloromethane (3×10 mL). The combined organic fractions were dried (MgSO$_4$) and the solvent was evaporated under reduced pressure. The residue was purified by flash column chromatography on silica gel, eluting with CH$_2$Cl$_2$/MeOH/NH$_3$(Aq.) (120:8:1), to give the title compound as colorless foam (113 mg, 60%). m/z (ES$^+$) 572 (M+1).

EXAMPLE 166

Trans-(RS)-N-(4-[(2-Chloroethoxy)carbonylamino]-1-phenylcyclohexyl)-α-methyl-3,5-bis(trifluoromethyl)benzeneacetamide 2-Chloroethyl chloroformate (253 μL, 2.45 mmol) was added to a stirred, cooled (0° C.) solution of trans-(RS)-N-(4-amino-1-phenylcyclohexyl)-α-methyl-3,5-bis(trifluoromethyl)benzeneacetamide (Example 39, 630 mg, 1.38 mmol) and triethylamine (770 μL, 5.5 mmol) in dichloromethane (10 mL) and the mixture was stirred at 0° C. for 1 hour, then at room temperature for 1 hour. Further 2-chloroethyl chloroformate (30 μL, 0.3 mmol) was added and the mixture was stirred at room temperature for 10 minutes. Saturated aqueous sodium hydrogen carbonate (25 mL) was added and the mixture was extracted with dichloromethane (3×20 mL). The combined organic fractions were washed with brine, dried (MgSO$_4$) and the solvent was evaporated under reduced pressure. The residue was purified by flash column chromatography on silica gel, eluting with isohexane/EtOAc (75:25 increasing to 0:100), to give the title compound as a colorless solid (537 mg, 69%). m/z (ES$^+$) 565 (M+1).

EXAMPLE 167

Trans-(RS)-α-Methyl-N-[4-(2-oxo-3-oxazolidinyl)-phenylcyclohexyl]-3,5-bis(trifluoromethyl)benzeneacetamide Sodium hydride (60% dispersion in mineral oil, 80 mg, 2.0 mmol) was added to a stirred, cooled (0° C.) solution of trans-(RS)-N-(4-[(2-chloroethoxy)carbonylamino]-1-phenylcyclohexyl)-α-methyl-3,5-bis(trifluoromethyl)benzeneacetamide (Example 166, 530 mg, 0.94 mmol) in dimethylformamide (4 mL) and the mixture was stirred at room temperature for 20 hours. The mixture was poured into water (200 mL) and extracted with ethyl acetate (3×100 mL). The combined organic fractions were washed with water (3×50 mL) and brine, dried (MgSO$_4$) and the solvent was evaporated under reduced pressure. The residue was purified by chromatography on a short column of silica gel, eluting with EtOAc, to give the title compound as a colorless foam (371 mg, 75%). m/z (ES$^+$) 529 (M+1).

EXAMPLE 168

Trans-(RS)-α-Methyl-N-[4-(2-hydroxy-N-methylethylamino)-1-phenylcyclohexyl]-3,5-bis(trifluoromethylbenzeneacetamide Lithium borohydride (2M in tetrahydrofuran, 0.1 mL, 0.2 mmol) was added to a solution of trans-(RS)-N-methyl-N-[4-({1-oxo-2-[3,5-bis(trifluoromethyl)phenyl]propyl}amino)-4-phenylcyclohexyl]glycine methyl ester (Example 44, 35 mg, 0.064 mmol) in tetrahydrofuran/toluene (3:1, 4 mL) and the mixture was heated at 50° C. overnight. The mixture was cooled, poured into water (25 mL), acidified with hydrochloric acid (2M) and extracted with ethyl acetate (2×25 mL). The combined organic fractions were washed with brine, dried (MgSO$_4$) and the solvent was evaporated under reduced pressure. The residue was dissolved in methanol (1.5 mL) and poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure and the residue was purified by flash column chromatography on silica gel, eluting with CH$_2$Cl$_2$/MeOH/NH$_3$(Aq.) (95:5:0.5), to give the title compound (12.5 mg, 38%). m/z (ES$^+$) 517 (M+1).

EXAMPLE 169

Trans-(RS)-α-Methyl-N-[4-(4-hydroxypiperidin-1-yl)-1-phenylcyclohexyl]-3,5-bis(trifluoromethylbenzeneacetamide Sodium borohydride (3 mg, 0.092 mmol) was added to a solution of trans-(RS)-α-methyl-N-[4-(4-oxopiperidin-1-yl)-1-phenylcyclohexyl]-3,5-bis(trifluoromethyl)benzeneacetamide (Example 38, 50 mg, 0.092 mmol) in ethanol (3 mL) and the mixture was stirred at room temperature for 1 hour. The mixture was carefully quenched with saturated aqueous ammonium chloride (0.5 mL), basified with aqueous sodium carbonate (10%, 10 mL) and extracted with ethyl acetate (2×20 mL). The combined organic fractions were washed with brine dried (MgSO$_4$) and the solvent was evaporated under reduced pressure. The residue was dissolved in methanol (1.5 mL) and poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure and the residue was purified by flash column chromatography on silica gel, eluting with CH$_2$Cl$_2$/MeOH/NH$_3$(Aq.) (95:5:0.5), to give the title compound (25 mg, 50%). m/z (ES$^+$) 543 (M+1).

EXAMPLE 170

(2R*,4'R*)-Trans- and (2S*,4R*)-Trans-α-Methyl-N-[4-(4-methyl-3-oxopiperidin-1-yl)-1-phenylcyclohexyl]-3,5-bis(trifluoromethylbenzeneacetamide 1,1,1-Tris(acetyloxy)-1,1-dihydro-1,2-benziodoxol-3(1H)-one (50 mg, 0.13 mmol) was added to a solution of trans- (2R*,3'R*,4'S*)- and trans-2S*,3'R*,4'S*)-α-methyl-N-[4-(3-hydroxy-4-methylpiperidin-1-y)-1-phenylcyclohexyl]-3,5-bis(trifluoromethyl)benzeneacetamide (Mixture of diastereoisomers, Example 75, 30 mg, 0.053 mmol) in dichloromethane (5 mL) and the mixture was stirred at room temperature for 20 minutes. Aqueous sodium bisulfite (10%, 1 mL) was added and the mixture was stirred at room temperature for 5 minutes. Saturated aqueous sodium hydrogen carbonate (2 mL) was added and the layers were separated. The organic fraction was poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure and the residue was purified by preparative thin layer chromatography on silica gel, eluting with $CH_2Cl_2$/MeOH/($NH_3$(Aq.) (90:10:1), to give the title compound (4 mg, 13%). m/z ($ES^+$) 555 (M+1).

EXAMPLE 171

Trans-(3R,2'R)-3-Methyl-1-[4-({1-oxo-2-[3,5-bis(trifluoromethyl)phenyl]propyl}amino)-4-phenylcyclohexyl]-3-piperidinecarboxylic acid Aqueous sodium hydroxide (4M, 1 mL, 4 mmol) was added to a solution of trans-3R,2'R)-ethyl 3-Methyl-1-[4-({1-oxo-2-[3,5-bis(trifluoromethyl)phenyl]propyl}amino)-4-phenylcyclohexyl]-3-piperidinecarboxylate (Example 73, 50 mg, 0.08 mmol) in methanol (6 mL) and the mixture was stirred at 60° C. for 18 hours. The mixture was cooled, acetic acid (252 µL, 4.4 mmol) was added and the solvent was evaporated under reduced pressure. Toluene was added and evaporated under reduced pressure. Water and dichloromethane were added and the layers were separated. The organic layer was dried ($MgSO_4$) and the solvent was evaporated under reduced pressure to give the title compound as a colorless solid (40 mg, 86%). m/z ($ES^+$) 584 (M+1).

EXAMPLE 172

Trans-(RS)-4-Methyl-1-[-4-({1-oxo-2-[3,5-bis(trifluoromethyl)phenyl]propyl}amino)-4-phenylcyclohexyl]piperidine-4-carboxylic Acid Palladium on carbon (5%, 1 mg) was added to a solution of trans-(RS)-phenylmethyl 4-methyl-1-[4-({(1-oxo-2-[3,5-bis(trifluoromethyl)phenyl]propyl}amino)-4-phenylcyclohexyl]piperidine-4-carboxylate (Example 72, 6 mg, 9 µmol) in methanol and the mixture was shaken under an atmosphere of hydrogen (50 psi) overnight. The mixture was filtered through a glass fibre pad and the solvent was evaporated under reduced pressure to the title compound (6 mg, 100%). m/z ($ES^+$) 585 (M+1).

EXAMPLE 173

Trans-(RS)-α-Methyl-N-[4-(1,4-dioxa-8-azaspiro[4.5]decan-8-yl)-1-phenylcyclohexyl]-3,5-bis(trifluoromethyl)benzeneacetamide A mixture of trans-(RS)-α-methyl-N-[-4-(4-oxopiperidin-1-yl)-1-phenylcyclohexyl]-3,5-bis(trifluoromethyl)benzeneacetamide (Example 38, 4.5 g, 8.3 mmol), ethylene glycol (2 mL) and p-toluenesulphonic acid (1.74 g, 9.13 mmol) in tetrahydrofuran (45 mL) was heated at 65° C. for 1 hour. The mixture was cooled, poured into aqueous sodium carbonate (10%, 50 mL) and extracted with ethyl acetate (50 mL). The organic fraction was washed with brine, dried ($MgSO_4$) and the solvent was evaporated under reduced pressure. The residue was purified by flash column chromatography on silica gel, eluting with $CH_2Cl_2$/MeOH/$NH_3$(Aq.) (95:5:0.5), and the residue was recrystallized from isopropanol (60 mL) to give the title compound (1.2 g, 25%). $^1$H NMR (360 MHz, $CDCl_3$) δ 7.75 (1H, s), 7.65 (2H, s), 7.39–7.23 (5H, m), 5.47 (1H, s), 3.91 (4H, s), 3.49 (1H, q, J 7 Hz), 2.68–2.38 (7H, m), 2.17–2.04 (2H, m), 1.75–1.64 (6H, m), 1.48–36 (2H, m), and 1.42 (3H, d, J 7 Hz). m/z ($ES^+$) 585 (M+1).

EXAMPLE 174

Trans-(2R*,5'R*)- and Trans-(2S*,5R*)-α-Methyl-N-[4-(2-oxa-6,7-dioxo-8-azaspiro[4.5]decan-8-yl)-1-phenylcyclohexyl]-3,5-bis(trifluoromethyl)benzeneacetamide 4-Methylmorpholine N-oxide (11 mg, 0.08 mmol) and 4 Å molecular sieves were added to a solution of trans-(2R*,5'R*,6'R*)- and trans-(2S*,5'R*,6'R*)-α-methyl-N-[4-(6-hydroxy-2-oxa-8-azaspiro[4.5]decan-8-yl)-1-phenylcyclohexyl]-3,5-bis(trifluoromethyl)benzeneacetamide (Mixture of diastereoisomers, Example 106, 32 mg, 0.053 mmol) in dichloromethane (2 mL) and the mixture was stirred at room temperature for 10 minutes. Tetrapropylammonium perruthenate (0.9 mg, 0.0027 mmol) was added and the mixture was stirred at room temperature for 2 hours. The mixture was filtered through Celite™, diluted with dichloromethane (10 mL), washed with aqueous sodium bisulfite (10%, 10 mL), aqueous copper sulphate (5%, 10 mL) and brine, dried ($MgSO_4$) and the solvent was evaporated under reduced pressure. The residue was purified by flash column chromatography on silica gel, eluting with $CH_2Cl_2$/MeOH/$NH_3$ (Aq.) (95:5:0.5), followed by preparative HPLC (ABZ+plus 250×21.0 mm i.d.; 0.1% TFA-$H_2O$/40% MeCN; 20 mL/min; 210 nm; 25 µl injections of a 50 mg/mL solution in MeOH) to give the title compound (3 mg, 9%). m/z ($ES^+$) 611 (M+1).

EXAMPLE 175

Trans-(2R*,5'R*)- and Trans-(2S*,5'R*)-α-Methyl-N-[4-(2-oxa-6-oxo-8-azaspiro[4.5]decan-8-yl)-1-phenylcyclohexyl]-3,5-bis(trifluoromethyl)benzeneacetamide Prepared from trans-2R*,5'R*,6'S*)- and trans-2S*,5'R*,6'S*)-α-methyl-N-[4-(6-hydroxy-2-oxa-8-azaspiro[4.5]decan-8-yl)-1-phenylcyclohexyl]-3,5-bis(trifluoromethyl)benzeneacetamide (Mixture of diastereoisomers, Example 108) according to the method of Example 174. m/z ($ES^+$) 597 (M+1).

EXAMPLE 176

Trans-(RS)-α-Methyl-N-[4-(2-oxa-4-oxo-8-azaspiro[4.5]decan-8-yl)-1-phenylcyclohexyl]-3,5-bis(trifluoromethyl)benzeneacetamide Hydrochloride 1,1,1-Tris(acetyloxy)-1,1-dihydro-1,2-benziodoxol-3(1H)-one (37 mg, 0.083 mmol) was added to a solution of (2R*,4'R*)-trans- and (2S*,4R*)-trans-α-methyl-N-[4-(4-hydroxy-2-oxa-8-azaspiro[4.5]decan-8-yl)-1-phenylcyclohexyl]-3,5-bis(trifluoromethyl)benzeneacetamide (Mixture of diastereoisomers, Example 104, 50 mg, 0.083 mmol) in dichloromethane (7 mL) and the mixture was stirred at room temperature for 15 minutes. Aqueous sodium bisulfite (10%, 1 mL) was added and the mixture was stirred at room temperature for 5 minutes. Saturated aqueous sodium hydrogen carbonate (2 mL) was added and the layers were separated. The organic layer was poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure and the residue was purified by preparative thin layer chromatography on silica gel. The residue was suspended in diethyl ether (5 mL) and treated with ethereal hydrogen chloride (1M, 0.1 mL). The solid was collected and dried in vacuo to give the title compound (10 mg, 20%). $^1$H NMR (400 MHz, CD$_3$OD) δ 1.34 (3H, d, J 6.8 Hz), 1.35–1.46 (4H, m), 1.48–1.58 (3H, m), 1.68–1.75 (2H, m), 1.78–1.94 (3H, m), 2.17–2.22 (2H, m), 2.37–2.39 (1H, m), 2.58–2.64 (1H, m), 2.82–2.86 (3H, m), 3.81 (1H, q, J 6.8 Hz), 3.94 (1H, s), 4.01 (1H, s), 7.12–7.44 (5H, m), 7.77 (2H, s), and 7.79 (1H, s). m/z (ES$^+$) 597 (M+1).

EXAMPLE 177

Trans-(RS)-α-Methyl-N-[4-(1-oxa-9-azaspiro[5.5]undecan-9-yl)-1-phenylcyclohexyl]-3,5-bis(trifluoromethyl)benzeneacetamide Palladium on carbon (8 mg) was added to a solution of trans-(RS)-α-methyl-N-[4-(1-oxa-9-azaspiro[5.5]undec-3-en-9-yl)-1-phenylcyclohexyl]-3,5-bis(trifluoromethyl)benzeneacetamide (Example 123, 20 mg, 003 mmol) in ethyl acetate (2 mL) and the mixture was stirred under hydrogen (1 atm.) for 3 hours. The mixture was filtered through a glass fibre pad and the solvent was evaporated under reduced pressure to give the title compound (15 mg, 84%). $^1$H NMR (360 MHz, CDCl$_3$) δ 7.72 (1H, s), 7.67 (2H, s), 7.40–7.21 (5H, m), 3.65–3.55 (3H, s), 2.85 (1H, d, J 11.6 Hz), 2.70 (5H, m), 2.12–2.02 (2H, m), 1.92 (4H, d, J 13.3 Hz), 1.79 (2H, m), 1.58–1.42 (9H, m), and 1.38 (3H, d, J 7 Hz). m/z (ES$^+$) 597 (M+1).

EXAMPLE 178

Trans-(2R*,3'R*)- and Trans-(2R*,3S*)-α-Methyl-N-[4-(3-hydroxy-1-oxa-9-azaspiro[5.5]undecan-9-yl)-1-phenylcyclohexyl]-3,5-bis(trifluoromethyl)benzeneacetamide and Trans-(2R*,4'R*)- and Trans-(2R*,4'S*)-α-Methyl-N-[4-(4-hydroxy-1-oxa-9-azaspiro[5.5]undecan 9-yl)-1-phenylcyclohexyl]-3,5-bis(trifluoromethyl)benzeneacetamide Prepared from trans-(RS)-α-methyl-N-[4-(1-oxa-9-azaspiro[5.5]undec-3-en-9-yl)-1-phenylcyclohexyl]-3,5-bis(trifluoromethyl)benzeneacetamide (Example 123) according to the method of Description 133 to give trans-(2R*,3'R*)- and trans-(2R*,3'S*)-α-methyl-N-[4-(3-hydroxy-1-oxa-9-azaspiro[5.5]undecan-9-yl)-1-phenylcyclohexyl]-3,5-bis(trifluoromethyl)benzeneacetamide as a mixture of diastereoisomers; $^1$H NMR (400 MHz, CDCl$_3$) δ 7.75 (1H, s), 7.64 (2H, s), 7.40–7.38 (2H, m), 7.33–7.29 (2H, m), 7.26–7.22 (1H, m), 5.60 (1H, s), 3.71–3.65 (2H, m), 3.51 (1H, q, J 7 Hz), 3.43–3.38 (1H, m), 2.71 (1H, d, J 12.4 Hz), 2.62–2.38 (5H, m), 2.15–2.07 (2×, m), 1.90–1.80 (6H, m), 1.70–1.59 (4H, m), 1.50–1.35 (31H, m), and 1.41 (3H, d, J 7 Hz); m/z (ES$^+$) 613 (M+1); and trans-(2R*,4R*)- and trans-(2R*4'S*)-α-4-methyl-N-[4-(4-hydroxy-1-oxa-9-azaspiro[5.5]undecan-9-yl)-1-phenylcyclohexyl]-3,5-bis(trifluoromethyl)benzeneacetamide; $^1$H NMR (400 MHz, CDCl$_3$) δ 7.74 (1H, s), 7.64 (2H, s), 7.39–7.23 (5H, m), 5.75 (1H, s), 3.97–3.90 (1H, m), 3.81–3.76 (1H, m), 3.55–3.45 (2H, m), 2.84–2.62 (6H, m), 2.60–2.50 (1H, m), 2.16–2.09 (3H, m), 1.97–1.78 (7H, m), 1.53–1.41 (3H, m), 1.40 (3×, d, J 7 Hz), and 1.34–1.26 (1H, m); m/z (ES$^+$) 613 (M+1).

EXAMPLE 179

Trans-(RS)-α-methyl-N-[4-(1-oxa-3-oxa-9-azaspiro[5.5]undecan-9-yl)-1-phenylcyclohexyl]-3,5-bis(trifluoromethyl)benzeneacetamide Prepared from trans-(2R*,3'R*)- and trans-(2R*,3S*)-α-methyl-N-[4-(3-hydroxy-1-oxa-9-azaspiro[5.5]undecan-9-yl)-1-phenylcyclohexyl]-3,5-bis(trifluoromethyl)benzeneacetamide (Example 178) according to the method of Description 120. $^1$H NMR (400 MHz, CDCl$_3$) δ 7.75 (1H, s), 7.65 (2H, s), 7.40–7.38 (2H, m), 7.33–7.30 (2H, m), 7.26–7.22 (1H, m), 5.48 (1H, s), 3.52–3.47 (2H, m), 2.67–2.64 (1H, m), 2.61–2.38 (7H, m), 2.17–2.10 (2H, m), 1.86–1.38 (12H, m), and 1.42 (3H, d, J 7H). m/z (ES$^+$) 611 (M+1).

EXAMPLE 180

Trans-(RS)-α-Methyl-N-{4-[4-(phenylmethyl)piperazin-1-yl]-phenylcyclohexyl}-3,5-bis(trifluoromethyl)benzeneacetamide Oxalyl chloride (2.3 mL, 26.4 mmol) was added slowly to a stirred, cooled (0° C.) solution of (RS)-α-methyl-3,5-bis(trifluoromethyl)benzeneacetic acid (Description 4, 3.77 g, 13.2 mmol) and dimethylformamide (1 drop) in dichloromethane (50 mL) and the mixture was allowed to warm to room temperature and stirred for 1 hour. The solvent was evaporated under reduced pressure and the residue was dissolved in dichloromethane (20 mL) and added to a stirred, cooled (0° C.) solution of trans-4-[4-phenylmethyl)piperazin-1-yl]-1-phenylcyclohexylamine (Description 188, 3.07 g, 8.8 mmol) and triethylamine (6.1 mL, 44 mmol) in dichloromethane (50 mL). The mixture was stirred at room temperature for 18 hours, diluted with dichloromethane (100 mL) and washed with water. The organic fraction was dried (MgSO$_4$) and the solvent was evaporated under reduced pressure. The residue was purified by flash column chromatography on silica gel, eluting with CH$_2$Cl$_2$/MeOH (95:5), to give the title compound as a light brown solid (4.4 g, 81%). $^1$H NMR (400 MHz, CDCl$_3$) δ 7.75 (1H, s), 7.65 (2H, s), 7.34–7.20 (10H, m), 5.45 (1H, br s), 3.50 (1H, q, J 7.1 Hz), 3.46 (2H, s), 2.60–2.37 (10H, m), 2.32–2.22 (1H, m), 2.16–2.07 (2H, m), 1.78–1.55 (3H, m), 1.50–1.35 (1H, m), and 1.43 (3H, d, J 7.1 Hz). m/z (ES$^+$) 618.

EXAMPLE 181

Trans-(RS)-α-Methyl-N-[4-(piperazin-1-yl)-1-phenylcyclohexyl]-3,5-bis(trifluoromethyl)benzeneacetamide Palladium hydroxide on carbon (5%, 0.5 g) was added to a solution of trans-(RS)-α-methyl-N-{4-[4-(phenylmethyl)

piperazin-1-yl]-1-phenylcyclohexyl}-3,5-bis(trifluoromethyl)benzeneacetamide (Example 180, 4 g, 6.48 mmol) in ethyl acetate (20 mL) and the mixture was shaken under an atmosphere of hydrogen (50 psi) for 24 hours. The mixture was filtered through Hyflo™ and the solvent was evaporated under reduced pressure to give the title compound as a colorless foam (1.5 g, 44(%). m/z (ES$^+$) 528 (M+1).

EXAMPLE 182

Trans-(RS)-α-Methyl-N-[4-(4-methylpiperazin-1-yl)-1-phenylcyclohexyl]-3,5-bis(trifluoromethyl)benzeneacetamide Palladium hydroxide on carbon (5%, 50 mg) was added to a solution of trans-(RS)-α-methyl-N-[4-(piperazin-1-yl)-1-phenylcyclohexyl]-3,5-bis(trifluoromethyl)benzeneacetamide (Example 181, 50 mg, 0.095 mmol) and formaldehyde (2 mL) in methanol (10 mL) and the mixture was shaken under an atmosphere of hydrogen (50 psi) for 24 hours. The mixture was filtered through Hyflo™ and the filtrate was poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure to give the title compound as a light brown solid (42 mg, 82%). $^1$H NMR (400 MHz, CDCl$_3$) δ 7.76 (1H, s), 7.66 (2H, s), 7.38–7.21 (5H, m), 5.46 (1H, s), 3.51 (1H, q, J 7.0 Hz), 2.61–2.27 (10H, m), 2.24 (3H, s), 2.16–2.07 (2H, m), 1.75–1.60 (3H, m), 1.49–1.37 (1H, m), and 1.43 (3H, d, J 7.1 Hz). m/z (ES$^+$) 542 (M+1).

EXAMPLE 183

Trans-(RS)-α-Methyl-N-{4-[4-(1-methylethyl)piperazin-1-yl]-1-phenylcyclohexyl}-3,5-bis(trifluoromethyl)benzeneacetamide A mixture of sodium cyanoborohydride (6 mg, 0.095 mmol) and zinc chloride (6.5 mg, 0.0475 mmol) in methanol (2 mL) was added to a solution of trans-(RS)-α-methyl-N-[4-(piperazin-1-yl)-1-phenylcyclohexyl]-3,5-bis(trifluoromethyl)benzeneacetamide (Example 181, 50 mg, 0.095 mmol) and acetone (35 μl, 0.25 mmol) in methanol (5 mL) and the mixture was stirred at room temperature for 18 hours. The mixture was poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure to give the title compound as a colorless solid (50 mg (93%). $^1$H NMR (400 MHz, CDCl$_3$) δ 7.76 (1H, s), 7.65 (2H, s), 7.38–7.21 (5H, m), 5.46 (1H, br s), 3.50 (1H, q, J 7.1 Hz), 2.61–2.58 (2H, m), 2.55–2.45 (8H, m), 2.30–2.23 (1H, m), 2.17–2.09 (2H, m), 1.51–1.35 (3H, m), 1.43 (3×, d, J 7.1 Hz), and 1.03 (6H, d, J 6.5 Hz). m/z (ES$^+$) 570 (M+1).

The following compounds were prepared from trans-(RS)-α-methyl-N-[4-(piperazin-1-yl)-1-phenylcyclohexyl]-3,5-bis(trifluoromethyl)benzeneacetamide (Example 181) according to the method of Example 183, substituting a suitable ketone or aldehyde for acetone.

| Ex. | X | A | B | —NR$_2$ | Stereochemistry | Formula | M.W. | m/z (ES$^+$) (M + 1). |
|---|---|---|---|---|---|---|---|---|
| 184 | H | Me | H | piperazine-N-CH$_2$CH$_2$C(CH$_3$)$_3$ | Trans-(RS)- | C$_{33}$H$_{43}$F$_6$N$_3$O | 611 | 612 |
| 185 | H | Me | H | piperazine-N-(tetrahydropyran-4-yl) | Trans-(RS)- | C$_{32}$H$_{39}$F$_6$N$_3$O$_2$ | 611 | 612 |

EXAMPLE 186

Trans-(RS)-α-Methyl-N-[4-(2-oxo-1-piperazinyl)-phenylcyclohexyl]-3,5-bis(trifluoromethyl)benzeneacetamide Bromoacetyl bromide (104 μL, 1.2 mmol) was added dropwise to a stirred, cooled (0° C.) solution of trans-(RS)-α-methyl-N-{4-[(2-{[(1,1-dimethylethoxy)carbonyl]amino}ethyl)amino]-1-phenylcyclohexyl)-3,5-bis(trifluoromethyl)benzeneacetamide (Example 33, 400 mg, 0.66 mmol) and triethylamine (368 μL, 2.6 mmol) in dichloromethane (15 mL) and the mixture was stirred at 0° C. for 30 minutes. Saturated aqueous sodium hydrogen carbonate (25 mL) and water (25 mL) were added and the mixture was extracted with dichloromethane (3×20 mL). The combined organic fractions were washed with aqueous citric acid (10%, 25 mL) and saturated aqueous sodium hydrogen carbonate (25 mL), dried (MgSO$_4$) and the solvent was evaporated under reduced pressure. The residue was dissolved in dichloromethane (10 mL) cooled to 0° C. and trifluoroacetic acid (2 mL) was added. The mixture was stirred at room temperature for 2 hours, then the solvent was evaporated under reduced pressure. The residue was dissolved in dichloromethane (20 mL), triethylamine (6 mL) was added and the mixture was stirred at room temperature for 20 hours. The solvent was evaporated under reduced pressure, water (25 mL) was added and the pH was adjusted to 12 with aqueous sodium hydroxide (4M). The mixture was extracted with dichloromethane (3×40 mL) and the combined organic fractions were washed with brine, dried ($MgSO_4$) and the solvent was evaporated under reduced pressure. The residue was purified by flash column chromatography on silica gel, eluting with $CH_2C_2$/MeOH/$NH_3$ (Aq.) (90:8:1), to give the title compound as an off-white solid (262 mg, 73%). m/z ($ES^+$) 542 (M+1).

EXAMPLE 187

Trans-(RS)-α-Methyl-N-[4-(4-methyl-2-oxo-1-piperazinyl)-1-phenylcyclohexyl]-3,5-bis(trifluoromethyl)benzeneacetamide Aqueous formaldehyde (38%, 22 μL, 0.3 mmol) was added to a solution of trans-(RS)-α-methyl-N-[4-(2-oxo-1-piperazinyl)-1-phenylcyclohexyl]-3,5-bis(trifluoromethyl)benzeneacetamide (Example 186, 15 mg, 0.03 mmol) in formic acid (1 mL) and the mixture was stirred at 70° C. for 1 hour. The mixture was cooled and the solvent was evaporated under reduced pressure. Saturated aqueous sodium hydrogen carbonate was added and the mixture was extracted with dichloromethane (3×1 mL). The combined organic fractions were poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure and the residue was purified by chromatography on silica, eluting with $CH_2Cl_2$/MeOH/$NH_3$(Aq.) (120:8:1), to give the title compound as a colorless glass (5 mg, 30%). m/z ($ES^+$) 556 (M+1).

EXAMPLE 188

Trans-(RS)-α-Methyl-N-{4-[4-(1-methylethyl)-2-oxo-1-piperazinyl]-1-phenylcyclohexyl}-3,5-bis(trifluoromethyl)benzeneacetamide Sodium triacetoxyborohydride (23 mg, 0.1 mmol) was added to a solution of trans-(RS)-α-methyl-N-[4-(2-oxo-1-piperazinyl)-1-phenylcyclohexyl]-3,5-bis(trifluoromethyl) benzeneacetamide (Example 186, 10 mg, 0.02 mmol) and acetone (8 μL, 0.11 mmol) in 1,2-dichloroethane (1 mL) and the mixture was stirred at room temperature for 19 hours. Saturated aqueous sodium hydrogen carbonate (2 mL) was added and the mixture was extracted with dichloromethane (3×1 mL). The combined organic fractions were poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure to give the title compound (10.2 mg, 87%). $^1$H NMR (400 MHz, $CD_3OD$) δ 1.02 (6H, d, J 6.5 Hz), 1.31 (3H, d, J 7.0 Hz), 1.46–1.56 (2H, m), 1.60–1.66 (2H, m), 1.88–1.96 (2H, m), 2.62–2.69 (3H, m), 2.77–2.81 (1H, m), 3.00–3.04 (2H, m), 3.09–3.16 (3H, m), 3.75 (1H, q, J 7.0 Hz), 4.44–4.46 (1H, m), 7.16–7.18 (1H, m), 7.24–7.28 (2H, m), 7.43–7.46 (2H, m), 7.72 (2H, s), and 7.78 (1H, s). m/z ($ES^+$) 584 (M+1).

The following compounds were prepared from trans-(RS)-α-methyl-N-[4-(2-oxo-1-piperazinyl)-1-phenylcyclohexyl]-3,5-bis(trifluoromethyl)benzeneacetamide (Example 186) according to the method of Example 188, substituting a suitable ketone or aldehyde for acetone.

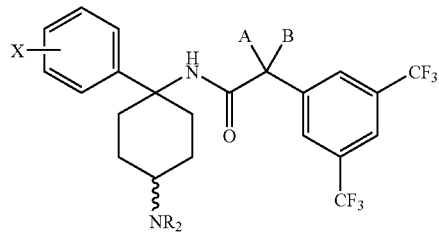

| Ex. | X | A | B | —NR2 | Stereochemistry | Formula | M.W. | m/z ($ES^+$) (M + 1) |
|---|---|---|---|---|---|---|---|---|
| 189 | H | Me | H | | Trans-(RS)- | $C_{34}H_{35}F_6N_3O_2$ | 631 | 632 |
| 190 | H | Me | H | | Trans-(RS)- | $C_{32}H_{37}F_6N_3O_3$ | 625 | 626 |

-continued

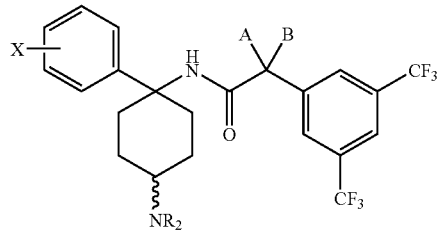

| Ex. | X | A | B | —NR₂ | Stereochemistry | Formula | M.W. | m/z (ES⁺) (M + 1). |
|---|---|---|---|---|---|---|---|---|
| 191 | H | Me | H | (3-oxopiperazinyl-piperidinyl) | Trans-(RS)- | $C_{33}H_{40}F_6N_4O_2$ | 638 | 639 |
| 192 | H | Me | H | (3-oxopiperazinyl-cyclohexyl) | Trans-(RS)- | $C_{33}H_{39}F_6N_3O_2$ | 623 | 624 |
| 193 | H | Me | H | (3-oxopiperazinyl-methylcyclopropyl) | Trans-(RS)- | $C_{31}H_{35}F_6N_3O_2$ | 595 | 596 |

EXAMPLE 194

Trans-(RS)-α-Methyl-N-[4-(2-oxo-4-phenyl-1-piperazinyl)-1-phenylcyclohexyl]3,5 bis(trifluoromethyl)benzeneacetamide (1R)-[,11'-Binaphthalene]-2,2'-diylbis[diphenylphosphine (2.8 mg, 0.0045 mmol) and tris[(1,2-η)-1,5-diphenyl-1,4-pentadien-3-one]palladium (4.1 mg, 0.0045 mmol) were added to a degassed mixture of trans-(RS)-α-methyl-N-[4-(2-oxo-1-piperazinyl)-1-phenylcyclohexyl]-3,5-bis(trifluoromethyl)benzeneacetamide (Example 186, 50 mg, 0.09 mmol), iodobenzene (15 μL, 0.14 mmol) and sodium t-butoxide (12 mg, 0.13 mmol) in toluene (5 mL). The mixture was degassed with bubbling nitrogen and stirred at 80° C. for 4 hours. Further (1R)-[1,1'-Binaphthalene]-2,2'-diylbis [diphenylphosphine (4.0 mg) and tris[(1,2-η)-1,5-diphenyl-1,4-pentadien-3-one]palladium (4.1 mg, 0.0045 mmol) were added and the mixture was stirred at 80° C. for 60 hours. Further iodobenzene (30 μL, 0.28 mmol), sodium t-butoxide (24 mg, 0.26 mmol), (1R)-[1,1'-binaphthalene]-2,2'-diylbis [diphenylphosphine (4.0 mg) and tris[(1,2-η)-1,5-diphenyl-1,4-pentadien-3-one]palladium (4.1 mg, 0.0045 mmol) were added and the mixture was degassed with bubbling argon and stirred at 80° C. for 20 hours. The mixture was cooled, poured into brine (10 mL) and water (10 mL) and extracted with ethyl acetate (2×20 mL). The combined organic fractions were washed with brine, dried (MgSO₄) and the solvent was evaporated under reduced pressure. The residue was dissolved in methanol (1.5 mL) and poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure and the residue was purified by flash column chromatography on silica gel, eluting with CH₂Cl₂/MeOH (98:2), then by preparative thin layer chromatography on silica gel, eluting with CH₂Cl₂/MeOH (98:2), to give the title compound as a colorless gum (9.1 mg, 16%). m/z (ES⁺) 618 (M+1).

EXAMPLE 195

Trans-(RS)-α-Methyl-N-{4-[(2-aminoethyl)amino]-1-phenylcyclohexyl}-3,5-bis(trifluoromethyl)benzeneacetamide Trifluoroacetic acid (1 mL) was added to a stirred, cooled (0° C.) solution of trans-(RS)-α-methyl-N-{4-[(2-{[(1,1-dimethylethoxy)carbonyl]amino}ethyl)amino]-1-phenylcyclohexyl}-3,5-bis(trifluoromethyl)benzeneacetamide (Example 33, 180 mg, 0.3 mmol) in dichloromethane (10 mL) and the mixture was stirred at 0° C. for 10 minutes, then at room temperature for 1 hour. The solvent was evaporated under reduced pressure and aqueous sodium hydroxide (1M, 25 mL) was added. The mixture was extracted with dichloromethane (3×10 mL), the combined organic fractions were dried (MgSO₄) and the solvent was evaporated under reduced pressure to give the title compound as a colorless glass (157 mg, 100%). m/z (ES⁺) 502 (M+1).

EXAMPLE 196

Trans-(RS)-α-Methyl-N-[4-(3,3-dimethyl-2-oxo-1-piperazinyl)-1-phenylcyclohexyl]-3,5-bis(trifluoromethyl)benzeneacetamide Aqueous sodium hydroxide (47%, 111 μL, 1.3 mmol), was added to a stirred, cooled (5° C.) mixture of trans-(RS)-α- methyl-N-{4-[(2-aminoethyl)amino]-1-phenylcyclohexyl}-3,5-bis(trifluoromethyl)benzeneacetamide (Example 195, 150 mg, 0.3 mmol), acetone (44 µL, 0.6 mmol), chloroform (29 µL, 0.36 mmol) and benzyltrimethylammonium chloride (2.7 mg, 0.012 mmol) in dichloromethane (2 mL) and the mixture was stirred at 5° C. for 20 hours. Further acetone (440 µL, 6.0 mmol), chloroform (290 µL, 3.6 mmol), benzyltrimethylammonium chloride (27 mg, 0.12 mmol) and aqueous sodium hydroxide (47%, 1.1 mL, 13 mmol) were added and the mixture was stirred at 5° C. for 24 hours. Dichloromethane was added and the mixture was stirred at room temperature for 1 hour. Water (20 mL) was added, the layers were separated and the aqueous layer was extracted with dichloromethane (2×20 mL). The combined organic fractions were dried ($MgSO_4$) and the solvent was evaporated under reduced pressure. The residue was purified by flash column chromatography on silica gel, eluting with $CH_2Cl_2$/MeOH/$NH_3$(Aq.) (120:8:1), to give the title compound as a colorless solid (55 mg, 32%). m/z ($ES^+$) 570 (M+1).

EXAMPLE 197

Trans-(RS)-α-Methyl-N-[4-(3,3-dimethyl-2-oxo-4-phenylmethyl-1-piperazinyl)-1-phenylcyclohexyl]-3,5-bis(trifluoromethyl)benzeneacetamide Sodium triacetoxyborohydride (19 mg, 0.09 mmol) was added to a solution of trans-(RS)-α-methyl-N-[4-(3,3-dimethyl-2-oxo-1-piperazinyl)-1-phenylcyclohexyl]-3,5-bis(trifluoromethyl)benzeneacetamide (Example 196, 10 mg, 0.018 mmol) and benzaldehyde (20 µL, 0.2 mmol) in 1,2-dichloroethane (1 mL) and the mixture was stirred at room temperature for 19 hours. Saturated aqueous sodium hydrogen carbonate (1 mL) was added and the mixture was extracted with dichloromethane (3×1 mL). The combined organic fractions were dried ($MgSO_4$) and the solvent was evaporated under reduced pressure. The residue was purified by flash column chromatography on silica gel, eluting with $CH_2Cl_2$/MeOH/$NH_3$(Aq.) (120:8:1), then by flash column chromatography on silica gel, eluting with $CH_2Cl_2$/MeOH (98:2), to give the title compound as a colorless glass (2.4 mg, 20%). m/z ($ES^+$) 660 (M+1).

EXAMPLE 198

Trans-(RS)-α-Methyl-N-[4-(2,2-dimethyl-4-phenylmethyl-1-piperazinyl)-1-phenylcyclohexyl]-3,5-bis(trifluoromethyl)benzeneacetamide Zirconium (IV) chloride (13 mg, 0.054 mmol) was added to stirred, cooled (−10° C.) solution of trans-(RS)-α-methyl-N-[4-(2-oxo-4-phenylmethyl-1-piperazinyl)-1-phenylcyclohexyl]-3,5-bis(trifluoromethyl)benzeneacetamide (Example 189, 18 mg, 0.027 mmol) in tetrahydrofuran (2 mL) and the mixture was stirred at −10° C. for 30 minutes. Methyl magnesium chloride (3M in tetrahydrofuran, 60 µL, 0.16 mmol) was added and the mixture was allowed to warm to room temperature and stirred for 16 hours. Further zirconium (IV) chloride (40 mg, 0.16 mmol) was added and the mixture was stirred at room temperature for 30 minutes. Methyl magnesium chloride (3M in tetrahydrofuran, 2 mL, 6 mmol) was added and the mixture was stirred at room temperature for 96 hours. Saturated aqueous ammonium chloride (10 mL) was added and the mixture was extracted with ethyl acetate (3×15 mL). The combined organic fractions were washed with brine, dried ($MgSO_4$) and the solvent was evaporated under reduced pressure. The residue was purified by preparative thin layer chromatography on silica gel, eluting with $CH_2Cl_2$/MeOH/$NH_3$(Aq.) (200:8:1), to give the title compound as a colorless solid (8.1 mg, 46%). $^1$H NMR (400 MHz, $CD_3OD$) δ 1.09 (6H, m), 1.31–1.34 (3H, m), 1.42–1.59 (4H, m), 1.83–1.91 (2H, m), 2.08 (2H, Br s), 2.25–2.38 (2H, m), 2.41–2.53 (2H, m), 2.69–2.72 (1H, m), 2.97–3.00 (2H, m), 3.37 (2H, s), 3.73 (1H, q, J 7.0 Hz), 7.13–7.26 (8H, m), 7.41 (2H, d, J 8.0 Hz), 7.72 (2H, s), and 7.78 (1H, s). m/z ($ES^+$) 646 (M+1).

EXAMPLE 199

Trans-(RS)-α-Methyl-N-{4-({N-[1,1-dimethylethoxy)carbonyl]-1,1-dimethylethyl)amino}ethylamino)-1-phenylcyohexyl}-3,5-bis(trifluoromethyl)benzeneacetamide 1,1-Dimethylethyl N-(1,1-dimethylethyl)-N-(2-oxoethyl)carbamate (Description 160, 86 mg, 0.4 mmol) was added to a solution of trans-(RS)-N-(4-amino-1-phenylcyclohexyl)-α-methyl-3,5-bis(trifluoromethyl)benzeneacetamide (Example 39, 100 mg, 0.22 mmol) in methanol (3 mL) and the mixture was stirred at room temperature for 65 hours. Sodium borohydride (30 mg, 0.8 mmol) was added and the mixture was stirred at room temperature for 1 hour. The solvent was evaporated under reduced pressure, saturated aqueous sodium hydrogen carbonate (15 mL) and water (15 mL) were added and the mixture was extracted with dichloromethane (3×20 mL). The combined organic fractions were dried ($MgSO_4$) and the solvent was evaporated under reduced pressure. The residue was purified by flash column chromatography on silica gel, eluting with $CH_2Cl_2$/MeOH/$NH_3$(Aq.) (200:8:1), to give the title compound as a colorless foam (120 mg, 83%). m/z ($ES^+$) 658 (M+1).

EXAMPLE 200

Trans-(RS)-α-Methyl-N-{4-[4-(1,1-dimethylethyl)-2-oxo-1-piperazinyl]-1-phenylcyclohexyl}-3,5-bis(trifluoromethyl)benzeneacetamide Bromoacetyl bromide (28 µL, 0.32 mmol) was added to a stirred, cooled (0° C.) solution of trans-(RS)-α-methyl-N-{4-({N-[(1,1-dimethylethoxy)carbonyl]-(1,1-dimethylethyl)amino}ethylamino)-1-phenylcyclohexyl}-3,5-bis(trifluoromethyl)benzeneacetamide (Example 199, 118 mg, 0.18 mmol) and triethylamine (100 µL, 0.72 mmol) in dichloromethane (5 mL) and the mixture was stirred at 0° C. for 1 hour. Saturated aqueous sodium hydrogen carbonate (10 mL) and water (10 mL) were added and the mixture was extracted with dichloromethane (2×20 mL). The combined organic fractions were washed with aqueous citric acid (10%, 20 mL) and saturated aqueous sodium hydrogen carbonate (20 mL), dried ($MgSO_4$) and the solvent was evaporated under reduced pressure. The residue was dissolved in dichloromethane (6 mL), trifluoroacetic acid (2 mL) was added and the mixture was stirred at room temperature for 45 minutes. The solvent was evaporated under reduced pressure, dichloromethane (5 mL) and triethylamine (3 mL) were added and the mixture was stirred at room temperature for 20 hours. The solvent was evaporated under reduced pressure, water (25 mL) was added and the pH was adjusted to 12 with aqueous sodium hydroxide (4M). The mixtures was extracted with dichloromethane (3×20 mL), the combined organic fractions were dried ($MgSO_4$) and the solvent was evaporated under reduced pressure. The residue was purified by flash column chromatography on silica gel, eluting with $CH_2Cl_2$/MeOH/$NH_3$(Aq.) (120:8:1), then by preparative thin layer chromatography on silica gel, eluting with CH$_2$Cl$_2$/MeOH/NH$_3$(Aq.) (200:8:1), to give the title compound as a colorless glass (13 mg, 12%). $^1$H NMR (400 MHz, CD$_3$OD) δ 1.05 (9H, s), 1.31 (3H, d, J 7.0 Hz), 1.42–1.64 (4H, m), 1.88–1.98 (2H, m), 2.66 (2H, t, J 5.2 Hz), 2.76–2.84 (1H, m), 2.99–3.01 (2H, m), 3.08–3.18 (1H, m), 3.30 (2H, s), 3.75 (1H, q, J 7.0 Hz), 4.39–4.49 (1H, m), 7.18 (1H, t, J 7.3 Hz), 7.24–78 (2H, m), 7.43–7.45 (2H, m), 7.72 (2H, s), and 7.78 (1H, s). m/z (ES$^+$) 598 (M+1).

EXAMPLE 201

Trans-(RS)-N-(2-{[(1,1-Dimethylethoxy)carbonyl] amino}ethyl)-N-[4-({1-Oxo-2-[3,5-bis(trifluoromethyl)phenyl]propyl}amino)-4-phenylcyclohexyl] glycine Methyl Ester Methyl bromoacetate (24 μL, 0.25 mmol) was added to a mixture of trans-(RS)-α-methyl-N-{4-[(2-{[(1,1-dimethylethoxy)carbonyl]amino}ethyl)amino]-1-phenylcyclohexyl}-3,5-bis(trifluoromethyl)benzeneacetamide (Example 33, 50 mg, 0.08 mmol) and potassium carbonate (69 mg, 0.5 mmol) in dimethylformamide (2 mL) and the mixture was stirred at room temperature for 20 hours. The mixture was diluted with water (20 mL) and extracted with ether (2×40 mL). The combined organic fractions were washed with water (4×10 mL) and brine (20 mL), dried (MgSO$_4$) and the solvent was evaporated under reduced pressure to give crude title compound as a colorless solid (60 mg). m/z (ES$^+$) 674 (M+1).

EXAMPLE 202

Trans-(RS)-α-Methyl-N-[4-(3-oxo-1-piperazinyl)-1-phenylcyclohexyl]-3,5-bis(trifluoromethyl)benzeneacetamide Trifluoroacetic acid (0.5 mL) was added to a solution of crude trans-(RS)-N-(2-{[(1,1-dimethylethoxy)carbonyl] amino}ethyl)-N-[4-({1-oxo-2-[3,5-bis(trifluoromethyl)phenyl]propyl}amino)-4-phenylcyclohexyl]glycine methyl ester (Example 201, 60 mg, 0.08 mmol) in dichloromethane (3 mL) and the mixture was stirred at room temperature for 20 hours. Further trifluoroacetic acid (1 mL) was added and the mixture was stirred at room temperature for 3 hours. The solvent was evaporated under reduced pressure, saturated aqueous potassium carbonate was added and the mixture was extracted with dichloromethane. The combined organic fractions were dried (MgSO$_4$) and the solvent was evaporated under reduced pressure The residue was purified by flash column chromatography on silica gel, eluting with CH$_2$Cl$_2$/MeOH/NH$_3$(Aq.) (120:8:1), to give the title compound as a colorless solid (20 mg, 46%). m/z (ES$^+$) 542 (M+1).

EXAMPLE 203

Trans-(RS)-α-Hydroxy-α-methyl-N-[4-(3-oxo-1-piperazinyl)-1-phenylcyclohexyl]-3,5-bis(trifluoromethyl)benzeneacetamide Sodium hydride (60% dispersion in mineral oil, 18 mg, 0.45 mmol) was added to a stirred, cooled (0° C.) solution of trans-(RS)-α-methyl-N-[4-(3-oxo-1-piperazinyl)-1-phenylcyclohexyl]-3,5-bis(trifluoromethyl)benzeneacetamide (Example 202, 100 mg, 0.18 mmol) in dimethylformamide (2 mL) and the mixture was stirred at 0° C. for 10 minutes. 2-Bromopropane (17 μL, 0.18 mmol) was added and the mixture was stirred at 50° C. for 18 hours. Further sodium hydride (60% dispersion in mineral oil, 18 mg, 0.45 mmol) and 2-bromopropane (17 μL, 0.18 mmol) were added the mixture was stirred at 70° C. for 3 hours. The mixture was cooled, diluted with water (50 mL) and extracted with ethyl acetate (2×25 mL). The combined organic fractions were washed with water (3×15 mL) and brine (15 mL), dried (MgSO$_4$) and the solvent was evaporated under reduced pressure. The residue was purified by preparative thin layer chromatography on silica gel, eluting with CH$_2$Cl$_2$/MeOH/ NH$_3$(Aq.) (200:8:1), to give the title compound as a yellow gum (6.5 mg, 7%). m/z (ES$^+$) 558 (M+1).

EXAMPLE 204

Trans-(RS)-N-(2-{N-[(1,1-Dimethylethoxy)carbonyl]-1,1-dimethylethylamino}ethyl)-N-[4-({1-Oxo-2-[3,5-bis(trifluoromethyl)phenyl]propyl}amino)-4-phenylcyclohexyl]glycine Methyl Ester Methyl bromoacetate (74 μL, 0.78 mmol) was added to a mixture of trans-(RS)-α-methyl-N-{4-({N-[(1,1-dimethylethoxy)carbonyl]-(1,1-dimethylethyl)amino}ethylamino)-1-phenylcyclohexyl}-3,5-bis(trifluoromethyl)benzeneacetamide (Example 199, 170 mg, 0.26 mmol) and potassium carbonate (215 mg, 1.56 mmol) in dimethylformamide (4 mL) and the mixture was stirred at room temperature for 17 hours. The mixture was diluted with water (50 mL) and extracted with ether (3×40 mL). The combined organic fractions were washed with water (4×10 mL) and brine (15 mL), dried (MgSO$_4$) and the solvent was evaporated under reduced pressure to give the title compound as a colorless foam (192 mg, 100%). m/z (ES$^+$) 674 (M+1).

EXAMPLE 205

Trans-(RS)-α-Methyl-N-{4-[4-(1,1-dimethylethyl)-3-oxo-1-piperazinyl]-1-phenylcyclohexyl}-3,5-bis (trifluoromethyl)benzeneacetamide Trifluoroacetic acid (2 mL) was added to a solution of trans-(RS)-N-(2-{N-[(1,1-dimethylethoxy)carbonyl]-1,1-dimethylethylamino}ethyl)-N-[4-({1-Oxo-2-[3,5-bis(trifluoromethyl)phenyl]propyl}amino)-4-phenylcyclohexyl] glycine methyl ester (Example 204, 190 mg, 0.7 mmol) in dichloromethane (5 mL) and the mixture was stirred at room temperature for 2 hours. Further trifluoroacetic acid (2 mL) was added and the mixture was stirred at room temperature for 1.5 hours. The solvent was evaporated under reduced pressure, dichloromethane (5 mL) and triethylamine (2 mL) were added and the mixture was stirred at room temperature for 20 hours. The solvent was evaporated under reduced pressure, methanol (5 mL) and triethylamine (1 mL) were added and the mixture was stirred under reflux for 3 hours, then at room temperature for 60 hours. The solvent was evaporated under reduced pressure, toluene (5 mL) was added and the mixture was heated under reflux for 20 hours. The mixture was cooled and the solvent was evaporated under reduced pressure. Saturated aqueous sodium hydrogen carbonate (10 mL) and water (10 mL) were added and the mixture was extracted with dichloromethane (3×15 mL). The combined organic fractions were washed with brine, dried (MgSO$_4$) and the solvent was evaporated under reduced pressure. The residue was dissolved in methanol (4 mL), sodium methoxide (7M in methanol, 60 μL, 0.4 mmol) was added and the mixture was stirred at room temperature for 2 hours. Further sodium methoxide (7M in methanol, 1 mL, 7 mmol) was added and the mixture was stirred at room temperature for 20 hours. Further sodium methoxide (7M in methanol, 2 mL, 14 mmol) was added and the mixture was stirred at 50° C. for 3 hours and at room temperature for 20 hours. The solvent was evaporated under reduced pressure, 1-(dimethylaminopropyl)-3-ethylcarbodiimide hydrochloride (672 mg, 3.5 mmol), 1-hydroxybenzotriazole (797 mg, 5.9 mmol), triethylamine (1.4 mL, 10 mmol) and tetrahydrofuran (15 mL) were added and the mixture was stirred at room temperature for 16 hours. The solvent was evaporated under reduced pressure, saturated aqueous sodium hydrogen carbonate (25 mL) was added and the mixture was extracted with dichloromethane (3×20 mL). The combined organic fractions were washed with brine, dried ($MgSO_4$) and the solvent was evaporated under reduced pressure. The residue was purified by flash column chromatography on silica gel, eluting with $CH_2Cl_2$/MeOH/$NH_3$(Aq.) (200:8:1), and the residue was dissolved in methanol (1.5 mL) and poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure to give the title compound as a colorless foam (33 mg, 8%). m/z ($ES^+$) 598 (M+1).

EXAMPLE 206

Trans-(RS)-α-Methyl-N-(4-{N-[2-(4-fluorophenyl)amino-2-oxoethyl]-(2-hydroxyethyl)amino}-1-phenylcyclohexyl)-3,5-bis(trifluoromethyl)benzeneacetamide Bromoacetyl bromide (1.1 mL, 12.6 mmol) was added slowly to a stirred, cooled (0° C.) mixture of 4-fluorobenzenamine (1 mL, 10.5 mmol) in dichloromethane (10 mL) and aqueous potassium hydrogen carbonate (20%, 10 mL) and the mixture was stirred at 0° C. for 10 minutes, then at room temperature for 1 hour. The mixture was diluted with water (100 mL) and extracted with ethyl acetate (3×50 mL). The combined organic fractions were dried ($MgSO_4$) and the solvent was evaporated under reduced pressure to give a purple solid (2.2 g). A sample (86 mg, 0.37 mmol), trans-(RS)-α-methyl-N-{4-[(2-hydroxyethyl)amino]-1-phenylcyclohexyl}-3,5-bis(trifluoromethyl)benzeneacetamide (Example 161, 100 mg, 0.19 mmol) and potassium carbonate (131 mg, 0.95 mmol) were suspended in acetonitrile (5 mL) and heated under reflux for 20 hours. The mixture was cooled, diluted with water (20 mL) and extracted with dichloromethane (3×20 mL). The aqueous layer was evaporated under reduced pressure and extracted with dichloromethane (3×20 mL). The combined organic fractions were dried ($MgSO_4$), the solvent was evaporated under reduced pressure and the residue was purified by flash column chromatography on silica gel, eluting with $CH_2Cl_2$/MeOH/$NH_3$(Aq.) (200:8:1). The residue was dissolved in methanol (1.5 mL) and poured onto an SCX cartridge (Varian Bond Elut™; 10 ml/500 mg). The cartridge was washed with methanol (4×2 mL), then eluted with methanolic ammonia (2M, 2×2 mL). The solvent was evaporated under reduced pressure to give the title compound as a colorless glass (114 mg, 92%). m/z ($ES^+$) 654 (M+1).

The following compounds were prepared according to the method of Example 206, substituting a suitable amine for 4-fluorobenzenamine.

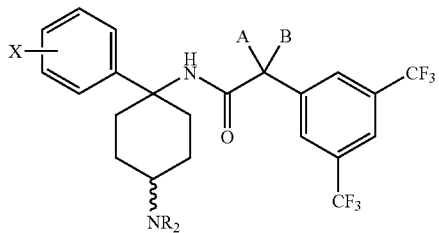

| Ex. | X | A | B | —$NR_2$ | Stereochemistry | Formula | M.W. | m/z ($ES^+$) (M + 1) |
|---|---|---|---|---|---|---|---|---|
| 207 | H | Me | H | (N-CH2-C(O)-NH-(2-methylphenyl), with N-CH2CH2OH) | Trans-(RS)- | $C_{34}H_{37}F_6N_3O_3$ | 649 | 650 |
| 208 | H | Me | H | (N-CH2-C(O)-NH-(3-methylphenyl), with N-CH2CH2OH) | Trans-(RS)- | $C_{34}H_{37}F_6N_3O_3$ | 649 | 650 |

-continued

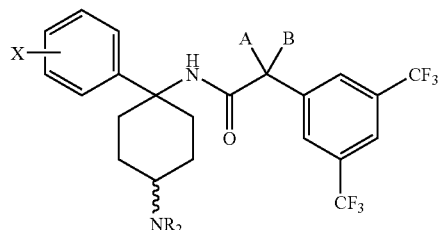

| Ex. | X | A | B | —NR₂ | Stereochemistry | Formula | M.W. | m/z (ES⁺) (M + 1). |
|---|---|---|---|---|---|---|---|---|
| 209 | H | Me | H | N-methyl, N-(2-hydroxyethyl), CH₂C(O)NH-(4-methylphenyl) | Trans-(RS)- | $C_{34}H_{37}F_6N_3O_3$ | 649 | 650 |
| 210 | H | Me | H | N-methyl, N-(2-hydroxyethyl), CH₂C(O)NH-(2,3-dimethylphenyl) | Trans-(RS)- | $C_{35}H_{39}F_6N_3O_3$ | 663 | 664 |
| 211 | H | Me | H | N-methyl, N-(2-hydroxyethyl), CH₂C(O)NH-(2,4-dimethylphenyl) | Trans-(RS)- | $C_{35}H_{39}F_6N_3O_3$ | 663 | 664 |
| 212 | H | Me | H | N-methyl, N-(2-hydroxyethyl), CH₂C(O)NH-(2,5-dimethylphenyl) | Trans-(RS)- | $C_{35}H_{39}F_6N_3O_3$ | 663 | 664 |
| 213 | H | Me | H | N-methyl, N-(2-hydroxyethyl), CH₂C(O)NH-(2,6-dimethylphenyl) | Trans-(RS)- | $C_{35}H_{39}F_6N_3O_3$ | 663 | 664 |
| 214 | H | Me | H | N-methyl, N-(2-hydroxyethyl), CH₂C(O)NH-(3,5-dimethylphenyl) | Trans-(RS)- | $C_{35}H_{39}F_6N_3O_3$ | 663 | 664 |
| 215 | H | Me | H | N-methyl, N-(2-hydroxyethyl), CH₂C(O)NH-(2-isopropylphenyl) | Trans-(RS)- | $C_{36}H_{41}F_6N_3O_3$ | 677 | 678 |

-continued

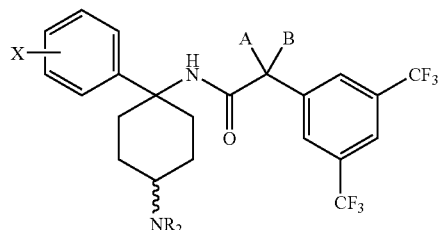

| Ex. | X | A | B | —NR₂ | Stereochemistry | Formula | M.W. | m/z (ES⁺) (M + 1). |
|---|---|---|---|---|---|---|---|---|
| 216 | H | Me | H | N-methyl-N-(2-hydroxyethyl), CH₂C(O)NH-(2-CF₃-phenyl) | Trans-(RS)- | $C_{34}H_{34}F_9N_3O_3$ | 703 | 704 |
| 217 | H | Me | H | N-methyl-N-(2-hydroxyethyl), CH₂C(O)NH-(3-CF₃-phenyl) | Trans-(RS)- | $C_{34}H_{34}F_9N_3O_3$ | 703 | 704 |
| 218 | H | Me | H | N-methyl-N-(2-hydroxyethyl), CH₂C(O)NH-(4-CF₃-phenyl) | Trans-(RS)- | $C_{34}H_{34}F_9N_3O_3$ | 703 | 704 |
| 219 | H | Me | H | N-methyl-N-(2-hydroxyethyl), CH₂C(O)NH-(2-OMe-phenyl) | Trans-(RS)- | $C_{34}H_{37}F_6N_3O_4$ | 665 | 666 |
| 220 | H | Me | H | N-methyl-N-(2-hydroxyethyl), CH₂C(O)NH-(3-OMe-phenyl) | Trans-(RS)- | $C_{34}H_{37}F_6N_3O_4$ | 665 | 666 |
| 221 | H | Me | H | N-methyl-N-(2-hydroxyethyl), CH₂C(O)NH-(4-OMe-phenyl) | Trans-(RS)- | $C_{34}H_{37}F_6N_3O_4$ | 665 | 666 |
| 222 | H | Me | H | N-methyl-N-(2-hydroxyethyl), CH₂C(O)NH-(2-OCF₃-phenyl) | Trans-(RS)- | $C_{34}H_{34}F_9N_3O_4$ | 719 | 720 |

-continued

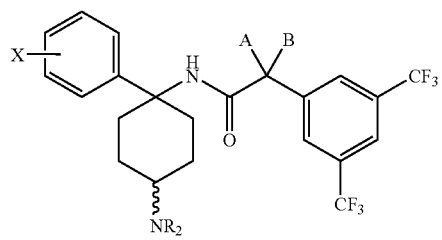

| Ex. | X | A | B | —NR₂ | Stereochemistry | Formula | M.W. | m/z (ES⁺) (M + 1). |
|---|---|---|---|---|---|---|---|---|
| 223 | H | Me | H | —N(Me)CH₂C(O)NH-C₆H₄-CO₂Me, with N-CH₂CH₂OH | Trans-(RS)- | $C_{35}H_{37}F_6N_3O_5$ | 693 | 694 |
| 224 | H | Me | H | —N(Me)CH₂C(O)NH-(2-F-C₆H₄), with N-CH₂CH₂OH | Trans-(RS)- | $C_{33}H_{34}F_7N_3O_3$ | 653 | 654 |
| 225 | H | Me | H | —N(Me)CH₂C(O)NH-(2-Cl-C₆H₄), with N-CH₂CH₂OH | Trans-(RS)- | $C_{33}H_{34}ClF_6N_3O_3$ | 669 671 | 670 672 |
| 226 | H | Me | H | —N(Me)CH₂C(O)NH-(3-Cl-C₆H₄), with N-CH₂CH₂OH | Trans-(RS)- | $C_{33}H_{34}ClF_6N_3O_3$ | 669 671 | 670 672 |
| 227 | H | Me | H | —N(Me)CH₂C(O)NH-(4-Cl-C₆H₄), with N-CH₂CH₂OH | Trans-(RS)- | $C_{33}H_{34}ClF_6N_3O_3$ | 669 671 | 670 672 |
| 228 | H | Me | H | —N(Me)CH₂C(O)NH-(2,6-Cl₂-C₆H₃), with N-CH₂CH₂OH | Trans-(RS)- | $C_{33}H_{33}Cl_2F_6N_3O_3$ | 703 705 | 704 706 |

-continued

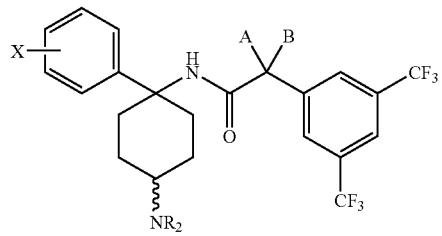

| Ex. | X | A | B | —NR₂ | Stereochemistry | Formula | M.W. | m/z (ES⁺) (M + 1) |
|---|---|---|---|---|---|---|---|---|
| 229 | H | Me | H | (structure with N-CH₂-C(O)-NH-CH₂-phenyl and -CH₂CH₂OH on N) | Trans-(RS)- | $C_{34}H_{37}F_6N_3O_3$ | 649 | 650 |

EXAMPLE 230

Trans-(RS)-α-Methyl-N-{4-[4-(4-fluorophenyl)-3-oxo-1-piperazinyl]-1-phenylcyclohexyl}-3,5-bis(trifluoromethyl)benzeneacetamide Di-t-butyl diazenedicarboxylate (76 mg, 0.33 mmol) was added to a stirred, cooled (0° C.) solution of trans-(RS)-α-methyl-N-(4-{N-[2-(4-fluorophenyl)amino-2-oxoethyl]-(2-hydroxyethyl)amino}-1-phenylcyclohexyl)-3,5-bis(trifluoromethyl)benzeneacetamide (Example 206, 72 mg, 0.11 mmol) and triphenylphosphine (86 mg, 0.33 mmol) in ethyl acetate (3 mL) and the mixture was stirred at 0° C. for 15 minutes, then at room temperature for 2 hours. Saturated aqueous sodium hydrogen carbonate (10 mL) and water (10 mL) were added and the mixture was extracted with ethyl acetate (2×20 mL). The combined organic fractions were poured onto an SCX cartridge (Varian Bond Elut™; 10 mL/500 mg). The cartridge was washed with methanol (4×2 m), then eluted with methanolic ammonia (2M, 2×2 mL). The solvent was evaporated under reduced pressure and the residue was purified by flash column chromatography on silica gel, eluting with CH₂Cl₂/MeOH/NH₃(Aq.) (200:8:1), then by preparative thin layer chromatography on silica gel, eluting with isohexane/EtOAc (25:75), to give the tide compound as a colorless foam (15 mg, 21%). ¹H NMR (400 MHz, CD₃OD) δ 1.38 (3H, d, J 7.0 Hz), 1.52–1.59 (1H, m), 1.66–1.75 (2H, m), 1.71–1.90 (1H, m), 1.99–2.09 (2H, m), 2.39–2.47 (2H, m), 2.58–2.61 (1H, m), 2.87 (2H, t, J 5.3 Hz), 3.65 (2H, t, J 5.3 Hz), 3.90 (1H, q, J 7.0 Hz), 7.11–7.18 (3H, m), 7.22–7.26 (2H, m), 7.28–7.34 (2H, m), 7.36–7.38 (2H, m), and 7.84 (3H, s). m/z (ES⁺) 636 (M+1).

The following compounds were prepared from the compounds of Example 207–229 according to the method of Example 230.

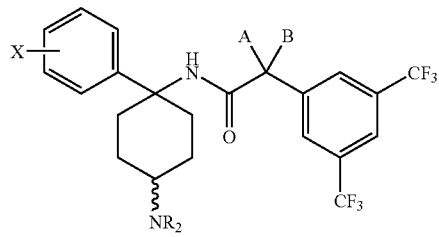

| Ex. | X | A | B | —NR₂ | Stereochemistry | Formula | M.W. | m/z (ES⁺) (M + 1) |
|---|---|---|---|---|---|---|---|---|
| 231 | H | Me | H | (piperazinone with o-tolyl) | Trans-(RS)- | $C_{34}H_{35}F_6N_3O_2$ | 631 | 632 |

-continued

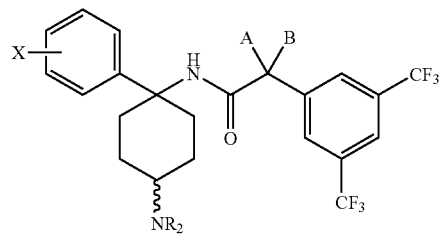

| Ex. | X | A | B | —NR₂ | Stereochemistry | Formula | M.W. | m/z (ES⁺) (M + 1). |
|---|---|---|---|---|---|---|---|---|
| 232 | H | Me | H | 3-methylphenyl-piperazinone-N-Me | Trans-(RS)- | $C_{34}H_{35}F_6N_3O_2$ | 631 | 632 |
| 233 | H | Me | H | 4-methylphenyl-piperazinone-N-Me | Trans-(RS)- | $C_{34}H_{35}F_6N_3O_2$ | 631 | 632 |
| 234 | H | Me | H | 2,3-dimethylphenyl-piperazinone-N-Me | Trans-(RS)- | $C_{35}H_{37}F_6N_3O_2$ | 645 | 646 |
| 235 | H | Me | H | 2,4-dimethylphenyl-piperazinone-N-Me | Trans-(RS)- | $C_{35}H_{37}F_6N_3O_2$ | 645 | 646 |
| 236 | H | Me | H | 2,5-dimethylphenyl-piperazinone-N-Me | Trans-(RS)- | $C_{35}H_{37}F_6N_3O_2$ | 645 | 646 |
| 237 | H | Me | H | 2,6-dimethylphenyl-piperazinone-N-Me | Trans-(RS)- | $C_{35}H_{37}F_6N_3O_2$ | 645 | 646 |
| 238 | H | Me | H | 3,5-dimethylphenyl-piperazinone-N-Me | Trans-(RS)- | $C_{35}H_{37}F_6N_3O_2$ | 645 | 646 |
| 239 | H | Me | H | 2-isopropylphenyl-piperazinone-N-Me | Trans-(RS)- | $C_{36}H_{39}F_6N_3O_2$ | 659 | 660 |

-continued

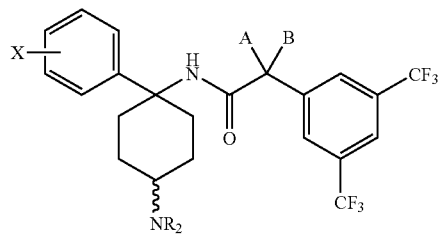

| Ex. | X | A | B | —NR₂ | Stereochemistry | Formula | M.W. | m/z (ES⁺) (M + 1). |
|---|---|---|---|---|---|---|---|---|
| 240 | H | Me | H | N-methylpiperazinone with 2-CF₃-phenyl | Trans-(RS)- | $C_{34}H_{32}F_9N_3O_2$ | 685 | 686 |
| 241 | H | Me | H | N-methylpiperazinone with 3-CF₃-phenyl | Trans-(RS)- | $C_{34}H_{32}F_9N_3O_2$ | 685 | 686 |
| 242 | H | Me | H | N-methylpiperazinone with 4-CF₃-phenyl | Trans-(RS)- | $C_{34}H_{32}F_9N_3O_2$ | 685 | 686 |
| 243 | H | Me | H | N-methylpiperazinone with 2-OMe-phenyl | Trans-(RS)- | $C_{34}H_{35}F_6N_3O_3$ | 647 | 648 |
| 244 | H | Me | H | N-methylpiperazinone with 3-OMe-phenyl | Trans-(RS)- | $C_{34}H_{35}F_6N_3O_3$ | 647 | 648 |
| 245 | H | Me | H | N-methylpiperazinone with 4-OMe-phenyl | Trans-(RS)- | $C_{34}H_{35}F_6N_3O_3$ | 647 | 648 |
| 246 | H | Me | H | N-methylpiperazinone with 2-OCF₃-phenyl | Trans-(RS)- | $C_{34}H_{32}F_9N_3O_3$ | 701 | 702 |
| 247 | H | Me | H | N-methylpiperazinone with 4-CO₂Me-phenyl | Trans-(RS)- | $C_{35}H_{35}F_6N_3O_4$ | 675 | 676 |
| 248 | H | Me | H | N-methylpiperazinone with 2-F-phenyl | Trans-(RS)- | $C_{33}H_{32}F_7N_3O_2$ | 635 | 636 |

-continued

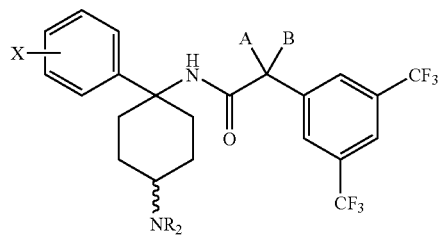

| Ex. | X | A | B | —NR₂ | Stereochemistry | Formula | M.W. | m/z (ES⁺) (M + 1). |
|---|---|---|---|---|---|---|---|---|
| 249 | H | Me | H | (1-methyl-4-(2-chlorophenyl)-3-oxopiperazinyl) | Trans-(RS)- | $C_{33}H_{32}ClF_6N_3O_2$ | 651 653 | 652 654 |
| 250 | H | Me | H | (1-methyl-4-(3-chlorophenyl)-3-oxopiperazinyl) | Trans-(RS)- | $C_{33}H_{32}ClF_6N_3O_2$ | 651 653 | 652 654 |
| 251 | H | Me | H | (1-methyl-4-(4-chlorophenyl)-3-oxopiperazinyl) | Trans-(RS)- | $C_{33}H_{32}ClF_6N_3O_2$ | 651 653 | 652 654 |
| 252 | H | Me | H | (1-methyl-4-(2,6-dichlorophenyl)-3-oxopiperazinyl) | Trans-(RS)- | $C_{33}H_{31}Cl_2F_6N_3O_2$ | 685 687 | 686 688 |
| 253 | H | Me | H | (1-methyl-4-benzyl-3-oxopiperazinyl) | Trans-(RS)- | $C_{34}H_{35}F_6N_3O_2$ | 631 | 632 |

EXAMPLE 254

Trans-(R)-α-Methyl-N-{4-[4-(4-fluorophenyl)-3-oxo-1-piperazinyl]-1-phenylcyclohexyl}-3,5-bis(trifluoromethyl)benzeneacetamide and Trans-(S)-α-Methyl-N-{4-[4-(4-fluorophenyl-3-oxo-1-piperazinyl]-1-phenylcyclohexyl}-3,5-bis(trifluoromethyl)benzeneacetamide Racemic trans-(RS)-α-methyl-N-{4-[4-(4-fluorophenyl)-3-oxo-1-piperazinyl]-1-phenylcyclohexyl}-3,5-bis(trifluoromethyl)benzeneacetamide (Example 249) was separated by preparative chiral HPLC [Chiralcel OD-H, 250×4.6 mm i.d.; isohexane/EtOH (95:5); 1 mL/min; 210 nm] to give trans-(R)-α-methyl-N-{4-[4-(4-fluorophenyl)-3-oxo-1-piperazinyl]-1-phenylcyclohexyl}-3,5-bis(trifluoromethyl)benzeneacetamide; m/z (ES⁺) 652 (M+1); and trans-(S)-α-methyl-N-{4-[4-(4-fluorophenyl)-3-oxo-1-piperazinyl]-1-phenylcyclohexyl}-3,5-bis(trifluoromethyl) benzeneacetamide; m/z (ES⁺) 652 (M+1).

The following compounds were prepared from according to the method of Example 1, substituting a suitable acid for 3,5-bis(trifluoromethyl)benzeneacetic acid and a suitable amine for 1,4-dioxa-8-phenylspiro[4.5]decan-8-amine.

| Ex. | R | A | B | —NR₂ | Stereochemistry | Formula | M.W. | m/z (ES⁺) (M + 1). |
|---|---|---|---|---|---|---|---|---|
| 255 | H | Me | Me | 3-oxo-4-phenylpiperazin-1-yl | Trans- | $C_{34}H_{35}F_6N_3O_2$ | 631 | 632 |
| 256 | H | Et | Et | 3-oxo-4-phenylpiperazin-1-yl | Trans- | $C_{36}H_{39}F_6N_3O_2$ | 659 | 660 |
| 257 | H | —CH₂CH₂— | | 3-oxo-4-phenylpiperazin-1-yl | Trans- | $C_{34}H_{33}F_6N_3O_2$ | 629 | 630 |
| 258 | H | CH₂OMe | H | 3-oxo-4-phenylpiperazin-1-yl | Trans-(RS)- | $C_{34}H_{35}F_6N_3O_3$ | 647 | 648 |
| 259 | H | Me | Me | 4-(2-chlorophenyl)-3-oxopiperazin-1-yl | Trans- | $C_{34}H_{34}ClF_6N_3O_2$ | 665 / 667 | 666 / 668 |
| 260 | H | H | H | 4-(2-chlorophenyl)-3-oxopiperazin-1-yl | Trans- | $C_{32}H_{30}ClF_6N_3O_2$ | 637 / 639 | 638 / 640 |
| 261 | Et | Me | H | 3-oxo-4-phenylpiperazin-1-yl | Trans-(RS)- | $C_{35}H_{37}F_6N_3O_2$ | 645 | 646 |
| 262 | Et | Me | H | 4-(2-chlorophenyl)-3-oxopiperazin-1-yl | Trans-(RS)- | $C_{36}H_{39}F_6N_3O_2$ | 659 | 660 |
| 263 | Et | Me | H | 4-(2-chlorophenyl)-3-oxopiperazin-1-yl | Trans-(RS)- | $C_{35}H_{36}ClF_6N_3O_2$ | 679 / 681 | 680 / 682 |

EXAMPLE 264

Trans-(RS)-Methyl 3-[-4-({1-Oxo-2-[3,5-bis(trifluoromethyl)phenyl]propyl}amino)-4-phenylcyclohexylamino]propanoate Methyl acrylate (218 µL, 2.42 mmol) in methanol (2 mL) was added dropwise to a stirred, cooled (0° C.) solution of trans-(RS)-N-(4-amino-1-phenylcyclohexyl)-α-methyl-3,5-bis(trifluoromethyl)benzeneacetamide (Example 39, 1.0 g, 2.2 mmol) in methanol (5 mL) and the mixture was stirred at room temperature for 16 hours. The solvent was evaporated under reduced pressure to give the title compound as a foam (1.2 g, 97%). m/z (ES$^+$) 544 (M+1).

EXAMPLE 265

Trans-(RS)-Methyl 3-{N-(3-Methoxy-1,3-dioxopropyl-[4-({1-oxo-2-[3,5-bis)trifluoromethylphenyl]propyl}amino)-4-phenylcyclohexyl]amino}propanoate Dimethyl malonate (5 mL) was added to trans-(RS)-methyl 3-[4-({1-oxo-2-[3,5-bis(trifluoromethyl)phenyl]propyl}amino)-4-phenylcyclohexylamino]propanoate (Example 264) and the mixture was stirred at 160–170° C. for 2 hours, then at room temperature for 16 hours. The residue was purified by flash column chromatography on silica gel, eluting with isohexane/EtOAc (50:50 increasing to 0:100) to give the title compound as a colorless foam (823 mg, 95%). m/z (ES$^+$) 645 (M+1).

EXAMPLE 266

Trans-(RS)-α-Methyl-N-[4-(2,4-dioxopiperidin-1-yl)-1-phenylcyclohexyl]-3,5-bis(trifluoromethyl)benzeneacetamide Sodium hydride (60% dispersion in mineral oil, 56 mg, 1.4 mmol) was added to a solution of trans-(RS)-methyl 3-{N-(3-methoxy-1,3-dioxopropyl)-[4-({1-oxo-2-[3,5-bis(trifluoromethyl)phenyl]propyl}amino)-4-phenylcyclohexyl]amino}propanoate (Example 265, 820 mg, 1.27 mmol) in toluene (5 mL) and the mixture was stirred at room temperature for 1 hour. Further sodium hydride (60% dispersion in mineral oil, 56 mg, 1.4 mmol) was added and the mixture was stirred at room temperature for 15 minutes, then under reflux for 3 hours. The mixture was cooled, the solvent was evaporated under reduced pressure and aqueous acetic acid (10%, 20 mL) was added. The mixture was heated under reflux for 4 hours, cooled and the pH was adjusted to 12.0 with saturated aqueous sodium hydrogen carbonate. The mixture was extracted with dichloromethane (3×40 mL), the combined organic fractions were dried (MgSO$_4$) and the solvent was evaporated under reduced pressure. The residue was purified by flash column chromatography on silica gel, eluting with EtOAc, to give the title compound as a colorless foam (301 mg, 43%). m/z (ES$^+$) 555 (M+1).

EXAMPLE 267

Trans-(RS)-α-Methyl-N-{4-[2-oxo-4-(piperidin-1-yl)piperidin-1-yl]-1-phenylcyclohexyl}-3,5-bis(trifluoromethyl)benzeneacetamide Piperidine hydrochloride (4.4 mg, 0.04 mmol) was added to a solution of trans-(RS)-α-methyl-N-[4-(2,4-dioxopiperidin-1-yl)-1-phenylcyclohexyl]-3,5-bis(trifluoromethyl)benzeneacetamide (Example 266, 20 mg, 0.04 mmol) in methanol (1 mL) and the mixture was stirred at room temperature for 48 hours. Further piperidine (4 µL, 0.04 mmol) and acetic acid (1 drop) were added and the mixture was stirred at room temperature for 20 hours. Further piperidine (4 µL, 0.04 mmol) and acetic acid (1 drop) were added and the mixture was stirred at room temperature for 96 hours. The solvent was evaporated under reduced pressure and toluene was added and evaporated under reduced pressure. The residue was dissolved in acetic acid (2 mL), palladium on carbon (5%, 20 mg) was added and the mixture was stirred under an atmosphere of hydrogen (1 Atm.) for 16 hours. The mixture was filtered and poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure and the residue was purified by preparative thin layer chromatography on silica gel, eluting with CH$_2$Cl$_2$/MeOH/NH$_3$(Aq.) (200:8:1), to give the title compound as a colorless glass (1.4 mg, 6%). $^1$H NMR (360 MHz, CD$_3$OD) δ 0.88–4.91 (5H, m), 1.28–1.65 (10H, m), 1.86–1.94 (2H, m), 2.05–2.08 (1H, m), 2.33–2.40 (1H, m), 2.55–2.72 (4H, m), 2.77–2.81 (2H, m), 2.92–3.13 (3H, m), 3.75 (1H, q, J 7.0 Hz), 4.46 (1H, m), 7.18 (1H, t, J 7.2 Hz), 7.24–7.29 (1H, m), 7.44–7.46 (2H, m), 7.72 (2H, s), and 7.78 (1H, s). m/z (ES$^+$) 624 (M+1).

EXAMPLE 268

Trans-(RS)-α-Methyl-N-[4-(4-oxopiperidin-1-yl)methyl-1-phenylcyclohexyl]-3,5-bis(trifluoromethylbenzeneacetamide Trans-(RS)-N-(4-Aminomethyl-1-phenylcyclohexyl)-α-methyl-3,5-bis(trifluoromethyl)benzeneacetamide hydrochloride (Example 46, 40 mg, 0.074 mmol) in methanol (1 mL) and 1,5-dichloropentan-3-one (11 mg, 0.074 mmol) in methanol (1 mL) were added simultaneously to a refluxing suspension of sodium carbonate (25 mg, 0.1 mmol) in methanol over 30 minutes. The mixture was heated under reflux for 2 hours, cooled and the solvent was evaporated under reduced pressure. Dichloromethane and water were added and the layers were separated. The organic fraction was dried (MgSO$_4$) and the solvent was evaporated under reduced pressure The residue was dissolved in methanol (1.5 mL) and poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure and the residue was purified by preparative thin layer chromatography on silica gel, eluting with CH$_2$Cl$_2$/MeOH/NH$_3$(Aq.) (96:4:1), to give the title compound (23 mg, 56%). $^1$H NMR (400 MHz, CDCl$_3$) δ 1.43 (3H, d, J 8.8 Hz), 1.67–1.81 (6H, m), 2.09–2.22 (4H, m), 2.36–2.40 (4H, m), 2.41–2.58 (2, m), 2.63–2.68 (3H, m), 4.10–4.35 (1, m), 7.20–7.42 (5H, m), 7.68 (2H, s), and 7.78 (1H, s). m/z (ES$^+$) 555 (M+1).

EXAMPLE 269

Trans-(RS)-α-Methyl-N-[4-(4-hydroxypiperidin-1-yl)-methyl-1-phenylcyclohexyl]-3,5-bis(trifluoromethylbenzeneacetamide Sodium borohydride (6 mg, 0.36 mmol) was added to a solution of trails-(RS)-α-methyl-N-[4-(4-oxopiperidin-1-yl) methyl-1-phenylcyclohexyl]-3,5-bis(trifluoromethylbenzeneacetamide (Example 268, 20 mg, 0.036 mmol) in methanol (1 mL) and the mixture was stirred at room temperature for 1 hour. The solvent was evaporated under reduced pressure and the residue was purified by preparative thin layer chromatography on silica gel, eluting with $CH_2Cl_2$/ MeOH/$NH_3$(Aq.) (92:8:1), to give the title compound (15 mg, 73%). $^1$H NMR (400 MHz, $CDCl_3$) δ 1.08–1.42 (5H, m), 1.36 (3H, d, J 6.8 Hz), 1.50–2.38 (12H, m), 2.48–2.56 (1H, m), 2.72–2.77 (2H, m), 3.57–3.59 (1H, m), 3.83–3.90 (1H, m), 7.09–7.40 (5H, m), and 7.81 (3H, s). m/z ($ES^+$) 557 (M+1).

EXAMPLE 270

(RS)-α-Methyl-N-(4-methylene-1-phenylcyclohexyl)-3,5-bis(trifluoromethyl) benzeneacetamide n-Butyllithium (1.6 Mol solution in hexanes, 10.3 mL) was added slowly to a stirred, cooled (0° C.) suspension of methyl triphenylphosphonium bromide (5.86 g, 16.4 mmol) in tetrahydrofuran (60 mL) and the mixture was stirred at room temperature for 3 hours. The mixture was cooled to 0° C. and (RS)-α-methyl-N-(4-oxo-1-phenylcyclohexyl)-3,5-bis(trifluoromethyl)benzeneacetamide (Example 3, 3.0 g, 6.56 mmol) in tetrahydrofuran (20 mL) was added. The mixture was stirred at room temperature for 1 hour, then under reflux for 3 hours. The mixture was cooled, poured into water and extracted with ethyl acetate. The combined organic fractions were dried ($MgSO_4$) and the solvent was evaporated under reduced pressure. The residue was purified by chromatography on a short column of silica gel, eluting with dichloromethane, to give the title compound as a colorless solid (2.27 g, 91%). $^1$H NMR (400 MHz, $CDCl_3$) δ 7.80 (1H, s), 7.75 (2H, s), 7.26–7.20 (5H, m), 5.59 (1H, s), 4.68 (2H, m), 3.70 (1H, d, J 7.1 Hz), 2.53–2.45 (1H, m), 2.38–2.31 (1H, m), 2.29–2.04 (4H, m), 2.00–1.85 (2H, m), and 1.52 (3H, d, J, 7.1 Hz).

EXAMPLE 271

Cis-(RS) and Trans-(RS)-α-Methyl-N-(4-hydroxymethyl-1-phenylcyclohexyl)-3,5-bis(trifluoromethyl) benzeneacetamide Borane-tetrahydrofuran complex (1M in tetrahydrofuran, 12 mL, 12 mmol) was added to a solution of (RS)-α-methyl-N-(4-methylene-1-phenylcyclohexyl)-3,5-bis(trifluoromethyl)benzeneacetamide (Example 270, 2.0 g, 7.84 mmol) in tetrahydrofuran (50 mL) and the mixture was stirred at room temperature overnight. Aqueous sodium hydroxide (4M, 9.8 mL) and aqueous hydrogen peroxide (30%, 9.8 mL) were added and the mixture was stirred at room temperature for 3 hours. Water was added and the mixture was extracted with ethyl acetate. The combined organic fractions were dried ($MgSO_4$) and the solvent was evaporated under reduced pressure. The residue was purified by flash column chromatography on silica gel, eluting with isohexane:EtOAc (50:50 increasing to 20:80), to give the title compound as a colorless solid (1.5 g, 40%) as a 1:1 mixture of cis and trans isomers. $^1$H NMR (400 MHz, $CD_3OD$) δ 8.13 (1H, s), 8.05 (1H, s), 7.93 (2H, s), 7.86 (1H, s), 7.81 (3H, s), 7.36–7.33 (2H, m), 7.27–7.11 (8H, m), 4.03 (1H, q, J 7.0 Hz), 3.86 (1H, q, J 7.0 Hz), 3.39–3.37 (2H, m), 3.32–3.26 (4H, m), 2.58–2.43 (3H, m), 2.39–2.32 (1H, m), 1.99–1.92 (2H, m), 1.77–1.58 (6H, m), 1.52–1.49 (1H, m), 1.45 (3H, d, J 7.0 Hz), 1.37 (3H, d, J 7.0 Hz), 1.31–1.29 (1H, m), 1.25–1.15 (1H, m), and 1.02–0.96 (1H, m).

EXAMPLE 272

Trans-(RS)-α-Methyl-N-(4-methanesulfonyloxymethyl-1-phenylcyclohexyl)-3,5-bis(trifluoromethyl) benzeneacetamide Methanesulfonyl chloride (0.34 mL, 4.44 mmol) was added to a solution of cis RS) and trans-(RS)-α-methyl-N-(4-hydroxymethyl-1-phenylcyclohexyl)-3,5-bis(trifluoromethyl)benzeneacetamide (Mixture of diastereoisomers, Example 271, 0.7 g, 1.48 mmol) and pyridine (0.6 mL, 7.4 mmol) in dichloromethane (20 mL) and the mixture was stirred at room temperature for 24 hours. The solvent was evaporated under reduced pressure and the residue was dissolved in ethyl acetate. The mixture was washed with aqueous citric acid (10%), aqueous sodium hydroxide (1M), dried ($MgSO_4$) and the solvent was evaporated under reduced pressure. The residue was purified by flash column chromatography on silica gel, eluting with isohexane:EtOAc (70:30), to give the title compound as a colorless foam (335 mg, 41%). $^1$H NMR (400 MHz, $CD_3OD$) δ 7.81 (3H, s), 7.37–7.34 (2H, m), 7.25–7.21 (2H, m), 7.17–7.15 (1H, m), 4.08 (2H, d, J 7.0 Hz), 3.87 (1H, q, J 7.1 Hz), 3.02 (3H, s), 2.61–2.54 (1H, m), 2.40–2.32 (1H, m), 2.07–1.89 (3H, m), 1.82–1.77 (1H, m), 1.71–1.62 (1H, m), 1.40–1.32 (1H, m), 1.37 (3H, d, J 7.1 Hz), and 1.29–1.22 (1H, m).

EXAMPLE 273

(1R*,2'R*)- and (1R*,2'S*)-Ethyl [1-({1-Oxo-2-[3,5-bis(trifluoromethyl)phenyl]propyl}amino)-1-phenylcyclohex-4-ylidine]acetate Ethyl (diethoxyphosphinyl)acetate (158 mL, 8.03 mmol) was added dropwise to a slurry of sodium hydride (60% dispersion in mineral oil, 320 mg, 8.00 mmol) in tetrahydrofuran (20 mL) and the mixture was stirred at room temperature for 1 hours. (RS)-α-Methyl-N-(4-oxo-1-phenylcyclohexyl)-3,5-bis(trifluoromethyl)benzeneacetamide (Example 3, 2.00 g, 4.37 mmol) in tetrahydrofuran (20 mL) was added dropwise over 10 minutes and the mixture was stirred at room temperature for 3 hours. Water (150 mL) was added and the mixture was extracted with ethyl acetate (3×150 mL). The combined organic fractions were washed with brine (100 mL), dried ($Na_2SO_4$) and the solvent was evaporated under reduced pressure. The residue was triturated with isohexane (×2) and the solid was collected and dried in vacuo to give the title compound (1.39 g, 60%) as a mixture of diastereoisomers. The filtrate was evaporated under reduced pressure and the residue was purified by chromatography on a short column of silica gel, eluting with $CH_2Cl_2$ to give additional title compound (0.61 g, 26%) as a mixture of diastereoisomers. $^1$H NMR (400 MHz, $CDCl_3$) δ 7.79 (1H, s), 7.75 and 7.73 (Total 2H, each s), 7.30–7.20

(5H, m), 5.69–5.61 (2H, m), 4.14 (2H, q, J 7 Hz), 3.68 (1H, q, J 7 Hz), 3.6–3.5 (1H, m), 2.8–1.9 (7H, m), 1.50 (3H, d, J 7 Hz), and 1.25 (3H, t, J 7 Hz).

EXAMPLE 274

Trans-(RS)-Ethyl [1-({1-Oxo-2-[3,5-bis(trifluoromethyl)phenyl]propyl}amino)-1-phenylcyclohex-4-yl] acetate Sodium borohydride (288 mg, 7.58 mmol) was added to a mixture of (1R*,2'R*)- and (1R*,2'S*)-ethyl [1-({1-oxo-2-[3,5-bis(trifluoromethyl)phenyl]propyl}amino)-1-phenylcyclohex-4-ylidine]acetate (Mixture of diastereoisomers, Example 273, 2.00 g, 3.80 mmol) and nickel (II) chloride hexahydrate (902 mg, 3.80 mmol) in ethanol (40 mL). The mixture was stirred at room temperature for 4 hours, then further nickel (II) chloride hexahydrate (450 mg, 1.90 mmol) and sodium borohydride (150 mg, 3.95 mmol) were added. The mixture was stirred at room temperature for 20 hours, then further nickel (II) chloride hexahydrate (450 mg, 1.90 mmol) and sodium borohydride (150 mg, 3.95 mmol) were added. The mixture was stirred at room temperature for 3 hours, then water (100 mL) was added and the ethanol was evaporated under reduced pressure. The residue was filtered through Hyflo™, washing with water (100 mL) and ethyl acetate (200 mL). The layers were separated and the aqueous layer was extracted with ethyl acetate (2×100 mL). The combined organic fractions were dried ($Na_2SO_4$), the solvent was evaporated under reduced pressure and the residue was purified by flash column chromatography and MPLC on silica gel, eluting with isohexane/EtOAc (75:25), to give the title compound (975 mg, 49%). $^1$H NMR (400 MHz, $CDCl_3$) δ 7.75 (1H, s), 7.64 (2H, s), 7.38–7.20 (5H, m), 5.49 (1H, br s), 4.10 (2H, q, J 7 Hz), 3.51 (1, q, J 7 Hz), 2.58 (1H, br d, J 14 Hz), 2.46 (1H, br d, J 14 Hz), 2.2–1.9 (5H, m), 1.75–1.6 (2H, m), 1.42 (3H, d, J 7 Hz), 1.22 (3H, t, J 7 Hz), and 1.25–1.05 (2H, m).

EXAMPLE 275

Trans-(RS)-α-Methyl-N-(4-hydroxyethyl-1-phenylcyclohexyl)-3,5-bis(trifluoromethyl)benzeneacetamide Lithium borohydride (500 mg, 22.7 mmol) was added to a solution of trans-(RS)-ethyl [1-({1-oxo-2-[3,5-bis(trifluoromethyl)phenyl]propyl}amino)-1-phenylcyclohex-4-yl]acetate (Example 274, 975 mg, 1.84 mmol) in tetrahydrofuran/toluene (50:50, 40 mL) and the mixture stirred at 60° C. for 6 hours. Additional lithium borohydride (200 mg, 9.10 mmol) was added and the mixture was stirred at 60° C. for 3 hours. The mixture was cooled to 0° C. and hydrochloric acid (2M, 30 mL) was added slowly. The mixture was poured into aqueous sodium carbonate (10%, 100 mL) and extracted with ethyl acetate (3×100 mL). The combined organic fractions were dried ($MgSO_4$) and the solvent was evaporated under reduced pressure to give the title compound (927 mg, 100%). $^1$H NMR (400 MHz, $CDCl_3$) δ 7.76 (1H, s), 7.65 (2H, s), 7.38–7.15 (5H, m), 5.48 (1H, br s), 3.64 (2H, t, J 6.5 Hz), 3.51 (1H, q, J 7 Hz), 2.55 (1H, br d, J 14 Hz), 2.44 (1H, br d, J 14 Hz), 2.08 (2H, dq, J 11, 3 Hz), 1.75–1.40 (5H, m), 1.42 (3H, d, J 7 Hz), and 1.2–1.0 (2H, m).

EXAMPLE 276

Trans-(RS)-α-Methyl-N-(4-methanesulfonyloxyethyl-1-phenylcyclohexyl)-3,5-bis(trifluoromethyl) benzeneacetamide Methanesulfonyl chloride (440 μL, 5.68 mmol) was added dropwise to a stirred, cooled (0° C.) solution of trans-(RS)-α-methyl-N-(4-hydroxyethyl-1-phenylcyclohexyl)-3,5-bis(trifluoromethyl)benzeneacetamide (Example 275, 920 mg, 1.89 mmol) and pyridine (760 μL, 9.4 mmol) in dichloromethane (20 mL) and the mixture was stirred at room temperature for 20 hours. Further pyridine (380 μL, 4.7 mmol) and methanesulfonyl chloride (220 μL, 2.84 mmol) were added and the mixture was stirred at room temperature for 20 hours. Dichloromethane (200 mL) was added and the mixture was washed with aqueous citric acid (10%, 100 mL), aqueous sodium hydroxide (1M, 100 mL), water (100 mL) and brine (100 mL), dried ($Na_2SO_4$) and the solvent was evaporated under reduced pressure to give the title compound (1.025 g, 96%). $^1$H NMR (400 MHz, $CDCl_3$) δ 7.76 (1H, s), 7.64 (2H, s), 7.38–7.2 (5H, m), 5.48 (1H, br s), 4.20 (2H, t, J 6.5 Hz), 3.48 (1H, q, J 7 Hz), 2.97 (3H, s), 2.58 (1H, br d, J 14 Hz), 2.48 (1H, br d, J 14 Hz), 2.20–2.05 (2H, m), 1.75–1.50 (5H, m), 1.42 (3H, d, J 7 Hz), and 1.20–1.00 (2H, m).

EXAMPLE 277

Trans-(RS)-α-Methyl-N-[4-(4-morpholinyl)methyl-1-phenylcyclohexyl]-3,5-bis(trifluoromethyl)benzeneacetamide Morpholine (31 μL, 0.36 mmol) was added to a solution of trans-(RS)-α-methyl-N-(4-methanesulfonyloxymethyl-1-phenylcyclohexyl)-3,5-bis(trifluoromethyl)benzeneacetamide (Example 272, 50 mg, 0.09 mmol) in acetonitrile (2 mL) and the mixture was stirred at 80° C. for 3 days. The mixture was cooled the solvent was evaporated under reduced pressure. Aqueous sodium hydroxide (1M) and dichloromethane were added. The layers were separated, the organic fraction was dried ($MgSO_4$) and the solvent was evaporated under reduced pressure. The residue was purified by flash column chromatography on silica gel, eluting with $CH_2Cl_2$/MeOH (95:5 increasing to 90:10), to give the title compound as a colorless solid (35 mg, 71%). m/z (ES$^+$) 543 (M+1).

The following compounds were prepared from trans-(RS)-α-methyl-N-(4-methanesulfonyloxymethyl-1-phenylcyclohexyl)-3,5-bis(trifluoromethyl)benzeneacetamide (Example 272) or trans-(RS)-α-methyl-N-(4-methanesulfonyloxyethyl-1-phenylcyclohexyl)-3,5-(trifluoromethyl)benzeneacetamide (Example 276) according to the method of Example 277, substituting a suitable amine for morpholine.

| Ex. | A | B | n | —NR₂ | Stereochemistry | Formula | M.W. | m/z (ES⁺) (M + 1). |
|---|---|---|---|---|---|---|---|---|
| 278 | Me | H | 1 | N-piperidinyl-CH₂OH | Trans-(RS)- | $C_{30}H_{36}F_6N_2O_2$ | 570 | 571 |
| 279 | Me | H | 1 | N-piperidinyl-CH₂CH₂OH | Trans-(RS)- | $C_{31}H_{38}F_6N_2O_2$ | 584 | 585 |
| 280 | Me | H | 1 | 2-oxa-8-azaspiro[4.5]decane | Trans-(RS)- | $C_{32}H_{38}F_6N_2O_2$ | 596 | 597 |
| 281 | Me | H | 1 | N-Me-piperidinyl-CO₂Et | -Trans-(3R,2'R)- Trans-(3R,2'S) | $C_{33}H_{40}F_6N_2O_3$ | 626 | 627 |
| 282 | Me | H | 1 | 4-phenyl-3-oxo-piperazinyl | Trans-(RS)- | $C_{34}H_{35}F_6N_3O_2$ | 631 | 632 |
| 283 | Me | H | 2 | piperidinyl | Trans-(RS)- | $C_{30}H_{36}F_6N_2O$ | 554 | 555 |
| 284 | Me | H | 2 | morpholinyl | Trans-(RS)- | $C_{29}H_{34}F_6N_2O_2$ | 556 | 557 |
| 285 | Me | H | 2 | 4-hydroxypiperidinyl | Trans-(RS)- | C30 H36 F6 N2 O2 | 570 | 571 |

-continued

| Ex. | A | B | n | —NR₂ | Stereochemistry | Formula | M.W. | m/z (ES⁺) (M + 1). |
|---|---|---|---|---|---|---|---|---|
| 286 | Me | H | 2 | (1-methylpiperidin-4-yl)methanol group | Trans-(RS)- | $C_{31}H_{38}F_6N_2O_2$ | 584 | 585 |
| 287 | Me | H | 2 | 2-(1-methylpiperidin-4-yl)ethanol group | Trans-(RS)- | $C_{32}H_{40}F_6N_2O_2$ | 598 | 599 |
| 288 | Me | H | 2 | ethyl 1-methylpiperidine-3-carboxylate group | Trans-(3R,2'R)- Trans-(3R,2'S)- | $C_{34}H_{43}F_6N_2O_3$ | 641 | 642 |
| 289 | Me | H | 2 | 8-methyl-2-oxa-8-azaspiro[4.5]decane group | Trans-(RS)- | $C_{33}H_{40}F_6N_2O_2$ | 610 | 611 |
| 290 | Me | H | 2 | 2,2,8-trimethyl-1-oxa-8-azaspiro[4.5]decane group | Trans-(RS)- | $C_{35}H_{44}F_6N_2O_2$ | 638 | 639 |
| 291 | Me | H | 2 | 4-methyl-1-phenylpiperazin-2-one group | Trans-(RS)- | $C_{35}H_{37}F_6N_3O_2$ | 645 | 646 |

EXAMPLE 292

Trans-(3R,2'R)- and Trans-(3R,2'S)-3-Methyl-1-[4-({1-oxo-2-[3,5-bis(trifluoromethyl)phenyl]propyl}amino)-4-phenylcycloxyl]ethyl-3-piperidinecarboxylic acid Prepared from trans-(3R,2'R)- and trans-(3R,2'S)-ethyl 3-methyl-1-[4-({1-oxo-2-[3,5-bis(trifluoromethyl)phenyl]propyl}amino)-4-phenylcyclohexyl]ethyl-3-piperidinecarboxylate (Mixture of diastereoisomers, Example 288) according to the method of Example 171. m/z (ES⁺) 614 (M+1).

EXAMPLE 293

Cis-(RS)-α-Methyl-N-(6-phenyl-1-oxaspiro[2.5]oct-6-yl)-3,5-bis(trifluoromethyl)benzeneacetamide 3-Chlorobenzenecarboperoxoic acid (50–55%, 150 mg, 0.44 mmol) was added to a solution of (RS)-α-methyl-N-(4-methylene-1-phenylcyclohexyl)-3,5-bis(trifluoromethyl)benzeneacetamide (Example 270, 135 mg, 0.297 mmol) in chloroform (5 mL) and the mixture was stirred at room temperature for 2 hours. Saturated aqueous sodium bisufite (10 mL) and aqueous sodium hydrogen carbonate (5%, 10 mL) were added and the mixture was stirred at room temperature for 1 hour. The layers were separated and the aqueous layer was extracted with dichloromethane (3×20 mL). The combined organic fractions were dried ($Na_2SO_4$) and the solvent was evaporated under reduced pressure. The residue was purified by flash column chromatography on silica gel, eluting with isohexane/EtOAc (75:25 increasing to 50:50), to give the title compound (30 mg, 21%). $^1$H NMR (400 MHz, $CDCl_3$) δ 7.80 (1H, s), 7.71 (2H, s), 7.3–7.18 (5H, m), 5.61 (1H, br s), 3.68 (1H, q, J 7 Hz), 2.66–2.53 (3H, m), 2.42–2.30 (1H, m), 2.25 (1H, ddd, J 14, 11, 4 Hz), 2.13 (1H, ddd, J 14, 11, 4 Hz), 1.9–1.7 (2H, m), 1.6–1.4 (2H, m), and 1.50 (3H, d, J 7 Hz).

EXAMPLE 294

Cis-(RS)-α-Methyl-N-[4-hydroxy-4-(1-oxa-8-aza-spiro[4.5]decan-8-yl)methyl-1-phenylcyclohexyl]-3,5-bis(trifluoromethyl)benzeneacetamide A mixture of cis (RS)-α-methyl-N-(6-phenyl-1-oxaspiro[2.5]oct-6-yl)-3,5-bis(trifluoromethyl)benzeneacetamide (Example 293, 24 mg, 0.051 mmol) and 1-oxa-8-azaspiro[4.5]decane (Description 75, 70 mg) was stirred in the absence of solvent at 90° C. for 18 hours. The mixture was cooled and purified by flash column chromatography on silica gel, eluting with $CH_2Cl_2$/MeOH/$NH_3$(Aq.) (95:5:0.5), to give the title compound (27 mg, 87%). $^1$H NMR (400 MHz, $CDCl_3$) δ 7.76 (1H, s), 7.64 (2H, s), 7.35–7.20 (5H, m), 5.61 (1H, br s), 3.80 (2H, t, J 7 Hz), 3.56 (1H, q, J 7 Hz), 2.75–2.62 (2H, m), 2.58–2.45 (2H, m), 2.36 (1H, t, J 6 Hz), 2.30 (2H, s), 2.17 (2H, t, J 6 Hz), 1.89 (2H, quin, J 7 Hz), 1.75–1.5 (7H, m), 1.42 (3H, d, J 7 Hz), and 1.50–1.30 (2H, m). m/z ($ES^+$) 613 (M+1).

EXAMPLE 295

(2R*,1'R*)- and (2S*,1'R*)-α-Methyl-N-[1-phenyl-4-(pyrid-3-yl)cyclohex-3-enyl]-3,5-bis(trifluoromethyl)benzeneacetamide Tetrakistriphenylphosphine palladium(0) (196 mg, 0.17 mmol) was added to a degassed mixture of (2R*,1'R*)- and (2S*,1'R*)-α-methyl-N-(1-phenyl-4-{[(trifluoromethyl)sulfonyl]-oxy}cyclohex-3-enyl)-3,5-bis(trifluoromethyl)benzeneacetamide (mixture of diastereoisomers, Description 203, 0.5 g, 8.45 mmol), 3-(tributylstannyl)pyridine (469 mg, 1.27 mmol) and lithium chloride (180 mg, 4.23 mmol) in toluene (25 mL) and the mixture was degassed and heated under reflux for 24 hours. The mixture was cooled, filtered and the solvent was evaporated under reduced pressure. The residue was purified by flash column chromatography on silica gel, eluting with isohexane/EtOAc (50:50) to give the title compound as a colorless solid (100 mg, 23%) as a 1:1 mixture of diastereoisomers. m/z ($ES^+$) 519 (M+1).

EXAMPLE 296

(2R*,1'R*) and (2S*,1'R*)-α-Methyl-N-[1-phenyl-4-(pyrid-2-yl)cyclohex-3-enyl]-3,5-bis(trifluoromethyl)benzeneacetamide Prepared from (2R*,1'R*)- and (2S*,1'R*)-α-methyl-N-(1-phenyl-4-{[(trifluoromethyl)sulfonyl]oxy}cyclohex-3-enyl)-3,5-bis(trifluoromethyl)benzeneacetamide (mixture of diastereoisomers, Description 203) and 2-(tributylstannyl)pyridine, according to the method of Example 295. m/z ($ES^+$) 519 (M+1).

EXAMPLE 297

(2R*,1'R*) and (2S*,1'R*)-α-Methyl-N-[1-phenyl-4-(pyrid-4-yl)cyclohex-3-enyl]-3,5-bis(trifluoromethyl)benzeneacetamide Tetrakistriphenylphosphine palladium(0) (75 mg, 0.07 mmol) was added to a degassed suspension of (2R*,1'R*)- and (2S*,1'R*)-α-methyl-N(1-phenyl-4-{[(trifluoromethyl)sulfonyl]oxy}cyclohex-3-enyl)-3,5-bis(trifluoromethyl)benzeneacetamide (mixture of diastereoisomers, Description 203, 418 mg, 0.71 mmol), 4-pyridinylboronic acid (96 mg, 0.78 mmol), potassium triphosphate (451 mg, 2.13 mmol) and ethylene glycol (45 L, 0.85 mmol) in dimethylformamide (10 mL), and the mixture was stirred at 100° C. for 2 hours. The mixture was cooled, poured into water (50 mL) and extracted with diethyl ether (2×50 mL). The combined organic fractions were dried ($MgSO_4$) and the solvent was evaporated under reduced pressure. The residue was purified by flash column chromatography on silica gel, eluting with isohexane/EtOAc (50:50) to give the title compound as a mixture of diastereoisomers (350 mg, 74%). m/z ($ES^+$) 519 (M+1).

EXAMPLE 298

(2R*,1'R*)- and (2S*,1'R*)-α-Methyl-N-[1-phenyl-4-(2-methyl-pyrid-5-yl)cyclohex-3-enyl]-3,5-bis(trifluoromethyl)benzeneacetamide Prepared from (2R*,1'R*)- and (2S*,1'R*)-α-methyl-N-(1-phenyl-4-{[(trifluoromethyl)sulfonyl]oxy}cyclohex-3-enyl)-3,5-bis(trifluoromethyl)benzeneacetamide (mixture of diastereoisomers, Description 203) and 2-methyl-5-(trimethylstannyl)pyridine (J. Med. Chem. 1996, 39, 1846–56), according to the method of Example 295. m/z ($ES^+$) 533 (M+1).

EXAMPLE 299

Trans-(RS)-α-Methyl-N-[1-phenyl-4-pyrid-3-yl)cyclohex]-3,5-bis(trifluoromethyl)benzeneacetamide Palladium on carbon (5%, 20 mg) was added to a solution of (2R*,1'R*)- and (2S*,1'R*)-α-methyl-N-[1-phenyl-4-(pyrid-3-yl)cyclohex-3-enyl]-3,5-bis(trifluoromethyl)benzeneacetamide (Example 295, 60 mg, 0.11 mmol) in ethyl acetate (20 mL) and the mixture was stirred under an atmosphere of hydrogen (1 Atm.) for 4 hours. The mixture was filtered and the solvent was evaporated under reduced pressure. The residue was purified by flash column chromatography on silica gel, eluting with isohexane:EtOAc (50:50 increasing to 25:75), to give the title compound as a colorless solid (12 mg, 21%). m/z ($ES^+$) 521 (M+1).

EXAMPLE 300

Trans-(RS)-α-Methyl-N-[1-phenyl-4-(pyrid-2-yl)cyclohexyl]-3,5-bis(trifluoromethyl)benzeneacetamide Prepared from (2R*,1'R*)- and (2S*,1'R*)-α-methyl-N-[1-phenyl-4-(pyrid-2-yl)cyclohex-3-enyl]-3,5-bis(trifluoromethyl)benzeneacetamide (mixture of diastereoisomers, Example 296), according to the method of Example 299. m/z ($ES^+$) 521 (M+1).

EXAMPLE 301

Cis-(RS)-α-Methyl-N-[1-phenyl-4-(pyrid-4-yl)cyclohexyl]-3,5-bis(trifluoromethyl)benzeneacetamide and Trans-(RS)-α-Methyl-N-[1-phenyl-4-(pyrid-4-yl)cyclohexyl]-3,5-bis(trifluoromethyl)benzeneacetamide A slurry of palladium on carbon (10%, 20 mg) in methanol (10 mL) was added to a solution of (2R*,1'R*)- and (2S*,1'R*)-α-methyl-N-(1-phenyl-4-(pyrid-4-yl)cyclohex-3-enyl]-3,5-bis(trifluoromethyl)benzeneacetamide (mixture of diastereoisomers, Description 297, 580 mg, 1.12 mmol) in ethanol (20 mL) and the mixture was stirred under hydrogen (1 atm.) for 2 hours. The mixture was filtered through Celite™ and the solvent was evaporated under reduced pressure. The residue was purified by flash column chromatography on silica gel, eluting with isohexane/EtOAc (55:45) to give cis-(RS)-α-methyl-N-[1-phenyl-4-(pyrid-4-yl)cyclohexyl]-3,5-bis(trifluoromethyl)benzeneacetamide (120 mg, 21%); $^1$H NMR (360 MHz, CD$_3$OD) δ 1.33–1.42 (1H, m), 1.47 (3H, d, J 7.2 Hz), 1.64–1.73 (2H, m), 1.81–2.01 (3H, m), 2.47 (1H, dd, J 13.7, 2.5 Hz), 2.63–2.71 (2H, m), 4.08 (1H, q, J 7.2 Hz), 7.05 (2H, dd, J 5.0, 1.4 Hz), 7.14–7.19 (1H, m), 7.22–7.27 (2H, m), 7.32–7.35 (2H, m), 7.91 (1H, s), 8.18 (1H, s), and 8.37 (2H, dd, J 5.0, 1.4 Hz); m/z (ES$^+$) 521 (M+1); and trans-(RS)-α-methyl-N-[1-phenyl-4-(pyrid-4-yl)cyclohexyl]-3,5-bis(trifluoromethyl)benzeneacetamide (50 mg, 9%); $^1$H NMR (360 MHz, CD$_3$OD) δ 1.39 (3H, d, J 7.2 Hz), 1.49–1.71 (2H, m), 1.80–1.92 (2H, m), 2.02–2.11 (2H, m), 2.68–2.83 (2H, m), 2.91–2.95 (1H, m), 3.92 (1H, q, J 7.2 Hz), 7.16 (2H, d, J 5.8 Hz), 7.20–7.28 (1H, m), 7.51–7.61 (2H, m), 7.62–7.67 (2H, m), 7.78 (2H, s), 7.80 (1H, s), and 8.37 (2H, d, J 5.8 Hz). m/z (ES$^+$) 521 (M+1).

EXAMPLE 302

Trans-(RS)-α-Methyl-N-[1-phenyl-4-(2-methylpyrid-5-yl)cyclohexyl]-3,5-bis(trifluoromethyl)benzeneacetamide Prepared from (2R*,1'R*)- and (2S*,1'R*)-α-methyl-N-[1-phenyl-4-(2-methyl-pyrid-5-yl)cyclohex-3-enyl]-3,5-bis(trifluoromethyl)benzeneacetamide (mixture of diastereoisomers, Example 298), according to the method of Example 299. m/z (ES$^+$) 535 (M+1).

EXAMPLE 303

Cis-(RS)-α-Methyl-N-[1-phenyl-4-(piperidin-4-yl)cyclohexyl]-3,5-bis(trifluoromethyl)benzeneacetamide, Trans-(RS)-α-Methyl-N-[1-phenyl-4-(piperidin-4-yl)cyclohexyl]-3,5-bis(trifluoromethyl)benzeneacetamide, Cis-(RS)-α-Methyl-N-{1-phenyl-4-[1-(phenylmethyl)piperidin-4-yl]cyclohexyl}-3,5-bis(trifluoromethyl)benzeneacetamide, and Trans-(RS)-α-Methyl-N-{1-phenyl-4-[1-(phenylmethyl)piperidin-4-yl]cyclohexyl}-3,5-bis(trifluoromethyl)benzeneacetamide Benzyl bromide (127 μL, 1.06 mmol) was added to a solution of (2R*,1'R*)- and (2S*,1'R*)-α-methyl-N-[1-phenyl-4-(pyrid-4-yl)cyclohex-3-enyl]-3,5-bis(trifluoromethyl)benzeneacetamide (Mixture of diastereoisomers, Description 297, 275 mg, 0.53 mmol) in acetone (15 mL) and the mixture was heated under reflux for 16 hours. The mixture was cooled and the solvent was evaporated under reduced pressure. The residue was dissolved in methanol (17 mL) and water (3 mL), sodium borohydride (80 mg, 2.12 mmol) was added, and the mixture was heated under reflux for 3 hours. The mixture was cooled and the solvent was evaporated under reduced pressure. Ethyl acetate (40 mL) and aqueous sodium hydrogen carbonate (10%, 40 mL) were added and the layers were separated. The organic fraction was dried (MgSO$_4$) and the solvent was evaporated under reduced pressure. The residue was dissolved in ethyl acetate (8 mL) and a slurry of palladium on carbon (10%, 20 mg) in ethyl acetate (10 mL) was added. The mixture was shaken under hydrogen (50 psi) for 16 hours. A slurry of palladium on carbon (10%, 20 mg) in ethanol (10 mL) and hydrochloric acid (2M, 2 mL) was added and the mixture was shaken under hydrogen (50 psi) for 72 hours. The mixture was filtered through Celite™, washing with ethanol, and the solvent was evaporated under reduced pressure. Ethyl acetate (10 mL) and aqueous sodium hydrogen carbonate (10%, 10 mL) were added and the layers were separated. The organic fraction was dried (MgSO$_4$) and the solvent was evaporated under reduced pressure. The residue was purified by MPLC chromatography on silica gel, eluting with CH$_2$Cl$_2$/MeOH/Et$_3$N (90:10:1), to give cis-(RS)-α-methyl-N-[1-phenyl-4-(piperidin-4-yl)cyclohexyl]-3,5-bis(trifluoromethyl)benzeneacetamide (60 mg, 21%); $^1$H NMR (360 MHz, CD$_3$OD) δ 0.84–4.90 (1H, m), 1.16–1.45 (6H, m), 1.43 (3H, d, J 7.2 Hz), 1.54–1.69 (5H, m), 2.32–2.37 (1H, m), 2.57–270 (3H, m), 3.17–3.22 (2H, m), 4.02 (1H, q, J 7.2H), 7.12–7.30 (5H, m), 7.88 (2H, s), and 7.95 (1H, s); m/z (ES$^+$) 527 (M+1); trans-(RS)-α-methyl-N-[1-phenyl-4-(piperidin-4-yl)cyclohexyl]-3,5-bis(trifluoromethyl)benzeneacetamide (26 mg, 9%); $^1$H NMR (400 MHz, CD$_3$OD) δ 0.98–1.45 (9H, m), 1.60–1.72 (1H, m), 1.88–1.91 (1H, m), 1.93–1.96 (4H, m), 2.47–2.53 (1H, m), 2.66–2.71 (1H, m), 2.84–2.91 (2H, m), 3.46–3.49 (2H, m), 3.82 (1H, q, J 7.2 Hz), 7.13–7.39 (5H, m), 7.78 (2H, s), and 7.80 (1H, s); m/z (ES$^+$) 527 (M+1); and a mixture of 2 isomeric compounds (20 mg) which were further purified by preparative thin layer chromatography on silica gel, eluting with CH$_2$Cl$_2$/MeOH/Et$_3$N (90:10:1), to give cis-(RS)-α-methyl-N-{1-phenyl-4-[1-(phenylmethyl)piperidin-4-yl]cyclohexyl}-3,5-bis(trifluoromethyl)benzeneacetamide (5 mg, 2%); $^1$H NMR (360 MHz, CDCl$_3$) δ 0.74–0.98 (2H, m), 1.04–1.39 (4H, m), 1.38 (3H, d, J 7.2 Hz), 1.39–1.73 (6H, m), 1.83–1.90 (2H, m), 2.32–2.46 (2H, m), 2.88–2.91 (2H, m), 3.49 (2H, s), 3.68 (1H, q, J 7.2 Hz), 7.13–7.32 (10H, m), and 7.77 (3H, s); m/z (ES$^+$) 617 (M+1); and trans-(RS)-α-methyl-N-{1-phenyl-4-[1-(phenylmethyl)piperidin-4-yl]cyclohexyl}-3,5-bis(trifluoromethyl)benzeneacetamide (3 mg, 1%); $^1$H NMR (360 MHz, CDCl$_3$) δ 0.94–1.25 (4H, m), 1.38 (3H, d, J 7.2 Hz), 1.50–1.68 (6H, m), 1.76–1.86 (2H, m), 1.97–2.05 (2H, m), 2.43–2.58 (2H, m), 2.83–2.87 (2H, m), 3.44–3.49 (3H, m), 7.20–7.37 (10H, m), 7.63 (2H, s), and 7.74 (1H, s). m/z (ES$^+$) 617 (M+1).

EXAMPLE 304

Trans-(RS)-α-Methyl-N-[1-phenyl-4-{1-(1-methylethyl)piperidin-4-yl]cyclohexyl}-3,5-bis(trifluoromethyl)benzeneacetamide A mixture of sodium cyanoborohydride (2.4 mg, 0.038 mmol) and zinc chloride (2.6 mg, 0.019 mmol) in methanol (2 mL) was sonicated until the solid dissolved, then added to a solution of trans-(RS)-α-methyl-N-[1-phenyl-4-(piperidin-4-yl)cyclohexyl]-3,5-bis(trifluoromethyl)benzeneacetamide (Example 303, 10 mg, 0.019 mmol) and acetone (7 μL, 0.019 mmol) in methanol (2 mL). The mixture was stirred at room temperature overnight, then the solvent was evaporated under reduced pressure and saturated aqueous sodium hydrogen carbonate (3 mL) and dichloromethane (3 mL) were added. The layers were separated and the organic fraction was poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure to give the title compound as a colorless oil. $^1$H NMR (400 MHz, CD$_3$OD) δ 1.03 (3H, d, J 7.2 Hz), 1.03–1.27 (4H, m), 1.33 (6H, d, J 7.0 Hz), 1.56–1.73 (5H, m), 1.85–1.96 (2H, m), 2.01–2.15 (2H, m), 2.41–2.49 (1H, m), 2.61–2.66 (2H, m), 2.86–2.90 (2H, m), 3.16–3.25 (1H, m), 3.82 (1H, q, J 7.2 Hz), 7.11–7.36 (5S, m), 7.78 (2H, s), and 7.79 (1H, s). m/z (ES$^+$) 569 (M+1).

EXAMPLE 305

Trans-(RS)-α-Methyl-N-{1-phenyl-4-[1-(tetrahydro-2H-pyran-4-yl)piperidin-4-yl]cyclohexyl}-3,5-bis(trifluoromethyl)benzeneacetamide Prepared from trans-(RS)-α-methyl-N-[1-phenyl-4-(piperidin-4-yl)cyclohexyl]-3,5-bis(trifluoromethyl)benzeneacetamide (Example 303) according to the method of Example 304, substituting pyran-4-one for acetone. m/z (ES$^+$) 611 (M+1).

EXAMPLE 306

Trans-(RS)-α-Methyl-N-{1-phenyl-4-[1,2,3,6-tetrahydro-1-(phenylmethyl)pyrid-4-yl]cyclohexyl}-3,5-bis(trifluoromethyl)benzeneacetamide Benzyl bromide (87 μL, 0.73 mmol) was added to a solution of trans-(RS)-α-methyl-N-[1-phenyl-4-(pyrid-4-yl)cyclohexyl]-3,5-bis(trifluoromethyl)benzeneacetamide (Example 301, 190 mg, 0.36 mmol) in acetone (3 mL) and the mixture was heated under reflux for 16 hours. The mixture was cooled and the solvent was evaporated under reduced pressure. The residue was dissolved in methanol/water (6:1, 14 mL) and sodium borohydride (54 mg 1.5 mmol) was added. The mixture was heated under reflux for 3 hours, cooled, and the solvent was evaporated under reduced pressure. Dichloromethane (10 mL) and aqueous sodium hydrogen carbonate (10%, 5 mL) were added and the layers were separated. The organic fraction was poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure and the residue was purified by preparative thin layer chromatography on silica gel to give the title compound (60 mg, 30%). m/z (ES$^+$) 614 (M+1).

EXAMPLE 307

(2R*,3'R*,4'R*)-Trans- and (2S*,3'R*,4'R*)-Trans-α-Methyl-N-{1-phenyl-4-[3-hydroxy-1-(phenylmethyl)piperidin-4-yl]cyclohexyl}-3,5-bis(trifluoromethyl)benzeneacetamide and (2R*,3'R*,4'R*)-Cis- and (2S*,3'R*,4'R*)-Cis-α-Methyl-N-{1-phenyl-4-[3-hydroxy-1-(phenylmethyl)piperidin-4-yl]cyclohexyl}-3,5-bis(trifluoromethyl)benzeneacetamide Borane-tetrahydrofuran complex (1M in tetrahydrofuran, 0.332 mL) was added to a solution of trans-(RS)-α-methyl-N-{1-phenyl-4-[1,2,3,6-tetrahydro-1-phenylmethyl)pyrid-4-yl]cyclohexyl}-3,5-bis(trifluoromethyl)benzeneacetamide (Example 306, 102 mg, 0.166 mmol) in tetrahydrofuran (5 mL) and the mixture was stirred at room temperature for 72 hours. A mixture of aqueous sodium hydroxide (4M, 2.5 mL) and aqueous hydrogen peroxide (37%, 2.5 mL) was added and the mixture was stirred at room temperature for 2 hours. The mixture was extracted with ethyl acetate (2×25 mL), the combined organic fractions were dried (MgSO$_4$) and the solvent was evaporated under reduced pressure. The residue was purified by preparative thin layer chromatography on silica gel to give (2R*,3'R*,4'R*)-trans- and (2S*,3'R*,4'R*)-trans-(RS)-α-methyl-N-{1-phenyl-4-[3-hydroxy-1-(phenylmethyl)piperidin-4-yl]cyclohexyl}-3,5-bis(trifluoromethyl)benzeneacetamide (mixture of diastereoisomers); $^1$H NMR (400 MHz, CD$_3$OD) δ 1.20–1.33 (6H, m), 1.42 (3H, d, J 7.2 Hz), 1.52–1.91 (6H, m), 2.23–2.79 (3H, m), 2.92–3.02 (1H, m), 3.38–3.53 (3H, m), 4.07 (1H, q, J 7.2 Hz), 7.12–7.42 (10H, m), and 7.72–7.79 (3H, m); m/z (ES$^+$) 633 (M+1); and (2R*,3'R*,4'R*)-cis- and (2S*,3'R*,4'R*)-cis-(RS)-α-methyl-N-[1-phenyl-4-{3-hydroxy-1-(phenylethyl)piperidin-4-yl]cyclohexyl}-3,5-bis(trifluoromethyl)benzeneacetamide (mixture of diastereoisomers); $^1$H NMR (400 MHz, CD$_3$OD) δ 0.82–4.96 (2H, m), 1.00–1.13 (1H, m), 1.19–1.49 (4H, m), 1.42 (3H, d, J 7.2 Hz), 1.62–1.90 (5H, m), 2.25–2.39 (1H, m), 2.50–2.69 (1H, m), 2.71–2.81 (1H, m), 2.97–3.01 (1H, m), 4.01 (1H, q, J 7.2 Hz), 7.11–7.75 (10H, m), and 7.79–8.01 (3H, m); m/z (ES$^+$) 633 (M+1).

EXAMPLE 308

(1R*,3S*,4R*)- and (1R*,3R*,4R*)-α,α-Dimethyl-N-[3-hydroxy-4-(1-oxa-8-azaspiro[4.5]decan-8-yl)-1-phenylcyclohexyl]-3,5-bis(trifluoromethyl)benzeneacetamide Prepared from cis-(RS)- and trans-(RS)-α,α-dimethyl-N-(3-hydroxy-4-oxo-1-phenylcyclohexyl)-3,5-bis(trifluoromethyl)benzeneacetamide (Mixture of diastereoisomers, Example 59) and 1-oxa-8-azaspiro[4.5]decane (Description 75) according to the method of Example 33. $^1$H NMR (400 MHz, CDCl$_3$) δ 7.75 (1H, s), 7.63 (2H, s), 7.40–7.20 (5H, m), 5.35 (1H, br s), 3.77 (2H, br t, J 7 Hz), 3.40–3.30 (1H, m), 2.90–2.65 (3H, m), 2.50–2.20 (4H, m), 2.10–1.55 (11H, m), 1.48 (3H, s), 1.47 (3H, s), and 1.25 (br q, J 13 Hz). m/z (ES$^+$) 613 (M+1).

EXAMPLE 309

(1R*,3S*,4R*)-α,α-Dimethyl-N-[3-fluoro-4-(2-oxa-8-azaspiro[4.5]decan-8-yl)-1-phenylcyclohexyl]-3,5-bis(trifluoromethyl)benzeneacetamide and (1S*,3S*,4R*)-α,α-Dimethyl-N-[3-fluoro-4-(2-oxa-8-azaspiro[4.5]decan-8-yl)-1-phenylcyclohexyl]-3,5-bis(trifluoromethyl)benzeneacetamide Sodium triacetoxyborohydride (307 mg, 1.45 mmol) was added to a mixture of (1R*,3S*)-α,α-dimethyl-N-[3-fluoro-4-oxo-1-phenylcyclohexyl]-3,5-bis(trifluoromethyl)benzeneacetamide (Example 58, 490 mg, 0.97 mmol), 2-oxa-8-azaspiro[4.5]decane hydrochloride (Description 86, 204 mg, 1.37 mmol) and triethylamine (1.34 mL, 9.7 mmol) in 1,2-dichloroethane (15 mL) and the mixture was stirred at room temperature for 3 days. Further sodium triacetoxyborohydride (103 mg, 0.49 mmol) was added and the mixture was stirred at room temperature for 24 hours. The mixture was basified with aqueous sodium hydroxide (1M) and extracted with dichloromethane. The combined organic fractions were dried (MgSO$_4$) and the solvent was evaporated under reduced pressure. The residue was purified by MPLC on silica gel, eluting with CH$_2$Cl$_2$/MeOH (97.5:2.5), to give (1R*,3S*,4R*)-α,α-dimethyl-N-[3-fluoro-4-(2-oxa-8-azaspiro[4.5]decan-8-yl)-1-phenylcyclohexyl]-3,5-bis(trifluoromethyl)benzeneacetamide as a colorless foam (18 mg, 3%); $^1$H NMR (400 MHz, CDCl$_3$) δ 7.81 (1H, s), 7.70 (2H, s), 7.36–7.23 (5H, m), 5.13 (1H, s), 4.98 (1H, br d, J 48.5 Hz), 3.81 (2H, t, J 7.2Hz), 2.89–2.68 (3H, m), 3.67–2.42 (4H, m), 2.41–2.38 (2H, m), 1.89–1.86 (1H, m), 1.73–1.71 (1H, m), 1.68 (2H, t, J 7.2 Hz), 1.63–1.58 (6H, m), and 1.53 (6H, d, 3.4 Hz). m/z (ES$^+$) 615 (M+1); and (1S*,3S*,4R*)-α,α-dimethyl-N-[3-fluoro-4-(2-oxa-8-azaspiro[4.5]decan-8-yl)-1-phenylcyclohexyl]-3,5-bis(trifluoromethyl)benzeneacetamide as a colorless foam (280 mg, 47%). $^1$H NMR (400 MHz, CDCl$_3$) δ 7.81 (2H, s), 7.79 (1H, s), 7.32–7.21 (1H, s), 6.41 (1H, d, J 10.5 Hz), 5.06 (1H, br d, J 50.0 Hz), 3.87–3.83 (2H, m), 3.00–2.96 (1H, m), 2.60–2.39 (4H, m), 2.30–2.22 (2H, m), 2.01–1.93 (1H, m), 1.77–1.70 (3H, m), 1.65–1.50 (8H, m), and 1.60 (6H, d, J 6.9 Hz). m/z (ES$^+$) 615 (M+1).

EXAMPLE 310

Trans-N-{4-[3-Oxa-4-phenylpiperazin-1-yl]-1-phenylcyclohexyl}-3,5-bis(trifluoromethyl)-α-oxobenzeneacetamide Hydrochloride Triethylamine (84 μL, 61 mg, 0.6 mmol) was added to a stirred, cooled (0° C.) mixture of trans-4-(3-oxo-4-phenyl-1-piperazinyl)-1-phenylcyclohexylamine (Description 193, 70 mg, 0.2 mmol), 3,5-bis(trifluoromethyl)-α-oxobenzeneacetic acid (Description 48, 86 mg, 0.3 mmol) and bis(2-oxo-3-oxazolidinyl)phosphinic chloride (76 mg, 0.3 mmol) in dichloromethane (5 mL) and the mixture was stirred at 0° C. for 5 minutes, then at room temperature for 22 hours. Saturated aqueous sodium hydrogen carbonate (20 mL) and water (10 mL) were added and mixture was extracted with dichloromethane (3×20 mL). The combined organic fractions were dried (MgSO$_4$), the solvent was evaporated under reduced pressure and the residue was purified by flash column chromatography on silica gel, eluting with CH$_2$Cl$_2$/MeOH/NH$_3$(Aq.) (98:2:0.2). The residue was dissolved in tetrahydrofuran (3 mL), cooled in ice and ethereal hydrogen chloride (1M, 0.2 mL) was added. The mixture was refrigerated and the solid was collected and dried in vacuo to give the title compound as a colorless solid (45 mg, 34%), m.p. 252–255° C. (Dec.). m/z (ES$^+$) 618 (M+1).

EXAMPLE 311

(RS)-Trans-N-{4-[3-Oxa-4-phenylpiperazin-1-yl]-1-phenylcyclohexyl}-3,5-bis(trifluoromethyl)-α-hydroxybenzeneacetamide Hydrochloride Sodium borohydride (9 mg, 0.24 mmol) was added to a stirred, cooled (0° C.) suspension of trans-N-{4-[3-oxa-4-phenylpiperazin-1-yl]-1-phenylcyclohexyl}-3,5-bis(trifluoromethyl)-α-oxobenzeneacetamide hydrochloride (Example 310, 54 mg, 82 μmol) in ethanol-water (95:5, 5 mL) and the mixture was stirred at 0° C. for 1 hour. The solvent was evaporated under reduced pressure, saturated aqueous sodium hydrogen carbonate (20 mL) and water (10 mL) were added and mixture was extracted with dichloromethane (3×20 mL). The combined organic fractions were dried (MgSO$_4$), the solvent was evaporated under reduced pressure and the residue was purified by MPLC on silica gel, eluting with CH$_2$Cl$_2$/MeOH/NH$_3$(Aq.) (97:3:0.3 increasing to 96:4:0.4). The residue was dissolved in ethanol (3 mL), cooled in ice and ethereal hydrogen chloride (1M, 0.15 mL) was added. The solvent was evaporated under reduced pressure and the residue was triturated with ether-ethanol (95:5, 3 mL). The solid was collected and dried in vacuo to give the title compound as a colorless solid (32 mg, 60%), m.p. 153–155° C. m/z (ES$^+$) 620 (M+1).

The invention claimed is:
1. A compound of the formula (I):

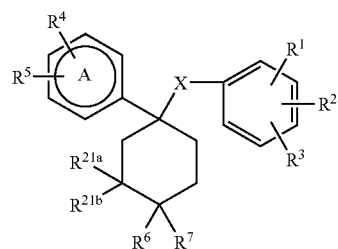

wherein
ring A is a phenyl or pyridyl ring;
X represents a linker selected from the group consisting of:

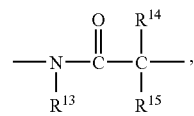

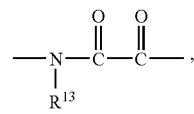

$R^1$ represents fluoroC$_{1-6}$alkyl or halogen;
$R^2$ represents hydrogen or halogen;
$R^3$ represents hydrogen, halogen, or fluoroC$_{1-6}$alkyl;
$R^4$ is hydrogen, halogen or CF$_3$;
$R^5$ is hydrogen, halogen or CF$_3$;
$R^6$ represents hydrogen, hydroxy or a C$_{1-4}$alkyl group optionally substituted by a hydroxy group;
$R^7$ represents —(CH$_2$)$_n$NR$^8$R$^9$, where $R^8$ and $R^9$, together with the nitrogen atom to which they are attached, represent a heteroaliphatic ring selected from the group consisting of:

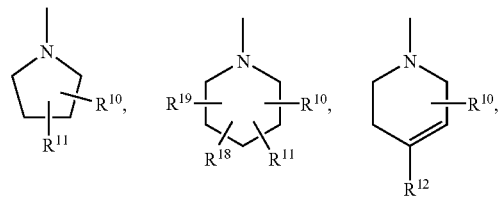

-continued

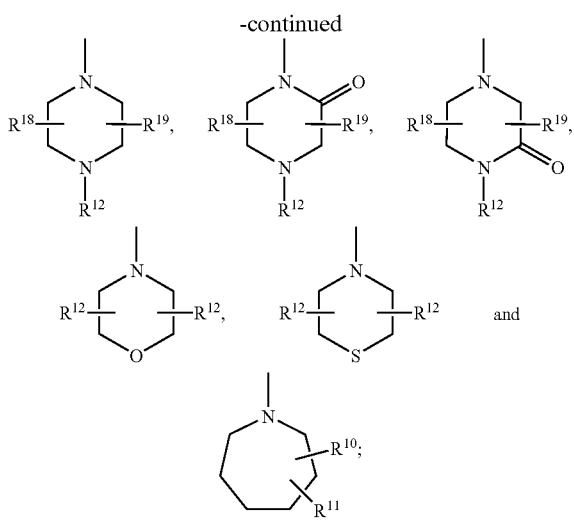

$R^{10}$ and $R^{11}$ each independently represent hydrogen, halogen, hydroxy, $C_{1-6}$alkyl, $C_{2-6}$alkenyl, $C_{2-6}$alkynyl, hydroxy$C_{1-6}$alkyl, fluoro$C_{1-6}$alkyl, $C_{1-6}$alkoxy, $(CH_2)_q$ $C_{3-7}$cycloalkyl, $(CH_2)_q$aryl, $(C_{2-6}$alkenyl)aryl, $(C_{2-6}$alkynyl)aryl, $(CH_2)_q$heterocyclyl, $(CH_2)_q NR^a R^b$, $O(CH_2)_q C_{3-7}$cycloalkyl, $O(CH_2)_q$aryl, $O(CH_2)_q$heterocyclyl, $O(CH_2)_q NR^a R^b$, $OC(O)C_{1-6}$alkyl, $C(O)C_{1-6}$alkyl, $C(O)(CH_2)_p$aryl, $C(O)(CH_2)_q$heterocyclyl, $C(O)(CH_2)_q NR^a R^b$, $CO_2 H$, $CO_2 C_{1-6}$alkyl, $CO_2 (CH_2)_q C_{3-7}$cycloalkyl, $CO_2 (CH_2)_q$aryl, $CO_2 (CH_2)_q$heterocyclyl or $CO_2 (CH_2)_p NR^a R^b$, where $R^a$ and $R^b$ each independently represent hydrogen, $C_{1-4}$alkyl, $C_{3-5}$cycloalkyl, fluoro$C_{1-4}$alkyl or $CH_2 CO_2 C_{1-4}$alkyl;

$R^{12}$ represents hydrogen, $C_{1-6}$alkyl, $(CH_2)_q C_{3-7}$cycloalkyl, $(CH_2)_q$aryl, $(CH_2)_q$heterocyclyl, CHO, $C(O)$ $C_{1-6}$alkyl, $C(O)(CH_2)_q C_{3-7}$cycloalkyl, $C(O)(CH_2)_q$aryl, $C(O)(CH_2)_q$heterocyclyl, $CO_2 C_{1-6}$alkyl, $CO_2 (CH_2)_q C_{3-7}$cycloalkyl, $CO_2 (CH_2)_q$aryl, $CO_2 (CH_2)_q$heterocyclyl or $CO_2 (CH_2)_p NR^a R^b$;

$R^{13}$ represents hydrogen, $C_{1-6}$alkyl or $C(O)C_{1-6}$alkyl;

$R^{14}$ and $R^{15}$ each independently represent hydrogen, hydroxy, $C_{1-6}$alkyl, $C_{1-6}$alkenyl, hydroxy$C_{1-6}$alkyl, $C_{1-4}$alkoxy$C_{1-4}$alkyl, $(CH_2)_p NR^a R^b$, CHO, $C(O)C_{1-6}$ alkyl or $CO_2 C_{1-6}$alkyl;

or, $R^{14}$ and $R^{15}$ together represent —$CH_2 CH_2$—;

$R^{18}$ and $R^{19}$ each independently represent hydrogen, halogen, hydroxy, $C_{1-6}$alkyl or oxo (=O);

$R^{20}$ represents hydrogen, halogen, hydroxy, $C_{1-4}$alkyl, hydroxy$C_{1-4}$alkyl or fluoro$C_{1-4}$alkyl;

$R^{21a}$ represents hydrogen, halogen or hydroxy and $R^{21b}$ represents hydrogen;

or $R^{21a}$ and $R^{21b}$ both represent fluorine or together represent oxo (=O);

n is zero, 1 or 2;
m is 1 or 2;
p is 1, 2, 3 or 4;
q is zero, 1, 2, 3 or 4; and
s is 1, 2 or 3;
or a pharmaceutically acceptable salt or an N-oxide thereof.

2. The compound of claim 1 wherein $R^1$ is $CF_3$.
3. The compound of claim 1 wherein $R^2$ is hydrogen.
4. The compound of claim 1 wherein $R^3$ is $CF_3$.
5. The compound of claim 1 wherein $R^4$ is hydrogen.
6. The compound of claim 1 wherein $R^5$ is halogen.
7. The compound of claim 6 wherein $R^5$ is fluorine.
8. The compound of claim 1 wherein $R^6$ is hydrogen.
9. The compound of claim 8 wherein $R^8$ and $R^9$ together with the nitrogen atom to which they are attached represent a heteroaliphatic ring selected from the group consisting of:

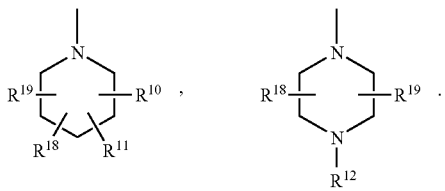

10. The compound as claimed in claim 9 wherein $R^{10}$ represents hydrogen, hydroxy, $C_{1-6}$alkyl, $C_{2-6}$alkenyl, $C_{2-6}$alkynyl, hydroxy$C_{1-6}$alkyl, fluoro$C_{1-6}$alkyl, $(C_{2-6}$alkynyl)aryl, $(CH_2)_q$aryl, $(CH_2)_q$heterocyclyl, $(CH_2)_q NR^a R^b$, $OC(O)C_{1-6}$alkyl, $C(O)(CH_2)_q NR^a R^b$, $CO_2 H$ or $CO_2 C_{1-6}$alkyl;

and $R^{11}$ represents hydrogen, halogen, hydroxy, $C_{1-6}$alkyl or $(CH_2)_q NR^a R^b$.

11. The compound of claim 9 wherein $R^{12}$ represents hydrogen, $C_{1-6}$alkyl, $(CH_2)_q C_{3-7}$cycloalkyl, $(CH_2)_q$aryl, $(CH_2)_q$heterocyclyl, CHO, $C(O)C_{1-6}$alkyl, $C(O)C_{3-7}$cycloalkyl, $C(O)(CH_2)_q$aryl or $CO_2 C_{1-6}$alkyl.

12. The compound of claim 1 wherein the ring A is a phenyl ring.

13. The compound of claim 1 wherein X is the linker:

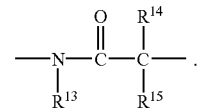

14. The compound of claim 13 wherein X is the linker:

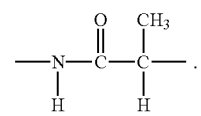

15. The compound of claim 1 of the formula (Ia):

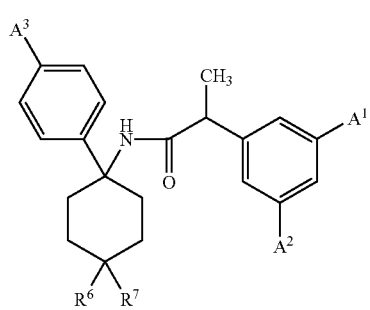

(Ia)

wherein
$A^1$ is fluorine or $CF_3$;
$A^2$ is fluorine or $CF_3$;
$A^3$ is fluorine or hydrogen;

or a pharmaceutically acceptable salt thereof.

16. A compound which selected from the group consisting of:

cis-(RS)- and trans-(RS)-α-methyl-N-{4-[4-hydroxymethyl-4-(methoxymethyl)piperidin-1-yl]-1-phenylcyclohexyl}-3,5-bis(trifluoromethylbenzeneacetamide;

trans-(RS)-α-methyl-N-[4-(1,4-dioxa-8-azaspiro[4.5]decan-8-yl)-1-phenylcyclohexyl]-3,5-bis(trifluoromethyl)benzeneacetamide;

trans-(RS)-α-methyl-N-[4-(2-oxa-4-oxo-8-azaspiro[4.5]decan-8-yl)-1-phenylcyclohexyl]-3,5-bis(trifluoromethyl)benzeneacetamide;

trans-(RS)-α-methyl-N-[4-(1-oxa-9-azaspiro[5.5]undecan-9-yl)-1-phenylcyclohexyl]-3,5-bis(trifluoromethyl)benzeneacetamide;

trans-(2R*,3'R*)- and trans-(2R*,3'S*)-α-methyl-N-[4-(3-hydroxy-1-oxa-9-azaspiro[5.5]undecan-9-yl)-1-phenylcyclohexyl]-3,5-bis(trifluoromethyl)benzeneacetamide;

trans-(2R*,4'R*)- and trans-(2R*,4'S*)-α-methyl-N-[4-(4-hydroxy-1-oxa-9-azaspiro[5.5]undecan-9-yl)-1-phenylcyclohexyl]-3,5-bis(trifluoromethyl)benzeneacetamide;

trans-(RS)-α-methyl-N-[4-(1-oxa-3-oxa-9-azaspiro[5.5]undecan-9-yl)-1-phenylcyclohexyl]-3,5-bis(trifluoromethyl)benzeneacetamide;

trans-(RS)-α-methyl-N-{4-[4-(phenylmethyl)piperazin-1-yl]-1-phenylcyclohexyl}-3,5-bis(trifluoromethyl)benzeneacetamide;

trans-(RS)-α-methyl-N-[4-(4-methylpiperazin-1-yl)-1-phenylcyclohexyl]-3,5-bis(trifluoromethyl)benzeneacetamide;

trans-(RS)-α-methyl-N-{4-[4-(1-methylethyl)piperazin-1-yl]-1-phenylcyclohexyl}-3,5-bis(trifluoromethyl)benzeneacetamide;

trans-(RS)-α-methyl-N-{4-[4-(1-methylethyl)-2-oxo-1-piperazinyl]-1-phenylcyclohexyl}-3,5-bis(trifluoromethyl)benzeneacetamide;

trans-(RS)-α-methyl-N-[4-(2,2-dimethyl-4-phenylmethyl-1-piperazinyl)-1-phenylcyclohexyl]-3,5-bis(trifluoromethyl)benzeneacetamide;

trans-(RS)-α-methyl-N-{4-[4-(1,1-dimethylethyl)-2-oxo-1-piperazinyl]-1-phenylcyclohexyl}-3,5-bis(trifluoromethyl)benzeneacetamide;

trans-(RS)-α-methyl-N-{4-[4-(4-fluorophenyl)-3-oxo-1-piperazinyl]-1-phenylcyclohexyl}-3,5-bis(trifluoromethyl)benzeneacetamide;

trans-(S)-α-methyl-N-{4-[4-(4-fluorophenyl)-3-oxo-1-piperazinyl]-1-phenylcyclohexyl}-3,5-bis(trifluoromethyl)benzeneacetamide;

trans-(RS)-α-methyl-N-{4-[2-oxo-4-(piperidin-1-yl)piperidin-1-yl]-1-phenylcyclohexyl}-3,5-bis(trifluoromethyl)benzeneacetamide;

trans-(RS)-α-methyl-N-[4-(4-oxopiperidin-1-yl)methyl]-1-phenylcyclohexyl]-3,5-bis(trifluoromethylbenzeneacetamide;

trans-(RS)-α-methyl-N-[4-(4-hydroxypiperidin-1-yl)methyl-1-phenylcyclohexyl]-3,5-bis(trifluoromethylbenzeneacetamide;

cis-(RS)-α-methyl-N-[4-hydroxy-4-(1-oxa-8-azaspiro[4.5]decan-8-yl)methyl-1-phenylcyclohexyl]-3,5-bis(trifluoromethyl)benzeneacetamide;

trans-(RS)-α-methyl-N-[1-phenyl-4-{1-(1-methylethyl)piperidin-4-yl]cyclohexyl}-3,5-bis(trifluoromethyl)benzeneacetamide;

(1R*,3S*,4R*)- and (1R*,3R*,4R*)-α,α-dimethyl-N-[3-hydroxy-4-(1-oxa-8-azaspiro[4.5]decan-8-yl)-1-phenylcyclohexyl]-3,5-bis(trifluoromethyl)benzeneacetamide;

(1R*,3S*,4R*)-α,α-dimethyl-N-[3-fluoro-4-(2-oxa-8-azaspiro[4.5]decan-8-yl)-1-phenylcyclohexyl]-3,5-bis(trifluoromethyl)benzeneacetamide;

or a pharmaceutically acceptable salt thereof.

17. The compound of claim 1 wherein the stereochemistry of the 1- and 4-positions is as shown in formula (Ib):

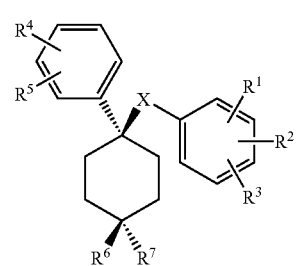

(Ib)

18. A pharmaceutical composition comprising the compound of claim 1 or a pharmaceutically acceptable salt thereof, and a pharmaceutically acceptable carrier or excipient.

19. A method for the treatment of pain, inflammation, migraine, emesis, postherpetic neuralgia, depression or anxiety, which method comprises administration to a patient in need thereof of a tachykinin reducing amount of the compound of claim 1 or a pharmaceutically acceptable salt thereof.

* * * * *